United States Patent
Wrobel et al.

(10) Patent No.: US 10,639,298 B2
(45) Date of Patent: May 5, 2020

(54) PRODRUGS OF RILUZOLE AND THEIR METHOD OF USE

(71) Applicant: Biohaven Pharmaceutical Holding Company Ltd., New Haven, CT (US)

(72) Inventors: Jay Edward Wrobel, Lawrenceville, NJ (US); Allen B. Reitz, Lansdale, PA (US); Jeffery Claude Pelletier, Lafayette Hill, PA (US); Garry Robert Smith, Royersford, PA (US); Haiyan Bian, Princeton, NJ (US)

(73) Assignee: Biohaven Therapeutics Ltd., New Haven, CT (US)

( * ) Notice: Subject to any disclaimer, the term of this patent is extended or adjusted under 35 U.S.C. 154(b) by 0 days.

(21) Appl. No.: 15/549,152

(22) PCT Filed: Feb. 26, 2016

(86) PCT No.: PCT/US2016/019773
§ 371 (c)(1),
(2) Date: Aug. 5, 2017

(87) PCT Pub. No.: WO2016/140878
PCT Pub. Date: Sep. 9, 2016

(65) Prior Publication Data
US 2018/0037557 A1    Feb. 8, 2018

Related U.S. Application Data

(60) Provisional application No. 62/127,684, filed on Mar. 3, 2015.

(51) Int. Cl.
| | | |
|---|---|---|
| C07D 277/82 | (2006.01) |
| A61K 31/428 | (2006.01) |
| C07D 417/12 | (2006.01) |
| A61K 31/496 | (2006.01) |
| A61K 38/05 | (2006.01) |
| A61K 31/454 | (2006.01) |
| A61K 31/5377 | (2006.01) |
| A61K 45/06 | (2006.01) |
| C07K 5/062 | (2006.01) |
| A61K 9/00 | (2006.01) |
| A61K 9/16 | (2006.01) |
| A61K 9/20 | (2006.01) |

(52) U.S. Cl.
CPC ........... *A61K 31/428* (2013.01); *A61K 9/006* (2013.01); *A61K 9/1617* (2013.01); *A61K 9/2004* (2013.01); *A61K 31/454* (2013.01); *A61K 31/496* (2013.01); *A61K 31/5377* (2013.01); *A61K 38/05* (2013.01); *A61K 45/06* (2013.01); *C07D 277/82* (2013.01); *C07D 417/12* (2013.01); *C07K 5/06026* (2013.01); *A61K 2300/00* (2013.01)

(58) Field of Classification Search
None
See application file for complete search history.

(56) References Cited

U.S. PATENT DOCUMENTS

| | | |
|---|---|---|
| 9,725,427 B2 | 8/2017 | Smith et al. |
| 2015/0045401 A1 | 2/2015 | Smith et al. |
| 2015/0148329 A1 | 5/2015 | Reitz et al. |
| 2017/0334870 A1 | 11/2017 | Smith et al. |
| 2018/0036290 A1 | 2/2018 | Wrobel et al. |
| 2018/0037557 A1 | 2/2018 | Wrobel et al. |

FOREIGN PATENT DOCUMENTS

| | | |
|---|---|---|
| WO | WO2013138753 | 9/2013 |
| WO | WO2013192610 | 12/2013 |
| WO | PCT/US2016/019773 | 8/2016 |
| WO | PCT/US2016/019787 | 8/2016 |
| WO | PCT/US2016/019787 | 9/2017 |

OTHER PUBLICATIONS

Cancer [online], [retrieved on Jul. 6, 2007] Retrieved from the Internet, URL: http://www.nlm.nih.gov/medlineplus/cancer.html (Year: 2007).*
Lala et al., Role of nitric oxide in tumor progression: Lessons from experimental tumors, Cancer and Metastasis Reviews (1998), 17, 91-106 (Year: 1998).*
Golub et al., Molecular Classification of Cancer: Class Discovery and Class Prediction by Gene Expression Monitoring, Science (1999), vol. 286, 531-537 (Year: 1999).*
Jeffery C. Pelletier, et al., Dipeptide Prodrugs of the Glutamate Modulator Riluzole, ACS Med. Chem. Lett. 2018, 9 752-756.

* cited by examiner

*Primary Examiner* — Kristin A Vajda

(57) ABSTRACT

Pharmaceutical compositions of the invention include substituted riluzole prodrugs useful for the treatment of cancers including melanoma, breast cancer, brain cancer, and prostate cancer through the release of riluzole. Prodrugs of riluzole have enhanced stability to hepatic metabolism and are delivered into systemic circulation by oral administration, and then cleaved to release riluzole in the plasma via either an enzymatic or general biophysical release process.

10 Claims, 4 Drawing Sheets

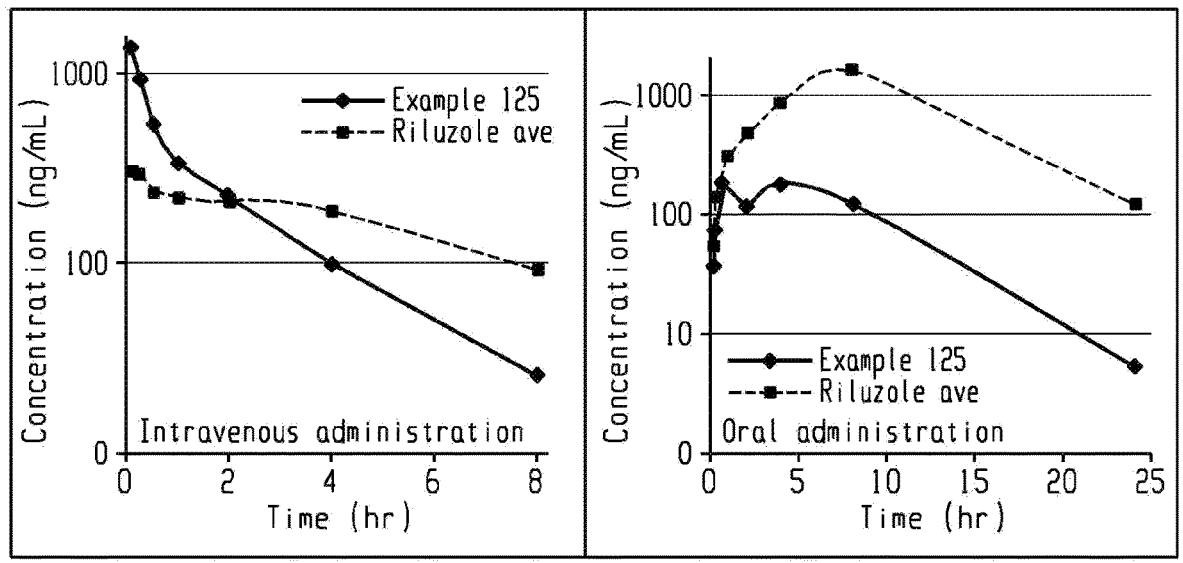
Fig. 1: Time concentration curve for example 125 and released riluzole via both intravenous and oral administration
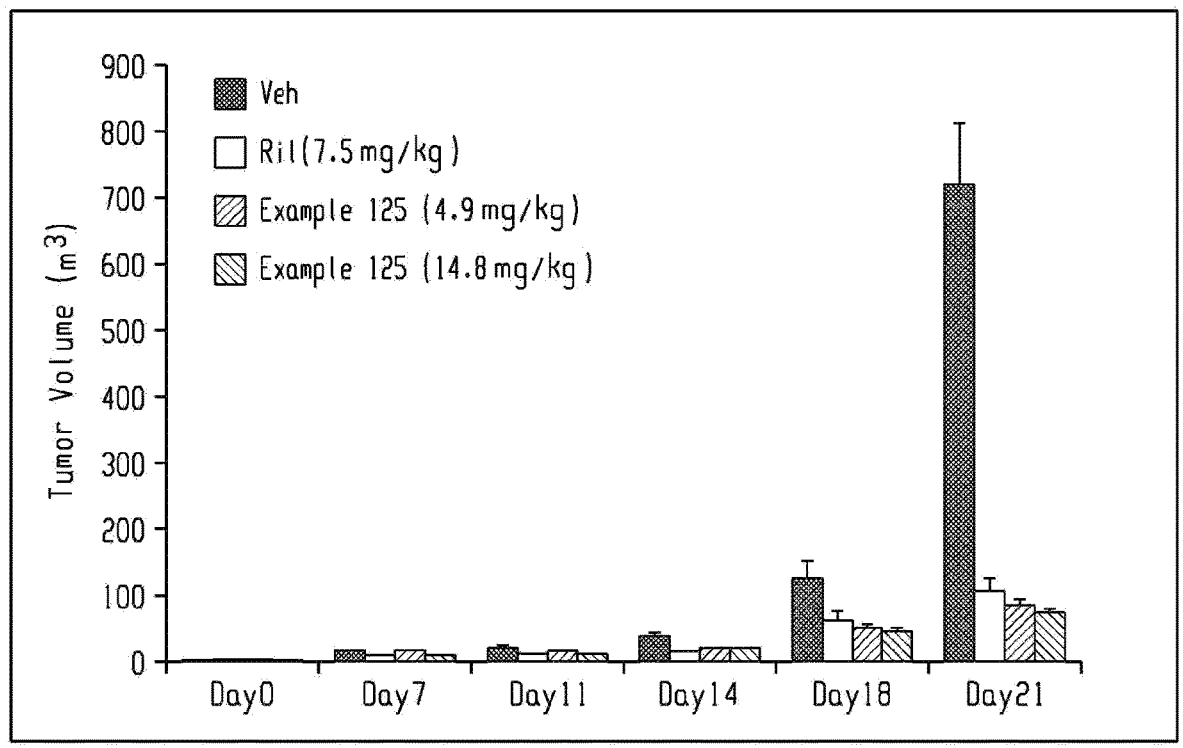
Fig. 2: Melanoma (C8161) xenograft study in nude mice with example 125 and riluzole given orally (RIL = Riluzole)

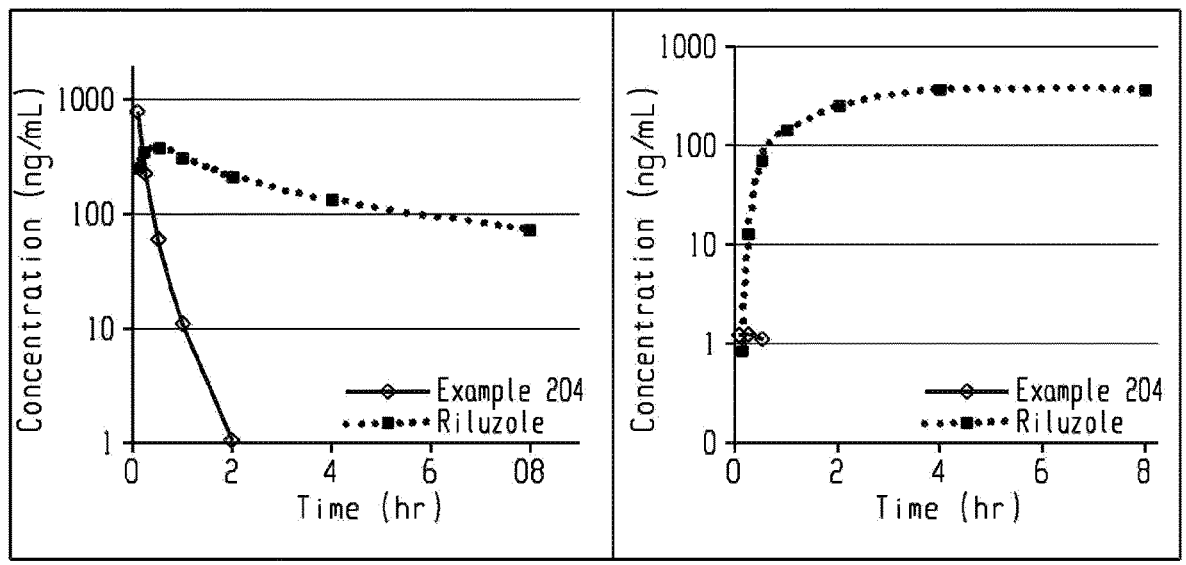
Fig. 3: Time-concentration curves for 2-Amino-N-{[methyl]({[6-(trifluoromethoxy)-1,3-benzo thiazol-2-yl]carbamoyl} acetamide (Example 204) and released riluzole via both intravenous and oral administration
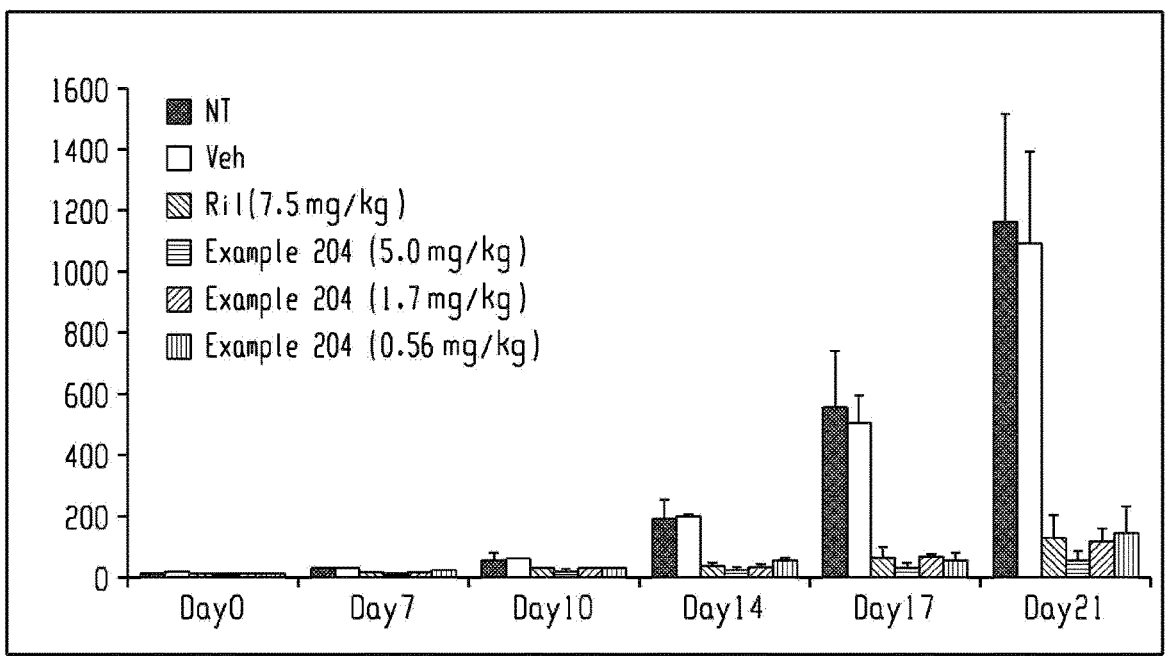
Fig. 4: Melanoma (C8161) xenograft study in nude mice with example 204 and riluzole given orally (RIL = Riluzole)

Fig. 5: PK in fasted male mice for Example 204, IV administration, 1 mg/kg, and PO administration 5 mg/kg. Monitor disappearance of Prodrug and appearance of riluzole.
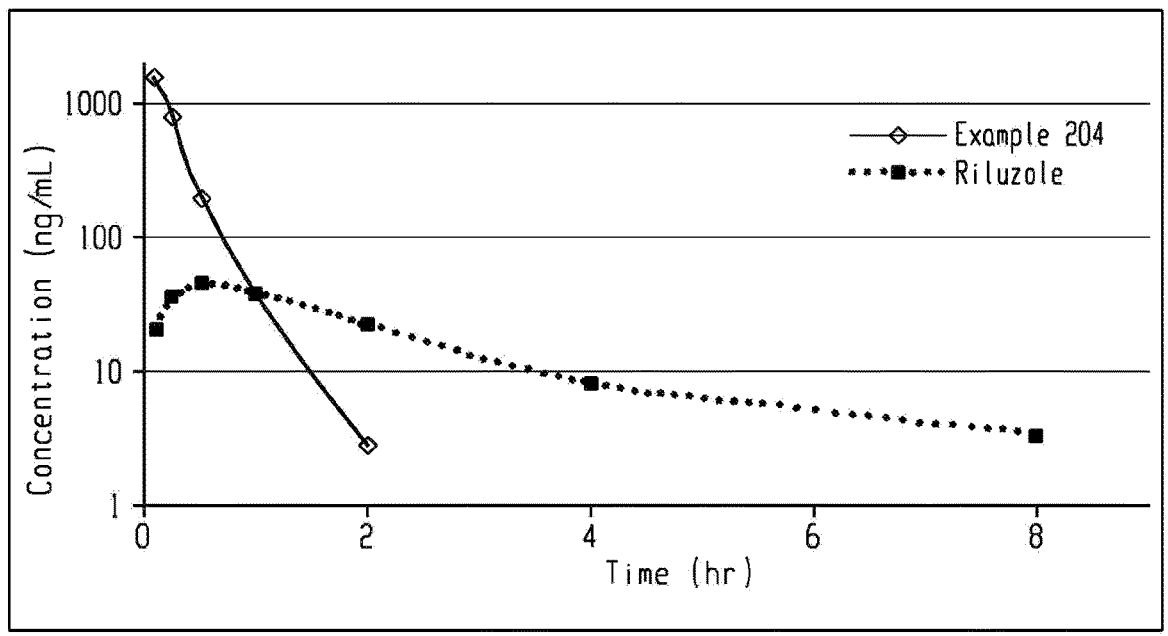
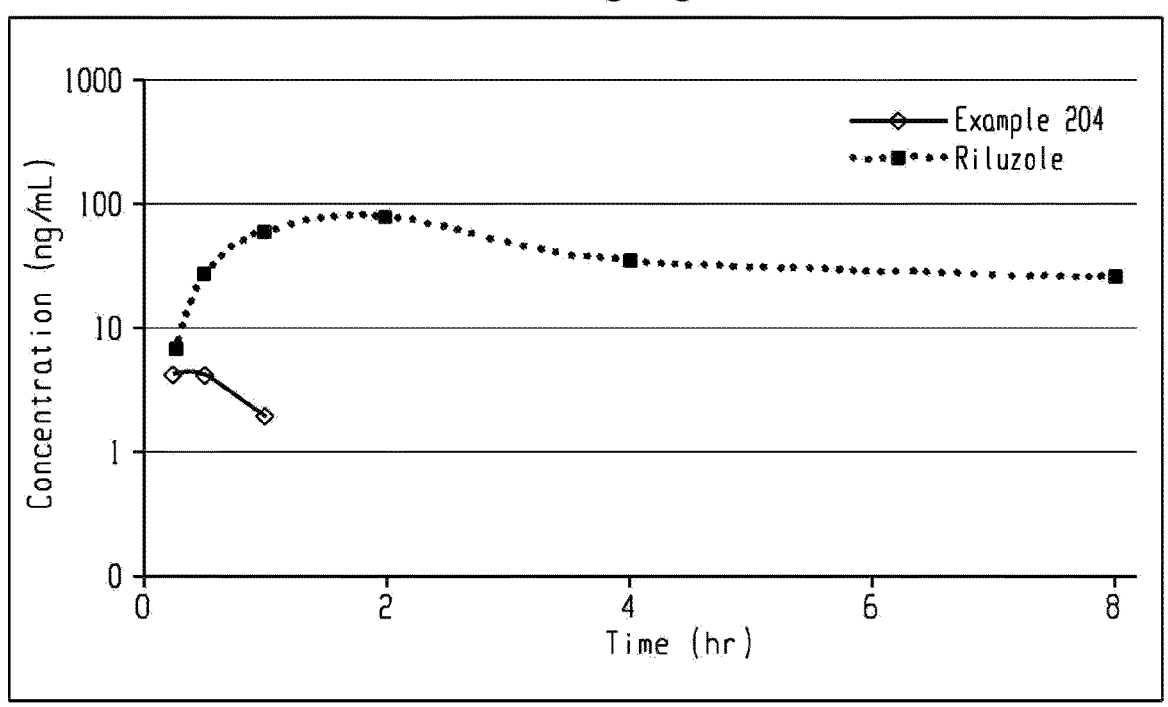

Fig. 6: PK in Cynomolgus Monkey for Example 204, IV administration, 1mg/kg, and PO administration 5mg/kg. Monitor appearance of riluzole.
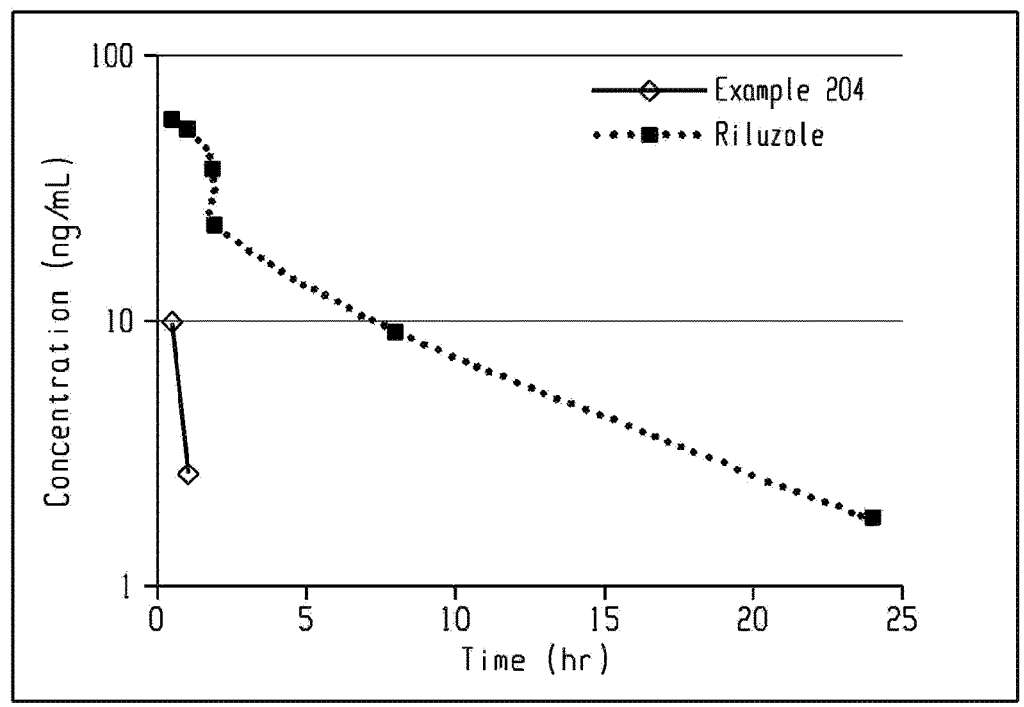
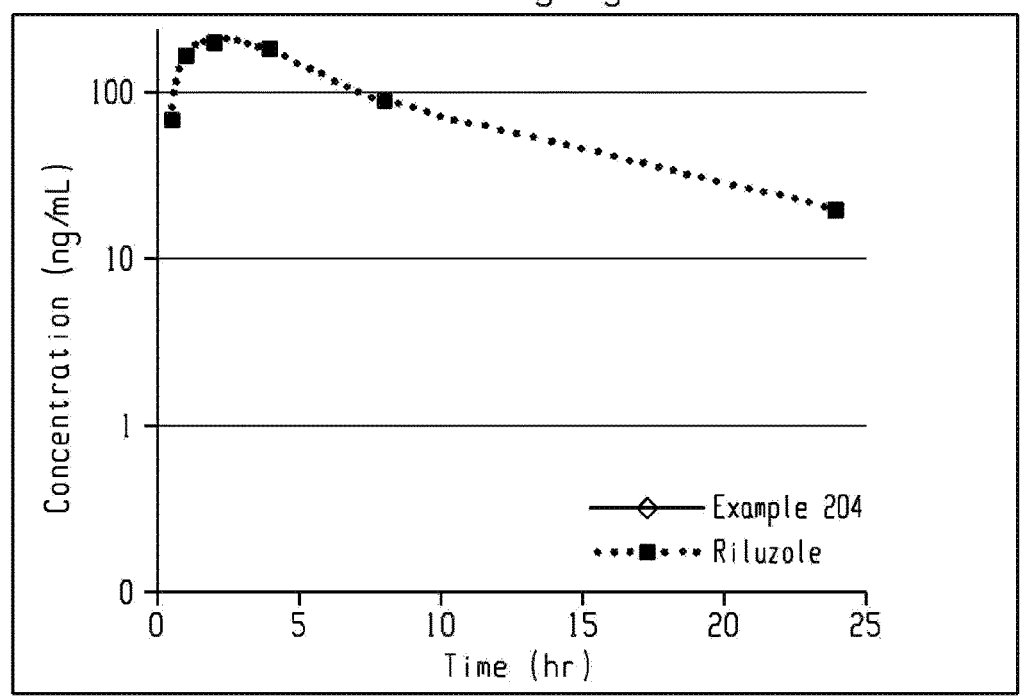

PRODRUGS OF RILUZOLE AND THEIR METHOD OF USE

CROSS-REFERENCE TO RELATED APPLICATIONS

This application is a national stage application under 35 U.S.C. § 371 of international application PCT/US2016/019773, filed Feb. 26, 2016 which claims the benefit of U.S. Provisional Application No. 62/127,684 filed Mar. 3, 2015, each of which are herein incorporated by reference in its entirety.

STATEMENT OF FEDERALLY FUNDED RESEARCH

This invention was made with government support under grant numbers R43 CA156781 and R44 CA156781 awarded by the National Institutes of Health. The government has certain rights in the invention.

FIELD OF INVENTION

The present invention describes compounds and methods useful as prodrug agents, useful for the treatment of cancers including melanoma through the release of riluzole.

BACKGROUND OF THE INVENTION

A recently conducted Phase 0 human clinical trial of riluzole (Rilutek™) demonstrated dramatic efficacy in certain melanoma patients after only 14 days of treatment. Riluzole, the only FDA approved drug to treat amyotrophic lateral sclerosis (ALS), showed clinical or radiologic evidence of tumor response in four of 12 patients with Stage III and IV melanoma, cancer with a poor prognosis and severely limited treatment options.

The use of riluzole (RILUTEK®) for cancers or other diseases is significantly constrained due to high levels of variability in hepatic metabolism of the drug, dose dependent effects on the liver, and a negative food effect associated with the drug when administered with meals. The approved USPI notes that that riluzole tablets should be taken at least 1 hour before, or 2 hours after, a meal to avoid food-related decreases in bioavailability that may interfere with the ability to achieve or maintain therapeutic blood concentrations. Such fasting requirements amount to six hours of fasting per day when administered twice daily. Despite riluzole's approval over 20 years ago, these multiple clinical constraints of riluzole have persisted and limited the clinical application of riluzole to other disease states. We describe here prodrugs of riluzole in order to improve the clinical efficacy of riluzole-based therapy, increase patient compliance, and relieve human suffering. Metastatic melanoma has few treatment options, and the current therapeutic standard of care is dacarbazine which is a highly cytotoxic drug with severe side effects including vomiting, headache and hair loss. Treatment with dacarbazine has a median progression-free enhancement of survival time of only 1.5 months. Riluzole (Rilutek™) is a generally non-toxic drug and currently the only FDA-approved treatment for amyotrophic lateral sclerosis (ALS or Lou Gehrig's disease).

We have recently shown that riluzole has dramatic anti-melanoma activity in vitro cellular assays, in mice and in a Phase 0 human clinical trial. In the clinic, four of twelve melanoma patients showed significant clinical or radiologic evidence of Stage III and IV tumor response. These results, along with the mild side-effect profile that riluzole has shown among ALS patients, suggests that this drug has significant potential for use as an improved treatment for metastatic melanoma. However, the therapeutic utility of riluzole itself in ALS and eventually for melanoma is very constrained by rapid first-pass metabolism in the liver and an exceptionally high level of patient-to-patient variability in the extent of the Cyp1A2-mediated oxidative metabolism that is observed.

Riluzole is also believed to be clinically relevant in additional disease states, including a variety of central nervous system ("CNS") and depression/anxiety states. These include, but are not limited to, bipolar disorder, treatment resistant and major depression, obsessive-compulsive disorder, general anxiety disorder, panic disorder, social anxiety, mood disorders, cognitive disorders, dementia, agitation, apathy, psychoses, post-traumatic stress disorders, irritability, disinhibition, learning disorders, memory loss, personality disorders, bipolar disorders, Rett syndrome, eating disorders, conduct disorder, neurodegenerative disorders, pain disorders, supranuclear palsy, frontotemporal dementia, frontotemporal lobar degeneration, delirium, Alzheimer's disease, mild cognitive impairment, mild cognitive impairment due to Alzheimer's disease, drug addiction, tinnitus, mental retardation, spinal muscular atrophy, radiation therapy, multiple sclerosis, chronic cerebellar ataxia, hereditary spinocerebellar ataxia, spinocerebellar ataxia, sporadic ataxia, episodic ataxia, Friedreich Ataxia, Multisystem Atrophy, ataxia associated with Anti-GAD antibodies target and onconeural antigen, essential tremor, cervical spondylotic myelopathy, spinal cord injury, hereditary cerebellar ataxia, Tourette syndrome, autism spectrum disorder, schizophrenia, fragile X syndrome, Parkinson's Disease, Progressive Supranuclear Palsy, Dementia with Lewy Bodies, and Huntington's disease. However, riluzole can have issues in liver metabolism. Pro-drugs of riluzole will provide more predictable pharmacokinetic properties and metabolic profiles for the parent compound, leading to an improved therapeutic effect in each of the aforementioned disease states. Riluzole has been approved for 25 years without solutions to the pharmacokinetic and metabolic limitations of the drug. The intrinsic property of the drug itself teaches away from the sublingual administration of riluzole. Riluzole has a very low solubility in water, poor oral palatability, pH dependent chemical stability, and intense as well as persistent numbness or burning sensation throughout the oral cavity. Techniques aimed at reducing these undesirable effects, such as use of chelating agents, would only facilitate the oral swallowing and gastric absorption rather than resulting in sublingual absorption It has also been demonstrated that riluzole is clinically relevant to generalized anxiety disorder (GAD) and is useful for the attenuation of presynaptic glutamate release. Riluzole is also useful for the normalization, enhancement or potentiation of the uptake of glutamate by glia (Coric et al. U.S. Pat. No. 8,778,979).

There is a long felt need for new treatments for melanoma that are both disease-modifying and effective in treating patients that are refractory to current treatments. The present invention addresses the need to identify new treatments for melanoma by identifying novel prodrugs of riluzole which possess enhanced stability to hepatic metabolism and are delivered into systemic circulation by oral administration. The present invention can also treat or prevent various neurological or CNS states as well as depression/anxiety states. The riluzole prodrugs are cleaved to release riluzole in the plasma via either an enzymatic or general biophysical release process.

BRIEF SUMMARY OF THE INVENTION

The present invention is directed toward riluzole derivatives of formula (I),

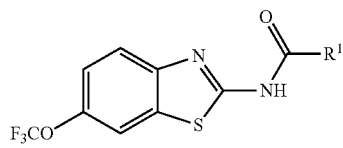

including enantiomers, diasteroemers, hydrates, solvates, pharmaceutically acceptable salts, and complexes thereof, wherein:
$R^1$ is selected from the group consisting of $C_1$-$C_6$ fluoroalkyl, $OR^2$, $(CR^{6a}R^{6b})_m NHR^7$, $CR^{10a}R^{10b}NR^{11}R^{12}$,

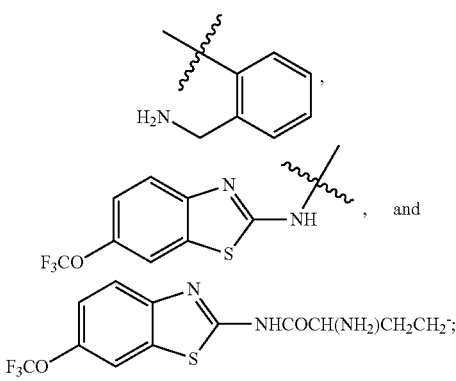, and $R^2$ is selected from the group consisting of $CH_2$ $(CH_2)_n NR^{3a}R^{3b}$,

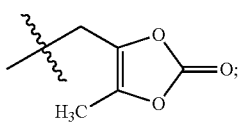 [SMILES: *Cc1oc(=O)oc1C]

$R^{3a}$ and $R^{3b}$ are independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl, and $CO_2R^4$;
$R^{3a}$ and $R^{3b}$ cannot both be $C_1$-$C_6$ alkyl;
$R^{3a}$ and $R^{3b}$ are taken together with the atom to which they are bound to form an optionally substituted three to six membered saturated heterocyclic ring consisting of two to five carbon atoms and a member selected from the group consisting of O, $NR^5$, S, and $SO_2$;
n is 1 or 2;
$R^4$ is selected from the group consisting of $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl, optionally substituted phenyl, and optionally substituted benzyl;
$R^5$ is selected from the group consisting of $C_1$-$C_6$ alkyl, $C_3$-$C_7$ branched alkyl, $C_3$-$C_7$ cycloalkyl, $C_2$-$C_6$ alkenyl, and $C_2$-$C_6$ alkynyl;

$R^{6a}$ and $R^{6b}$ are at each occurrence independently selected from the group consisting of hydrogen, optionally substituted $C_1$-$C_6$ alkyl, optionally substituted $C_3$-$C_7$ branched alkyl, optionally substituted $C_3$-$C_7$ cycloalkyl, $C_2$-$C_6$ alkenyl, and $C_2$-$C_6$ alkynyl;
$R^{6a}$ and $R^{6b}$ are taken together with the atom to which they are bound to form an optionally substituted 6 membered ring;
m is 1, 2, or 3;
$R^7$ is selected from the group consisting of $COCR^{8a}R^{8b}$ $(NHR^9)$,

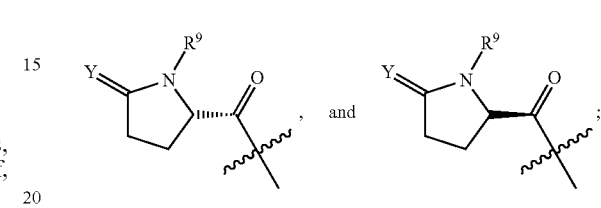

$R^{8a}$ and $R^{8b}$ are at each occurrence independently selected from the group consisting of hydrogen, $CH_3$, $CH(CH_3)_2$, $CH_2CH(CH_3)_2$, $CH(CH_3)CH_2CH_3$, $CH_2OH$, $CH(OH)CH_3$, $CH_2Ph$, $CH_2(4\text{-}OH\text{-}Ph)$, $(CH_2)_4NH_2$, $(CH_2)_3NHC(NH_2)$ NH, $CH_2(3\text{-indole})$, $CH_2(5\text{-imidazole})$, $CH_2CO_2H$, $CH_2CH_2CO_2H$, $CH_2CONH_2$, and $CH_2CH_2CONH_2$;
$R^9$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, and $C_2$-$C_6$ alkynyl;
Y is at each occurrence independently selected from the group consisting of $H_2$ or O;
$R^{10a}$ and $R^{10b}$ are at each occurrence independently selected from the group consisting of hydrogen, $CH_3$, $CH_2CH_3$, $CH(CH_3)_2$, $CH_2CH(CH_3)_2$, $CH(CH_3)CH_2CH_3$, $CH_2OH$, $CH_2OCH_2Ph$, $CH(OH)CH_3$, $CH_2Ph$, $CH_2(4\text{-}OH\text{-}Ph)$, $(CH_2)_4NH_2$, $(CH_2)_3NHC(NH_2)NH$, $CH_2(3\text{-indole})$, $CH_2(5\text{-imidazole})$, $CH_2(CCH)$, $CH_2(cyclohexyl)$, $CH_2CO_2H$, $CH_2CH_2CO_2H$, $CH_2CONH_2$, and $CH_2CH_2CONH_2$;
$R^{10a}$ and $R^{10b}$ are taken together with the atom to which they are bound to form an optionally substituted three to six membered saturated carbocyclic ring;
$R^{11}$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, $C_1$-$C_6$ haloalkyl, and $C_2$-$C_6$ alkynyl;
$R^{10a}$ and $R^{11}$ are taken together with the atoms to which they are bound to form an optionally substituted four to six membered ring containing one nitrogen atom, and $R^{12}$ is not hydrogen;
$R^{10b}$ and $R^{11}$ are taken together with the atoms to which they are bound to form an optionally substituted four to six membered ring containing one nitrogen atom, and $R^{12}$ is not hydrogen;
$R^{12}$ is at each occurrence independently selected from the group consisting of hydrogen, $C_1$-$C_6$ alkyl, $COCR^{13a}R^{13b}NR^{15a}R^{15b}$, $COCR^{13a}R^{13b}OR^{14}$, $SO_2CR^{13a}R^{13b}NR^{15a}R^{15b}$, $COCR^{13a}R^{13b}NHSO_2R^{15a}$,

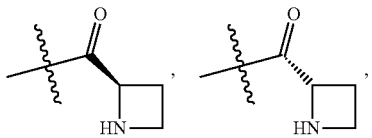

-continued

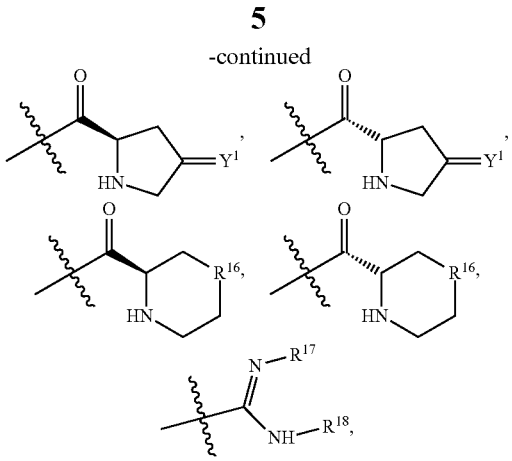

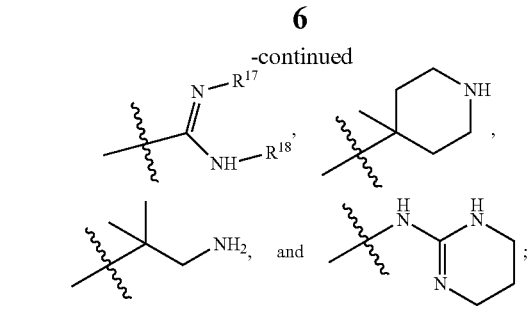

and $(CR^{19a}R^{19b})_q NHR^{20}$, and when $R^{12}$ is hydrogen, $R^{11}$ cannot be hydrogen;

$R^{11}$ and $R^{12}$ are taken together with the atom to which they are bound to form an optionally substituted four to six membered saturated heterocyclic ring containing a nitrogen atom and optionally containing an additional heteroatom from the group consisting of N and O;

$R^{13a}$ and $R^{13b}$ are at each occurrence independently selected from the group consisting hydrogen, $CH_3$, $CH_2CH_3$, $CH_2CH_2CH_3$, $CH_2CCH$, $CH(CH_3)_2$, $CH_2CH(CH_3)_2$, $CH(CH_3)CH_2CH_3$, $CH_2OH$, $CH_2OCH_2Ph$, $CH_2CH_2OCH_2Ph$, $CH(OH)CH_3$, $CH_2Ph$, $CH_2(cyclohexyl)$, $CH_2(4\text{-OH-Ph})$, $(CH_2)_4NH_2$, $(CH_2)_3NHC(NH_2)NH$, $CH_2(3\text{-indole})$, $CH_2(5\text{-imidazole})$, $CH_2CO_2H$, $CH_2CH_2CO_2H$, $CH_2CONH_2$, and $CH_2CH_2CONH_2$;

$R^{13a}$ and $R^{13b}$ are taken together with the atom to which they are bound to form an optionally substituted three to six membered saturated carbocyclic ring;

$R^{13a}$ and $R^{13b}$ are taken together with the atom to which they are bound to form an optionally substituted six membered saturated heterocyclic ring with one O atom within the ring;

$R^{14a}$ and $R^{14}$ are taken together with the atoms to which they are bound to form an optionally substituted four to six membered ring containing one nitrogen atom;

$R^{13a}$ and $R^{15a}$ are taken together with the atoms to which they are bound to form an optionally substituted four to six membered ring containing one nitrogen atom;

$Y^1$ is at each occurrence independently selected from the group consisting of $H_2$, O, and $-H/-OCH_2Ph$;

$R^{14}$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, and $C_2$-$C_6$ alkynyl;

$R^{15a}$ and $R^{15b}$ are at each occurrence independently selected from the group consisting of H, $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl $C_1$-$C_6$ fluoroalkyl, $COR^{21}$, $CH_2R^{21}$, $SO_2R^{22}$, an optionally substituted four to six membered saturated heterocyclic ring containing a heteroatom selected from the group consisting of $NR^{24}$ and O, $COCHR^{23}NH_2$,

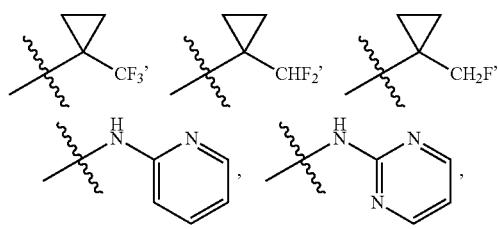

$R^{15a}$ and $R^{15b}$ are taken together with the atom to which they are bound to form an optionally substituted three to six membered saturated heterocyclic ring consisting of two to five carbon atoms and a member selected from the group consisting of O, $NR^5$, S, and $SO_2$;

$R^{16}$ is at each occurrence independently selected from the group consisting of $CH_2$, O, $C=O$, and NH;

$R^{17}$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, and $C_2$-$C_6$ alkynyl;

$R^{18}$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, and $C_2$-$C_6$ alkynyl;

$R^{17}$ and $R^{18}$ are taken together with the atoms to which they are bound to form an optionally substituted five or six membered ring containing two nitrogen atoms;

$R^{19a}$ and $R^{19b}$ are at each occurrence independently selected from the group consisting of hydrogen, optionally substituted $C_1$-$C_6$ alkyl, optionally substituted $C_3$-$C_7$ branched alkyl, optionally substituted $C_3$-$C_7$ cycloalkyl, optionally substituted $C_2$-$C_6$ alkenyl, and optionally substituted $C_2$-$C_6$ alkynyl;

$R^{19a}$ and $R^{19b}$ are taken together with the atom to which they are bound to form an optionally substituted 3 to 6 membered carbocyclic ring;

$R^{20}$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, and $C_2$-$C_6$ alkynyl; q is 1, or 2;

$R^{21}$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl, $C_1$-$C_6$ fluoroalkyl, optionally substituted aryl, and optionally substituted heteroaryl;

$R^{22}$ is at each occurrence independently selected from the group consisting of $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl, optionally substituted aryl, optionally substituted heteroaryl;

$R^{23}$ is selected from the group consisting H, $CH_3$, $CH_2CH_3$, $CH_2CH_2CH_3$, $CH_2CCH$, $CH(CH_3)_2$, $CH_2CH(CH_3)_2$, $CH(CH_3)CH_2CH_3$, $CH_2OH$, $CH_2OCH_2Ph$, $CH_2CH_2OCH_2Ph$, $CH(OH)CH_3$, $CH_2Ph$, $CH_2(cyclohexyl)$, $CH_2(4\text{-OH-Ph})$, $(CH_2)_4NH_2$, $(CH_2)_3NHC(NH_2)NH$, $CH_2(3\text{-indole})$, $CH_2(5\text{-imidazole})$, $CH_2CO_2H$, $CH_2CH_2CO_2H$, $CH_2CONH_2$, and $CH_2CH_2CONH_2$;

$R^{24}$ is at each occurrence independently selected from the group consisting of H, $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl, optionally substituted aryl, optionally substituted heteroaryl, $COR^{25}$, and $SO_2$—$C_{1-6}$alkyl;

$R^{25}$ is at each occurrence independently selected from the group consisting of H, $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl, optionally substituted aryl, optionally substituted heteroaryl, $C_1$-$C_6$ alkoxy, and $C_1$-$C_6$ alkylamino.

The compounds of the present invention include compounds having formula (II):

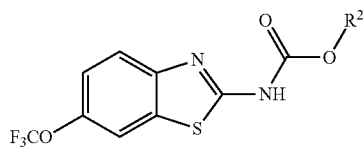

II including enantiomers, diasteroemers, hydrates, solvates, pharmaceutically acceptable salts, and complexes thereof.

The compounds of the present invention include compounds having formula (III):

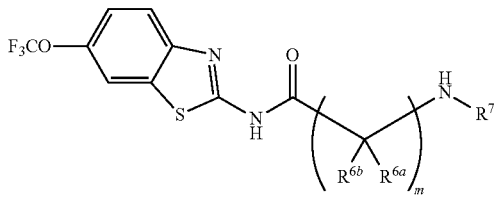

III including enantiomers, diasteroemers, hydrates, solvates, pharmaceutically acceptable salts, and complexes thereof.

The compounds of the present invention include compounds having formula (IV):

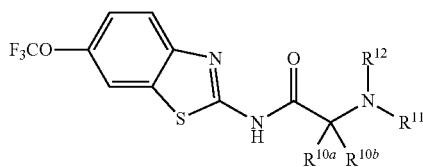

IV including enantiomers, diasteroemers, hydrates, solvates, pharmaceutically acceptable salts, and complexes thereof.

The compounds of the present invention include compounds having formula (V):

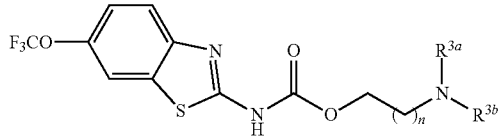

V including enantiomers, diasteroemers, hydrates, solvates, pharmaceutically acceptable salts, and complexes thereof.

The compounds of the present invention include compounds having formula (VI):

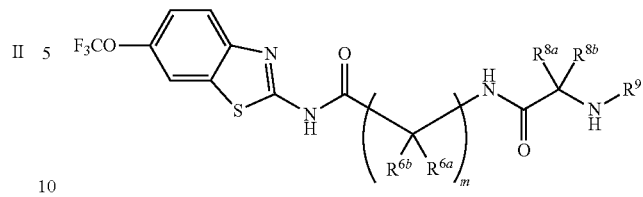

VI including enantiomers, diasteroemers, hydrates, solvates, pharmaceutically acceptable salts, and complexes thereof.

The compounds of the present invention include compounds having formula (VII):

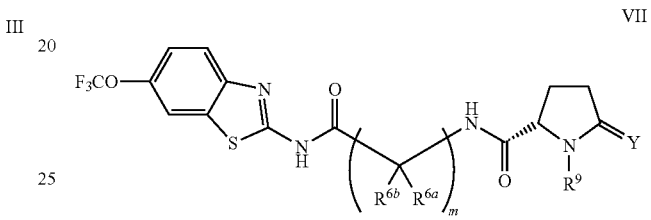

VII including enantiomers, diasteroemers, hydrates, solvates, pharmaceutically acceptable salts, and complexes thereof.

The compounds of the present invention include compounds having formula (VIII):

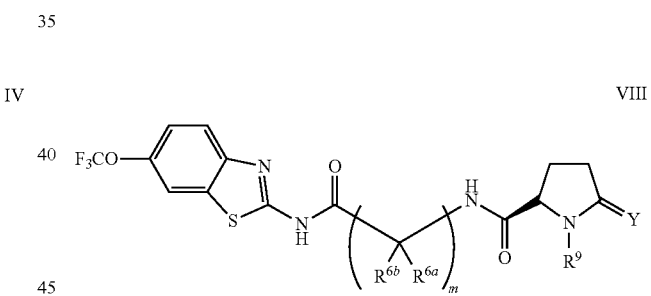

VIII including enantiomers, diasteroemers, hydrates, solvates, pharmaceutically acceptable salts, and complexes thereof.

The compounds of the present invention include compounds having formula (IX):

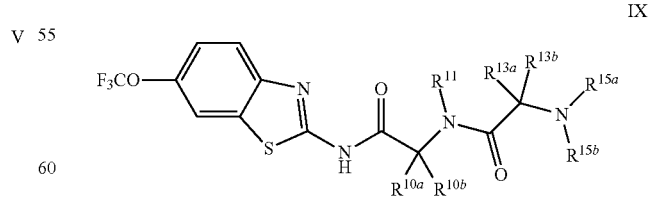

IX including enantiomers, diasteroemers, hydrates, solvates, pharmaceutically acceptable salts, and complexes thereof.

The compounds of the present invention include compounds having formula (X):

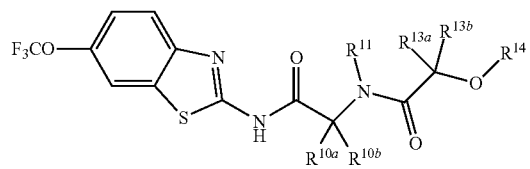

X including enantiomers, diasteroemers, hydrates, solvates, pharmaceutically acceptable salts, and complexes thereof.

The compounds of the present invention include compounds having formula (XI):

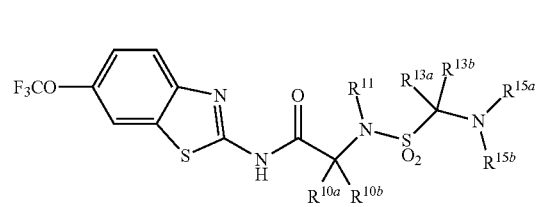

XI including enantiomers, diasteroemers, hydrates, solvates, pharmaceutically acceptable salts, and complexes thereof.

The compounds of the present invention include compounds having formula (XII):

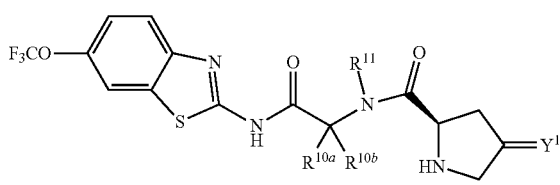

XII including enantiomers, diasteroemers, hydrates, solvates, pharmaceutically acceptable salts, and complexes thereof.

The compounds of the present invention include compounds having formula (XIII):

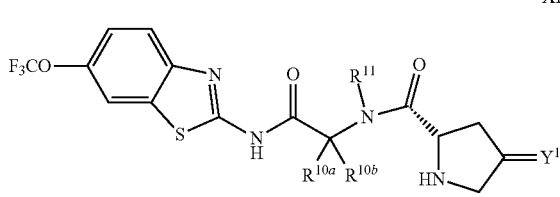

XIII including enantiomers, diasteroemers, hydrates, solvates, pharmaceutically acceptable salts, and complexes thereof.

The compounds of the present invention include compounds having formula (XIV):

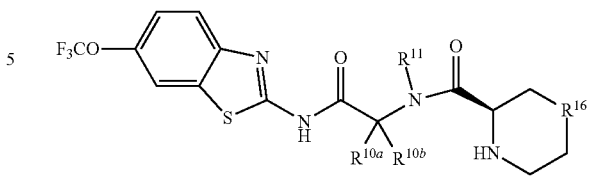

XIV including enantiomers, diasteroemers, hydrates, solvates, pharmaceutically acceptable salts, and complexes thereof.

The compounds of the present invention include compounds having formula (XV):

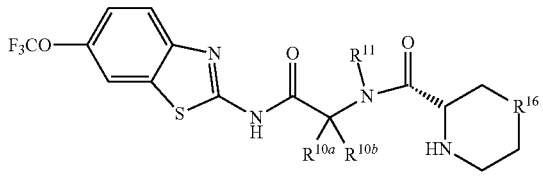

XV including enantiomers, diasteroemers, hydrates, solvates, pharmaceutically acceptable salts, and complexes thereof.

The compounds of the present invention include compounds having formula (XVI):

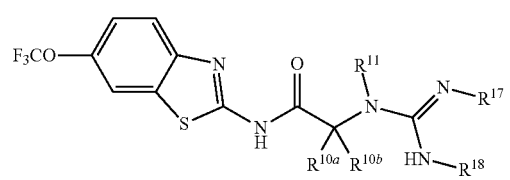

XVI including enantiomers, diasteroemers, hydrates, solvates, pharmaceutically acceptable salts, and complexes thereof.

The compounds of the present invention include compounds having formula (XVII):

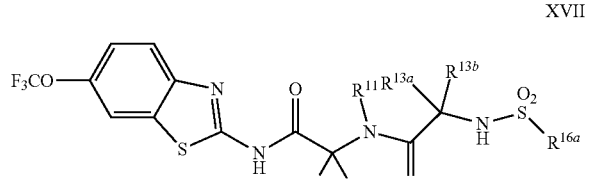

XVII including enantiomers, diasteroemers, hydrates, solvates, pharmaceutically acceptable salts, and complexes thereof.

The compounds of the present invention include compounds having formula (XVIII)

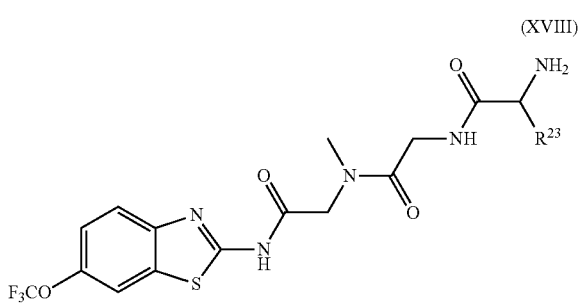

(XVIII)

including enantiomers, diasteroemers, hydrates, solvates, pharmaceutically acceptable salts, and complexes thereof, wherein:

$R^{23}$ is selected from the group consisting H, $CH_3$, $CH_2CH_3$, $CH_2CH_2CH_3$, $CH_2CCH$, $CH(CH_3)_2$, $CH_2CH(CH_3)_2$, $CH(CH_3)CH_2CH_3$, $CH_2OH$, $CH_2OCH_2Ph$, $CH_2CH_2OCH_2Ph$, $CH(OH)CH_3$, $CH_2Ph$, $CH_2(cyclohexyl)$, $CH_2(4\text{-}OH\text{-}Ph)$, $(CH_2)_4NH_2$, $(CH_2)_3NHC(NH_2)NH$, $CH_2(3\text{-}indole)$, $CH_2(5\text{-}imidazole)$, $CH_2CO_2H$, $CH_2CH_2CO_2H$, $CH_2CONH_2$, and $CH_2CH_2CONH_2$.

The present invention further relates to compositions comprising:

an effective amount of one or more compounds according to the present invention and an excipient.

The present invention yet further relates to an effective amount of one or more compounds according to the present invention and an anticancer agent.

The present invention also relates to a method for treating or preventing cancer, particularly melanoma, said method comprising administering to a subject an effective amount of a compound or composition according to the present invention, possibly in conjunction with an excipient and/or an anticancer agent.

The present invention also relates to a method for treating or preventing disease or conditions associated with cancer, particularly melanoma. Said methods comprise administering to a subject an effective amount of a compound or composition according to the present invention, possibly in conjunction with an excipient and/or an anticancer agent.

Cancers that may be treated or prevented by administering to a subject an effective amount of a compound or composition according to the present invention, or a pharmaceutically acceptable salt, solvate, anomer, enantiomer or hydrate thereof, possibly with an excipient or an anticancer agent, include ovarian cancer, cervical cancer, breast cancer, prostate cancer, testicular cancer, lung cancer, renal cancer, colorectal cancer, melanoma and nonmelanoma skin cancer, brain cancer including glioma, glioblastoma, and leukemia. The present invention also provides a sublingual or sustained release formulation which may comprise an effective amount of riluzole or a pharmaceutically acceptable salts, solvate, anomers, enantiomers, hydrate or prodrugs thereof to treat cancers in combination with immunotherapies (including alone or in combination with vaccines, anti-PD1, anti-PDL1, anti-CTLA4 or other immunotherapy or checkpoint inhibitor targets including: CTLA4, cytotoxic T-lymphocyte-associated antigen 4; Ig, immunoglobulin; LAG3, lymphocyte activation gene 3; mAbs, monoclonal antibodies; PD1, programmed cell death protein 1; PDL, PD1 ligand; TIM3, T cell membrane protein 3; CD40L, A2aR, adenosine A2a receptor; B7RP1, B7-related protein 1; BTLA, B and T lymphocyte attenuator; GAL9, galectin 9; HVEM, herpesvirus entry mediator; ICOS, inducible T cell co-stimulator; IL, interleukin; KIR, killer cell immunoglobulin-like receptor; LAG3, lymphocyte activation gene 3; PD1, programmed cell death protein 1; PDL, PD1 ligand; TGFβ, transforming growth factor-β; TIM3, T cell membrane protein 3; CD27).

The present invention also relates to a method for treating or preventing various neurological or CNS states as well as depression/anxiety states in which riluzole is clinically relevant including, but are not limited to, bipolar disorder, treatment resistant and major depression, general anxiety disorder, panic disorder, social anxiety, mood disorders, cognitive disorders, dementia, agitation, apathy, psychoses, post-traumatic stress disorders, irritability, disinhibition, learning disorders, memory loss, personality disorders, bipolar disorders, Rett syndrome, eating disorders, conduct disorder, neurodegenerative disorders, pain disorders, supranuclear palsy, frontotemporal dementia, frontotemporal lobar degeneration, delirium, Alzheimer's disease, mild cognitive impairment, mild cognitive impairment due to Alzheimer's disease, drug addiction, tinnitus, mental retardation, obsessive-compulsive disorder, spinal muscular atrophy, radiation therapy, multiple sclerosis, chronic cerebellar ataxia, hereditary spinocerebellar ataxia, spinocerebellar ataxia, sporadic ataxia, episodic ataxia, Friedreich Ataxia, Multisystem Atrophy, ataxia associated with Anti-GAD antibodies target and onconeural antigen, essential tremor, cervical spondylotic myelopathy, spinal cord injury, hereditary cerebellar ataxia, Tourette syndrome, autism spectrum disorder, schizophrenia, fragile X syndrome, Parkinson's Disease, Progressive Supranuclear Palsy, Dementia with Lewy Bodies, and Huntington's disease, said method comprising administering to a subject an effective amount of a compound or composition according to the present invention, possibly with an excipient or other CNS drug such as serotonin reuptake inhibitor (SRI).

The present invention yet further relates to a method of enhancing the activity of a serotonin reuptake inhibitor (SRI) in an individual in need thereof. The methods comprise co-administering to the individual an effective amount of a compound or composition according to the present invention and a SRI.

In certain embodiments, the serotonin reuptake inhibitor can be citalopram, escitalopram, fluoxetine, fluvoxamine, paroxetine, sertraline, trazodone, venlafaxine, mirtazapine, clomipramine, or combinations with other psychotropic medications including an anti-psychotic, an anticonvulsant, a tricyclic antidepressant, a monoamine oxidase inhibitor, a selective serotonin reuptake inhibitor, a selective serotonin-norepinephrine reuptake inhibitor, a norepinephrine dopamine reuptake inhibitor, a serotonin-2 antagonist reuptake inhibitor, a benzodiazepine, a wakefulness promoting agent, anti-manic agent, or a combination of one or more of the foregoing. The present invention further relates to a process for preparing the riluzole prodrugs of the present invention.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

BRIEF DESCRIPTION OF THE DRAWINGS

FIG. 1: Time concentration curve for example 125 and released riluzole via both intravenous and oral administration.

FIG. 2: Melanoma (C8161) xenograft study in nude mice with example 125 and riluzole given orally (RIL=Riluzole).

FIG. 3: Time-concentration curves for 2-Amino-N-{[methyl({[6-(trifluoromethoxy)-1,3-benzo thiazol-2-yl] carbamoyl}methyl)carbamoyl]methyl}acetamide (Example 204) and released riluzole via both intravenous and oral administration.

FIG. 4: Melanoma (C8161) xenograft study in nude mice with example 204 and riluzole given orally (RIL=Riluzole).

FIG. 5: PK in fasted male mice for Example 204, IV administration, 1 mg/kg. and PO administration 5 mg/kg. Monitor disappearance of Prodrug and appearance of riluzole.

FIG. 6: PK in Cynomolgus Monkey for Example 204, IV administration, 1 mg/kg. and PO administration 5 mg/kg. Monitor appearance of riluzole.

DETAILED DESCRIPTION OF THE INVENTION

The prodrugs of the present invention are capable of treating and preventing cancers such as melanoma by releasing riluzole in vivo. Prodrugs of riluzole have enhanced stability to hepatic metabolism and are delivered into systemic circulation by oral administration, and are then cleaved to release riluzole in the plasma via either an enzymatic or general biophysical release process. Riluzole has dramatic anti-melanoma activity in vitro, in mice and in a Phase 0 human clinical trial. The pro-drugs of the present invention are also capable of treating and preventing other disease states in which riluzole is clinically relevant including, but are not limited to, amyotrophic lateral sclerosis (ALS) bipolar disorder, treatment resistant and major depression, general anxiety disorder, panic disorder, social anxiety, mood disorders, cognitive disorders, dementia, agitation, apathy, psychoses, post-traumatic stress disorders, irritability, disinhibition, learning disorders, memory loss, personality disorders, bipolar disorders, Rett syndrome, eating disorders, conduct disorder, neurodegenerative disorders, pain disorders, supranuclear palsy, frontotemporal dementia, frontotemporal lobar degeneration, delirium, Alzheimer's disease, mild cognitive impairment, mild cognitive impairment due to Alzheimer's disease, drug addiction, tinnitus, mental retardation, obsessive-compulsive disorder, spinal muscular atrophy, radiation therapy, multiple sclerosis, chronic cerebellar ataxia, hereditary spinocerebellar ataxia, spinocerebellar ataxia, sporadic ataxia, episodic ataxia, Friedreich Ataxia, Multisystem Atrophy, ataxia associated with Anti-GAD antibodies target and onconeural antigen, essential tremor, cervical spondylotic myelopathy, spinal cord injury, hereditary cerebellar ataxia, Tourette syndrome, autism spectrum disorder, schizophrenia, fragile X syndrome, Parkinson's Disease, Progressive Supranuclear Palsy, Dementia with Lewy Bodies, and Huntington's disease.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from the group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise. It should be understood that the order of steps or order for performing certain actions is immaterial so long as the present teachings remain operable. Moreover, two or more steps or actions can be conducted simultaneously As used herein, the term "halogen" shall mean chlorine, bromine, fluorine and iodine.

As used herein, unless otherwise noted, "alkyl" and "aliphatic" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_1$-$C_6$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as ($C_1$-$C_6$ alkyl)$_2$amino, the alkyl groups may be the same or different.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Cycloalkyl rings can be optionally substituted. Nonlimiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., —$CF_3$, $CF_2CF_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

The term "alkoxy" refers to the group —O-alkyl, wherein the alkyl group is as defined above. Alkoxy groups optionally may be substituted. The term v cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "aryl," wherein used alone or as part of another group, is defined herein as an unsaturated, aromatic monocyclic ring of 6 carbon members or to an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino) phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "arylalkyl" or "aralkyl" refers to the group alkyl-aryl, where the alkyl and aryl groups are as defined herein. Aralkyl groups of the present invention are optionally substituted. Examples of arylalkyl groups include, for example, benzyl, 1-phenylethyl, 2-phenylethyl, 3-phenylpropyl, 2-phenylpropyl, fluorenylmethyl and the like.

The terms "heterocyclic" and/or "heterocycle" and/or "heterocylyl," whether used alone or as part of another group, are defined herein as one or more ring having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted. Non-limiting examples of heterocyclic units having a single ring include: diazirinyl, aziridinyl, urazolyl, azetidinyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydro-quinoline. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-Dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiophenyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, benzo[d]thiazolyl, 1H-indolyl, 4,5,6,7-tetrahydro-1-H-indolyl, quinoxalinyl, 5-methylquinoxalinyl, quinazolinyl, quinolinyl, 8-hydroxyquinolinyl, and isoquinolinyl.

Unless otherwise noted, when two substituents are taken together to form a ring having a specified number of ring atoms (e.g., $R^2$ and $R^3$ taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted. For the purposed of the present invention fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

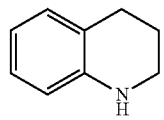

is, for the purposes of the present invention, considered a heterocyclic unit. 6,7-Dihydro-5H-cyclopentapyrimidine having the formula:

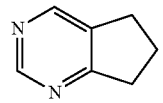

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

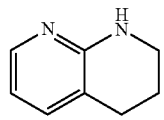

is, for the purposes of the present invention, considered a heteroaryl unit.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, cycloalkyl, alkoxy, aryloxy, aryl, heterocycle and heteroaryl groups defined herein, whether used alone or as part of another group, can be optionally substituted. Optionally substituted groups will be so indicated.

The following are non-limiting examples of substituents which can substitute for hydrogen atoms on a moiety: halogen (chlorine ($C_1$), bromine (Br), fluorine (F) and iodine (I)), —CN, —NO$_2$, oxo (=O), —OR$^{26}$, —SR$^{26}$, —N(R$^{26}$)$_2$, —NR$^{26}$C(O)R$^{26}$, —SO$_2$R$^{26}$, —SO$_2$OR$^{26}$, —SO$_2$N(R$^{26}$)$_2$, —C(O)R$^{26}$, —C(O)OR$^{26}$, —C(O)N(R$^{26}$)$_2$, $C_{1-6}$ alkyl, $C_{1-6}$ haloalkyl, $C_{1-6}$ alkoxy, $C_{2-8}$ alkenyl, $C_{2-8}$ alkynyl, $C_{3-14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, —NO$_2$, oxo, and R$^{26}$; wherein R$^{26}$, at each occurrence, independently is hydrogen, —OR$^{27}$, —SR$^{27}$, —C(O)R$^{27}$, —C(O)OR$^{27}$, —C(O)N(R$^{27}$)$_2$, —SO$_2$R$^{27}$, —S(O)$_2$OR$^{27}$, —N(R$^{27}$)$_2$, —NR$^{27}$C(O)R$^{27}$, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two R$^{26}$ units taken together with the atom(s) to which they are bound form an optionally substituted carbocycle or heterocycle wherein said carbocycle or heterocycle has 3 to 7 ring atoms; wherein R$^{27}$, at each occurrence, independently is hydrogen, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two R$^{27}$ units taken together with the atom(s) to which they are bound form an optionally substituted carbocycle or heterocycle wherein said carbocycle or heterocycle preferably has 3 to 7 ring atoms.

In some embodiments, the substituents are selected from
i) OR$^{28}$; for example, —OH, —OCH$_3$, —OCH$_2$CH$_3$, —OCH$_2$CH$_2$CH$_3$;
ii) —C(O)R$^{28}$; for example, —COCH$_3$, —COCH$_2$CH$_3$, —COCH$_2$CH$_2$CH$_3$;
iii) —C(O)OR$^{28}$; for example, —CO$_2$CH$_3$, —CO$_2$CH$_2$CH$_3$, —CO$_2$CH$_2$CH$_2$CH$_3$;
iv) —C(O)N(R$^{28}$)$_2$; for example, —CONH$_2$, —CONHCH$_3$, —CON(CH$_3$)$_2$;
v) —N(R$^{28}$)$_2$; for example, —NH$_2$, —NHCH$_3$, —N(CH$_3$)$_2$, —NH(CH$_2$CH$_3$);
vi) halogen: —F, —Cl, —Br, and —I;
vii) —CH$_e$X$_g$; wherein X is halogen, m is from 0 to 2, e+g=3; for example, —CH$_2$F, —CHF$_2$, —CF$_3$, —CCl$_3$, or —CBr$_3$;
viii) —SO$_2$R$^{28}$; for example, —SO$_2$H; —SO$_2$CH$_3$; —SO$_2$C$_6$H$_5$;
ix) $C_1$-$C_6$ linear, branched, or cyclic alkyl;
x) Cyano
xi) Nitro;
xii) N(R$^{28}$)C(O)R$^{28}$;
xiii) Oxo (=O);
xiv) Heterocycle; and
xv) Heteroaryl.
wherein each R$^{28}$ is independently hydrogen, optionally substituted $C_1$-$C_6$ linear or branched alkyl (e.g., optionally substituted $C_1$-$C_4$ linear or branched alkyl), or optionally substituted $C_3$-$C_6$ cycloalkyl (e.g optionally substituted $C_3$-$C_4$ cycloalkyl); or two R$^{28}$ units can be taken together to form a ring comprising 3-7 ring atoms. In certain aspects, each R$^{28}$ is independently hydrogen, $C_1$-$C_6$ linear or branched alkyl optionally substituted with halogen or $C_3$-$C_6$ cycloalkyl or $C_3$-$C_6$ cycloalkyl.

At various places in the present specification, substituents of compounds are disclosed in groups or in ranges. It is specifically intended that the description include each and every individual subcombination of the members of such groups and ranges. For example, the term "$C_1$-$C_6$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$, alkyl.

For the purposes of the present invention the terms "compound," "analog," and "composition of matter" stand equally well for the prodrug agent described herein, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include $NaHCO_3$, $Na_2CO_3$, $KHCO_3$, $K_2CO_3$, $Cs_2CO_3$, $LiOH$, $NaOH$, $KOH$, $NaH_2PO_4$, $Na_2HPO_4$, and $Na_3PO_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, naphthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in $N(R^{13})_2$, each $R^{13}$ may be the same or different than the other). Combinations of substituents and/or variables are permissible only if such combinations result in stable compounds.

The term "neuropsychiatric disorder", as used herein, is a mental or neurologic disorder which is associated with the nervous system. For example, the neuropsychiatric disorder may include anxiety disorders, mood disorders, neurodegenerative disorders, neurodevelopmental disorders, autism, pervasive developmental disorder, pain disorders, neuropathic pain, ALS, cognitive disorders, Huntington's disease, Parkinson's disease, supranuclear palsy, frontal temporal dementia, schizophrenia, delirium, Alzheimer's disease, depression, mania, attention deficit disorders, drug addiction, dementia, agitation, apathy, anxiety, psychoses, post-traumatic stress disorders, irritability, and disinhibition, learning disorders, memory loss, mental retardation, dementia, personality disorders, bipolar disorders, bipolar depression, generalized anxiety disorder, panic disorder, obsessive-compulsive disorders, trichotillomania, eating disorders, and the like. More specifically, neuropsychiatric disorders includes those listed in the Diagnostic and Statistical Manual of Mental Disorders (American Psychiatric Association, 5th Edition): Neurodevelopmental disorders, Intellectual disabilities, Intellectual disability (intellectual developmental disorder), Global developmental delay, Unspecified intellectual disability (Intellectual developmental disorder), Communication disorders, Language disorder, Speech sound disorder, Childhood-onset fluency disorder (stuttering), Social (pragmatic) communication disorder, Unspecified communication disorder, Autism spectrum disorder, Rett Syndrome, Attention deficit hyperactivity disorder (ADHD), Unspecified attention-deficit/Hyperactivity disorder, Specific learning disorder, Motor disorders, Developmental coordination disorder, Stereotypic movement disorder, Tic disorders, Tourette's disorder, Persistent (Chronic) motor or vocal tic disorder, Provisional tic disorder, Other specified tic disorder, Unspecified tic disorder, Other neurodevelopmental disorders, Unspecified neurodevelopmental disorder, Schizophrenia spectrum and other psychotic disorders, Delusional disorder, Brief psychotic disorder, Schizophreniform disorder, Schizophrenia, Schizoaffective disorder, Major depressive or manic mood disorder concurrent with primary symptoms of schizophrenia, Substance/Medication-induced psychotic disorder, Psychotic disorder due to another medical condition, Catatonia, Other specified schizophrenia spectrum and other psychotic disorder, Unspecified schizophrenia spectrum and other psychotic disorder, Bipolar and related disorders, Anxiety disorders, Obsessive-compulsive and related disorders, Trauma- and stressor-related disorders, Reactive attachment disorder, Disinhibited social engagement disorder, Posttraumatic stress disorder, Acute stress disorder, Adjustment disorder, Other specified Trauma- and stressor-related disorder, Unspecified trauma- and stressor-related disorder, Dissociative disorders, Dissociative identity disorder, Dissociative amnesia, Depersonalization/Derealization disorder, Somatic symptom disorders, Encopresis, other elimination disorder, Disruptive, impulse-control and conduct disorders in DSM-5, Oppositional defiant disorder, Intermittent explosive disorder, Conduct disorder, Other specified disruptive, conduct disorder, unspecified disruptive, and conduct disorder, Substance-Related and Addictive Disorders, Substance-Related Disorders, Alcohol-Related Disorders, Alcohol Use Disorder, Alcohol Withdrawal, Cannabis-Related Disorders, Cannabis Use Disorder, Gambling Disorder, Cluster A personality disorders, Paranoid personality disorder, Schizoid personality disorder, Schizotypal personality disorder, Cluster B personality disorders, Antisocial personality disorder, Borderline personality disorder, Histrionic personality disorder, Narcissistic personality disorder, Cluster C personality disorders, Avoidant personality disorder, Dependent personality disorder, Obsessive-compulsive personality disorder, Paraphilic disorders.

The term "DSM" refers to a Diagnostic and Statistical Manual of Mental Disorders as provided by American Psychiatric Association's (APA) classification and diagnostic tool. Diagnostic and Statistical Manual of Mental Disorders, Fifth Edition (DSM-5 or DSM-V) is updated in 2013 and exemplary disorders in DSM-V are listed in Appendix A. In addition, the DSM-V has a structure that includes broad categories and subdiagnoses indicating disorders, conditions and problems.

"Neuropsychiatric disorders" could also include neurodegenerative or neurologic disorders including: Alzheimer's disease, dementia, vascular dementia, mixed dementia, Parkinson's disease, Huntington's disease, Amyotrophic lateral sclerosis (ALS), pseudobulbar affect, agitation in Alzheimer's disease, dementia, cerebellar ataxia, hereditary ataxias, multiple sclerosis, Progressive Supranuclear Palsy, pain disorders, neuropathic pain, neuropathies, stroke, seizure, Fragile X, etc. The neuropsychiatric symptoms may include anxiety, depression, stress, fatigue, feelings of panic, fear, uneasiness, problems in sleeping, cold or sweaty hands and/or feet, shortness of breath, heart palpitations, social phobia, fear of public speaking, an inability to be still and calm, dry mouth, numbness or tingling in the hands or feet, nausea, muscle tension, dizziness apathy, elation, disinhibition, irritability, wandering, and the like. Additionally, neuropsychiatric symptoms could include: delusions, hallucinations, disorganized thinking or speech, derailment of focal topic or loose associations, incoherence, grossly disorganized or abnormal motor behavior (including catatonia), negative symptoms—reduced emotional expression, avolition, alogia, anhedonia, asociality, dyskinesias (including tardive dyskinesia), anhedonia and dysphoria, anger and aggression, or symptoms of dissociation, or some combination of these.

Other disorders treated could include cancer (including Acute Lymphoblastic Leukemia (ALL), Acute Myeloid Leukemia (AML), Adrenocortical Carcinoms, Childhood cancers, AIDS-Related Cancers, Kaposi Sarcoma, AIDS-Related Lymphoma, Primary CNS Lymphoma, Anal Cancer, Astrocytomas, Atypical Teratoid/Rhabdoid Tumor, Basal Cell Carcinoma, Skin Cancer (Nonmelanoma), Bile Duct Cancer, Bladder Cancer, Bone Cancer, Ewing Sarcoma Family of Tumors, Osteosarcoma and Malignant Fibrous Histiocytoma, Brain Stem Glioma, Atypical Teratoid/Rhabdoid Tumor, Embryonal Tumors, Germ Cell Tumors, Craniopharyngioma, Ependymoma, Breast Cancer, Bronchial Tumors, Burkitt Lymphoma, Non-Hodgkin Lymphoma, Carcinoid Tumor, Gastrointestinal Carcinoma, Cardiac (Heart) Tumors, Primary Lymphoma, Cervical Cancer, Cholangiocarcinoma, Chordoma, Chronic Lymphocytic Leukemia (CLL), Chronic Myelogenous Leukemia (CML), Chronic Myeloproliferative Neoplasms, Colon Cancer, Colorectal Cancer, Craniopharyngioma, Cutaneous T-Cell Lymphoma, Mycosis Fungoides and Sezary Syndrome, Ductal Carcinoma In Situ (DCIS), Embryonal Tumors, Endometrial Cancer, Ependymoma, Esophageal Cancer, Esthesioneuroblastoma, Extracranial Germ Cell Tumor, Extragonadal Germ Cell Tumor, Eye Cancer, Intraocular Melanoma, Retinoblastoma, Fallopian Tube Cancer, Fibrous Histiocytoma of Bone, Malignant, and Osteosarcoma, Gallbladder Cancer, Gastric (Stomach) Cancer, Gastrointestinal Carcinoid Tumor, Gastrointestinal Stromal Tumors (GIST), Germ Cell Tumor, Ovarian, Testicular, Gestational Trophoblastic Disease, Glioma, Hairy Cell Leukemia, Head and Neck Cancer, Hepatocellular (Liver) Cancer, Histiocytosis, Langerhans Cell, Hodgkin Lymphoma, Hypopharyngeal Cancer, Islet Cell Tumors, Pancreatic Neuroendocrine Tumors, Kaposi Sarcoma, Kidney, Renal Cell, Wilms Tumor, Langerhans Cell Histiocytosis, Laryngeal Cancer, Leukemia, Acute Lymphoblastic (ALL), Acute Myeloid (AML), Chronic Lymphocytic (CLL), Chronic Myelogenous (CML), Hairy Cell, Lip and Oral Cavity Cancer, Liver Cancer (Primary), Lung Cancer, Non-Small Cell, Small Cell, Lymphoma, Hodgkin, Non-Hodgkin, Macroglobulinemia, Waldenström, Male Breast Cancer, Melanoma, Merkel Cell Carcinoma, Mesothelioma, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic (CML), Myeloid Leukemia, Acute (AML) Myeloma, Multiple, Myeloproliferative Neoplasms, Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip and Oropharyngeal Cancer, Osteosarcoma and Malignant Fibrous Histiocytoma of Bone, Ovarian Cancer, Low Malignant Potential Tumor, Pancreatic Cancer, Pancreatic Neuroendocrine Tumors (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Pregnancy and Breast Cancer, Primary Central Nervous System (CNS) Lymphoma, Primary Peritoneal Cancer, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Rhabdomyosarcoma, Uterine, Small Intestine Cancer, Soft Tissue Sarcoma, squamous Cell Carcinoma, Squamous Neck Cancer with Occult Primary, Metastatic, Ttomach (Gastric) Cancer, T-Cell Lymphoma, Testicular Cancer, Throat Cancer, Thymoma and Thymic Carcinoma, Thyroid Cancer, Transitional Cell Cancer of the Renal Pelvis and Ureter, Unknown Primary, Ureter and Renal Pelvis, Transitional Cell Cancer, Urethral Cancer, Uterine Cancer, Endometrial, Uterine Sarcoma, Vaginal Cancer, Vulvar Cancer, Waldenström Macroglobulinemia, Wilms Tumor.

The term "treatment" as used herein includes any treatment of a condition or disease in a subject, or particularly a human, and may include: (i) preventing the disease or condition from occurring in the subject which may be predisposed to the disease but has not yet been diagnosed as having it; (ii) inhibiting the disease or condition, i.e., arresting its development; relieving the disease or condition, i.e., causing regression of the condition; or (iii) ameliorating or relieving the conditions caused by the disease, i.e., symptoms of the disease. "Treatment" could be in combination with other standard therapies or alone.

As used herein, "therapeutically effective" and "effective dose" refer to a substance or an amount that elicits a desirable biological activity or effect.

As used herein, the term "riluzole prodrug" shall mean a compound that are cleaved to release riluzole in the plasma via either an enzymatic or general biophysical release process.

As used herein, the term "prodrug agent" shall mean a compound that are cleaved to release riluzole in the plasma via either an enzymatic or general biophysical release process.

As used herein, the term "anticancer agent" shall mean a compound that is useful for the treatment or prevention of cancer, including but not limited to melanoma, ovarian cancer, cervical cancer, breast cancer, prostate cancer, testicular cancer, lung cancer, renal cancer, colorectal cancer, skin cancer, brain cancer, and leukemia.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

The prodrug agents:

The prodrug agents of the present invention are N-substituted riluzole analogs, and include all enantiomeric and diastereomeric forms and pharmaceutically accepted salts thereof having the formula (I):

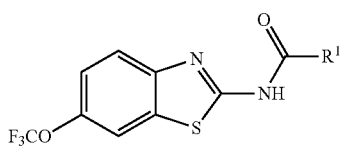

I including hydrates, solvates, pharmaceutically acceptable salts, and complexes thereof, wherein:

$R^1$ is selected from the group consisting of $C_1$-$C_6$ fluoroalkyl, $OR^2$, $(CR^{6a}R^{6b})_m NHR^7$, $CR^{10a}R^{10b}NR^{11}R^{12}$,

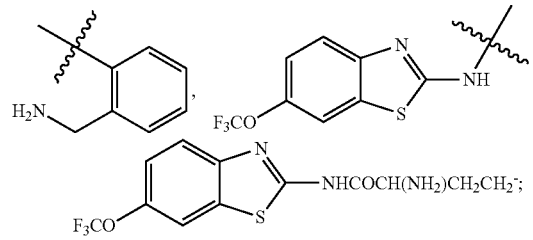

$R^2$ is selected from the group consisting of $CH_2$ $(CH_2)_n NR^{3a}R^{3b}$,

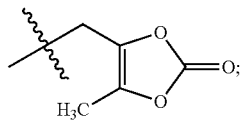 [SMILES: *Cc1oc(=O)oc1C]

$R^{3a}$ and $R^{3b}$ are independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl, and $CO_2R^4$;

$R^{3a}$ and $R^{3b}$ cannot both be $C_1$-$C_6$ alkyl;

$R^{3a}$ and $R^{3b}$ are taken together with the atom to which they are bound to form an optionally substituted three to six membered saturated heterocyclic ring consisting of two to five carbon atoms and a member selected from the group consisting of O, $NR^5$, S, and $SO_2$;

n is 1 or 2;

$R^4$ is selected from the group consisting of $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl, optionally substituted phenyl, and optionally substituted benzyl;

$R^5$ is selected from the group consisting of $C_1$-$C_6$ alkyl, $C_3$-$C_7$ branched alkyl, $C_3$-$C_7$ cycloalkyl, $C_2$-$C_6$ alkenyl, and $C_2$-$C_6$ alkynyl;

$R^{6a}$ and $R^{6b}$ are at each occurrence independently selected from the group consisting of hydrogen, optionally substituted $C_1$-$C_6$ alkyl, optionally substituted $C_3$-$C_7$ branched alkyl, optionally substituted $C_2$-$C_6$ alkenyl, optionally substituted $C_2$-$C_6$ alkynyl, and optionally substituted $C_3$-$C_7$ cycloalkyl;

$R^{6a}$ and $R^{6b}$ are taken together with the atom to which they are bound to form an optionally substituted 6 membered ring;

m is 1, 2, or 3;

$R^7$ is selected from the group consisting of COC $R^{8a}R^{8b}$ $(NHR^9)$,

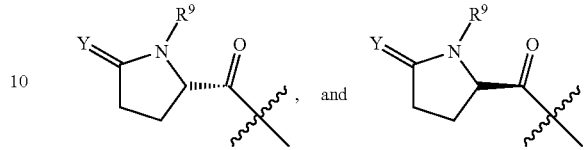

$R^{8a}$ and $R^{8b}$ are at each occurrence independently selected from the group consisting of hydrogen, $CH_3$, $CH(CH_3)_2$, $CH_2CH(CH_3)_2$, $CH(CH_3)CH_2CH_3$, $CH_2OH$, $CH(OH)CH_3$, $CH_2Ph$, $CH_2(4\text{-OH-Ph})$, $(CH_2)_4NH_2$, $(CH_2)_3NHC(NH_2)NH$, $CH_2(3\text{-indole})$, $CH_2(5\text{-imidazole})$, $CH_2CO_2H$, $CH_2CH_2CO_2H$, $CH_2CONH_2$, and $CH_2CH_2CONH_2$;

$R^9$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, and $C_2$-$C_6$ alkynyl;

Y is at each occurrence independently selected from the group consisting of $H_2$ or O;

$R^{10a}$ and $R^{10b}$ are at each occurrence independently selected from the group consisting of hydrogen, $CH_3$, $CH_2CH_3$, $CH(CH_3)_2$, $CH_2CH(CH_3)_2$, $CH(CH_3)CH_2CH_3$, $CH_2OH$, $CH_2OCH_2Ph$, $CH(OH)CH_3$, $CH_2Ph$, $CH_2(4\text{-OH-Ph})$, $(CH_2)_4NH_2$, $(CH_2)_3NHC(NH_2)NH$, $CH_2(3\text{-indole})$, $CH_2(5\text{-imidazole})$, $CH_2(CCH)$, $CH_2(cyclohexyl)$, $CH_2CO_2H$, $CH_2CH_2CO_2H$, $CH_2CONH_2$, and $CH_2CH_2CONH_2$;

$R^{10a}$ and $R^{10b}$ are taken together with the atom to which they are bound to form an optionally substituted three to six membered saturated carbocyclic ring;

$R^{11}$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, $C_1$-$C_6$ haloalkyl, and $C_2$-$C_6$ alkynyl;

$R^{10a}$ and $R^{11}$ are taken together with the atoms to which they are bound to form an optionally substituted four to six membered ring containing one nitrogen atom, and $R^{12}$ is not hydrogen;

$R^{10b}$ and $R^{11}$ are taken together with the atoms to which they are bound to form an optionally substituted four to six membered ring containing one nitrogen atom, and $R^{12}$ is not hydrogen;

$R^{12}$ is at each occurrence independently selected from the group consisting of hydrogen, $C_1$-$C_6$ alkyl, $COCR^{13a}R^{13b}NR^{15a}R^{15b}$, $COCR^{13a}R^{13b}OR^{14}$, $SO_2CR^{13a}R^{13b}NR^{15a}R^{15b}$, $COCR^{13a}R^{13b}NHSO_2R^{15a}$,

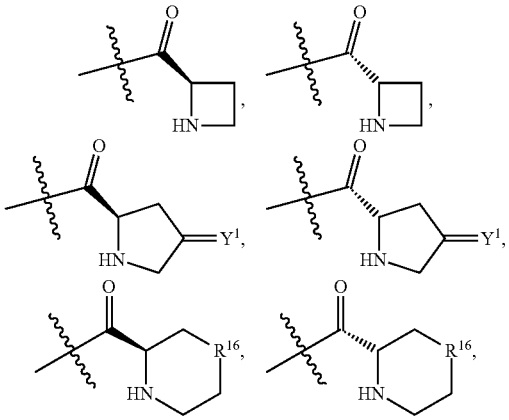

-continued

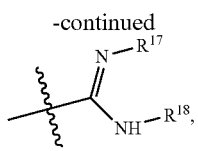

and $(CR^{19a}R^{19b})_q NHR^{20}$, and when $R^{12}$ is hydrogen, $R^{11}$ cannot be hydrogen;

$R^{11}$ and $R^{12}$ are taken together with the atom to which they are bound to form an optionally substituted four to six membered saturated heterocyclic ring containing a nitrogen atom and optionally containing an additional heteroatom from the group consisting of N and O;

$R^{13a}$ and $R^{13b}$ are at each occurrence independently selected from the group consisting hydrogen, $CH_3$, $CH_2CH_3$, $CH_2CH_2CH_3$, $CH_2CCH$, $CH(CH_3)_2$, $CH_2CH(CH_3)_2$, $CH(CH_3)CH_2CH_3$, $CH_2OH$, $CH_2OCH_2Ph$, $CH_2CH_2OCH_2Ph$, $CH(OH)CH_3$, $CH_2Ph$, $CH_2(cyclohexyl)$, $CH_2(4\text{-}OH\text{-}Ph)$, $(CH_2)_4NH_2$, $(CH_2)_3NHC(NH_2)NH$, $CH_2(3\text{-indole})$, $CH_2(5\text{-imidazole})$, $CH_2CO_2H$, $CH_2CH_2CO_2H$, $CH_2CONH_2$, and $CH_2CH_2CONH_2$;

$R^{13a}$ and $R^{13b}$ are taken together with the atom to which they are bound to form an optionally substituted three to six membered saturated carbocyclic ring;

$R^{13a}$ and $R^{13b}$ are taken together with the atom to which they are bound to form an optionally substituted six membered saturated heterocyclic ring with one O atom within the ring;

$R^{13a}$ and $R^{14}$ are taken together with the atoms to which they are bound to form an optionally substituted four to six membered ring containing one nitrogen atom;

$R^{13a}$ and $R^{15a}$ are taken together with the atoms to which they are bound to form an optionally substituted four to six membered ring containing one nitrogen atom;

$Y^1$ is at each occurrence independently selected from the group consisting of $H_2$, O, and $—H/—OCH_2Ph$;

$R^{14}$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, and $C_2$-$C_6$ alkynyl;

$R^{15a}$ and $R^{15b}$ are at each occurrence independently selected from the group consisting of H, $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl, $C_1$-$C_6$ fluoroalkyl, $COR^{21}$, $CH_2R^{21}$, $SO_2R^{22}$, an optionally substituted four to six membered saturated heterocyclic ring containing a heteroatom selected from the group consisting of $NR^{24}$ and O, $COCHR^{23}NH_2$,

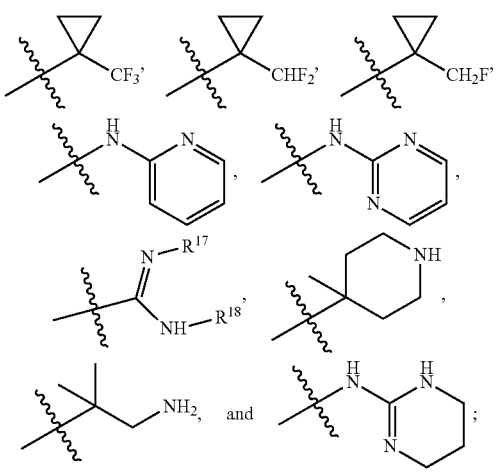

$R^{15a}$ and $R^{15b}$ are taken together with the atom to which they are bound to form an optionally substituted four to six membered saturated heterocyclic ring optionally containing one O atom within the ring;

$R^{16}$ is at each occurrence independently selected from the group consisting of $CH_2$, O, C=O, and NH;

$R^{17}$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, and $C_2$-$C_6$ alkynyl;

$R^{18}$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, and $C_2$-$C_6$ alkynyl;

$R^{17}$ and $R^{18}$ are taken together with the atoms to which they are bound to form an optionally substituted five or six membered ring containing two nitrogen atoms;

$R^{19a}$ and $R^{19b}$ are at each occurrence independently selected from the group consisting of hydrogen, optionally substituted $C_1$-$C_6$ alkyl, optionally substituted $C_3$-$C_7$ branched alkyl, optionally substituted $C_3$-$C_7$ cycloalkyl, optionally substituted $C_2$-$C_6$ alkenyl, and optionally substituted $C_2$-$C_6$ alkynyl;

$R^{19a}$ and $R^{19b}$ are taken together with the atom to which they are bound to form an optionally substituted 3 to 6 membered carbocyclic ring;

$R^{20}$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, and $C_2$-$C_6$ alkynyl;

q is 1, or 2;

$R^{21}$ is at each occurrence independently selected from the group consisting of hydrogen, $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl, $C_1$-$C_6$ fluoroalkyl, optionally substituted aryl, and optionally substituted heteroaryl;

$R^{22}$ is at each occurrence independently selected from the group consisting of $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl optionally substituted aryl, optionally substituted heteroaryl;

$R^{23}$ is selected from the group consisting H, $CH_3$, $CH_2CH_3$, $CH_2CH_2CH_3$, $CH_2CCH$, $CH(CH_3)_2$, $CH_2CH(CH_3)_2$, $CH(CH_3)CH_2CH_3$, $CH_2OH$, $CH_2OCH_2Ph$, $CH_2CH_2OCH_2Ph$, $CH(OH)CH_3$, $CH_2Ph$, $CH_2(cyclohexyl)$, $CH_2(4\text{-}OH\text{-}Ph)$, $(CH_2)_4NH_2$, $(CH_2)_3NHC(NH_2)NH$, $CH_2(3\text{-indole})$, $CH_2(5\text{-imidazole})$, $CH_2CO_2H$, $CH_2CH_2CO_2H$, $CH_2CONH_2$, and $CH_2CH_2CONH_2$;

$R^{24}$ is at each occurrence independently selected from the group consisting of H, $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl, optionally substituted aryl, optionally substituted heteroaryl, $COR^{25}$, and $SO_2$—$C_{1-6}$alkyl;

$R^{25}$ is at each occurrence independently selected from the group consisting of H, $C_1$-$C_6$ alkyl, $C_3$-$C_7$ branched alkyl, $C_3$-$C_7$ cycloalkyl, $C_2$-$C_6$ alkenyl, $C_2$-$C_6$ alkynyl, optionally substituted aryl, optionally substituted heteroaryl, $C_1$-$C_6$alkoxy, and $C_1$-$C_6$ alkylamino.

The compounds of the present invention include compounds having formula (II):

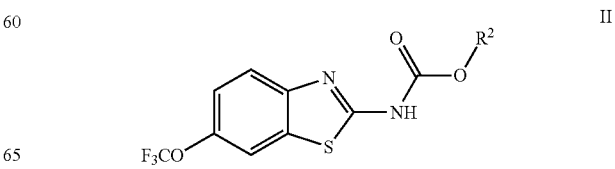

including enantiomers, diasteroemers, hydrates, solvates, pharmaceutically acceptable salts, and complexes thereof.

The compounds of the present invention include compounds having formula (III):

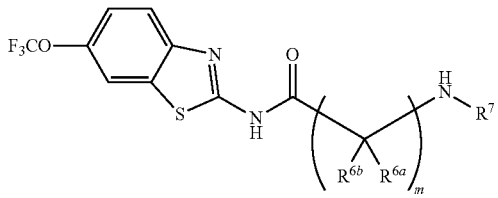

III including enantiomers, diasteroemers, hydrates, solvates, pharmaceutically acceptable salts, and complexes thereof.

The compounds of the present invention include compounds having formula (IV):

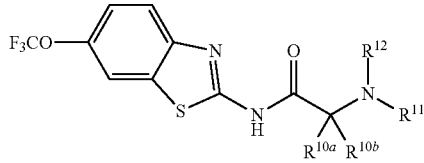

IV including enantiomers, diasteroemers, hydrates, solvates, pharmaceutically acceptable salts, and complexes thereof.

The compounds of the present invention include compounds having formula (V):

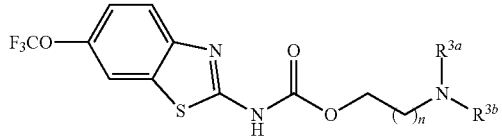

V including enantiomers, diasteroemers, hydrates, solvates, pharmaceutically acceptable salts, and complexes thereof.

The compounds of the present invention include compounds having formula (VI):

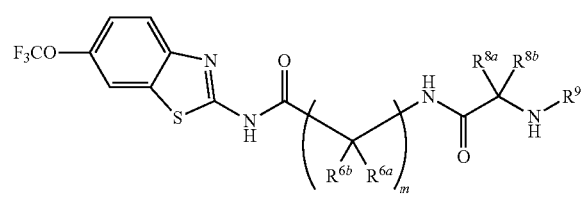

VI including enantiomers, diasteroemers, hydrates, solvates, pharmaceutically acceptable salts, and complexes thereof.

The compounds of the present invention include compounds having formula (VII):

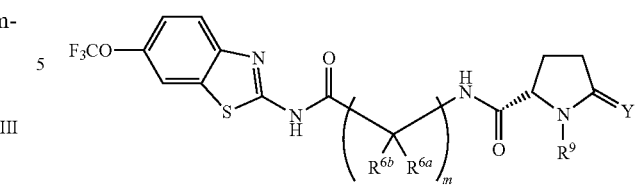

VII including enantiomers, diasteroemers, hydrates, solvates, pharmaceutically acceptable salts, and complexes thereof.

The compounds of the present invention include compounds having formula (VIII):

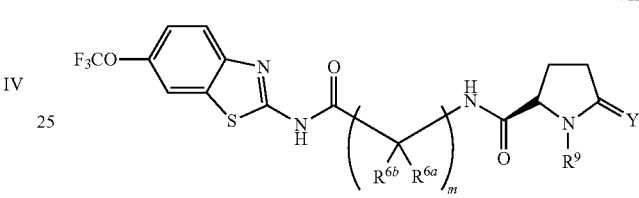

VIII including enantiomers, diasteroemers, hydrates, solvates, pharmaceutically acceptable salts, and complexes thereof.

The compounds of the present invention include compounds having formula (IX):

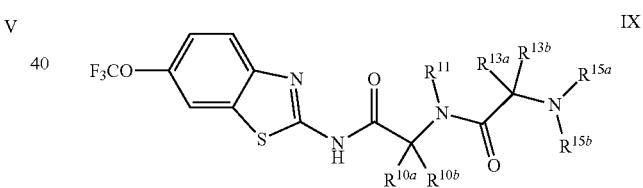

IX including enantiomers, diasteroemers, hydrates, solvates, pharmaceutically acceptable salts, and complexes thereof.

The compounds of the present invention include compounds having formula (X):

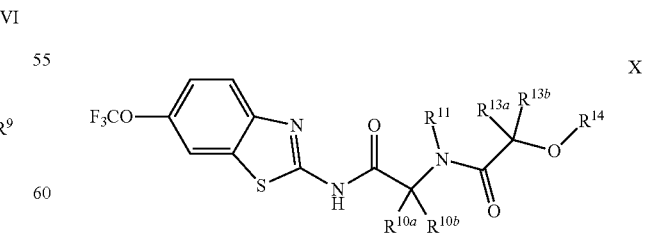

X including enantiomers, diasteroemers, hydrates, solvates, pharmaceutically acceptable salts, and complexes thereof.

The compounds of the present invention include compounds having formula (XI):

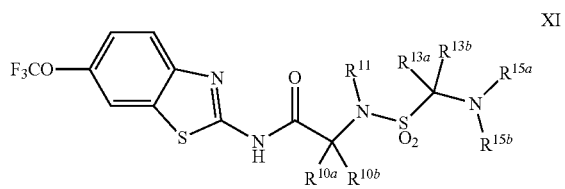
XI including enantiomers, diasteroemers, hydrates, solvates, pharmaceutically acceptable salts, and complexes thereof.

The compounds of the present invention include compounds having formula (XII):

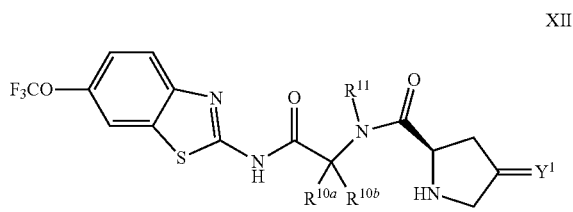
XII including enantiomers, diasteroemers, hydrates, solvates, pharmaceutically acceptable salts, and complexes thereof.

The compounds of the present invention include compounds having formula (XIII):

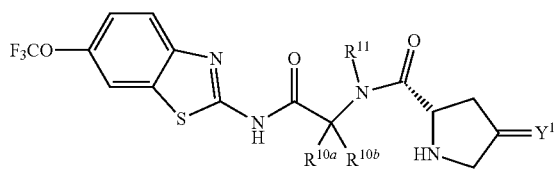
XIII including enantiomers, diasteroemers, hydrates, solvates, pharmaceutically acceptable salts, and complexes thereof.

The compounds of the present invention include compounds having formula (XIV):

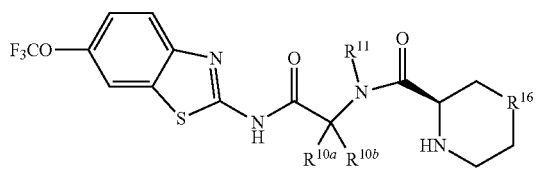
XIV including enantiomers, diasteroemers, hydrates, solvates, pharmaceutically acceptable salts, and complexes thereof.

The compounds of the present invention include compounds having formula (XV):

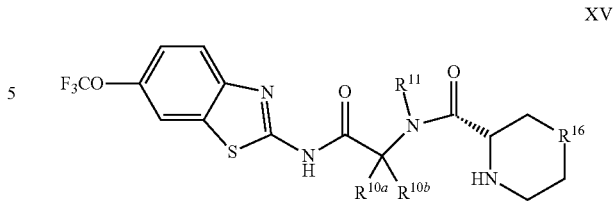
XV including enantiomers, diasteroemers, hydrates, solvates, pharmaceutically acceptable salts, and complexes thereof.

The compounds of the present invention include compounds having formula (XVI):

XVI

F$_3$CO including enantiomers, diasteroemers, hydrates, solvates, pharmaceutically acceptable salts, and complexes thereof.

The compounds of the present invention include compounds having formula (XVII):

XVII including enantiomers, diasteroemers, hydrates, solvates, pharmaceutically acceptable salts, and complexes thereof.

The compounds of the present invention include compounds having formula (XVIII)

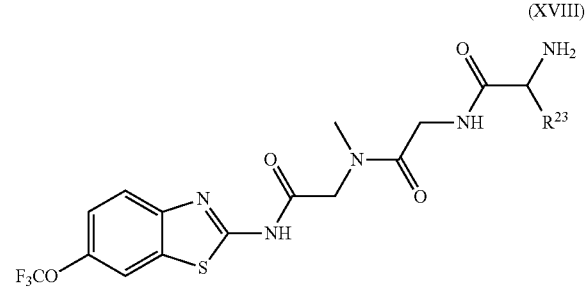
(XVIII)

including enantiomers, diasteroemers, hydrates, solvates, pharmaceutically acceptable salts, and complexes thereof, wherein:

$R^{23}$ is selected from the group consisting H, CH$_3$, CH$_2$CH$_3$, CH$_2$CH$_2$CH$_3$, CH$_2$CCH, CH(CH$_3$)$_2$, CH$_2$CH (CH$_3$)$_2$, CH(CH$_3$)CH$_2$CH$_3$, CH$_2$OH, CH$_2$OCH$_2$Ph, CH$_2$CH$_2$OCH$_2$Ph, CH(OH)CH$_3$, CH$_2$Ph, CH$_2$(cyclohexyl), CH$_2$(4-OH-Ph), (CH$_2$)$_4$NH$_2$, (CH$_2$)$_3$NHC(NH$_2$)NH, CH$_2$(3- indole), CH$_2$(5-imidazole), CH$_2$CO$_2$H, CH$_2$CH$_2$CO$_2$H, CH$_2$CONH$_2$, and CH$_2$CH$_2$CONH$_2$.

In some embodiments R$^1$ is C$_1$-C$_6$ fluoroalkyl.
In some embodiments R$^1$ is OR$^2$.
In some embodiments R$^1$ is (CR$^{6a}$R$^{6b}$)$_m$NHR$^7$.
In some embodiments R$^1$ is CR$^{10a}$R$^{10b}$NR$^{11}$R$^{12}$.
In some embodiments R$^1$ is

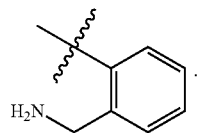

In some embodiments R$^1$ is

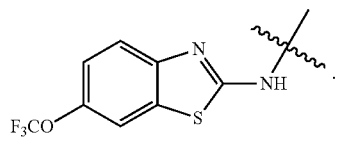

In some embodiments R$^1$ is

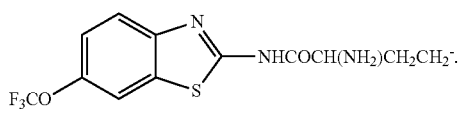

some embodiments R$^2$ is CH$_2$(CH$_2$)$_n$NR$^{3a}$R$^{3b}$.
In some embodiments R$^2$ is

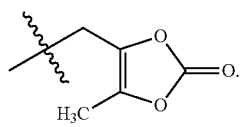

In some embodiments R$^{3a}$ is hydrogen.
In some embodiments R$^{3a}$ is C$_1$-C$_6$ alkyl.
In some embodiments R$^{3a}$ is C$_3$-C$_7$ cycloalkyl.
In some embodiments R$^{3a}$ is C$_3$-C$_7$ branched alkyl.
In some embodiments R$^{3a}$ is C$_2$-C$_6$ alkenyl.
In some embodiments R$^{3a}$ is C$_2$-C$_6$ alkynyl.
In some embodiments R$^{3a}$ is CO$_2$R$^4$.
In some embodiments R$^{3b}$ is hydrogen.
In some embodiments R$^{3b}$ is C$_1$-C$_6$ alkyl.
In some embodiments R$^{3b}$ is C$_3$-C$_7$ cycloalkyl.
In some embodiments R$^{3b}$ is C$_3$-C$_7$ branched alkyl.
In some embodiments R$^{3b}$ is C$_2$-C$_6$ alkenyl.
In some embodiments R$^{3b}$ is C$_2$-C$_6$ alkynyl.
In some embodiments R$^{3b}$ is CO$_2$R$^4$.
In some embodiments R$^{3a}$ and R$^{3b}$ are taken together with the atom to which they are bound to form an optionally substituted three to six membered saturated heterocyclic ring consisting of two to five carbon atoms and a member selected from the group consisting of O, NR$^5$, S, and SO$_2$;
In some embodiments n is 1.
In some embodiments n is 2.
In some embodiments R$^4$ is C$_1$-C$_6$ alkyl.
In some embodiments R$^4$ is C$_3$-C$_7$ branched alkyl.
In some embodiments R$^4$ is C$_3$-C$_7$ cycloalkyl.
In some embodiments R$^4$ is C$_2$-C$_6$ alkenyl.
In some embodiments R$^4$ is C$_2$-C$_6$ alkynyl.
In some embodiments R$^4$ is optionally substituted phenyl.
In some embodiments R$^4$ is benzyl.
In some embodiments R$^5$ is C$_1$-C$_6$ alkyl
In some embodiments R$^5$ is C$_3$-C$_7$ branched alkyl
In some embodiments R$^5$ is C$_3$-C$_7$ cycloalkyl.
In some embodiments R$^5$ is C$_2$-C$_6$ alkenyl.
In some embodiments R$^5$ is C$_2$-C$_6$ alkynyl.
In some embodiments R$^{6a}$ is hydrogen.
In some embodiments R$^{6a}$ is optionally substituted C$_1$-C$_6$ alkyl.
In some embodiments R$^{6a}$ is optionally substituted C$_3$-C$_7$ branched alkyl.
In some embodiments R$^{6a}$ is optionally substituted C$_3$-C$_7$ cycloalkyl.
In some embodiments R$^{6a}$ is optionally substituted C$_2$-C$_6$ alkenyl.
In some embodiments R$^{6a}$ is optionally substituted C$_2$-C$_6$ alkynyl.
In some embodiments R$^{6b}$ is hydrogen.
In some embodiments R$^{6b}$ is optionally substituted C$_1$-C$_6$ alkyl.
In some embodiments R$^{6b}$ is optionally substituted C$_3$-C$_7$ branched alkyl.
In some embodiments R$^{6b}$ is optionally substituted C$_3$-C$_7$ cycloalkyl.
In some embodiments R$^{6b}$ is optionally substituted C$_2$-C$_6$ alkenyl.
In some embodiments R$^{6b}$ is optionally substituted C$_2$-C$_6$ alkynyl.
In some embodiments R$^{6a}$ and R$^{6b}$ are taken together with the atom to which they are bound to form an optionally substituted 6 membered ring.
In some embodiments m is 1.
In some embodiments m is 2.
In some embodiments m is 3.
In some embodiments R$^7$ is COC R$^{8a}$R$^{8b}$(NHR$^9$).
In some embodiments R$^7$ is

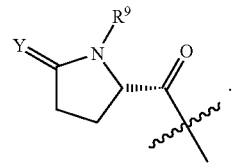

In some embodiments R$^7$ is

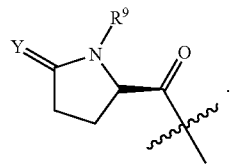

In some embodiments R$^{8a}$ is hydrogen.
In some embodiments R$^{8a}$ is CH$_3$.
In some embodiments R$^{8a}$ is CH(CH$_3$)$_2$.
In some embodiments R$^{8a}$ is CH$_2$CH(CH$_3$)$_2$.
In some embodiments R$^{8a}$ is CH(CH$_3$)CH$_2$CH$_3$.
In some embodiments R$^{8a}$ is CH$_2$OH.

In some embodiments $R^{8a}$ is CH(OH)CH$_3$.
In some embodiments $R^{8a}$ is CH$_2$Ph.
In some embodiments $R^{8a}$ is CH$_2$(4-OH-Ph).
In some embodiments $R^{8a}$ is (CH$_2$)$_4$NH$_2$.
In some embodiments $R^{8a}$ is (CH$_2$)$_3$NHC(NH$_2$)NH.
In some embodiments $R^{8a}$ is CH$_2$(3-indole).
In some embodiments $R^{8a}$ is CH$_2$(5-imidazole).
In some embodiments $R^{8a}$ is CH$_2$CO$_2$H.
In some embodiments $R^{8a}$ is CH$_2$CH$_2$CO$_2$H.
In some embodiments $R^{8a}$ is CH$_2$CONH$_2$.
In some embodiments $R^{8a}$ is CH$_2$CH$_2$CONH$_2$.
In some embodiments $R^{8b}$ is hydrogen.
In some embodiments $R^{8b}$ is CH$_3$.
In some embodiments $R^{8b}$ is CH(CH$_3$)$_2$.
In some embodiments $R^{8b}$ is CH$_2$CH(CH$_3$)$_2$.
In some embodiments $R^{8b}$ is CH(CH$_3$)CH$_2$CH$_3$.
In some embodiments $R^{8b}$ is CH$_2$OH.
In some embodiments $R^{8b}$ is CH(OH)CH$_3$.
In some embodiments $R^{8b}$ is CH$_2$Ph.
In some embodiments $R^{8b}$ is CH$_2$(4-OH-Ph).
In some embodiments $R^{8b}$ is (CH$_2$)$_4$NH$_2$.
In some embodiments $R^{8b}$ is (CH$_2$)$_3$NHC(NH$_2$)NH.
In some embodiments $R^{8b}$ is CH$_2$(3-indole).
In some embodiments $R^{8b}$ is CH$_2$(5-imidazole).
In some embodiments $R^{8b}$ is CH$_2$CO$_2$H.
In some embodiments $R^{8b}$ is CH$_2$CH$_2$CO$_2$H.
In some embodiments $R^{8b}$ is CH$_2$CONH$_2$.
In some embodiments $R^{8b}$ is CH$_2$CH$_2$CONH$_2$.
In some embodiments $R^9$ is hydrogen.
In some embodiments $R^9$ is C$_1$-C$_6$ alkyl.
In some embodiments $R^9$ is C$_3$-C$_7$ branched alkyl.
In some embodiments $R^9$ is C$_3$-C$_7$ cycloalkyl.
In some embodiments $R^9$ is C$_2$-C$_6$ alkenyl.
In some embodiments $R^9$ is C$_2$-C$_6$ alkynyl.
In some embodiments Y is H$_2$.
In some embodiments Y is O.
In some embodiments $R^{10a}$ is hydrogen.
In some embodiments $R^{10a}$ is CH$_3$.
In some embodiments $R^{10a}$ is CH$_2$CH$_3$.
In some embodiments $R^{10a}$ is CH(CH$_3$)$_2$.
In some embodiments $R^{10a}$ is CH$_2$CH(CH$_3$)$_2$.
In some embodiments $R^{10a}$ is CH(CH$_3$)CH$_2$CH$_3$.
In some embodiments $R^{10a}$ is CH$_2$OH.
In some embodiments $R^{10a}$ is CH$_2$OCH$_2$Ph.
In some embodiments $R^{10a}$ is CH(OH)CH$_3$.
In some embodiments $R^{10a}$ is CH$_2$Ph.
In some embodiments $R^{10a}$ is CH$_2$(4-OH-Ph).
In some embodiments $R^{10a}$ is (CH$_2$)$_4$NH$_2$.
In some embodiments $R^{10a}$ is (CH$_2$)$_3$NHC(NH$_2$)NH.
In some embodiments $R^{10a}$ is CH$_2$(3-indole).
In some embodiments $R^{10a}$ is CH$_2$(5-imidazole).
In some embodiments $R^{10a}$ is CH$_2$(CCH).
In some embodiments $R^{10a}$ is CH$_2$(cyclohexyl),
In some embodiments $R^{10a}$ is CH$_2$CO$_2$H.
In some embodiments $R^{10a}$ is CH$_2$CH$_2$CO$_2$H.
In some embodiments $R^{10a}$ is CH$_2$CONH$_2$.
In some embodiments $R^{10a}$ is CH$_2$CH$_2$CONH$_2$.
In some embodiments $R^{10b}$ is hydrogen.
In some embodiments $R^{10b}$ is CH$_3$.
In some embodiments $R^{10b}$ is CH$_2$CH$_3$.
In some embodiments $R^{10b}$ is CH(CH$_3$)$_2$.
In some embodiments $R^{10b}$ is CH$_2$CH(CH$_3$)$_2$.
In some embodiments $R^{10b}$ is CH(CH$_3$)CH$_2$CH$_3$.
In some embodiments $R^{10b}$ is CH$_2$OH.
In some embodiments $R^{10b}$ is CH$_2$OCH$_2$Ph.
In some embodiments $R^{10b}$ is CH(OH)CH$_3$.
In some embodiments $R^{10b}$ is CH$_2$Ph.
In some embodiments $R^{10b}$ is CH$_2$(4-OH-Ph).
In some embodiments $R^{10b}$ is (CH$_2$)$_4$NH$_2$.
In some embodiments $R^{10b}$ is (CH$_2$)$_3$NHC(NH$_2$)NH.
In some embodiments $R^{10b}$ is CH$_2$(3-indole).
In some embodiments $R^{10b}$ is CH$_2$(5-imidazole).
In some embodiments $R^{10b}$ is CH$_2$(CCH).
In some embodiments $R^{10b}$ is CH$_2$(cyclohexyl),
In some embodiments $R^{10b}$ is CH$_2$CO$_2$H.
In some embodiments $R^{10b}$ is CH$_2$CH$_2$CO$_2$H.
In some embodiments $R^{10b}$ is CH$_2$CONH$_2$.
In some embodiments $R^{10b}$ is CH$_2$CH$_2$CONH$_2$.
In some embodiments $R^{10a}$ and $R^{10b}$ are taken together with the atom to which they are bound to form an optionally substituted three to six membered saturated carbocyclic ring.
In some embodiments $R^{11}$ is hydrogen.
In some embodiments $R^{11}$ is of C$_1$-C$_6$ alkyl.
In some embodiments $R^{11}$ is C$_3$-C$_7$ branched alkyl.
In some embodiments $R^{11}$ is C$_3$-C$_7$ cycloalkyl.
In some embodiments $R^{11}$ is C$_2$-C$_6$ alkenyl.
In some embodiments $R^{11}$ is C$_1$-C$_6$ haloalkyl.
In some embodiments $R^{11}$ is C$_2$-C$_6$ alkynyl.
In some embodiments $R^{10a}$ and $R^{11}$ are taken together with the atoms to which they are bound to form an optionally substituted four to six membered ring containing one nitrogen atom, and $R^{12}$ is not hydrogen.
In some embodiments $R^{10b}$ and $R^{11}$ are taken together with the atoms to which they are bound to form an optionally substituted four to six membered ring containing one nitrogen atom, and $R^{12}$ is not hydrogen.
In some embodiments $R^{12}$ is hydrogen.
In some embodiments $R^{12}$ is C$_1$-C$_6$ alkyl.
In some embodiments $R^{12}$ is COCR$^{13a}$R$^{13b}$NR$^{15a}$R$^{15b}$.
In some embodiments $R^{12}$ is COCR$^{13a}$R$^{13b}$OR$^{14}$.
In some embodiments $R^{12}$ is SO$_2$CR$^{13a}$R$^{13b}$NR$^{15a}$R$^{15b}$.
In some embodiments $R^{12}$ is COCR$^{13a}$R$^{13b}$NHSO$_2$R$^{15a}$.
In some embodiments $R^{12}$ is

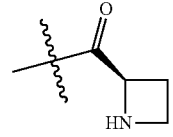

In some embodiments $R^{12}$ is

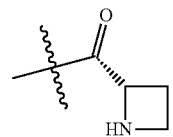

In some embodiments $R^{12}$ is

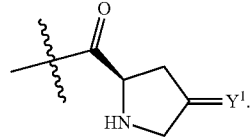

In some embodiments $R^{12}$ is

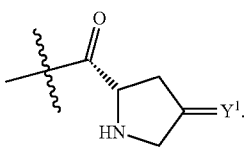

In some embodiments $R^{12}$ is

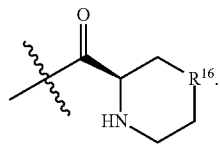

In some embodiments $R^{12}$ is

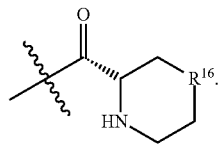

In some embodiments $R^{12}$ is

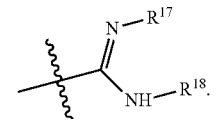

In some embodiments $R^{12}$ is $(CR^{19a}R^{19b})_q NHR^{20}$.

In some embodiments $R^{11}$ and $R^{12}$ are taken together with the atom to which they are bound to form an optionally substituted four to six membered saturated heterocyclic ring containing a nitrogen atom and optionally containing an additional heteroatom from the group consisting of N and O.

In some embodiments $R^{13a}$ is hydrogen.
In some embodiments $R^{13a}$ is $CH_3$.
In some embodiments $R^{13a}$ is $CH_2CH_3$.
In some embodiments $R^{13a}$ is $CH_2CH_2CH_3$
In some embodiments $R^{13a}$ is $CH_2CCH$.
In some embodiments $R^{13a}$ is $CH(CH_3)_2$.
In some embodiments $R^{13a}$ is $CH_2CH(CH_3)_2$.
In some embodiments $R^{13a}$ is $CH(CH_3)CH_2CH_3$.
In some embodiments $R^{13a}$ is $CH_2OH$.
In some embodiments $R^{13a}$ is $CH_2OCH_2Ph$.
In some embodiments $R^{13a}$ is $CH_2CH_2OCH_2Ph$.
In some embodiments $R^{13a}$ is $CH(OH)CH_3$.
In some embodiments $R^{13a}$ is $CH_2Ph$.
In some embodiments $R^{13a}$ is $CH_2(cyclohexyl)$.
In some embodiments $R^{13a}$ is $CH_2(4\text{-OH-Ph})$.
In some embodiments $R^{13a}$ is $(CH_2)_4NH_2$.
In some embodiments $R^{13a}$ is $(CH_2)_3NHC(NH_2)NH$.
In some embodiments $R^{13a}$ is $CH_2(3\text{-indole})$.
In some embodiments $R^{13a}$ is $CH_2(5\text{-imidazole})$.
In some embodiments $R^{13a}$ is $CH_2CO_2H$.
In some embodiments $R^{13a}$ is $CH_2CH_2CO_2H$.
In some embodiments $R^{13a}$ is $CH_2CONH_2$.
In some embodiments $R^{13a}$ is $CH_2CH_2CONH_2$.
In some embodiments $R^{13b}$ is hydrogen.
In some embodiments $R^{13b}$ is $CH_3$.
In some embodiments $R^{13b}$ is $CH_2CH_3$.
In some embodiments $R^{13b}$ is $CH_2CH_2CH_3$.
In some embodiments $R^{13b}$ is $CH_2CCH$.
In some embodiments $R^{13b}$ is $CH(CH_3)_2$.
In some embodiments $R^{13b}$ is $CH_2CH(CH_3)_2$.
In some embodiments $R^{13b}$ is $CH(CH_3)CH_2CH_3$.
In some embodiments $R^{13b}$ is $CH_2OH$.
In some embodiments $R^{13b}$ is $CH_2OCH_2Ph$.
In some embodiments $R^{13b}$ is $CH_2CH_2OCH_2Ph$.
In some embodiments $R^{13b}$ is $CH(OH)CH_3$.
In some embodiments $R^{13b}$ is $CH_2Ph$.
In some embodiments $R^{13b}$ is $CH_2(cyclohexyl)$.
In some embodiments $R^{13b}$ is $CH_2(4\text{-OH-Ph})$.
In some embodiments $R^{13b}$ is $(CH_2)_4NH_2$.
In some embodiments $R^{13b}$ is $(CH_2)_3NHC(NH_2)NH$.
In some embodiments $R^{13b}$ is $CH_2(3\text{-indole})$.
In some embodiments $R^{13b}$ is $CH_2(5\text{-imidazole})$.
In some embodiments $R^{13b}$ is $CH_2CO_2H$.
In some embodiments $R^{13b}$ is $CH_2CH_2CO_2H$.
In some embodiments $R^{13b}$ is $CH_2CONH_2$.
In some embodiments $R^{13b}$ is $CH_2CH_2CONH_2$.

In some embodiments $R^{13a}$ and $R^{13b}$ are taken together with the atom to which they are bound to form an optionally substituted three to six membered saturated carbocyclic ring.

In some embodiments $R^{13a}$ and $R^{13b}$ are taken together with the atom to which they are bound to form an optionally substituted six membered saturated heterocyclic ring with one O atom within the ring.

In some embodiments $R^{13a}$ and $R^{14}$ are taken together with the atoms to which they are bound to form an optionally substituted four to six membered ring containing one nitrogen atom.

In some embodiments $R^{13a}$ and $R^{15a}$ are taken together with the atoms to which they are bound to form an optionally substituted four to six membered ring containing one nitrogen atom. In some embodiments $Y^1$ is In some embodiments $Y^1$ is $H_2$.
In some embodiments $Y^1$ is O.
In some embodiments $Y^1$ is —H/—$OCH_2Ph$.
In some embodiments $R^{14}$ is hydrogen.
In some embodiments $R^{14}$ is $C_1$-$C_6$ alkyl.
In some embodiments $R^{14}$ is $C_3$-$C_7$ branched alkyl.
In some embodiments $R^{14}$ is $C_3$-$C_7$ cycloalkyl.
In some embodiments $R^{14}$ is $C_2$-$C_6$ alkenyl.
In some embodiments $R^{14}$ is $C_2$-$C_6$ alkynyl.
In some embodiments $R^{15a}$ is hydrogen.
In some embodiments $R^{15a}$ is $C_1$-$C_6$ alkyl.
In some embodiments $R^{15a}$ is $C_3$-$C_7$ branched alkyl.
In some embodiments $R^{15a}$ is $C_3$-$C_7$ cycloalkyl.
In some embodiments $R^{15a}$ is $C_2$-$C_6$ alkenyl.
In some embodiments $R^{15a}$ is $C_2$-$C_6$ alkynyl.
In some embodiments $R^{15a}$ is $C_1$-$C_6$ fluoroalkyl.
In some embodiments $R^{15a}$ is $COR^{21}$.
In some embodiments $R^{15a}$ is $CH_2R^{21}$.
In some embodiments $R^{15a}$ is $SO_2R^{22}$.

In some embodiments $R^{15a}$ is an optionally substituted four to six membered saturated heterocyclic ring containing a heteroatom selected from the group consisting of $NR^{24}$ and O, In some embodiments $R^{15a}$ is $COCHR^{23}NH_2$.
In some embodiments $R^{15a}$ is

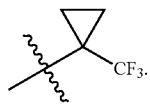 [SMILES: *C1(C(F)(F)F)CC1]

In some embodiments $R^{15a}$ is

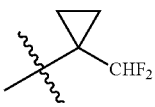

In some embodiments $R^{15a}$ is

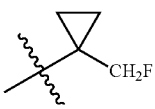

In some embodiments $R^{15a}$ is

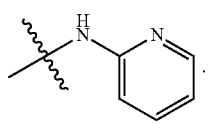 [SMILES: *Nc1ccccn1]

In some embodiments $R^{15a}$ is

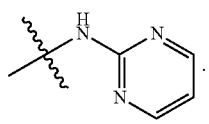

In some embodiments $R^{15a}$

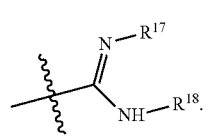

In some embodiments $R^{15a}$ is

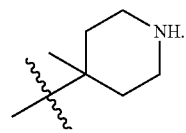 [SMILES: *C1(C)CCNCC1]

In some embodiments $R^{15a}$ is

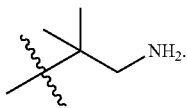 [SMILES: *C(C)(C)CN]

In some embodiments $R^{15a}$ is

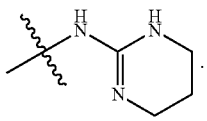

In some embodiments $R^{15b}$ is hydrogen.
In some embodiments $R^{15b}$ is $C_1$-$C_6$ alkyl.
In some embodiments $R^{15b}$ is $C_3$-$C_7$ branched alkyl.
In some embodiments $R^{15b}$ is $C_3$-$C_7$ cycloalkyl.
In some embodiments $R^{15b}$ is $C_2$-$C_6$ alkenyl.
In some embodiments $R^{15b}$ is $C_2$-$C_6$ alkynyl.
In some embodiments $R^{15b}$ is $C_1$-$C_6$ fluoroalkyl.
In some embodiments $R^{15b}$ is $COR^{21}$.
In some embodiments $R^{15b}$ is $CH_2R^{21}$.
In some embodiments $R^{15b}$ is $SO_2R^{22}$.
In some embodiments $R^{15b}$ is an optionally substituted four to six membered saturated heterocyclic ring containing a heteroatom selected from the group consisting of $NR^{24}$ and O,
In some embodiments $R^{15b}$ is $COCHR^{23}NH_2$.
In some embodiments $R^{15b}$ is

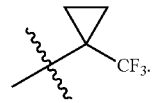 [SMILES: *C1(C(F)(F)F)CC1]

In some embodiments $R^{15b}$ is

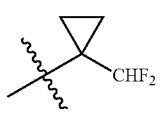 [SMILES: *C1(C(F)F)CC1]

In some embodiments $R^{15b}$ is

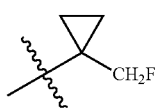

In some embodiments $R^{15b}$ is

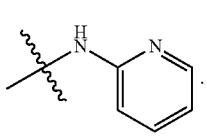 [SMILES: *Nc1ccccn1]

In some embodiments $R^{15b}$ is

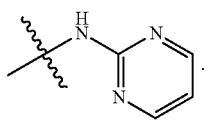 [SMILES: *Nc1ncccn1]

In some embodiments $R^{15b}$ is

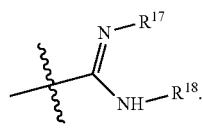

In some embodiments $R^{15b}$ is

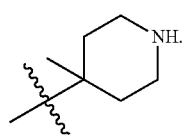 [SMILES: *C1(C)CCNCC1]

In some embodiments $R^{15b}$ is

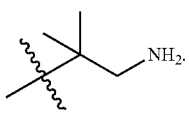 [SMILES: *C(C)(C)CN]

In some embodiments $R^{15b}$ is

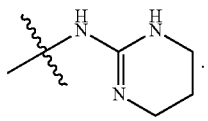 [SMILES: *NC1=NCCCN1]

In some embodiments $R^{15a}$ and $R^{15b}$ are taken together with the atom to which they are bound to form an optionally substituted four to six membered saturated heterocyclic ring optionally containing one O atom within the ring.
In some embodiments $R^{16}$ is $CH_2$.
In some embodiments $R^{16}$ is O.
In some embodiments $R^{16}$ is C=O.
In some embodiments $R^{16}$ is NH.
In some embodiments $R^{17}$ is hydrogen.
In some embodiments $R^{17}$ is $C_1$-$C_6$ alkyl.
In some embodiments $R^{17}$ is $C_3$-$C_7$ branched alkyl.
In some embodiments $R^{17}$ is $C_3$-$C_7$ cycloalkyl.
In some embodiments $R^{17}$ is $C_2$-$C_6$ alkenyl.
In some embodiments $R^{17}$ is $C_2$-$C_6$ alkynyl.
In some embodiments $R^{18}$ is hydrogen.
In some embodiments $R^{18}$ is $C_1$-$C_6$ alkyl.
In some embodiments $R^{18}$ is $C_3$-$C_7$ branched alkyl.
In some embodiments $R^{18}$ is $C_3$-$C_7$ cycloalkyl.
In some embodiments $R^{18}$ is $C_2$-$C_6$ alkenyl.
In some embodiments $R^{18}$ is $C_2$-$C_6$ alkynyl.
In some embodiments $R^{17}$ and $R^{18}$ are taken together with the atoms to which they are bound to form an optionally substituted five or six membered ring containing two nitrogen atoms.

In some embodiments $R^{19a}$ is hydrogen.
In some embodiments $R^{19a}$ is optionally substituted $C_1$-$C_6$ alkyl.
In some embodiments $R^{19a}$ is optionally substituted $C_3$-$C_7$ branched alkyl.
In some embodiments $R^{19a}$ is optionally substituted $C_3$-$C_7$ cycloalkyl.
In some embodiments $R^{19a}$ is optionally substituted $C_2$-$C_6$ alkenyl.
In some embodiments $R^{19a}$ is optionally substituted $C_2$-$C_6$ alkynyl.
In some embodiments $R^{19b}$ is hydrogen.
In some embodiments $R^{19b}$ is optionally substituted $C_1$-$C_6$ alkyl.
In some embodiments $R^{19b}$ is optionally substituted $C_3$-$C_7$ branched alkyl.
In some embodiments $R^{19b}$ is optionally substituted $C_3$-$C_7$ cycloalkyl.
In some embodiments $R^{19b}$ is optionally substituted $C_2$-$C_6$ alkenyl.
In some embodiments $R^{19b}$ is optionally substituted $C_2$-$C_6$ alkynyl.
In some embodiments $R^{19a}$ and $R^{19b}$ are taken together with the atom to which they are bound to form an optionally substituted 3 membered carbocyclic ring.
In some embodiments $R^{19a}$ and $R^{19b}$ are taken together with the atom to which they are bound to form an optionally substituted 4 membered carbocyclic ring.
In some embodiments $R^{19a}$ and $R^{19b}$ are taken together with the atom to which they are bound to form an optionally substituted 5 membered carbocyclic ring.
In some embodiments $R^{19a}$ and $R^{19b}$ are taken together with the atom to which they are bound to form an optionally substituted 6 membered carbocyclic ring.
In some embodiments $R^{20}$ is hydrogen.
In some embodiments $R^{20}$ is $C_1$-$C_6$ alkyl.
In some embodiments $R^{20}$ is $C_3$-$C_7$ branched alkyl.
In some embodiments $R^{20}$ is $C_3$-$C_7$ cycloalkyl.
In some embodiments $R^{20}$ is $C_2$-$C_6$ alkenyl.
In some embodiments $R^{20}$ is $C_2$-$C_6$ alkynyl.
In some embodiments q is 1.
In some embodiments q is 2.
In some embodiments $R^{21}$ is hydrogen.
In some embodiments $R^{21}$ is $C_1$-$C_6$ alkyl.
In some embodiments $R^{21}$ is $C_3$-$C_7$ branched alkyl.
In some embodiments $R^{21}$ is $C_3$-$C_7$ cycloalkyl.
In some embodiments $R^{21}$ is $C_2$-$C_6$ alkenyl.
In some embodiments $R^{21}$ is $C_2$-$C_6$ alkynyl.
In some embodiments $R^{21}$ is $C_1$-$C_6$ fluoroalkyl.
In some embodiments $R^{21}$ is optionally substituted aryl.
In some embodiments $R^{21}$ is optionally substituted heteroaryl.
In some embodiments $R^{22}$ is $C_1$-$C_6$ alkyl.
In some embodiments $R^{22}$ is $C_3$-$C_7$ branched alkyl.
In some embodiments $R^{22}$ is $C_3$-$C_7$ cycloalkyl.
In some embodiments $R^{22}$ is $C_2$-$C_6$ alkenyl.
In some embodiments $R^{22}$ is $C_2$-$C_6$ alkynyl.
In some embodiments $R^{22}$ is optionally substituted aryl.
In some embodiments $R^{22}$ is optionally substituted heteroaryl
In some embodiments $R^{23}$ is hydrogen.
In some embodiments $R^{23}$ is $CH_3$.
In some embodiments $R^{23}$ is $CH_2CH_3$.
In some embodiments $R^{23}$ is $CH_2CH_2CH_3$
In some embodiments $R^{23}$ is $CH_2CCH$.
In some embodiments $R^{23}$ is $CH(CH_3)_2$.
In some embodiments $R^{23}$ is $CH_2CH(CH_3)_2$.

In some embodiments $R^{23}$ is $CH(CH_3)CH_2CH_3$.
In some embodiments $R^{23}$ is $CH_2OH$.
In some embodiments $R^{23}$ is $CH_2OCH_2Ph$.
In some embodiments $R^{23}$ is $CH_2CH_2OCH_2Ph$.
In some embodiments $R^{23}$ is $CH(OH)CH_3$.
In some embodiments $R^{23}$ is $CH_2Ph$.
In some embodiments $R^{23}$ is $CH_2(cyclohexyl)$.
In some embodiments $R^{23}$ is $CH_2(4\text{-}OH\text{-}Ph)$.
In some embodiments $R^{23}$ is $(CH_2)_4NH_2$.
In some embodiments $R^{23}$ is $(CH_2)_3NHC(NH_2)NH$.
In some embodiments $R^{23}$ is $CH_2(3\text{-indole})$.
In some embodiments $R^{23}$ is $CH_2(5\text{-imidazole})$.
In some embodiments $R^{23}$ is $CH_2CO_2H$.
In some embodiments $R^{23}$ is $CH_2CH_2CO_2H$.
In some embodiments $R^{23}$ is $CH_2CONH_2$.
In some embodiments $R^{23}$ is $CH_2CH_2CONH_2$.
In some embodiments $R^{24}$ is hydrogen.
In some embodiments $R^{24}$ is $C_1\text{-}C_6$ alkyl.
In some embodiments $R^{24}$ is $C_3\text{-}C_7$ branched alkyl.
In some embodiments $R^{24}$ is $C_3\text{-}C_7$ cycloalkyl.
In some embodiments $R^{24}$ is $C_2\text{-}C_6$ alkenyl.
In some embodiments $R^{24}$ is $C_2\text{-}C_6$ alkynyl.
In some embodiments $R^{24}$ is optionally substituted aryl.
In some embodiments $R^{24}$ is optionally substituted heteroaryl.
In some embodiments $R^{24}$ is $COR^{25}$.
In some embodiments $R^{24}$ is $SO_2$—$C_{1\text{-}6}$alkyl.
In some embodiments $R^{25}$ is hydrogen.
In some embodiments $R^{25}$ is $C_1\text{-}C_6$ alkyl.
In some embodiments $R^{25}$ is $C_3\text{-}C_7$ branched alkyl.
In some embodiments $R^{25}$ is $C_3\text{-}C_7$ cycloalkyl.
In some embodiments $R^{25}$ is $C_2\text{-}C_6$ alkenyl.
In some embodiments $R^{25}$ is $C_2\text{-}C_6$ alkynyl.
In some embodiments $R^{25}$ is optionally substituted aryl.
In some embodiments $R^{25}$ is optionally substituted heteroaryl.
In some embodiments $R^{25}$ is $C_1\text{-}C_6$ alkoxy.
In some embodiments $R^{25}$ is $C_1\text{-}C_6$ alkylamino.

Exemplary non-limiting embodiments of the invention include
2-(methylamino)-N-(2-oxo-2-((6-(trifluoromethoxy) benzo[d]thiazol-2-yl)amino)ethyl)acetamide;
(S)—N-(2-oxo-2-((6-(trifluoromethoxy)benzo[d]thiazol-2-yl)amino)ethyl)pyrrolidine-2-carboxamide;
(R)-2-amino-N-(2-oxo-2-((6-(trifluoromethoxy)benzo [d]thiazol-2-yl)amino)ethyl)propanamide; 3-amino-N-(2-oxo-2-((6-(trifluoromethoxy)benzo[d] thiazol-2-yl) amino)ethyl) propanamide;
1-amino-N-(2-oxo-2-((6-(trifluoromethoxy)benzo[d] thiazol-2-yl)amino)ethyl) cyclopropane-1-carboxamide;
(S)—N-(2-oxo-2-((6-(trifluoromethoxy)benzo[d]thiazol-2-yl)amino)ethyl)azetidine-2-carboxamide; 2-amino-2-methyl-N-(2-oxo-2-((6-(trifluoromethoxy) benzo[d]thiazol-2-yl)amino)ethyl)propanamide;
(S)-2-(methylamino)-N-(2-oxo-2-((6-(trifluoromethoxy) benzo[d]thiazol-2-yl)amino)ethyl)propanamide;
(R)-2-(methylamino)-N-(2-oxo-2-((6-(trifluoromethoxy) benzo[d]thiazol-2-yl)amino)ethyl)propanamide;
(R)-2-amino-3-hydroxy-N-(2-oxo-2-((6-(trifluoromethoxy) benzo[d]thiazol-2-yl)amino)ethyl)propanamide;
(R)-2-amino-N-(2-oxo-2-((6-(trifluoromethoxy)benzo[d] thiazol-2-yl)amino)ethyl)pent-4-ynamide;
(S)-2-amino-N-(2-oxo-2-((6-(trifluoromethoxy) benzo[d] thiazol-2-yl)amino)ethyl)pent-4-ynamide;
(R)—N-(2-oxo-2-((6-(trifluoromethoxy)benzo[d] thiazol-2-yl)amino)ethyl)pyrrolidine-2-carboxamide;
1-amino-N-(2-oxo-2-((6-(trifluoromethoxy)benzo [d]thiazol-2-yl)amino)ethyl)cyclobutane-1-carboxamide;
(S)-2-amino-N-(2-oxo-2-((6-(trifluoromethoxy) benzo[d]thiazol-2-yl)amino)ethyl)pentanamide;
(R)-2-amino-3-methyl-N-(2-oxo-2-((6-(trifluoro methoxy) benzo[d]thiazol-2-yl)amino)ethyl)butanamide;
(S)-4-oxo-N-(2-oxo-2-((6-(trifluoromethoxy)benzo [d]thiazol-2-yl)amino)ethyl)pyrrolidine-2-carboxamide;
(S)—N-(2-oxo-2-((6-(trifluoromethoxy)benzo[d] thiazol-2-yl)amino)ethyl)piperidine-2-carboxamide;
(S)—N-(2-oxo-2-((6-(trifluoromethoxy)benzo[d] thiazol-2-yl)amino)ethyl)morpholine-3-carboxamide;
(R)—N-(2-oxo-2-((6-(trifluoromethoxy)benzo[d] thiazol-2-yl)amino)ethyl)morpholine-3-carboxamide;
(R)-2-amino-4-methyl-N-(2-oxo-2-((6-(trifluoro methoxy) benzo[d]thiazol-2-yl)amino)ethyl)pentanamide;
(R)-4-oxo-N-(2-oxo-2-((6-(trifluoromethoxy)benzo[d]thiazol-2-yl)amino)ethyl)piperidine-2-carboxamide;
4-amino-N-(2-oxo-2-((6-(trifluoromethoxy)benzo[d] thiazol-2-yl)amino)ethyl)tetrahydro-2H-pyran-4-carboxamide;
(R)-2-amino-N1-(2-oxo-2-((6-(trifluoromethoxy) benzo[d]thiazol-2-yl)amino)ethyl)pentanediamide;
(R)-2-amino-N-(2-oxo-2-((6-(trifluoromethoxy) benzo[d]thiazol-2-yl)amino)ethyl)-3-phenylpropanamide;
(R)-2-amino-3-cyclohexyl-N-(2-oxo-2-((6-(trifluoro methoxy)benzo[d] thiazol-2-yl)amino)ethyl)propanamide;
(R)-2-amino-3-(benzyloxy)-N-(2-oxo-2-((6-(trifluoro methoxy)benzo[d]thiazol-2-yl)amino)ethyl)propanamide;
(S)-2-amino-3-(benzyloxy)-N-(2-oxo-2-((6-(trifluoro methoxy)benzo[d]thiazol-2-yl)amino)ethyl)propanamide;
(R)-2-amino-3-(1H-indol-3-yl)-N-(2-oxo-2-((6-(trifluoro methoxy)benzo[d]thiazol-2-yl)amino)ethyl)propanamide;
(2S,4R)-4-(benzyloxy)-N-(2-oxo-2-((6-(trifluoro methoxy) benzo[d]thiazol-2-yl)amino)ethyl)pyrrolidine-2-carboxamide;
(S)—N-(2-oxo-2-((6-(trifluoromethoxy)benzo[d] thiazol-2-yl)amino)ethyl)piperazine-2-carboxamide;
(R)-2-amino-4-(benzyloxy)-N-(2-oxo-2-((6-(trifluoro methoxy)benzo[d]thiazol-2-yl)amino)ethyl)butanamide;
(R)-1-(N,N-dimethyl-L-valyl)-N-(6-(trifluoromethoxy) benzo [d]thiazol-2-yl)pyrrolidine-2-carboxamide;
(R)-1-(L-valyl)-N-(6-(trifluoromethoxy)benzo[d]thiazol-2-yl)pyrrolidine-2-carboxamide;
(R)-1-D-valyl-N-(6-(trifluoromethoxy)benzo[d]thiazol-2-yl) pyrrolidine-2-carboxamide;
(R)-1-glycinyl-N-(6-(trifluoromethoxy)benzo[d]thiazol-2-yl) pyrrolidine-2-carboxamide;
(R)-1-N-ethylglycinyl-N-(6-(trifluoromethoxy)benzo[d]thiazol-2-yl) pyrrolidine-2-carboxamide;
(R)-1-N-isopropylglycinyl-N-(6-(trifluoromethoxy) benzo [d]thiazol-2-yl) pyrrolidine-2-carboxamide;
(R)-1-N-t-butylglycinyl-N-(6-(trifluoromethoxy) benzo[d] thiazol-2-yl)pyrrolidine-2-carboxamide;
(R)-1-(3-amino-2,2-dimethylpropanoyl)-N-(6-(trifluoromethoxy)benzo[d]thiazol-2-yl)pyrrolidine-2-carboxamide;
(R)-1-(1-(aminomethyl)cyclopropane-1-carbonyl)-N-(6-(trifluoromethoxy)benzo[d] thiazol-2-yl)pyrrolidine-2-carboxamide;
(R)-1-(1-(aminomethyl)cyclopentane-1-carbonyl)-N-(6-(trifluoromethoxy)benzo[d] thiazol-2-yl)pyrrolidine-2-carboxamide;

(R)-1-(1-(aminomethyl)cyclohexane-1-carbonyl)-N-(6-(trifluoromethoxy)benzo [d]thiazol-2-yl)pyrrolidine-2-carboxamide;
(S)-1-(3-amino-2,2-dimethylpropanoyl)-N-(6-(trifluoromethoxy)benzo[d]thiazol-2-yl)pyrrolidine-2-carboxamide;
(S)-1-(1-(aminomethyl)cyclopropane-1-carbonyl)-N-(6-(trifluoromethoxy)benzo[d] thiazol-2-yl)pyrrolidine-2-carboxamide;
(S)-1-(1-(aminomethyl)cyclopentane-1-carbonyl)-N-(6-(trifluoromethoxy)benzo[d]thiazol-2-yl)pyrrolidine-2-carboxamide;
(S)-1-(D-valyl)-N-(6-(trifluoromethoxy)benzo[d]thiazol-2-yl)pyrrolidine-2-carboxamide;
(S)-1-(L-valyl)-N-(6-(trifluoromethoxy)benzo[d]thiazol-2-yl)pyrrolidine-2-carboxamide;
(S)-1-glycyl-N-(6-(trifluoromethoxy)benzo[d]thiazol-2-yl)pyrrolidine-2-carboxamide;
(S)-1-(D-alanyl)-N-(6-(trifluoromethoxy)benzo [d]thiazol-2-yl)pyrrolidine-2-carboxamide;
(S)-1-(methylglycyl)-N-(6-(trifluoromethoxy)benzo [d]thiazol-2-yl)pyrrolidine-2-carboxamide;
(S)-1-(ethylglycyl)-N-(6-(trifluoromethoxy)benzo[d]thiazol-2-yl)pyrrolidine-2-carboxamide;
(S)-1-(isopropylglycyl)-N-(6-(trifluoromethoxy)benzo[d]thiazol-2-yl)pyrrolidine-2-carboxamide;
(S)-1-(tert-butylglycyl)-N-(6-(trifluoromethoxy)benzo[d]thiazol-2-yl)pyrrolidine-2-carboxamide;
(S)-1-(D-leucyl)-N-(6-(trifluoromethoxy)benzo[d]thiazol-2-yl)pyrrolidine-2-carboxamide;
(S)-1-(3-aminopropanoyl)-N-(6-(trifluoromethoxy)benzo[d]thiazol-2-yl)pyrrolidine-2-carboxamide;
(S)-1-glycyl-N-(6-(trifluoromethoxy)benzo[d]thiazol-2-yl)azetidine-2-carboxamide;
(S)-1-(3-aminopropanoyl)-N-(6-(trifluoromethoxy)benzo[d]thiazol-2-yl)azetidine-2-carboxamide;
(S)-1-(1-(aminomethyl)cyclopropane-1-carbonyl)-N-(6-(trifluoromethoxy)benzo[d]thiazol-2-yl)azetidine-2-carboxamide;
(S)-1-(1-(aminomethyl)cyclopentane-1-carbonyl)-N-(6-(trifluoromethoxy)benzo[d]thiazol-2-yl)azetidine-2-carboxamide;
(S)-1-glycyl-N-(6-(trifluoromethoxy)benzo[d]thiazol-2-yl)piperidine-2-carboxamide;
(S)-1-(3-aminopropanoyl)-N-(6-(trifluoromethoxy)benzo [d] thiazol-2-yl)piperidine-2-carboxamide;
(S)-1-(3-aminopropanoyl)-N-(6-(trifluoromethoxy)benzo[d]thiazol-2-yl)piperidine-2-carboxamide;
(R)-1-(methylglycyl)-N-(6-(trifluoromethoxy)benzo[d] thiazol-2-yl)piperidine-2-carboxamide;
1-(2-aminoacetamido)-N-(6-(trifluoromethoxy)benzo[d]thiazol-2-yl)cyclopropane-1-carboxamide;
1-(2-(methylamino)acetamido)-N-(6-(trifluoromethoxy)benzo[d]thiazol-2-yl)cyclopropane-1-carboxamide;
1-(2-aminoacetamido)-N-(6-(trifluoromethoxy)benzo[d]thiazol-2-yl)cyclobutane-1-carboxamide;
1-(2-(methylamino)acetamido)-N-(6-(trifluoromethoxy)benzo[d]thiazol-2-yl)cyclobutane-1-carboxamide;
1-(3-amino-2,2-dimethylpropanamido)-N-(6-(trifluoromethoxy)benzo[d]thiazol-2-yl)cyclobutane-1-carboxamide;
1-(aminomethyl)-N-(1-((6-(trifluoromethoxy)benzo[d]thiazol-2-yl)carbamoyl)cyclobutyl) cyclopentane-1-carboxamide;
1-(2-(isopropylamino)acetamido)-N-(6-(trifluoromethoxy)benzo[d]thiazol-2-yl)cyclobutane-1-carboxamide;
1-(2-(isopropylamino)acetamido)-N-(6-(trifluoromethoxy)benzo[d]thiazol-2-yl)cyclobutane-1-carboxamide;
1-(aminomethyl)-N-(1-((6-(trifluoromethoxy)benzo[d]thiazol-2-yl)carbamoyl)cyclobutyl) cyclohexane-1-carboxamide;
(R)-1-(2-aminopropanamido)-N-(6-(trifluoromethoxy)benzo [d]thiazol-2-yl)cyclobutane-1-carboxamide;
(R)-1-(2-amino-3-methylbutanamido)-N-(6-(trifluoromethoxy)benzo[d]thiazol-2-yl)cyclobutane-1-carboxamide;
(S)-2-(2-aminoacetamido)-3-phenyl-N-(6-(trifluoromethoxy)benzo[d]thiazol-2-yl)propanamide;
(S)-2-(2-(methylamino)acetamido)-3-phenyl-N-(6-(trifluoromethoxy)benzo[d]thiazol-2-yl)propanamide;
(S)-2-((R)-2-aminopropanamido)-3-phenyl-N-(6-(trifluoromethoxy)benzo[d]thiazol-2-yl)propanamide;
(S)-2-((S)-2-aminopropanamido)-3-phenyl-N-(6-(trifluoromethoxy)benzo[d]thiazol-2-yl)propanamide;
(R)-2-amino-3-methyl-N—((S)-1-oxo-3-phenyl-1-((6-(trifluoromethoxy)benzo[d]thiazol-2-yl)amino)propan-2-yl)butanamide;
(S)-2-amino-2-methyl-N-(1-oxo-3-phenyl-1-((6-(trifluoromethoxy)benzo [d]thiazol-2-yl)amino)propan-2-yl)propanamide;
(S)-1-amino-N-(1-oxo-3-phenyl-1-((6-(trifluoromethoxy)benzo[d]thiazol-2-yl)amino)propan-2-yl)cyclopropane-1-carboxamide;
(S)-1-amino-N-(1-oxo-3-phenyl-1-((6-(trifluoromethoxy)benzo[d]thiazol-2-yl)amino)propan-2-yl)cyclobutane-1-carboxamide;
1-(3-amino-2,2-dimethylpropanamido)-N-(6-(trifluoromethoxy)benzo[d]thiazol-2-yl)cyclobutane-1-carboxamide;
(R)-2-(2-aminopropanamido)-2-methyl-N-(6-(trifluoromethoxy)benzo[d]thiazol-2-yl)propanamide;
(S)-2-(2-aminopropanamido)-2-methyl-N-(6-(trifluoromethoxy)benzo[d]thiazol-2-yl)propanamide;
2-(2-aminoacetamido)-2-methyl-N-(6-(trifluoromethoxy)benzo[d]thiazol-2-yl)propanamide;
(R)-2-amino-N-(2-methyl-1-oxo-1-((6-(trifluoromethoxy)benzo[d]thiazol-2-yl)amino)propan-2-yl)-3-phenylpropanamide;
(S)-2-amino-3-(benzyloxy)-N-(2-methyl-1-oxo-1-((6-(trifluoromethoxy)benzo[d]thiazol-2-yl)amino)propan-2-yl)propanamide;
1-amino-N-(2-methyl-1-oxo-1-((6-(trifluoromethoxy)benzo[d]thiazol-2-yl)amino)propan-2-yl)cyclopropane-1-carboxamide;
1-amino-N-(2-methyl-1-oxo-1-((6-(trifluoromethoxy)benzo[d]thiazol-2-yl)amino)propan-2-yl)cyclobutane-1-carboxamide;
2-amino-2-methyl-N-(2-methyl-1-oxo-1-((6-(trifluoromethoxy)benzo[d]thiazol-2-yl)amino)propan-2-yl)propanamide;
3-amino-2,2-dimethyl-N-(2-methyl-1-oxo-1-((6-(trifluoromethoxy)benzo[d]thiazol-2-yl)amino)propan-2-yl)propanamide;
1-(aminomethyl)-N-(2-methyl-1-oxo-1-((6-(trifluoromethoxy)benzo[d]thiazol-2-yl)amino)propan-2-yl)cyclopropane-1-carboxamide;
1-(aminomethyl)-N-(2-methyl-1-oxo-1-((6-(trifluoromethoxy)benzo[d]thiazol-2-yl)amino)propan-2-yl)cyclopentane-1-carboxamide;
1-(aminomethyl)-N-(2-methyl-1-oxo-1-((6-(trifluoromethoxy)benzo[d]thiazol-2-yl)amino)propan-2-yl)cyclohexane-1-carboxamide;

2-methyl-2-(2-(methylamino)acetamido)-N-(6-(trifluoromethoxy)benzo[d]thiazol-2-yl)propanamide;
2-(2-(ethylamino)acetamido)-2-methyl-N-(6-(trifluoromethoxy)benzo[d]thiazol-2-yl)propanamide;
2-(2-(isopropylamino)acetamido)-2-methyl-N-(6-(trifluoromethoxy)benzo[d]thiazol-2-yl)propanamide;
2-(2-(tert-butylamino)acetamido)-2-methyl-N-(6-(trifluoromethoxy)benzo[d]thiazol-2-yl)propanamide;
(S)-2-(2-aminoacetamido)-N-(6-(trifluoromethoxy) benzo[d]thiazol-2-yl)propanamide;
(S)-2-amino-N—((S)-1-oxo-1-((6-(trifluoromethoxy)benzo[d]thiazol-2-yl)amino)propan-2-yl)propanamide;
(R)-2-amino-N—((S)-1-oxo-1-((6-(trifluoromethoxy)benzo[d] thiazol-2-yl)amino)propan-2-yl)propanamide;
3-Amino-N,2,2-trimethyl-N-(2-oxo-2-((6-(trifluoromethoxy)benzo[d]thiazol-2-yl)amino)ethyl)propanamide;
1-(aminomethyl)-N-methyl-N-(2-oxo-2-((6-(trifluoromethoxy)benzo[d]thiazol-2-yl)amino)ethyl)cyclopropane-1-carboxamide;
1-(aminomethyl)-N-methyl-N-(2-oxo-2-((6-(trifluoromethoxy)benzo[d]thiazol-2-yl)amino)ethyl)cyclopentane-1-carboxamide;
1-(aminomethyl)-N-methyl-N-(2-oxo-2-((6-(trifluoromethoxy)benzo[d]thiazol-2-yl)amino)ethyl)cyclohexane-1-carboxamide;
N-methyl-2-(methylamino)-N-(2-oxo-2-((6-(trifluoromethoxy)benzo[d]thiazol-2-yl)amino)ethyl)acetamide;
2-(ethylamino)-N-methyl-N-(2-oxo-2-((6-(trifluoromethoxy)benzo[d]thiazol-2-yl)amino)ethyl)acetamide;
2-(isopropylamino)-N-methyl-N-(2-oxo-2-((6-(trifluoromethoxy)benzo[d]thiazol-2-yl)amino)ethyl)acetamide;
2-(tert-butylamino)-N-methyl-N-(2-oxo-2-((6-(trifluoromethoxy)benzo[d]thiazol-2-yl)amino)ethyl)acetamide;
2-(dimethylamino)-N-methyl-N-(2-oxo-2-((6-(trifluoromethoxy)benzo[d]thiazol-2-yl) amino)ethyl)acetamide;
2-amino-N-methyl-N-(2-oxo-2-((6-(trifluoromethoxy)benzo[d]thiazol-2-yl)amino) ethyl)acetamide;
(S)-2-amino-N-methyl-N-(2-oxo-2-((6-(trifluoromethoxy)benzo[d]thiazol-2-yl)amino) ethyl)propanamide;
(R)-2-amino-N-methyl-N-(2-oxo-2-((6-(trifluoromethoxy)benzo[d]thiazol-2-yl)amino) ethyl)propanamide;
3-amino-N-methyl-N-(2-oxo-2-((6-(trifluoromethoxy)benzo [d]thiazol-2-yl)amino)ethyl) propanamide;
2-amino-N-ethyl-N-(2-oxo-2-((6-(trifluoromethoxy)benzo[d]thiazol-2-yl)amino) ethyl)acetamide;
2-amino-N-isopropyl-N-(2-oxo-2-((6-(trifluoromethoxy)benzo [d]thiazol-2-yl)amino)ethyl)acetamide;
2-(aminomethyl)-N-(6-(trifluoromethoxy)benzo [d]thiazol-2-yl)benzamide;
tert-butyl (4-oxo-4-((6-(trifluoromethoxy)benzo[d]thiazol-2-yl)amino)butyl)carbamate;
4-amino-N-(6-(trifluoromethoxy)benzo[d]thiazol-2-yl)butanamide;
(S)—N-(4-oxo-4-((6-(trifluoromethoxy)benzo[d]thiazol-2-yl)amino)butyl) pyrrolidine-2-carboxamide;
(S)-2-amino-4-methyl-N-(4-oxo-4-((6-(trifluoromethoxy)benzo[d]thiazol-2-yl)amino) butyl)pentanamide;
4-(2-aminoacetamido)-N-(6-(trifluoromethoxy)benzo[d]thiazol-2-yl)butanamide;
(S)-4-(2-aminopropanamido)-N-(6-(trifluoromethoxy) benzo [d]thiazol-2-yl)butanamide;
(S)-2-amino-3-methyl-N-(4-oxo-4-((6-(trifluoromethoxy)benzo[d]thiazol-2-yl)amino) butyl)butanamide;
(S)-5-oxo-N-(4-oxo-4-((6-(trifluoromethoxy)benzo[d]thiazol-2-yl)amino)butyl) pyrrolidine-2-carboxamide;
(2S,3S)-2-amino-3-methyl-N-(4-oxo-4-((6-(trifluoromethoxy)benzo[d]thiazol-2-yl) amino)butyl)pentanamide;
(S)-4-amino-5-oxo-5-((4-oxo-4-((6-(trifluoromethoxy) benzo [d]thiazol-2-yl)amino)butyl) amino)pentanoic acid;
(S)-2-amino-4-(methylthio)-N-(4-oxo-4-((6-(trifluoromethoxy)benzo[d]thiazol-2-yl)amino)butyl)butanamide;
(S)-4-(2-amino-3-phenylpropanamido)-N-(6-(trifluoromethoxy)benzo [d]thiazol-2-yl)butanamide;
(S)-3-amino-4-oxo-4-((4-oxo-4-((6-(trifluoromethoxy) benzo [d]thiazol-2-yl)amino) butyl)amino)butanoic acid;
(S)-4-amino-5-oxo-5-((4-oxo-4-((6-(trifluoromethoxy) benzo[d]thiazol-2-yl)amino)butyl) amino)pentanoic acid;
(S)-4-(2-amino-3-(1H-indol-3-yl)propanamido)-N-(6-(trifluoromethoxy)benzo[d]thiazol-2-yl)butanamide;
(S)—N-((1-(2-oxo-2-((6-(trifluoromethoxy)benzo[d]thiazol-2-yl)amino)ethyl)cyclohexyl) methyl)pyrrolidine-2-carboxamide;
(S)—N-((1-(2-oxo-2-((6-(trifluoromethoxy)benzo[d]thiazol-2-yl)amino) ethyl)cyclohexyl) methyl)pyrrolidine-2-carboxamide;
(S)-2-amino-4-methyl-N-((1-(2-oxo-2-((6-(trifluoromethoxy) benzo[d]thiazol-2-yl)amino) ethyl)cyclohexyl)methyl)pentanamide;
(S)-2-amino-3-methyl-N-((1-(2-oxo-2-((6-(trifluoromethoxy)benzo[d]thiazol-2-yl)amino)ethyl)cyclohexyl) methyl)butanamide;
2-amino-N-((1-(2-oxo-2-((6-(trifluoromethoxy)benzo[d]thiazol-2-yl)amino) ethyl) cyclohexyl)methyl)acetamide;
(S)-2-amino-N-((1-(2-oxo-2-((6-(trifluoromethoxy)benzo[d] thiazol-2-yl)amino)ethyl) cyclohexyl)methyl)propanamide;
2-(methylamino)-N-((1-(2-oxo-2-((6-(trifluoromethoxy) benzo[d]thiazol-2-yl)amino)ethyl) cyclohexyl)methyl)acetamide;
(R)-2-amino-3-methyl-N-((1-(2-oxo-2-((6-(trifluoromethoxy)benzo[d]thiazol-2-yl)amino) ethyl)cyclohexyl) methyl)butanamide;
(S)-5-oxo-N-((1-(2-oxo-2-((6-(trifluoromethoxy)benzo[d] thiazol-2-yl)amino)ethyl) cyclohexyl)methyl)pyrrolidine-2-carboxamide;
(S)-2-amino-N1-((1-(2-oxo-2-((6-(trifluoromethoxy)benzo [d]thiazol-2-yl)amino)ethyl) cyclohexyl)methyl)pentanediamide;
(S)-2-amino-4-(methylthio)-N-((1-(2-oxo-2-((6-(trifluoromethoxy)benzo[d]thiazol-2-yl)amino)ethyl)cyclohexyl) methyl)butanamide;
(S)-2-amino-N-((1-(2-oxo-2-((6-(trifluoromethoxy)benzo [d] thiazol-2-yl)amino)ethyl) cyclohexyl)methyl)-3-phenylpropanamide;
(S)-3-amino-4-oxo-4-(((1-(2-oxo-2-((6-(trifluoromethoxy) benzo[d]thiazol-2-yl)amino) ethyl)cyclohexyl)methyl) amino)butanoic acid;
(S)-4-amino-5-oxo-5-(((1-(2-oxo-2-((6-(trifluoromethoxy) benzo[d]thiazol-2-yl)amino) ethyl)cyclohexyl)methyl) amino)pentanoic acid;
(S)-2-amino-3-(1H-indol-3-yl)-N-((1-(2-oxo-2-((6-(trifluoromethoxy)benzo [d]thiazol-2-yl)amino)ethyl)cyclohexyl)methyl)propanamide;
(R)-2-amino-3-methyl-N-(4-oxo-4-((6-(trifluoromethoxy) benzo[d]thiazol-2-yl)amino) butyl)butanamide;
(R)—N-(4-oxo-4-((6-(trifluoromethoxy)benzo[d]thiazol-2-yl)amino)butyl)pyrrolidine-2-carboxamide;
(R)-5-oxo-N-(4-oxo-4-((6-(trifluoromethoxy)benzo[d]thiazol-2-yl)amino)butyl) pyrrolidine-2-carboxamide;

(R)-2-amino-3-methyl-N-((1-(2-oxo-2-((6-(trifluoro methoxy)benzo[d]thiazol-2-yl)amino)ethyl) cyclohexyl) methyl)butanamide;
(S)—N-((1-(2-oxo-2-((6-(trifluoromethoxy)benzo[d]thiazol-2-yl)amino)ethyl)cyclohexyl) methyl)pyrrolidine-2-carboxamide;
(R)-5-oxo-N-((1-(2-oxo-2-((6-(trifluoromethoxy)benzo[d]thiazol-2-yl)amino)ethyl)cyclohexyl) methyl)pyrrolidine-2-carboxamide;
4-amino-3,3-dimethyl-N-(6-(trifluoromethoxy)benzo[d]thiazol-2-yl)butanamide;
(S)-3-(benzyloxy)-2-morpholino-N-(6-(trifluoromethoxy)benzo[d]thiazol-2-yl)propanamide;
(S)-3-(benzyloxy)-2-(dimethylamino)-N-(6-(trifluoromethoxy)benzo[d]thiazol-2-yl)propanamide;
(S)-1-methyl-N-(6-(trifluoromethoxy)benzo[d]thiazol-2-yl) pyrrolidine-2-carboxamide;
2-(ethylamino)-N-methyl-N-(2-oxo-2-((6-(trifluoromethoxy) benzo[d]thiazol-2-yl)amino)ethyl)acetamide;
2-(isopropylamino)-N-methyl-N-(2-oxo-2-((6-(trifluoromethoxy)benzo[d]thiazol-2-yl)amino)ethyl)acetamide;
(R)-1-(1-(aminomethyl)cyclohexane-1-carbonyl)-N-(6-(trifluoromethoxy)benzo[d] thiazol-2-yl)pyrrolidine-2-carboxamide;
N-methyl-2-(methylsulfonamido)-N-(2-oxo-2-((6-(trifluoromethoxy)benzo[d]thiazol-2-yl)amino)ethyl)acetamide;
2-(tert-butoxy)-N-methyl-N-(2-oxo-2-((6-(trifluoromethoxy) benzo[d]thiazol-2-yl)amino)ethyl)acetamide;
N,4,4-trimethyl-N-(2-oxo-2-((6-(trifluoromethoxy)benzo[d]thiazol-2-yl)amino)ethyl) pentanamide;
tert-Butyl (2-(methyl(2-oxo-2-((6-(trifluoromethoxy)benzo[d]thiazol-2-yl)amino)ethyl)amino)-2-oxoethyl)(1-(trifluoromethyl)cyclopropyl)carbamate;
N-methyl-N-(2-oxo-2-((6-(trifluoromethoxy)benzo[d]thiazol-2-yl)amino)ethyl)-2-((1-(trifluoromethyl)cyclopropyl)amino)acetamide;
N-methyl-N-(2-oxo-2-((6-(trifluoromethoxy)benzo[d] thiazol-2-yl)amino)ethyl)-2-((2,2,2-trifluoroethyl)amino)acetamide hydrochloride;
2-acetamido-N-methyl-N-(2-oxo-2-((6-(trifluoromethoxy) benzo[d]thiazol-2-yl)amino)ethyl) acetamide;
N-(2-(methyl(2-oxo-2-((6-(trifluoromethoxy)benzo[d] thiazol-2-yl)amino)ethyl)amino)-2-oxoethyl)propionamide;
N-(2-(methyl(2-oxo-2-((6-(trifluoromethoxy)benzo[d]thiazol-2-yl)amino)ethyl)amino)-2-oxoethyl)butyramide;
N-(2-(methyl(2-oxo-2-((6-(trifluoromethoxy)benzo[d]thiazol-2-yl)amino)ethyl)amino)-2-oxoethyl)isobutyramide;
N-(2-(methyl(2-oxo-2-((6-(trifluoromethoxy)benzo[d]thiazol-2-yl)amino)ethyl)amino)-2-oxoethyl)benzamide;
2,2,2-trifluoro-N-(2-(methyl(2-oxo-2-((6-(trifluoromethoxy) benzo[d]thiazol-2-yl)amino)ethyl) amino)-2-oxoethyl)acetamide;
N-methyl-N-(2-oxo-2-((6-(trifluoromethoxy)benzo[d] thiazol-2-yl)amino)ethyl)-2-((1,1,1-trifluoro-2-methylpropan-2-yl)amino)acetamide;
2-(2-oxopiperazin-1-yl)-N-(6-(trifluoromethoxy)benzo [d]thiazol-2-yl)acetamide;
(S)—N-methyl-N-(2-oxo-2-((6-(trifluoromethoxy)benzo[d] thiazol-2-yl)amino)ethyl) piperazine-2-carboxamide;
(R)—N-methyl-N-(2-oxo-2-((6-(trifluoromethoxy)benzo[d] thiazol-2-yl)amino)ethyl) piperazine-2-carboxamide;
Benzyl (2-(((6-(trifluoromethoxy)benzo[d]thiazol-2-yl)carbamoyl)oxy)ethyl)carbamate;
2-aminoethyl (6-(trifluoromethoxy)benzo[d]thiazol-2-yl) carbamate;
Benzyl ethyl(2-(((6-(trifluoromethoxy)benzo[d]thiazol-2-yl)carbamoyl)oxy) ethyl)carbamate;
2-(Ethylamino)ethyl (6-(trifluoromethoxy)benzo[d]thiazol-2-yl)carbamate;
Benzyl methyl(2-(((6-(trifluoromethoxy)benzo[d]thiazol-2-yl)carbamoyl)oxy) ethyl)carbamate;
2-(Methylamino)ethyl (6-(trifluoromethoxy)benzo [d]thiazol-2-yl)carbamate;
Benzyl isopropyl(2-(((6-(trifluoromethoxy)benzo[d]thiazol-2-yl)carbamoyl)oxy)ethyl)carbamate;
2-(Isopropylamino)ethyl (6-(trifluoromethoxy)benzo[d] thiazol-2-yl)carbamate;
(5-methyl-2-oxo-1,3-dioxol-4-yl)methyl (5-(trifluoro methoxy)benzo[d]thiazol-2-yl)carbamate;
4-amino-2,2-dimethyl-N-(6-(trifluoromethoxy)benzo [d]thiazol-2-yl)butanamide;
(S)-2-amino-N1,N5-bis(6-(trifluoromethoxy)benzo[d]thiazol-2-yl)pentanediamide;
2-(dimethylamino)-N-(6-(trifluoromethoxy)benzo[d]thiazol-2-yl)acetamide;
and 1,3-bis(6-(trifluoromethoxy)benzo[d]thiazol-2-yl)urea.

Exemplary embodiments include compounds having the formula (I) through (XVI) or a pharmaceutically acceptable salt form thereof, in combination with an anticancer agent. Exemplary embodiments of anticancer agents include but are not limited to Vemurafenib, Ipilimumab, Masitinib, Sorafenib, Lenalidomide, Oblimersen, Trametinib, Dabrafenib, RO5185426, Veliparib, Bosentan, YM155, CNTO 95, CR011-veMMAE, CY503, Lenvatinib, Avastin, Tasidotin, Ramucirumab, IPI-504, Tasisulam, KW2871, MPC-6827, RAF265, Dovitinib, Everolimus, MEK162, BKM120, Nilotinib, Reolysin, 825A, Tremelimumab, PI-88, Elesclomol, STA9090, and Allovectin-7.

For the purposes of the present invention, a compound depicted by the racemic formula will stand equally well for either of the two enantiomers or mixtures thereof, or in the case where a second chiral center is present, all diastereomers.

For the purposes of the present invention, a compound depicted by the racemic formula will stand equally well for either of the two enantiomers or mixtures thereof, or in the case where a second chiral center is present, all diastereomers.

In all of the embodiments provided herein, examples of suitable optional substituents are not intended to limit the scope of the claimed invention. The compounds of the invention may contain any of the substituents, or combinations of substituents, provided herein.

Process

Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., *Protective Groups in Organic Synthesis*, 2d. Ed. (Wiley & Sons, 1991), the entire disclosure of which is incorporated by reference herein for all purposes.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of these teachings can be prepared by methods known in the art of organic chemistry. The reagents used in the preparation of the compounds of these teachings can be either commercially obtained or can be prepared by standard procedures described in the literature. For example, compounds of the present invention can be prepared according to the method illustrated in the General Synthetic Schemes:

General Synthetic Schemes for Preparation of Compounds

The reagents used in the preparation of the compounds of this invention can be either commercially obtained or can be prepared by standard procedures described in the literature. In accordance with this invention, compounds in the genus may be produced by one of the following reaction schemes. Compounds of formula (I) may be prepared according to the process outlined in schemes 1-21.

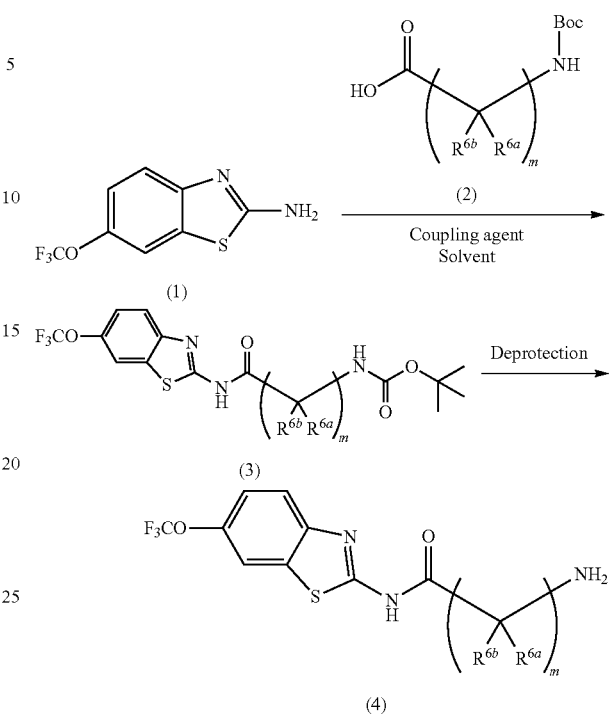

Scheme 1

Riluzole (1), a known compound, is reacted with a compound of the formula (2), a known compound or a compound made by known methods, in the presence of a coupling agent such as 0-(benzotriazol-1-yl)-N,N,N',N'-tetramethyluronium hexafluorophosphate, N,N'-dicyclohexylcarbodiimide, 1-ethyl-3-(3-dimethylaminopropyl) carbodiimide, 1-[Bis(dimethylamino)methylene]-1H-1,2,3-triazolo[4,5-b]pyridinium 3-oxid hexafluorophosphate, 1-hydroxy-7-azabenzotriazole and the like, optionally in the presence of a base such as triethylamine, diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (3). A compound of the formula (3) is reacted with an acid such as trifluoroacetic acid, hydrochloric acid, and the like in a solvent such as methylene chloride, 1,2-dichloroethane, tetrahydrofuran, 1,4-dioxane, and the like to provide a compound of the formula (4).

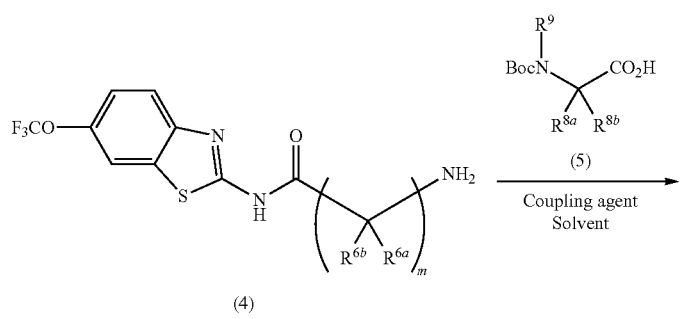

Scheme 2

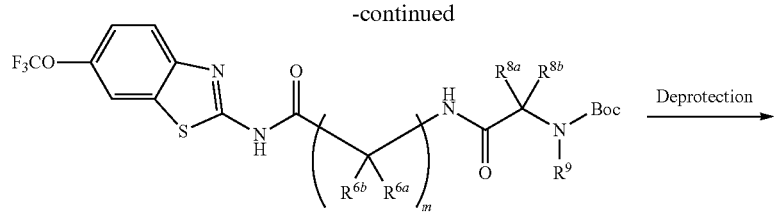

(6)

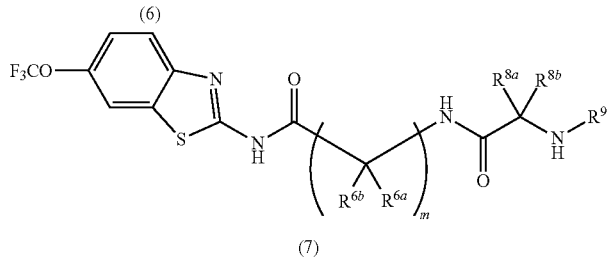

(7)

A compound of the formula (4) is reacted with a compound of the formula (5), a known compound or a compound made by known methods, in the presence of a coupling agent such as 0-(benzotriazol-1-yl)-N,N,N',N'-tetramethyluronium hexafluorophosphate, N,N'-dicyclohexylcarbodiimide, 1-ethyl-3-(3-dimethylaminopropyl) carbodiimide, 1-[Bis(dimethylamino)methylene]-1H-1,2,3-triazolo[4,5-b]pyridinium 3-oxid hexafluorophosphate, 1-hydroxy-7-azabenzotriazole and the like, optionally in the presence of a base such as triethylamine, diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (6). A compound of the formula (6) is reacted with an acid such as trifluoroacetic acid, hydrochloric acid, and the like in a solvent such as methylene chloride, 1,2-dichloroethane, tetrahydrofuran, 1,4-dioxane, and the like to provide a compound of the formula (7).

Scheme 3

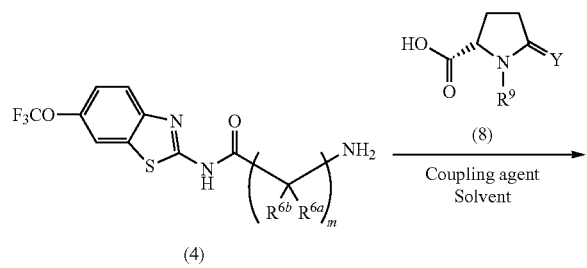

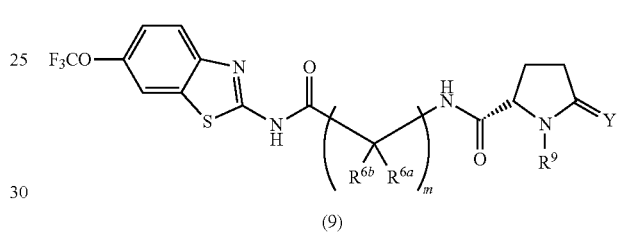

(9)

A compound of the formula (4) is reacted with a compound of (8), a known compound or a compound made by known methods, in the presence of a coupling agent such as O-(benzotriazol-1-yl)-N,N,N',N'-tetramethyluronium hexafluorophosphate, N,N'-dicyclohexylcarbodiimide, 1-ethyl-3-(3-dimethylaminopropyl) carbodiimide, 1-[Bis(dimethylamino)methylene]-1H-1,2,3-triazolo[4,5-b]pyridinium 3-oxid hexafluorophosphate, 1-hydroxy-7-azabenzotriazole and the like, optionally in the presence of a base such as triethylamine, diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (9).

Scheme 4

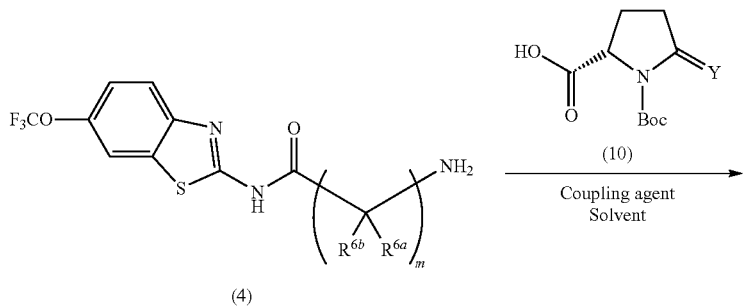

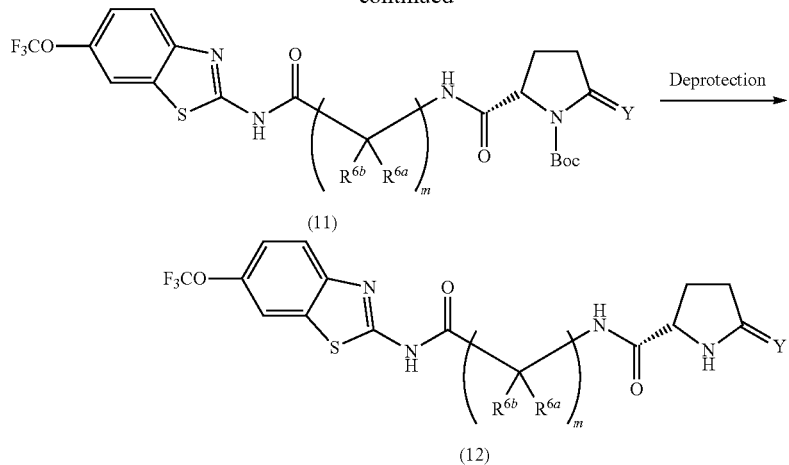

A compound of the formula (4) is reacted with a compound of (10), a known compound or a compound made by known methods, in the presence of a coupling agent such as O-(benzotriazol-1-yl)-N,N,N',N'-tetramethyluronium hexafluorophosphate, N,N'-dicyclohexylcarbodiimide, 1-ethyl-3-(3-dimethylaminopropyl) carbodiimide, 1-[Bis(dimethylamino)methylene]-1H-1,2,3-triazolo[4,5-b]pyridinium 3-oxid hexafluorophosphate, 1-hydroxy-7-azabenzotriazole and the like, optionally in the presence of a base such as triethylamine, diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (11). A compound of the formula (11) is reacted with an acid such as trifluoroacetic acid, hydrochloric acid, and the like in a solvent such as methylene chloride, 1,2-dichloroethane, tetrahydrofuran, 1,4-dioxane, and the like to provide a compound of the formula (12).

Scheme 5

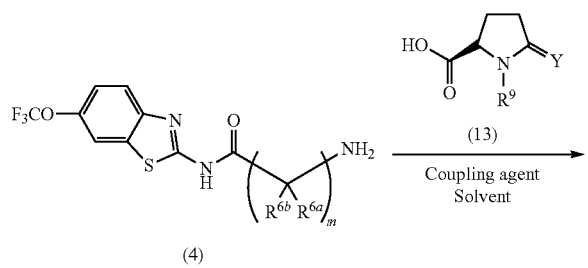

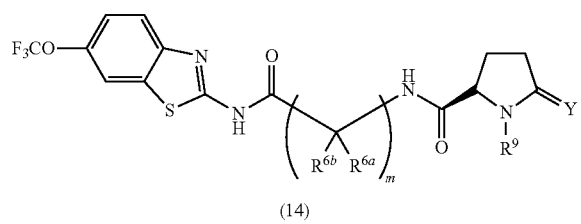

A compound of the formula (4) is reacted with a compound of (13), a known compound or a compound made by known methods, in the presence of a coupling agent such as O-(benzotriazol-1-yl)-N,N,N',N'-tetramethyluronium hexafluorophosphate, N,N'-dicyclohexylcarbodiimide, 1-ethyl-3-(3-dimethylaminopropyl) carbodiimide, 1-[Bis(dimethylamino)methylene]-1H-1,2,3-triazolo[4,5-b]pyridinium 3-oxid hexafluorophosphate, 1-hydroxy-7-azabenzotriazole and the like, optionally in the presence of a base such as triethylamine, diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (14).

Scheme 6

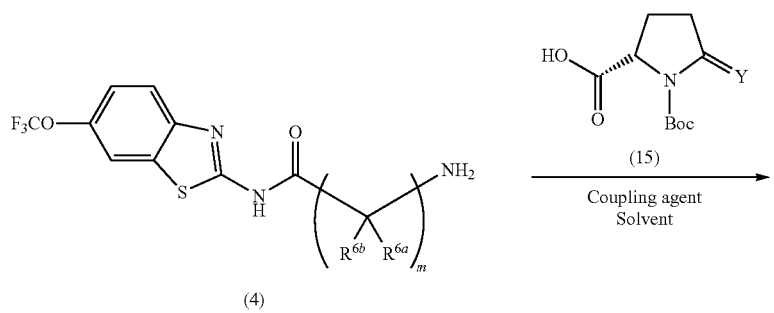

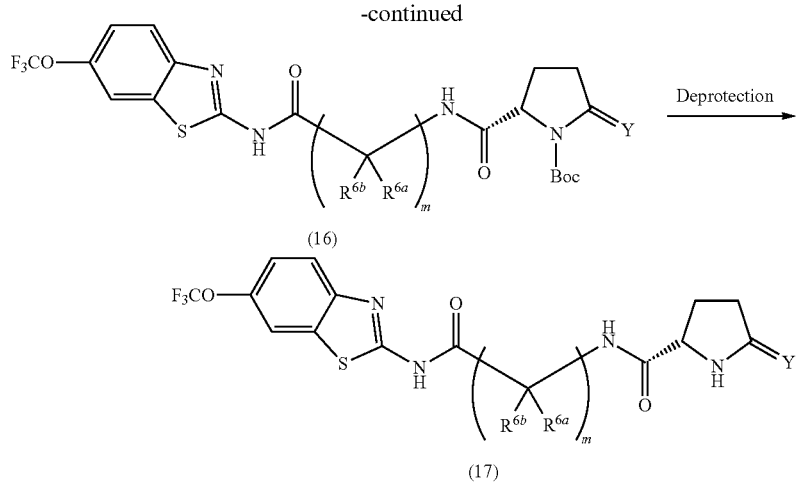

A compound of the formula (4) is reacted with a compound of (15), a known compound or a compound made by known methods, in the presence of a coupling agent such as O-(benzotriazol-1-yl)-N,N,N',N'-tetramethyluronium hexafluorophosphate, N,N'-dicyclohexylcarbodiimide, 1-ethyl-3-(3-dimethylaminopropyl) carbodiimide, 1-[Bis(dimethylamino)methylene]-1H-1,2,3-triazolo[4,5-b]pyridinium 3-oxid hexafluorophosphate, 1-hydroxy-7-azabenzotriazole and the like, optionally in the presence of a base such as triethylamine, diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (16). A compound of the formula (16) is reacted with an acid such as trifluoroacetic acid, hydrochloric acid, and the like in a solvent such as methylene chloride, 1,2-dichloroethane, tetrahydrofuran, 1,4-dioxane, and the like to provide a compound of the formula (17).

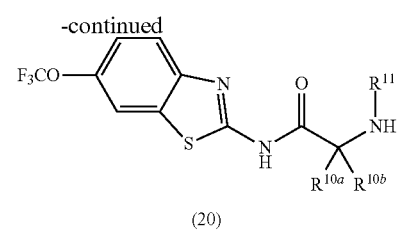

Riluzole (1), a known compound, is reacted with a compound of the formula (18), a known compound or a compound made by known methods, in the presence of a coupling agent such as O-(benzotriazol-1-yl)-N,N,N',N'-tetramethyluronium hexafluorophosphate, N,N'-dicyclohexylcarbodiimide, 1-ethyl-3-(3-dimethylaminopropyl) carbodiimide, 1-[Bis(dimethylamino)methylene]-1H-1,2,3-triazolo[4,5-b]pyridinium 3-oxid hexafluorophosphate, 1-hydroxy-7-azabenzotriazole and the like, optionally in the presence of a base such as triethylamine, diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (19). A compound of the formula (19) is reacted with an acid such as trifluoroacetic acid, hydrochloric acid, and the like in a solvent such as methylene chloride, 1,2-dichloroethane, tetrahydrofuran, 1,4-dioxane, and the like to provide a compound of the formula (20).

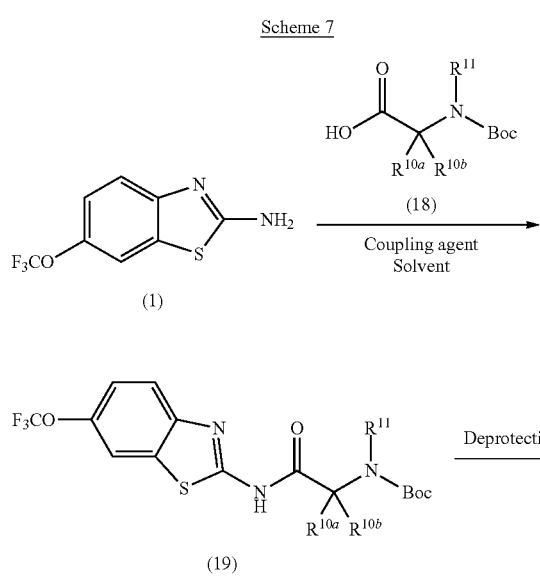

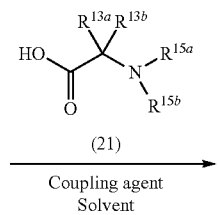

57

-continued

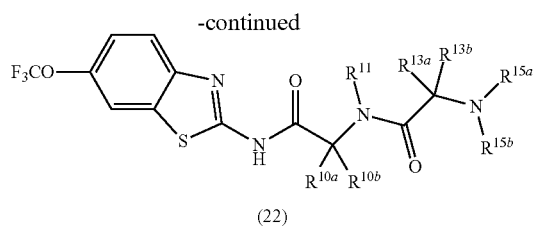

(22)

A compound of the formula (20) is reacted with a compound of (21), a known compound or a compound made by known methods, in the presence of a coupling agent such as O-(benzotriazol-1-yl)-N,N,N',N'-tetramethyluronium hexafluorophosphate, N,N'-dicyclohexylcarbodiimide, 1-ethyl-3-(3-dimethylaminopropyl) carbodiimide, 1-[Bis(dimethylamino)methylene]-1H-1,2,3-triazolo[4,5-b]pyridinium 3-oxid hexafluorophosphate, 1-hydroxy-7-azabenzotriazole and the like, optionally in the presence of a base such as triethylamine, diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (22).

Scheme 9

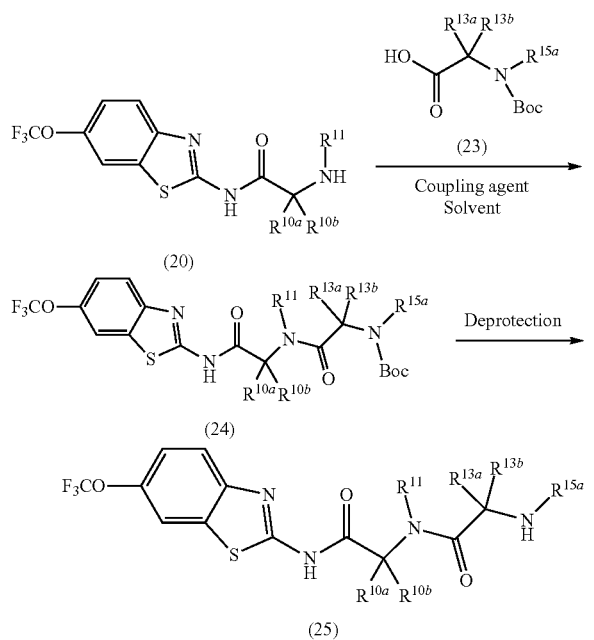

A compound of the formula (20) is reacted with a compound of (23), a known compound or a compound made by known methods, in the presence of a coupling agent such as O-(benzotriazol-1-yl)-N,N,N',N'-tetramethyluronium hexafluorophosphate, N,N'-dicyclohexylcarbodiimide, 1-ethyl-3-(3-dimethylaminopropyl) carbodiimide, 1-[Bis(dimethylamino)methylene]-1H-1,2,3-triazolo[4,5-b]pyridinium 3-oxid hexafluorophosphate, 1-hydroxy-7-azabenzotriazole and the like, optionally in the presence of a base such as triethylamine, diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (24). A compound of the formula (24) is reacted with an acid such as trifluoroacetic acid, hydrochloric acid, and the like in a solvent such as methylene chloride, 1,2-dichloroethane, tetrahydrofuran, 1,4-dioxane, and the like to provide a compound of the formula (25).

Scheme 10

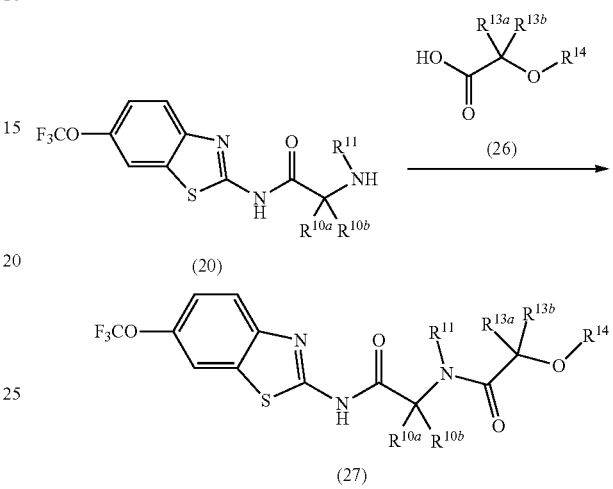

A compound of the formula (20) is reacted with a compound of (26), a known compound or a compound made by known methods, in the presence of a coupling agent such as O-(benzotriazol-1-yl)-N,N,N',N'-tetramethyluronium hexafluorophosphate, N,N'-dicyclohexylcarbodiimide, 1-ethyl-3-(3-dimethylaminopropyl) carbodiimide, 1-[Bis(dimethylamino)methylene]-1H-1,2,3-triazolo[4,5-b]pyridinium 3-oxid hexafluorophosphate, 1-hydroxy-7-azabenzotriazole and the like, optionally in the presence of a base such as triethylamine, diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (27).

Scheme 11

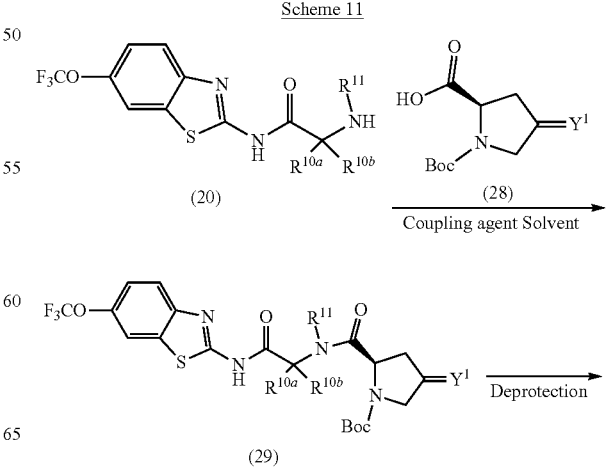

-continued

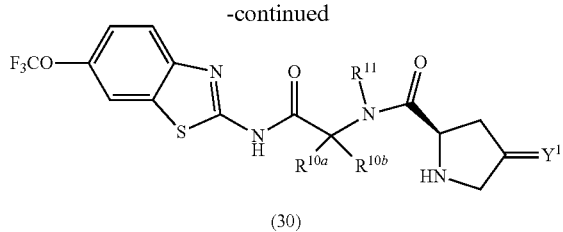

(30)

A compound of the formula (20) is reacted with a compound of (28), a known compound or a compound made by known methods, in the presence of a coupling agent such as O-(benzotriazol-1-yl)-N,N,N',N'-tetramethyluronium hexafluorophosphate, N,N'-dicyclohexylcarbodiimide, 1-ethyl-3-(3-dimethylaminopropyl) carbodiimide, 1-[Bis(dimethylamino)methylene]-1H-1,2,3-triazolo[4,5-b]pyridinium 3-oxid hexafluorophosphate, 1-hydroxy-7-azabenzotriazole and the like, optionally in the presence of a base such as triethylamine, diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (29). A compound of the formula (29) is reacted with an acid such as trifluoroacetic acid, hydrochloric acid, and the like in a solvent such as methylene chloride, 1,2-dichloroethane, tetrahydrofuran, 1,4-dioxane, and the like to provide a compound of the formula (30).

Scheme 12

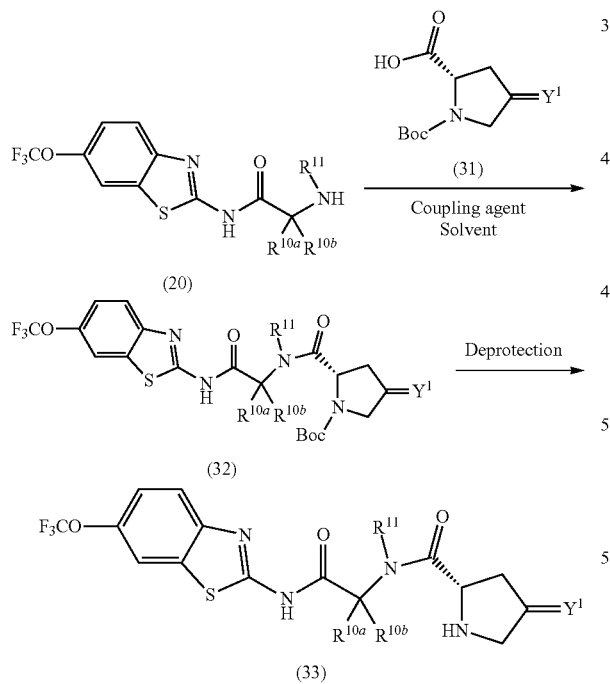

A compound of the formula (20) is reacted with a compound of (31), a known compound or a compound made by known methods, in the presence of a coupling agent such as O-(benzotriazol-1-yl)-N,N,N',N'-tetramethyluronium hexafluorophosphate, N,N'-dicyclohexylcarbodiimide, 1-ethyl-3-(3-dimethylaminopropyl) carbodiimide, 1-[Bis(dimethylamino)methylene]-1H-1,2,3-triazolo[4,5-b]pyridinium 3-oxid hexafluorophosphate, 1-hydroxy-7-azabenzotriazole and the like, optionally in the presence of a base such as triethylamine, diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (32). A compound of the formula (32) is reacted with an acid such as trifluoroacetic acid, hydrochloric acid, and the like in a solvent such as methylene chloride, 1,2-dichloroethane, tetrahydrofuran, 1,4-dioxane, and the like to provide a compound of the formula (33).

Scheme 13

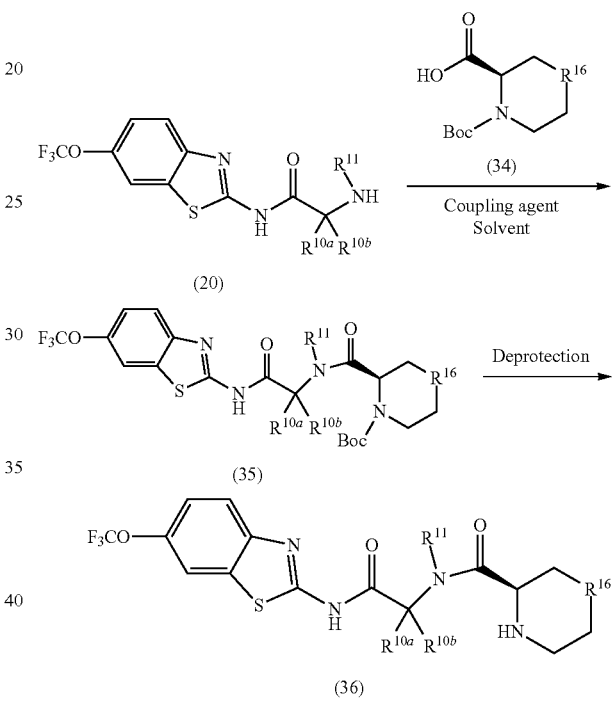

A compound of the formula (20) is reacted with a compound of (34), a known compound or a compound made by known methods, in the presence of a coupling agent such as O-(benzotriazol-1-yl)-N,N,N',N'-tetramethyluronium hexafluorophosphate, N,N'-dicyclohexylcarbodiimide, 1-ethyl-3-(3-dimethylaminopropyl) carbodiimide, 1-[Bis(dimethylamino)methylene]-1H-1,2,3-triazolo[4,5-b]pyridinium 3-oxid hexafluorophosphate, 1-hydroxy-7-azabenzotriazole and the like, optionally in the presence of a base such as triethylamine, diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (35). A compound of the formula (35) is reacted with an acid such as trifluoroacetic acid, hydrochloric acid, and the like in a solvent such as methylene chloride, 1,2-dichloroethane, tetrahydrofuran, 1,4-dioxane, and the like to provide a compound of the formula (36).

Scheme 14

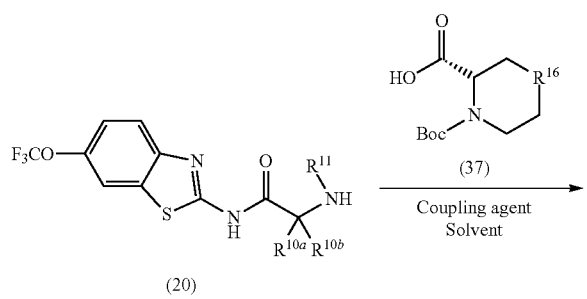

(20) + (37) →[Coupling agent, Solvent]

1-ethyl-3-(3-dimethylaminopropyl) carbodiimide, 1-[Bis(dimethylamino)methylene]-1H-1,2,3-triazolo[4,5-b]pyridinium 3-oxid hexafluorophosphate, 1-hydroxy-7-azabenzotriazole and the like, optionally in the presence of a base such as triethylamine, diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (38). A compound of the formula (38) is reacted with an acid such as trifluoroacetic acid, hydrochloric acid, and the like in a solvent such as methylene chloride, 1,2-dichloroethane, tetrahydrofuran, 1,4-dioxane, and the like to provide a compound of the formula (39).

Scheme 15

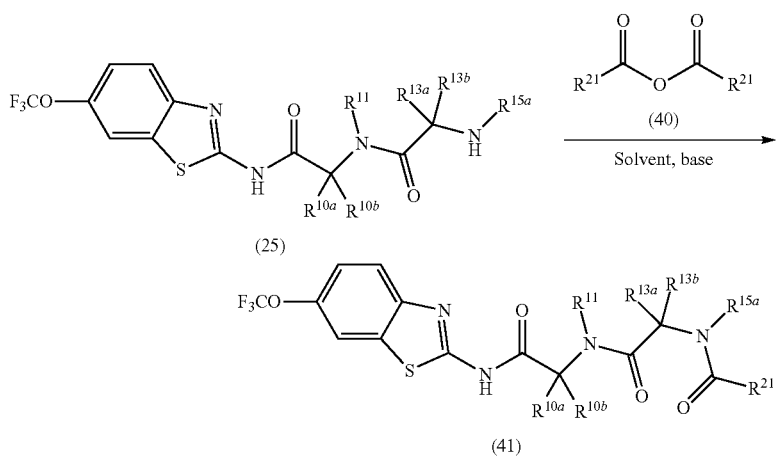

-continued

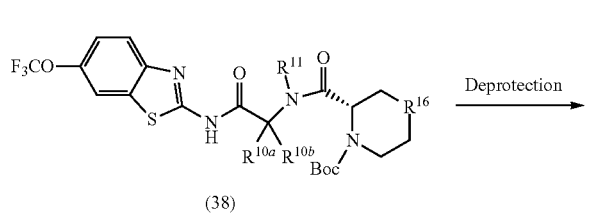

(38) →[Deprotection] (39)

A compound of the formula (20) is reacted with a compound of (37), a known compound or a compound made by known methods, in the presence of a coupling agent such as O-(benzotriazol-1-yl)-N,N,N',N'-tetramethyluronium hexafluorophosphate, N,N'-dicyclohexylcarbodiimide, A compound of the formula (25) is reacted with a compound of (40), a known compound or a compound made by known methods, in the presence of a base such as triethylamine, diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (41).

Scheme 16

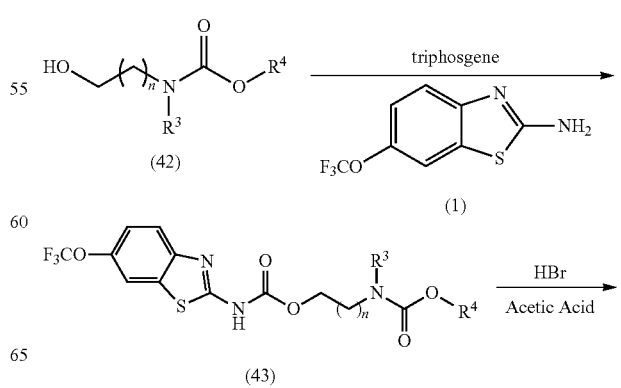

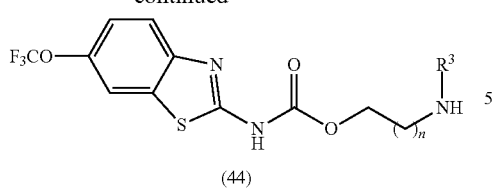

(44)

A compound of the formula (42), a known compound or a compounds prepared by known methods, is reacted with triphosgene in the presence of a solvent such as N,N-dimethylformamide, 1,4-dioxane, tetrahydrofuran, methylene chloride, chloroform, and the like. The resulting product is then reacted with a compound of the formula (1) in the presence of a base such as triethylamine, diisopropylethylamine, N-methylmorpholine and the like, in the presence of a solvent such as N, N-dimethylformamide, 1,4-dioxane, tetrahydrofuran, methylene chloride and the like, optionally with heating, optionally with microwave irradiation to provide a compound of the formula (43). A compound of the formula (44) is reacted with hydrogen bromide in the presence of acetic acid, optionally in the presence of a solvent such as N, N-dimethylformamide, 1,4-dioxane, tetrahydrofuran, methylene chloride and the like, optionally with heating, optionally with microwave irradiation to provide a compound of the formula (44).

Scheme 17

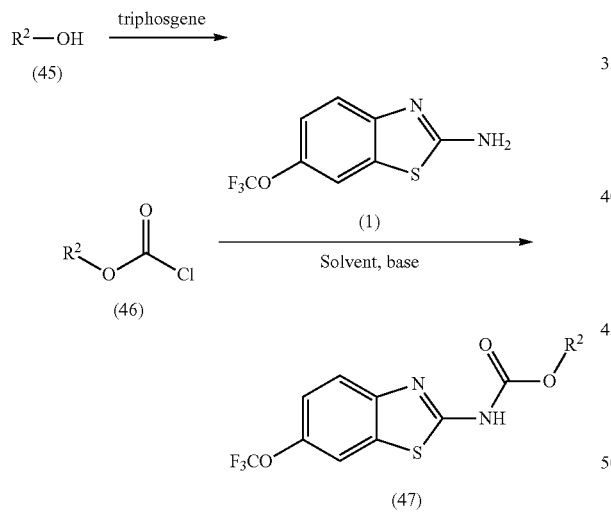

A compound of the formula (45), a known compound or a compounds prepared by known methods, is reacted with triphosgene in the presence of a solvent such as N,N-dimethylformamide, 1,4-dioxane, tetrahydrofuran, methylene chloride, chloroform, and the like to provide a compound of the formula (46). A compound of the formula (46) is reacted with a compound of the formula (I) in the presence of a base such as triethylamine, diisopropylethylamine, N-methylmorpholine, and the like, in the presence of a solvent such as N, N-dimethylformamide, 1,4-dioxane, tetrahydrofuran, methylene chloride and the like, optionally with heating, optionally with microwave irradiation to provide a compound of the formula (43).

Scheme 18

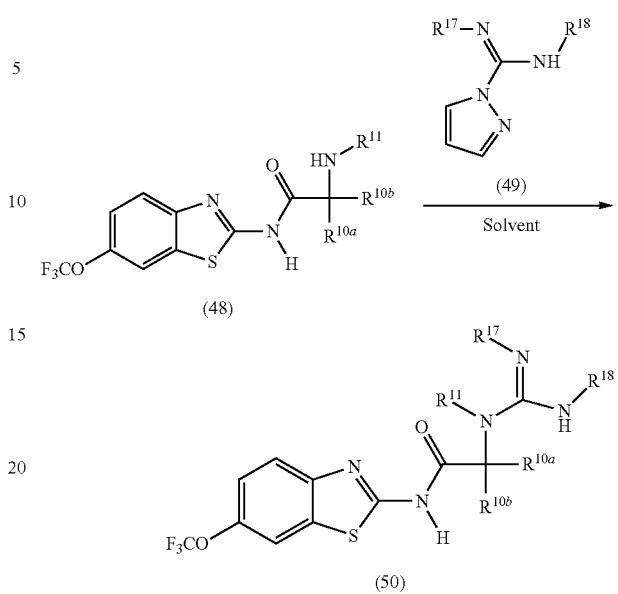

A compound of the formula (48), a known compound or a compounds prepared by known methods, is reacted with a compound of the formula (49), a known compound or a compounds prepared using known methods, in the presence of a solvent such as N, N-dimethylformamide, 1,4-dioxane, tetrahydrofuran, methylene chloride and the like, optionally with heating, optionally with microwave irradiation to provide a compound of the formula (50).

Scheme 19

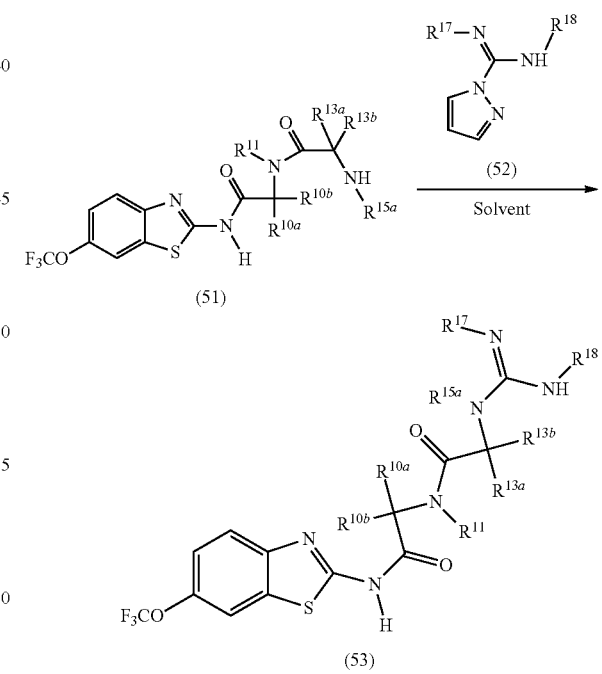

A compound of the formula (51), a known compound or a compounds prepared by known methods, is reacted with a compound of the formula (52), a known compound or a compounds prepared using known methods, in the presence of a solvent such as N, N-dimethylformamide, 1,4-dioxane, tetrahydrofuran, methylene chloride and the like, optionally with heating, optionally with microwave irradiation to provide a compound of the formula (53).

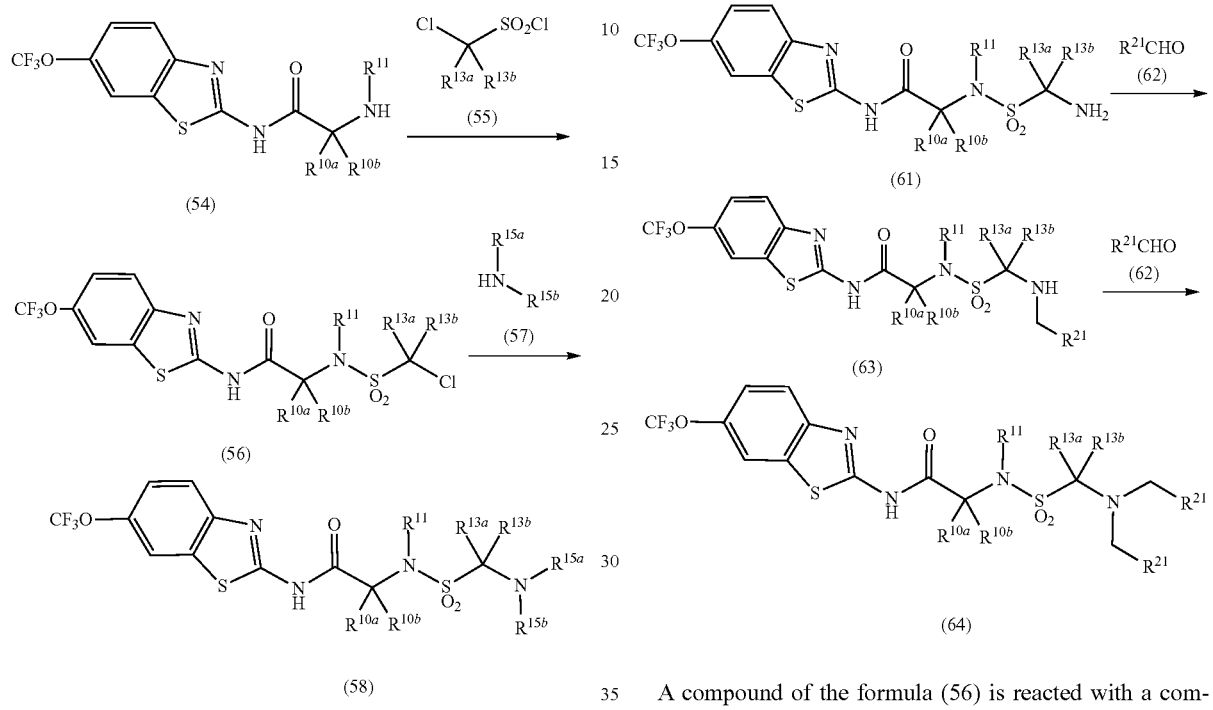

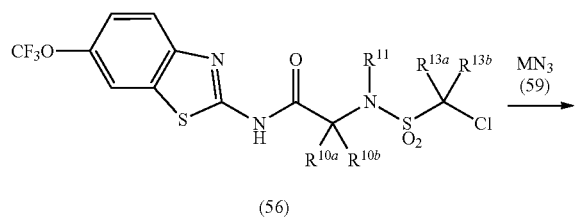

A compound of the formula (54), a known compound or a compounds prepared by known methods, is reacted with a compound of the formula (55), a known compound or a compounds prepared using known methods, in the presence of a base such as triethylamine, diisopropylethylamine, N-methylmorpholine and the like, in the presence of a solvent such as N, N-dimethylformamide, 1,4-dioxane, tetrahydrofuran, methylene chloride and the like, optionally with heating, optionally with microwave irradiation to provide a compound of the formula (56). A compound of the formula (56) is reacted with a compound of the formula (57), a known compound or a compounds prepared by known methods, in the presence of a solvent such as N, N-dimethylformamide, dimethylsulfoxide, 1,4-dioxane, tetrahydrofuran, methylene chloride and the like, optionally with heating, optionally with microwave irradiation to provide a compound of the formula (58).

A compound of the formula (56) is reacted with a compound of the formula (59), a known compound or a compounds prepared by known methods wherein M is a counter ion such as sodium, potassium, tetrabutyl ammonium, and the like, in the presence of a solvent such as N, N-dimethylformamide, dimethylsulfoxide, 1,4-dioxane, tetrahydrofuran, methylene chloride and the like, optionally with heating, optionally with microwave irradiation to provide a compound of the formula (60). A compound of the formula (60) is reacted with hydrogen in the presence of a catalyst such as palladium on carbon, palladium on barium sulfate, palladium (II) acetate, tetrakis(triphenylphosphine)palladium(0), dichlorobis (triphenylphosphine)palladium(II), palladium on carbon, bis(acetonitrile)dichloropalladium(II), and the like, in an organic solvent such as methanol, ethanol, ethyl acetate, tetrahydrofuran, 1,4-dioxane, dichloromethane, chloroform, 1,2-dichloroethane, N,N-dimethylformamide, and the like, to provide a compound of the formula (61). A compound of the formula (61) is reacted with a compound of the formula (62), a known compound or a compound prepared by known methods, in the presence of a hydride source such as sodium borohydride, sodium cyanoborohydride, sodium triacetoxy borohydride, and the like, optionally in the presence of an acid such as acetic acid, trifluoroacetic acid, formic acid, and the like, in an organic solvent such as methanol, ethanol, ethyl acetate, tetrahydrofuran, 1,4-dioxane, dichloromethane, chloroform, 1,2-dichloroethane, N,N-dimethylformamide, and the like, optionally with heating, optionally with microwave irradiation to provide a compound of the formula (63). A compound of the formula (63) is reacted with a compound of the formula (62), a known compound or a compound prepared by known methods, in the presence of a hydride source such as sodium borohydride, sodium cyanoborohydride, sodium triacetoxyborohydride, and the like, optionally in the presence of an acid such as acetic acid, trifluoroacetic acid, formic acid, and the like, in an organic solvent such as methanol, ethanol, ethyl acetate, tetrahydrofuran, 1,4-dioxane, dichloromethane, chloroform, 1,2-dichloroethane, N,N-dimethylformamide, and the like, optionally with heating, optionally with microwave irradiation to provide a compound of the formula (64).

Schemes 1-21 describe the preparation of compounds containing chiral centers. Those skilled in the art of organic synthesis will recognize that the chemistry described in schemes 1-21 can be applied to prepare the enantiomer of the compounds described employing starting material containing the opposite stereochemistry. In the case of compounds with multiple chiral centers those skilled in the art of organic synthesis will recognize that the chemistry described in schemes 1-21 can be employed to prepare compounds of the disclosure from starting materials containing the desired chirality and each chiral center.

EXAMPLES

Example 1-267 provides methods for preparing representative compounds of formula (I). The skilled practitioner will know how to substitute the appropriate reagents, starting materials and purification methods known to those skilled in the art, in order to prepare additional compounds of the present invention.

The following procedures were employed to purify and analyze compounds of the disclosure. Those skilled in the art would understand that alternate methods could be employed to analyze and purify the compounds of the disclosure.

Method A: LC/MS data were determined with a Waters Alliance 2695 HPLC/MS (Waters Symmetry C18, 4.6×75 mm, 3.5 µm) with a 2996 diode array detector from 210-400 nm; the solvent system is 5-95% acetonitrile in water (with 0.1% TFA) over nine minutes using a linear gradient, and retention times are in minutes. Mass spectrometry was performed on a Waters ZQ using electrospray in positive mode.

Method B: Preparative reversed phase HPLC was performed on a Waters Sunfire column (19×50 mm, C18, 5 µm) with a 10 min mobile phase gradient of 10% acetonitrile/water to 90% acetonitrile/water with 0.1% TFA as buffer using 214 and 254 nm as detection wavelengths. Injection and fraction collection were performed with a Gilson 215 liquid handling apparatus using Trilution LC software.

Method C: LC/MS data were determined on a Shimadzu LC 20AD instrument with a Phenomenex Luna C18 (3 µm) 50×3.0 mm column. Mobile phase consisted of water and acetonitrile with 0.1% formic acid buffer. Gradient was 10-90% acetonitrile over three minutes and held at 90% acetonitrile for two minutes. Detection was performed on diode array detector from 210-400 nm and retention times are in minutes. Mass spectra were determined on an Applied Biosystems MDS Sciex API 2000 instrument using electrospray ionization.

Example 1: Synthesis of 2-amino-N-(6-(trifluoromethoxy)benzo[d]thiazol-2-yl)acetamide

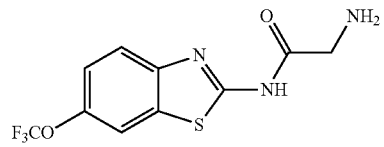 [SMILES: NCC(=O)Nc1nc2ccc(OC(F)(F)F)cc2s1]

To a solution of 2-amino-6-(trifluoromethoxy)benzimidazole (0.50 g, 2.1 mmol), N-(t-butyloxycarbonyl) glycine (0.56 g, 3.2 mmol) and N,N-diisopropylethylamine (0.41 g, 3.2 mmol, 0.57 ml) in dimethylformamide (7 ml) was added 1-[Bis(dimethylamino)methylene]-1H-1,2,3-triazolo[4,5-b]pyridinium 3-oxid hexafluorophosphate (HATU, 1.2 g, 3.2 mmol) and the mixture stirred at 20° C. for 18 hours. Ethyl acetate (100 ml) was added and the mixture was washed with water (2×75 ml), 1N HCl (75 ml), water (75 ml), 1M sodium carbonate solution (75 ml) and brine. The organic layer was dried over sodium sulfate and evaporated. The residue was chromatographed on silica gel eluted with a gradient of ethyl acetate in hexanes (50% to 75%) to leave the product as a white foamy solid (0.78 g, 95%). LC/MS method A: $R_t$=5.92 min., $(M+H)^+$=392. The product was dissolved in 4N HCl/1,4-dioxane and stirred for 2 h. The solvents were evaporated in an HCl compatible Genevac evaporator to leave a white solid mono HCl product (0.69 g, 100%, 95% overall yield). LC/MS method A: $R_t$=3.53 min., $(M+H)^+$=292.

Example 2: Synthesis of 2-(Methylamino)-N-(6-(trifluoromethoxy)benzo[d]thiazol-2-yl) acetamide Hydrochloride

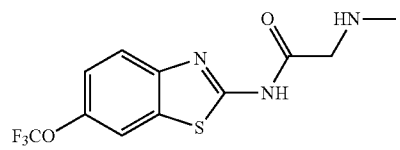

2-(Methylamino)-N-(6-(trifluoromethoxy)benzo[d]thiazol-2-yl) acetamide hydrochloride was prepared according to the procedure of example 1 from 2-amino-6-(trifluoromethoxy) benzimidazole (0.50 g, 2.1 mmol) and N-(t-butyloxycarbonyl)sarcosine (0.60 g, 3.2 mmol). Yield for intermediate=0.96 g (100%). LC/MS method A: $R_t$=5.92 min., $(M+H)^+$=406. Yield for final product (0.82 g, 100%, 100% overall). LC/MS method A: $R_t$=3.60 min., $(M+H)^+$=306.

Example 3: Synthesis of 2-(Ethylamino)-N-(6-(trifluoromethoxy)benzo[d]thiazol-2-yl)acetamide Hydrochloride

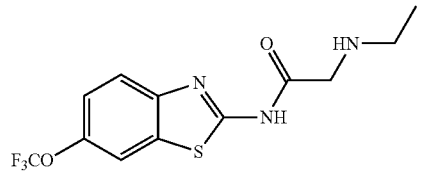 [SMILES: CCNCC(=O)Nc1nc2ccc(OC(F)(F)F)cc2s1]

2-(Ethylamino)-N-(6-(trifluoromethoxy)benzo[d]thiazol-2-yl)acetamide hydrochloride was prepared according to the procedure of example 1 from 2-amino-6-(trifluoromethoxy) benzimidazole (117 mg, 0.5 mmol) and N-t-butyloxycarbonyl-2-(ethylamino)acetic acid (122 mg, 0.6 mmol). Yield for Boc protected intermediate 182 mg (87%). LC/MS method A: $R_f$=6.20 min., $(M+H)^+$=420. Yield for final product (142 mg, 87% overall). LC/MS method A: $R_f$=3.67 min., $(M+H)^+$=320.

Example 4: Synthesis of 2-(Isopropylamino)-N-(6-(trifluoromethoxy)benzo[d]thiazol-2-yl)acetamide Hydrochloride

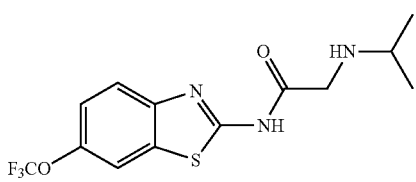 [SMILES: CC(C)NCC(=O)Nc1nc2ccc(OC(F)(F)F)cc2s1]

2-(Isopropylamino)-N-(6-(trifluoromethoxy)benzo[d]thiazol-2-yl)acetamide hydrochloride was prepared according to the procedure of example 1 from 2-amino-6-(trifluoromethoxy) benzimidazole (117 mg, 0.5 mmol) and N-t-butyloxycarbonyl-2-(isopropylamino)acetic acid (131 mg, 0.6 mmol). Yield for Boc protected intermediate 146 mg (67%). LC/MS method A: $R_f$=6.39 min., $(M+H)^+$=434. Yield for final product (110 mg, 67% overall). LC/MS method A: $R_f$=3.76 min., $(M+H)^+$=334.

Example 5: Synthesis of (S)—N-(6-(trifluoromethoxy)benzo[d]thiazol-2-yl)pyrrolidine-2-carboxamide

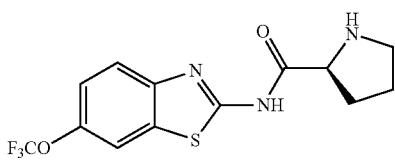 [SMILES: O=C(Nc1nc2ccc(OC(F)(F)F)cc2s1)[C@@H]1CCCN1]

To a solution of 2-amino-6-(trifluoromethoxy)benzimidazole (50 mg, 0.21 mmol), N-t-butyloxycarbonyl-L-proline (69 mg, 0.32 mmol), 1-Hydroxy-7-azabenzotriazole (42 mg, 0.32 mmol) and N,N-diisopropylethylamine (41 mg, 0.32 mmol, 57 μl) in N,N-dimethyl formamide (0.35 ml) was added 2-chloro-1-methylpyridinium iodide (82 mg, 0.32 mmol) and the yellow solution stirred for 72 hours. Water (0.25 ml) and methanol (1 ml) were added and the mixture was purified by reverse phase HPLC (method B). The product fractions were combined and the solvents were removed on a Genevac evaporator. This left 59 mg (59%) of foamy solid. LC/MS method A: $R_f$=6.21 min., $(M+H)^+$=432. The product was dissolved in 4N HCl/1,4-dioxane and stirred for 2 h. The solvents were evaporated in an HCl compatible Genevac evaporator to leave a white solid mono HCl product (45 mg, 100%, 59% overall yield). LC/MS method A: $R_f$=3.72 min., $(M+H)^+$=332.

Example 6: Synthesis of (R)—N-(6-(trifluoromethoxy)benzo[d]thiazol-2-yl)pyrrolidine-2-carboxamide

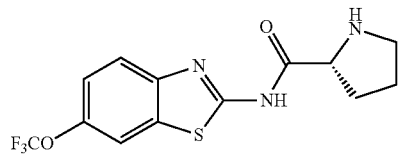 [SMILES: O=C(Nc1nc2ccc(OC(F)(F)F)cc2s1)[C@H]1CCCN1]

(R)—N-(6-(trifluoromethoxy)benzo[d]thiazol-2-yl)pyrrolidine-2-carboxamide was prepared according to the procedure of example 5 from 2-amino-6-(trifluoromethoxy) benzimidazole (50 mg, 0.21 mmol) and N-t-butyloxycarbonyl-D-proline (69 mg, 0.32 mmol). Yield for Boc protected intermediate 64 mg (71%). LC/MS method A: $R_f$=6.21 min., $(M+H)^+$=432. Yield for final product (46 mg, 60% overall). LC/MS method A: $R_f$=3.72 min., $(M+H)^+$=332.

Example 7: Synthesis of (R)-2-amino-3-phenyl-N-(6-(trifluoromethoxy)benzo[d] thiazol-2-yl) propanamide

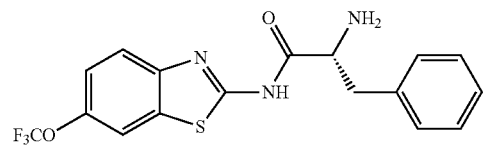 [SMILES: N[C@H](Cc1ccccc1)C(=O)Nc1nc2ccc(OC(F)(F)F)cc2s1]

(R)-2-amino-3-phenyl-N-(6-(trifluoromethoxy)benzo[d] thiazol-2-yl) propanamide was prepared according to the procedure of example 5 from 2-amino-6-(trifluoro methoxy) benzimidazole (100 mg, 0.42 mmol) and N-t-butyloxycarbonyl-D-phenylalanine (170 mg, 0.64 mmol). Yield for Boc protected intermediate 91 mg (44%). LC/MS method A: $R_f$=6.67 min., $(M+H)^+$=482. Yield for final product (70 mg, 89%, 39% overall). LC/MS method A: $R_f$=3.99 min., $(M+H)^+$=382.

Example 8: Synthesis of (S)-2-amino-3-phenyl-N-(6-(trifluoromethoxy)benzo[d] thiazol-2-yl) propanamide Hydrochloride

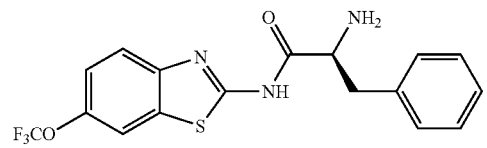 [SMILES: N[C@@H](Cc1ccccc1)C(=O)Nc1nc2ccc(OC(F)(F)F)cc2s1]

(S)-2-amino-3-phenyl-N-(6-(trifluoromethoxy)benzo[d] thiazol-2-yl) propanamide hydrochloride was prepared according to the procedure of example 5 from 2-amino-6-(trifluoro methoxy)benzimidazole (100 mg, 0.42 mmol) and N-t-butyloxycarbonyl-L-phenylalanine (170 mg, 0.64 mmol). Yield for Boc protected intermediate 70 mg (34%). LC/MS method A: $R_f$=6.66 min., $(M+H)^+$=482. Yield for final product (50 mg, 82%, 28% overall). LC/MS method A: $R_f$=3.99 min., $(M+H)^+$=382.

Example 9: Synthesis of (S)—N-(6-(trifluoromethoxy)benzo[d]thiazol-2-yl)azetidine-2-carboxamide

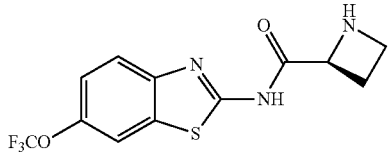 [SMILES: O=C(Nc1nc2ccc(OC(F)(F)F)cc2s1)[C@@H]1CCN1]

(S)—N-(6-(trifluoromethoxy)benzo[d]thiazol-2-yl)azetidine-2-carboxamide was prepared according to the procedure of example 5 from 2-amino-6-(trifluoromethoxy) benzimidazole (0.50 g, 2.1 mmol) and N-t-butyloxycarbonyl-L-azetidine-2-carboxylic acid (0.64 g, 3.2 mmol). Yield for Boc protected intermediate 0.62 g (71%). LC/MS method A: $R_t$=6.13 min., purity >95%, (M+H)$^+$=418. Yield for final product (0.52 g, 100%, 71% overall). LC/MS method A: $R_t$=3.66 min., purity >90%, (M+H)$^+$=318.

Example 10: Synthesis of (R)—N-(6-(trifluoromethoxy)benzo[d]thiazol-2-yl)azetidine-2-carboxamide

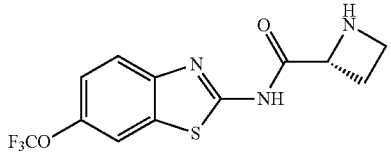 [SMILES: O=C(Nc1nc2ccc(OC(F)(F)F)cc2s1)[C@H]1CCN1]

(R)—N-(6-(trifluoromethoxy)benzo[d]thiazol-2-yl)azetidine-2-carboxamide was prepared according to the procedure of example 5 from 2-amino-6-(trifluoromethoxy) benzimidazole (0.50 g, 2.1 mmol) and N-t-butyloxycarbonyl-D-azetidine-2-carboxylic acid (0.64 g, 3.2 mmol). Yield for Boc protected intermediate 0.60 g (69%). LC/MS method A: $R_t$=6.13 min., (M+H)$^+$=418. Yield for final product (0.51 g, 100%, 69% overall). LC/MS method A: $R_t$=3.66 min., (M+H)$^+$=318.

Example 11: Synthesis of (R)—N-(6-(trifluoromethoxy)benzo[d]thiazol-2-yl)piperidine-2-carboxamide

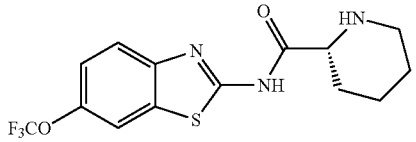 [SMILES: O=C(Nc1nc2ccc(OC(F)(F)F)cc2s1)[C@H]1CCCCN1]

(R)—N-(6-(trifluoromethoxy)benzo[d]thiazol-2-yl)piperidine-2-carboxamide was prepared according to the procedure of example 5 from 2-amino-6-(trifluoromethoxy) benzimidazole (234 mg, 1.0 mmol) and (R)-1-(tert-butoxycarbonyl)piperidine-2-carboxylic acid (300 mg, 1.3 mmol). Yield for Boc protected intermediate 78 mg (17%). LC/MS method A: $R_t$=6.72 min., (M+H)$^+$=446. Yield for final product (61 mg, 100%, 17% overall). LC/MS method A: $R_t$=3.78 min., (M+H)$^+$=346.

Example 12: Synthesis of (S)—N-(6-(trifluoromethoxy)benzo[d]thiazol-2-yl)piperidine-2-carboxamide

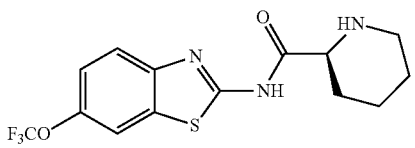 [SMILES: O=C(Nc1nc2ccc(OC(F)(F)F)cc2s1)[C@@H]1CCCCN1]

(S)—N-(6-(trifluoromethoxy)benzo[d]thiazol-2-yl)piperidine-2-carboxamide was prepared according to the procedure of example 5 from 2-amino-6-(trifluoromethoxy) benzimidazole (234 mg, 1.0 mmol) and (S)-1-(tert-butoxycarbonyl)piperidine-2-carboxylic acid (300 mg, 1.3 mmol). Yield for Boc protected intermediate 78 mg (17%). LC/MS method A: $R_t$=6.72 min. (M+H)$^+$=446. Yield for final product (61 mg, 100%, 17% overall). LC/MS method A: $R_t$=3.78 min., (M+H)$^+$=346.

Example 13: Synthesis of 2-amino-2-methyl-N-(6-(trifluoromethoxy)benzo[d]thiazol-2-yl)propanamide

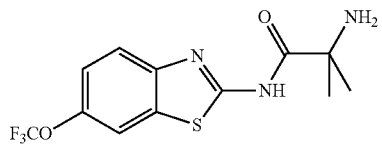 [SMILES: CC(C)(N)C(=O)Nc1nc2ccc(OC(F)(F)F)cc2s1]

2-amino-2-methyl-N-(6-(trifluoromethoxy)benzo[d]thiazol-2-yl)propanamide was prepared according to the procedure of example 1 from 2-amino-6-(trifluoromethoxy) benzimidazole (234 mg, 1.0 mmol) and N-t-butyloxycarbonyl-2-amino-2-methylpropanamide (305 mg, 1.5 mmol). Yield for Boc protected intermediate 280 mg (67%). LC/MS method A: $R_t$=6.22 min., (M+H)$^+$=420. Yield for final product (205 mg, 100%, 67% overall). LC/MS method A: $R_t$=3.68 min., (M+H)$^+$=320.

Example 14: Synthesis of 1-amino-N-(6-(trifluoromethoxy)benzo[d]thiazol-2-yl)cyclopropanecarboxamide

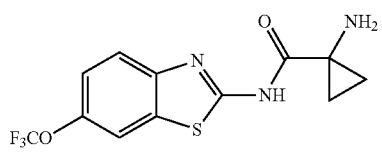 [SMILES: NC1(C(=O)Nc2nc3ccc(OC(F)(F)F)cc3s2)CC1]

1-amino-N-(6-(trifluoromethoxy)benzo[d]thiazol-2-yl)cyclopropanecarboxamide was prepared according to the procedure of example 1 from 2-amino-6-(trifluoromethoxy) benzimidazole (234 mg, 1.0 mmol) and N-t-butyloxycarbonyl-1-aminocyclopropanecarboxylic acid (261 mg, 1.3 mmol). Yield for Boc protected intermediate 281 mg (67%).

LC/MS method A: $R_t$=6.08 min., $(M+H)^+$=418. Yield for final product (227 mg, 100%, 67% overall). LC/MS method A: $R_t$=3.65 min., $(M+H)^+$=318.

Example 15: Synthesis of 1-amino-N-(6-(trifluoromethoxy)benzo[d]thiazol-2-yl)cyclobutanecarboxamide

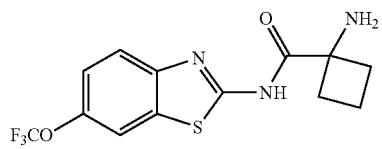 [SMILES: NC1(C(=O)Nc2nc3ccc(OC(F)(F)F)cc3s2)CCC1]

1-amino-N-(6-(trifluoromethoxy)benzo [d]thiazol-2-yl) cyclobutanecarboxamide was prepared according to the procedure of example 1 from 2-amino-6-(trifluoromethoxy) benzimidazole (234 mg, 1.0 mmol) and N-t-butyloxycarbonyl-1-aminocyclobutanecarboxylic acid (280 mg, 1.3 mmol). Yield for Boc protected intermediate 281 mg (65%). LC/MS method A: $R_t$=6.34 min., $(M+H)^+$=432. Yield for final product (248 mg, 100%, 65% overall). LC/MS method A: $R_t$=3.75 min., $(M+H)^+$=332.

Example 16: Synthesis of 2-(methylamino)-N-(2-oxo-2-((6-(trifluoromethoxy) benzo[d]thiazol-2-yl) amino)ethyl)acetamide

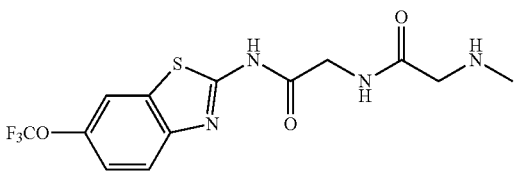

To a solution of 2-amino-N-(6-(trifluoromethoxy) benzo [d]thiazol-2-yl)acetamide hydrochloride from example 1 above (0.40 g, 1.2 mmol), N-(t-butyloxycarbonyl)sarcosine (0.28 g, 1.5 mmol) and N,N-diisopropylethylamine (0.39 g, 3.0 mmol, 0.54 ml) in N,N-dimethylformamide (10 ml) was added 1-[Bis(dimethylamino)methylene]-1H-1,2,3-triazolo[4,5-b]pyridinium 3-oxid hexafluorophosphate (HATU, 0.57 g, 1.5 mmol) and the reaction mixture stirred for 18 hours. Ethyl acetate (100 ml) was added and the mixture was washed with water (2×50 ml), 1N HCl (50 ml), saturated sodium bicarbonate solution (50 ml) and brine (25 ml). The organic solution was dried over sodium sulfate and evaporated to a light yellow foamy solid which was dissolved in 4N HCl in 1,4-dioxane. The mixture stirred 2 hours and the white precipitate was filtered on a glass frit (medium), washed with 1,4-dioxane and ether and dried under vacuum to leave 344 mg (76%) of white crystalline product. LC/MS method A: $R_t$=3.62 min., $(M+H)^+$=363.

Example 17: Synthesis of (S)—N-(2-oxo-2-((6-(trifluoromethoxy)benzo[d]thiazol-2-yl)amino)ethyl) pyrrolidine-2-carboxamide

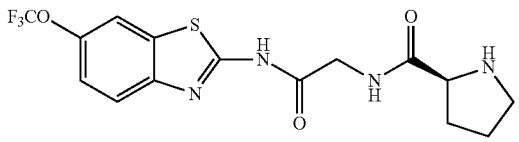 [SMILES: O=C(CNC(=O)[C@@H]1CCCN1)Nc1nc2ccc(OC(F)(F)F)cc2s1]

(S)—N-(2-oxo-2-((6-(trifluoromethoxy)benzo[d]thiazol-2-yl)amino)ethyl)pyrrolidine-2-carboxamide was prepared according to the procedures of example 16 from 2-amino-N-(6-(trifluoromethoxy)benzo[d]thiazol-2-yl)acetamide hydrochloride (60 mg, 0.25 mmol) and N-(t-butyloxycarbonyl)proline (89 mg, 0.32 mmol). Yield for Boc protected intermediate 62 mg (51%). LC/MS method A: $R_t$=6.34 min., $(M+H)^+$=432. Yield for final product (64 mg, 100%, 51% overall). LC/MS method A: $R_t$=3.74 min., $(M+H)^+$=389.

Example 18: Synthesis of (R)-2-amino-N-(2-oxo-2-((6-(trifluoromethoxy)benzo [d]thiazol-2-yl)amino) ethyl)propanamide

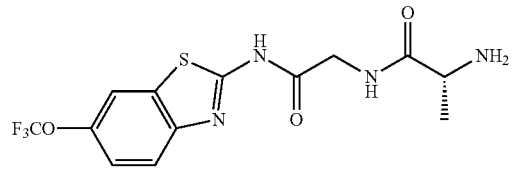 [SMILES: C[C@@H](N)C(=O)NCC(=O)Nc1nc2ccc(OC(F)(F)F)cc2s1]

A solution of 2-amino-N-(6-(trifluoromethoxy)benzo[d] thiazol-2-yl)acetamide hydrochloride from example 1 above (20 mg, 61 μmol), N-(t-butyloxycarbonyl)-D-alanine (15 mg, 79 μmol) and N,N-Diisopropylethylamine (20 mg, 0.16 mmol, 28 μl) in N,N-dimethylformamide (0.5 ml) was treated with 1-[Bis(dimethylamino)methylene]-1H-1,2,3-triazolo[4,5-b]pyridinium 3-oxid hexafluorophosphate (30 mg, 79 μmol) and shaken for 18 hours. The product was isolated following direct injection reverse phase HPLC (method B) and evaporation of the product fractions on a Genevac evaporator. The product weighed 23 mg (82%). The compound was dissolved in 4N HCl/1,4-dioxane, shaken 2 hours then evaporated on a Genevac evaporator to leave the product as a white solid (20 mg, 82%) mono HCl salt. LC/MS method A: $R_t$=3.59 min., $(M+H)^+$=363. The following compounds were prepared using the same method and scale as example 18.

Example 19: Synthesis of 3-amino-N-(2-oxo-2-((6-(trifluoromethoxy)benzo[d] thiazol-2-yl)amino) ethyl)propanamide

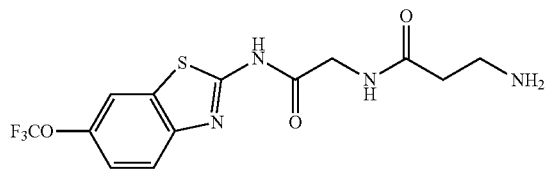 [SMILES: NCCC(=O)NCC(=O)Nc1nc2ccc(OC(F)(F)F)cc2s1]

3-amino-N-(2-oxo-2-((6-(trifluoromethoxy)benzo[d]thi-azol-2-yl)amino)ethyl)propanamide was prepared according to the procedure of example 18 from 2-amino-N-(6-(trifluoromethoxy)benzo[d] thiazol-2-yl)acetamide hydrochloride from example 1 above (20 mg, 61 µmol) and N-(t-butyloxy-carbonyl)-β-alanine (15 mg, 79 µmol). Yield=5.5 mg (23%). LC/MS method A: $R_t$=3.57 min., $(M+H)^+$=363.

Example 20: Synthesis of 1-amino-N-(2-oxo-2-((6-(trifluoromethoxy)benzo[d] thiazol-2-yl)amino)ethyl)cyclopropane-1-carboxamide

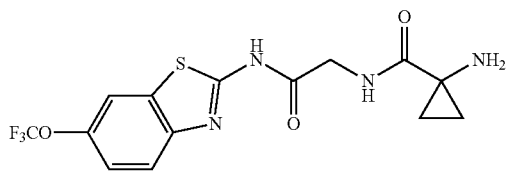 [SMILES: NC1(C(=O)NCC(=O)Nc2nc3ccc(OC(F)(F)F)cc3s2)CC1]

1-amino-N-(2-oxo-2-((6-(trifluoromethoxy)benzo [d]thi-azol-2-yl)amino)ethyl)cyclo propane-1-carboxamide was prepared according to the procedure of example 18 from 2-amino-N-(6-(trifluoromethoxy)benzo[d] thiazol-2-yl)ac-etamide hydrochloride from example 1 above (20 mg, 61 µmol) and N-1-(t-butyloxycarbonyl)aminocyclopropane-1-carboxylic acid (16 mg, 79 µmol). Yield=20 mg (80%). LC/MS method A: $R_t$=3.60 min., $(M+H)^+$=375.

Example 21: Synthesis of (S)—N-(2-oxo-2-((6-(trifluoromethoxy)benzo[d]thiazol-2-yl)amino)ethyl)azetidine-2-carboxamide

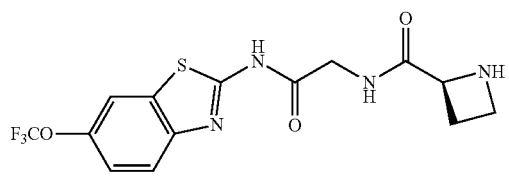 [SMILES: O=C(CNC(=O)[C@@H]1CCN1)Nc1nc2ccc(OC(F)(F)F)cc2s1]

(S)—N-(2-oxo-2-((6-(trifluoromethoxy)benzo[d]thiazol-2-yl)amino)ethyl)azetidine-2-carboxamide was prepared according to the procedure of example 18 from 2-amino-N-(6-(trifluoromethoxy)benzo[d] thiazol-2-yl)acetamide hydrochloride from example 1 above (20 mg, 61 µmol) and (S)—N-(t-butyloxycarbonyl)azetidine-2-carboxylic acid (16 mg, 79 µmol). Yield=20 mg (80%). LC/MS method A: $R_t$=3.62 min., $(M+H)^+$=375.

Example 22: Synthesis of 2-amino-2-methyl-N-(2-oxo-2-((6-(trifluoromethoxy) benzo[d]thiazol-2-yl)amino)ethyl)propanamide

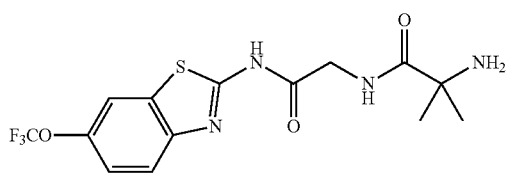 [SMILES: CC(C)(N)C(=O)NCC(=O)Nc1nc2ccc(OC(F)(F)F)cc2s1]

2-amino-2-methyl-N-(2-oxo-2-((6-(trifluoromethoxy)benzo [d]thiazol-2-yl)amino)ethyl) propanamide was prepared according to the procedure of example 18 from 2-amino-N-(6-(trifluoromethoxy)benzo[d] thiazol-2-yl)acetamide hydrochloride from example 1 above (20 mg, 6111 mol) and N-(t-butyloxycarbonyl)aminoisobutyric acid (16 mg, 79 µmol). Yield=20 mg (80%). LC/MS method A: $R_t$=3.63 min., $(M+H)^+$=377.

Example 23: Synthesis of (S)-2-(methylamino)-N-(2-oxo-2-((6-(trifluoromethoxy) benzo[d]thiazol-2-yl)amino)ethyl)propanamide

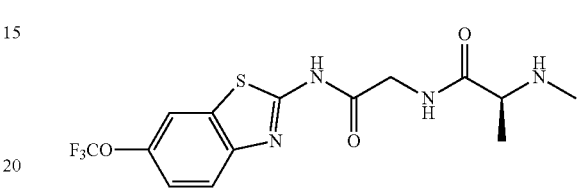

(S)-2-(methylamino)-N-(2-oxo-2-((6-(trifluoromethoxy)benzo [d]thiazol-2-yl)amino)ethyl) propanamide was prepared according to the procedure of example 18 from 2-amino-N-(6-(trifluoromethoxy)benzo[d] thiazol-2-yl)ac-etamide hydrochloride from example 1 above (20 mg, 61 µmol) and N-(t-butyloxycarbonyl)-N-methyl-L-alanine (16 mg, 79 µmol). Yield=20 mg (80%). LC/MS method A: $R_t$=3.64 min., $(M+H)^+$=377.

Example 24: Synthesis of (R)-2-(methylamino)-N-(2-oxo-2-((6-(trifluoromethoxy) benzo[d] thiazol-2-yl)amino)ethyl)propanamide

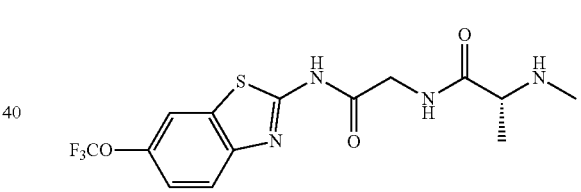

(R)-2-(methylamino)-N-(2-oxo-2-((6-(trifluoromethoxy)benzo[d]thiazol-2-yl)amino)ethyl) propanamide was prepared according to the procedure of example 18 from 2-amino-N-(6-(trifluoromethoxy)benzo[d] thiazol-2-yl)ac-etamide hydrochloride from example 1 above (20 mg, 61 µmol) and N-(t-butyloxycarbonyl)-N-methyl-D-alanine (16 mg, 79 µmol). Yield=18 mg (72%). LC/MS method A: $R_t$=3.64 min., $(M+H)^+$=377.

Example 25: Synthesis of (R)-2-amino-3-hydroxy-N-(2-oxo-2-((6-(trifluoromethoxy) benzo[d] thiazol-2-yl)amino)ethyl)propanamide

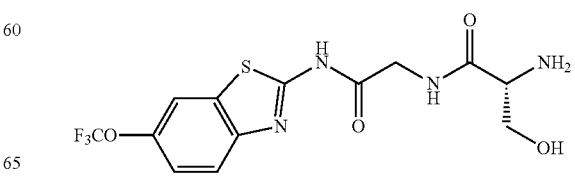

(R)-2-amino-3-hydroxy-N-(2-oxo-2-((6-(trifluoromethoxy)benzo[d]thiazol-2-yl)amino) ethyl)propanamide was prepared according to the procedure of example 18 from 2-amino-N-(6-(trifluoromethoxy)benzo[d] thiazol-2-yl)acetamide hydrochloride from example 1 above (20 mg, 61 µmol) and N-(t-butyloxycarbonyl)-D-serine (16 mg, 79 µmol). Yield=16 mg (63%). LC/MS method A: $R_t$=3.50 min., (M+H)$^+$=379.

Example 26: Synthesis of (R)-2-amino-N-(2-oxo-2-((6-(trifluoromethoxy)benzo[d] thiazol-2-yl)amino) ethyl)pent-4-ynamide

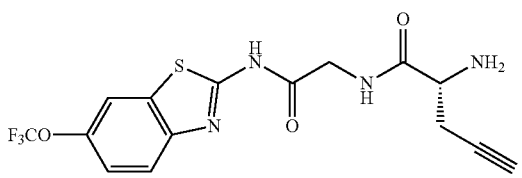 [SMILES: C#CC[C@@H](N)C(=O)NCC(=O)Nc1nc2ccc(OC(F)(F)F)cc2s1]

(R)-2-amino-N-(2-oxo-2-((6-(trifluoromethoxy) benzo[d]thiazol-2-yl)amino)ethyl)pent-4-ynamide was prepared according to the procedure of example 18 from 2-amino-N-(6-(trifluoromethoxy)benzo[d] thiazol-2-yl)acetamide hydrochloride from example 1 above (20 mg, 61 µmol) and N-(t-butyloxycarbonyl)-(R)-2-amino-4-pentynyl carboxylic acid (17 mg, 79 µmol). Yield=22 mg (85%). LC/MS method A: $R_t$=3.71 min., (M+H)$^+$=387.

Example 27: Synthesis of (S)-2-amino-N-(2-oxo-2-((6-(trifluoromethoxy) benzo[d]thiazol-2-yl)amino) ethyl)pent-4-ynamide

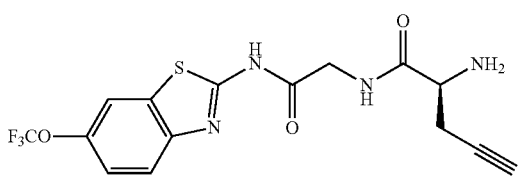 [SMILES: C#CC[C@H](N)C(=O)NCC(=O)Nc1nc2ccc(OC(F)(F)F)cc2s1]

(S)-2-amino-N-(2-oxo-2-((6-(trifluoromethoxy) benzo[d] thiazol-2-yl)amino)ethyl)pent-4-ynamide was prepared according to the procedure of example 18 from 2-amino-N-(6-(trifluoromethoxy)benzo[d] thiazol-2-yl)acetamide hydrochloride from example 1 above (20 mg, 61 µmol) and N-(t-butyloxycarbonyl)-(S)-2-amino-4-pentynyl carboxylic acid (17 mg, 79 µmol). Yield=22 mg (85%). LC/MS method A: $R_t$=3.71 min., (M+H)$^+$=387.

Example 28: Synthesis of (R)—N-(2-oxo-2-((6-(trifluoromethoxy)benzo[d] thiazol-2-yl)amino) ethyl)pyrrolidine-2-carboxamide

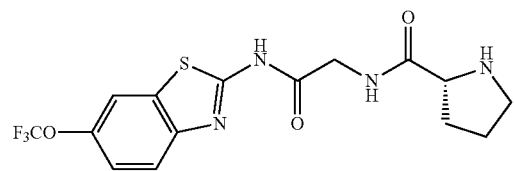 [SMILES: O=C(CNC(=O)[C@H]1CCCN1)Nc1nc2ccc(OC(F)(F)F)cc2s1]

(R)—N-(2-oxo-2-((6-(trifluoromethoxy)benzo[d] thiazol-2-yl)amino)ethyl)pyrrolidine-2-carboxamide was prepared according to the procedure of example 18 from 2-amino-N-(6-(trifluoromethoxy)benzo[d] thiazol-2-yl)acetamide hydrochloride from example 1 above (20 mg, 61 µmol) and N-(t-butyloxycarbonyl)-D-proline (17 mg, 79 Yield=21 mg (81%). LC/MS method A: $R_t$=3.70 min., (M+H)$^+$=389.

Example 29: Synthesis of 1-amino-N-(2-oxo-2-((6-(trifluoromethoxy)benzo [d]thiazol-2-yl)amino) ethyl)cyclobutane-1-carboxamide

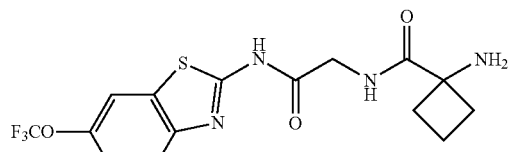

1-amino-N-(2-oxo-2-((6-(trifluoromethoxy)benzo [d]thiazol-2-yl)amino)ethyl)cyclobutane-1-carboxamide was prepared according to the procedure of example 18 from 2-amino-N-(6-(trifluoromethoxy)benzo[d] thiazol-2-yl)acetamide hydrochloride from example 1 above (20 mg, 61 µmol) and 1-(N-(t-butyloxycarbonyl)amino) cyclobutanecarboxylic acid (17 mg, 79 µmol). Yield=1.5 mg (5.8%). LC/MS method A: $R_t$=3.69 min., (M+H)$^+$=389.

Example 30: Synthesis of (S)-2-amino-N-(2-oxo-2-((6-(trifluoromethoxy) benzo[d]thiazol-2-yl)amino) ethyl)pentanamide

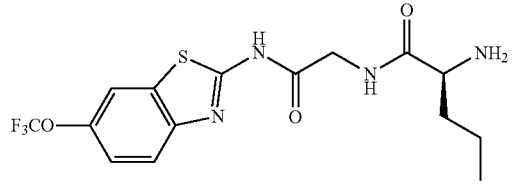 [SMILES: CCC[C@H](N)C(=O)NCC(=O)Nc1nc2ccc(OC(F)(F)F)cc2s1]

(S)-2-amino-N-(2-oxo-2-((6-(trifluoromethoxy) benzo[d] thiazol-2-yl)amino)ethyl) pentanamide was prepared according to the procedure of example 18 from 2-amino-N-(6-(trifluoromethoxy)benzo[d] thiazol-2-yl)acetamide hydrochloride from example 1 above (20 mg, 61 µmol) and (S)-2-(N-(t-butyloxycarbonyl)amino)pentanoic acid (17 mg, 79 µmol). Yield=19 mg (73%). LC/MS method A: $R_t$=3.88 min., (M+H)$^+$=391.

Example 31: Synthesis of (R)-2-amino-3-methyl-N-(2-oxo-2-((6-(trifluoro methoxy)benzo[d]thiazol-2-yl)amino)ethyl)butanamide

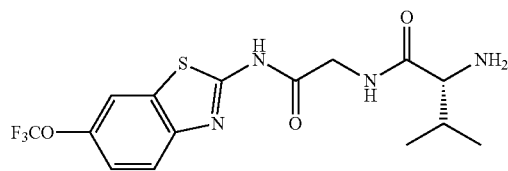 [SMILES: CC(C)[C@@H](N)C(=O)NCC(=O)Nc1nc2ccc(OC(F)(F)F)cc2s1]

(R)-2-amino-3-methyl-N-(2-oxo-2-((6-(trifluoromethoxy)benzo [d]thiazol-2-yl)amino) ethyl)butanamide was prepared according to the procedure of example 18 from 2-amino-N-(6-(trifluoromethoxy)benzo[d] thiazol-2-yl)acetamide hydrochloride from example 1 above (20 mg, 61 µmol) and (R)-2-(N-(t-butyloxycarbonyl)valine (17 mg, 79 µmol). Yield=21 mg (81%). LC/MS method A: $R_t$=3.83 min., (M+H)$^+$=391.

Example 32: Synthesis of (S)-4-oxo-N-(2-oxo-2-((6-(trifluoromethoxy)benzo [d]thiazol-2-yl)amino) ethyl)pyrrolidine-2-carboxamide

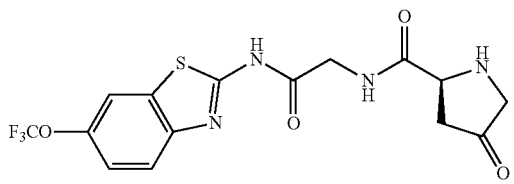 [SMILES: O=C1CN[C@H](C(=O)NCC(=O)Nc2nc3ccc(OC(F)(F)F)cc3s2)C1]

(S)-4-oxo-N-(2-oxo-2-((6-(trifluoromethoxy)benzo [d]thiazol-2-yl)amino)ethyl) pyrrolidine-2-carboxamide was prepared according to the procedure of example 18 from 2-amino-N-(6-(trifluoromethoxy)benzo[d] thiazol-2-yl)acetamide hydrochloride from example 1 above (20 mg, 61 µmol) and (S)—N-t-butyloxycarbonyl-4-oxopyrrolidine-2-carboxylic acid (18 mg, 79 µmol). Yield=16 mg (60%). LC/MS method A: $R_t$=3.64 min., (M+H)$^+$=403.

Example 33: (S)—N-(2-oxo-2-((6-(trifluoromethoxy)benzo[d] thiazol-2-yl)amino)ethyl)piperidine-2-carboxamide

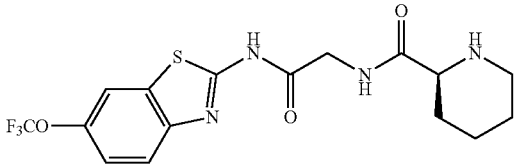 [SMILES: O=C(CNC(=O)[C@@H]1CCCCN1)Nc1nc2ccc(OC(F)(F)F)cc2s1]

(S)—N-(2-oxo-2-((6-(trifluoromethoxy)benzo[d] thiazol-2-yl)amino)ethyl)piperidine-2-carboxamide was prepared according to the procedure of example 18 from 2-amino-N-(6-(trifluoromethoxy)benzo[d] thiazol-2-yl)acetamide hydrochloride from example 1 above (20 mg, 61 µmol) and (S)—N-t-butyloxycarbonylpiperidine-2-carboxylic acid (18 mg, 79 µmol). Yield=20 mg (75%). LC/MS method A: 114=3.73 min., (M+H)$^+$=403.

Example 34: Synthesis of (S)—N-(2-oxo-2-((6-(trifluoromethoxy)benzo[d] thiazol-2-yl)amino) ethyl)morpholine-3-carboxamide

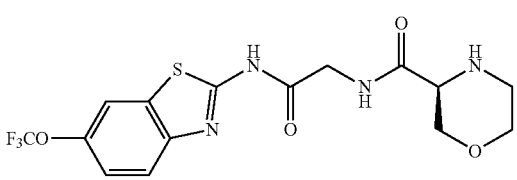 [SMILES: O=C(CNC(=O)[C@@H]1COCCN1)Nc1nc2ccc(OC(F)(F)F)cc2s1]

(S)—N-(2-oxo-2-((6-(trifluoromethoxy)benzo[d] thiazol-2-yl)amino)ethyl)morpholine-3-carboxamide was prepared according to the procedure of example 18 from 2-amino-N-(6-(trifluoromethoxy)benzo[d] thiazol-2-yl)acetamide hydrochloride from example 1 above (20 mg, 61 µmol) and (S)—N-t-butyloxycarbonylmorpholine-2-carboxylic acid (18 mg, 79 µmol). Yield=24 mg (89%). LC/MS method A: $R_t$=3.64 min., (M+H)$^+$=405.

Example 35: Synthesis of (R)—N-(2-oxo-2-((6-(trifluoromethoxy)benzo[d] thiazol-2-yl)amino) ethyl)morpholine-3-carboxamide

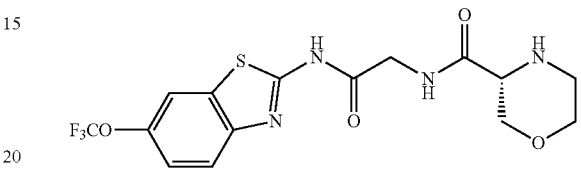

(R)—N-(2-oxo-2-((6-(trifluoromethoxy)benzo[d] thiazol-2-yl)amino)ethyl)morpholine-3-carboxamide was prepared according to the procedure of example 18 from 2-amino-N-(6-(trifluoromethoxy)benzo[d] thiazol-2-yl)acetamide hydrochloride from example 1 above (20 mg, 61 µmol) and (R)—N-t-butyloxycarbonylmorpholine-2-carboxylic acid (18 mg, 79 µmol). Yield=25 mg (93%). LC/MS method A: $R_t$=3.64 min., (M+H)$^+$=405.

Example 36: Synthesis of (R)-2-amino-4-methyl-N-(2-oxo-2-((6-(trifluoro methoxy)benzo[d]thiazol-2-yl)amino)ethyl)pentanamide

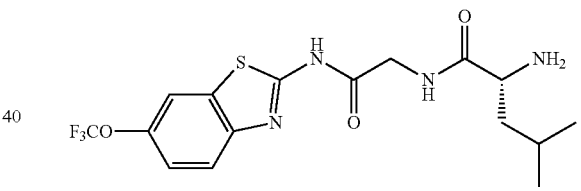

(R)-2-amino-4-methyl-N-(2-oxo-2-((6-(trifluoromethoxy)benzo[d]thiazol-2-yl)amino) ethyl)pentanamide was prepared according to the procedure of example 18 from 2-amino-N-(6-(trifluoromethoxy)benzo[d] thiazol-2-yl)acetamide hydrochloride from example 1 above (20 mg, 61 µmol) and N-t-butyloxycarbonyl-D-leucine (18 mg, 79 µmol). Yield=21 mg (78%). LC/MS method A: $R_t$=4.01 min., (M+H)$^+$=405.

Example 37: Synthesis of (R)-4-oxo-N-(2-oxo-2-((6-(trifluoromethoxy)benzo [d]thiazol-2-yl)amino) ethyl)piperidine-2-carboxamide

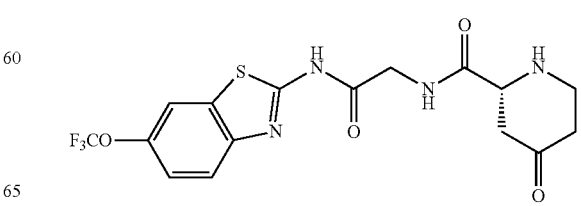

(R)-4-oxo-N-(2-oxo-2-((6-(trifluoromethoxy)benzo[d]thiazol-2-yl)amino)ethyl)piperidine-2-carboxamide was prepared according to the procedure of example 18 from 2-amino-N-(6-(trifluoromethoxy)benzo[d] thiazol-2-yl)acetamide hydrochloride from example 1 above (20 mg, 61 µmol) and (R)—N-t-butyloxycarbonyl-4-oxopiperidine-2-carboxylic acid (19 mg, 79 µmol). Yield=15 mg (54%). LC/MS method A: $R_t$=3.68 min., $(M+H)^+$=417.

Example 38: Synthesis of 4-amino-N-(2-oxo-2-((6-(trifluoromethoxy)benzo[d] thiazol-2-yl)amino)ethyl)tetrahydro-2H-pyran-4-carboxamide

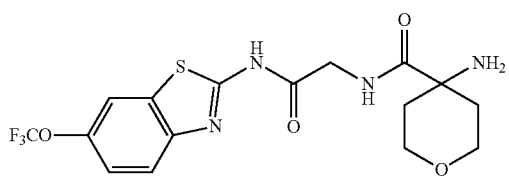 [SMILES: NC1(C(=O)NCC(=O)Nc2nc3ccc(OC(F)(F)F)cc3s2)CCOCC1]

4-amino-N-(2-oxo-2-((6-(trifluoromethoxy)benzo[d] thiazol-2-yl)amino)ethyl)tetrahydro-2H-pyran-4-carboxamide was prepared according to the procedure of example 18 from 2-amino-N-(6-(trifluoromethoxy)benzo[d] thiazol-2-yl)acetamide hydrochloride from example 1 above (20 mg, 61 µmol) and 4-N-t-butyloxycarbonylamino-2,3,5,6-tetrahydropyran-4H-4-carboxylic acid (19 mg, 79 µmol). Yield=24 mg (87%). LC/MS method A: $R_t$=3.63 min., $(M+H)^+$=419.

Example 39: (R)-2-amino-N1-(2-oxo-2-((6-(trifluoromethoxy) benzo[d]thiazol-2-yl)amino)ethyl)pentanediamide

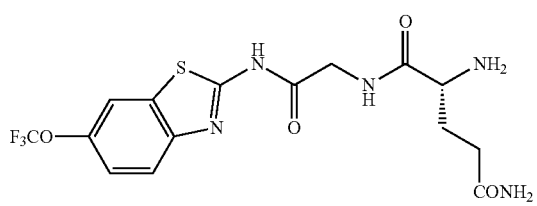 [SMILES: NC(=O)CC[C@@H](N)C(=O)NCC(=O)Nc1nc2ccc(OC(F)(F)F)cc2s1]

(R)-2-amino-N1-(2-oxo-2-((6-(trifluoromethoxy) benzo[d]thiazol-2-yl)amino)ethyl) pentanediamide: was prepared according to the procedure of example 18 from 2-amino-N-(6-(trifluoromethoxy)benzo[d] thiazol-2-yl)acetamide hydrochloride from example 1 above (20 mg, 61 µmol) and N-t-butyloxycarbonyl-D-glutamine (20 mg, 79 µmol). Yield=24 mg (72%). LC/MS method A: $R_t$=3.47 min., $(M+H)^+$=420.

Example 40: (R)-2-amino-N-(2-oxo-2-((6-(trifluoromethoxy) benzo[d]thiazol-2-yl)amino)ethyl)-3-phenylpropanamide

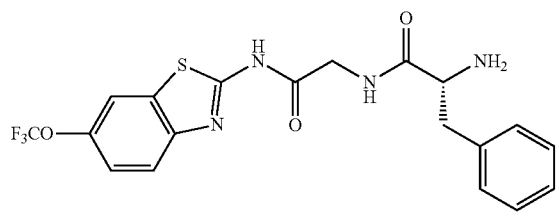 [SMILES: N[C@H](Cc1ccccc1)C(=O)NCC(=O)Nc1nc2ccc(OC(F)(F)F)cc2s1]

(R)-2-amino-N-(2-oxo-2-((6-(trifluoromethoxy) benzo[d]thiazol-2-yl)amino)ethyl)-3-phenylpropanamide was prepared according to the procedure of example 18 from 2-amino-N-(6-(trifluoromethoxy)benzo[d] thiazol-2-yl)acetamide hydrochloride from example 1 above (20 mg, 61 µmol) and N-t-butyloxycarbonyl-D-phenylalanine (21 mg, 79 µmol). Yield=22 mg (76%). LC/MS method A: $R_t$=4.11 min., $(M+H)^+$=439.

Example 41: (R)-2-amino-3-cyclohexyl-N-(2-oxo-2-((6-(trifluoro methoxy)benzo[d] thiazol-2-yl)amino)ethyl)propanamide

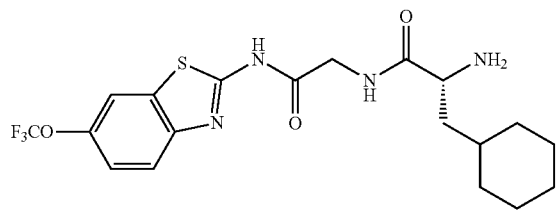 [SMILES: N[C@H](CC1CCCCC1)C(=O)NCC(=O)Nc1nc2ccc(OC(F)(F)F)cc2s1]

(R)-2-amino-3-cyclohexyl-N-(2-oxo-2-((6-(trifluoromethoxy)benzo[d]thiazol-2-yl)amino) ethyl)propanamide was prepared according to the procedure of example 18 from 2-amino-N-(6-(trifluoromethoxy)benzo[d] thiazol-2-yl)acetamide hydrochloride from example 1 above (20 mg, 61 µmol) and N-t-butyloxycarbonyl-D-cyclohexylalanine (21 mg, 79 µmol). Yield=15 mg (51%). LC/MS method A: $R_t$=4.43 min., $(M+H)^+$=445.

Example 42: Synthesis of (R)-2-amino-3-(benzyloxy)-N-(2-oxo-2-((6-(trifluoro methoxy)benzo[d]thiazol-2-yl)amino)ethyl)propanamide

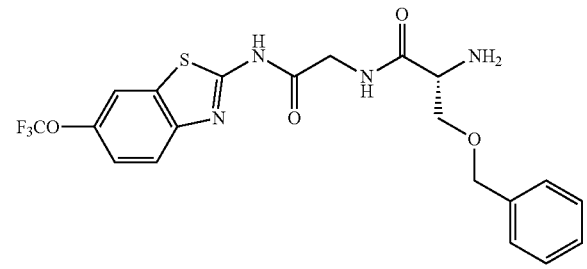 [SMILES: N[C@H](COCc1ccccc1)C(=O)NCC(=O)Nc1nc2ccc(OC(F)(F)F)cc2s1]

(R)-2-amino-3-(benzyloxy)-N-(2-oxo-2-((6-(trifluoromethoxy)benzo[d]thiazol-2-yl) amino)ethyl)propanamide was prepared according to the procedure of example 18 from 2-amino-N-(6-(trifluoromethoxy)benzo[d] thiazol-2-yl)acetamide hydrochloride from example 1 above (20 mg, 61 µmol) and N-t-butyloxycarbonyl-O-benzyl-D-serine (23 mg, 79 µmol). Yield=25 mg (81%). LC/MS method A: $R_t$=4.30 min., $(M+H)^+$=469.

Example 43: Synthesis of (S)-2-amino-3-(benzyloxy)-N-(2-oxo-2-((6-(trifluoromethoxy)benzo[d] thiazol-2-yl)amino)ethyl)propanamide

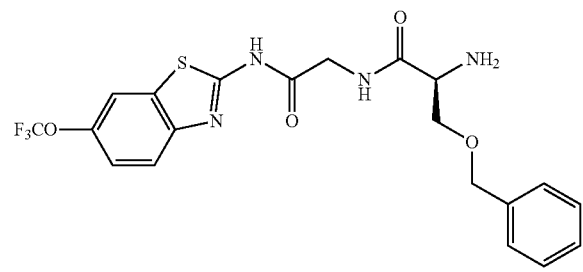 [SMILES: N[C@@H](COCc1ccccc1)C(=O)NCC(=O)Nc1nc2ccc(OC(F)(F)F)cc2s1]

(S)-2-amino-3-(benzyloxy)-N-(2-oxo-2-((6-(trifluoromethoxy)benzo[d]thiazol-2-yl) amino)ethyl)propanamide was prepared according to the procedure of example 18 from 2-amino-N-(6-(trifluoromethoxy)benzo[d] thiazol-2-yl)acetamide hydrochloride from example 1 above (20 mg, 61 µmol) and N-t-butyloxycarbonyl-O-benzyl-L-serine (23 mg, 79 µmol). Yield=26 mg (84%). LC/MS method A: $R_t$=4.30 min., $(M+H)^+$=469.

Example 44: Synthesis of (R)-2-amino-3-(1H-indol-3-yl)-N-(2-oxo-2-((6-(trifluoro methoxy)benzo[d] thiazol-2-yl)amino)ethyl)propanamide

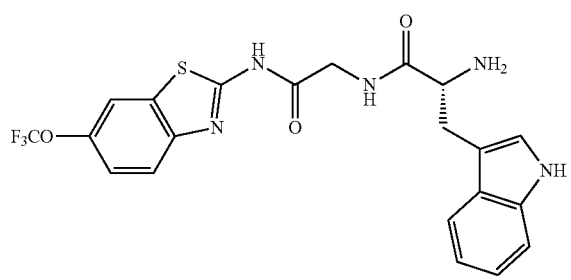 [SMILES: N[C@H](Cc1c[nH]c2ccccc12)C(=O)NCC(=O)Nc1nc2ccc(OC(F)(F)F)cc2s1]

(R)-2-amino-3-(1H-indol-3-yl)-N-(2-oxo-2-((6-(trifluoromethoxy)benzo[d]thiazol-2-yl)amino)ethyl)propanamide was prepared according to the procedure of example 18 from 2-amino-N-(6-(trifluoromethoxy)benzo[d] thiazol-2-yl)acetamide hydrochloride from example 1 above (20 mg, 61 µmol) and N-t-butyloxycarbonyl-L-tryptophan (24 mg, 79 µmol). Yield=22 mg (70%).

Example 45: Synthesis of (2S,4R)-4-(benzyloxy)-N-(2-oxo-2-((6-(trifluoro methoxy)benzo[d]thiazol-2-yl)amino)ethyl)pyrrolidine-2-carboxamide

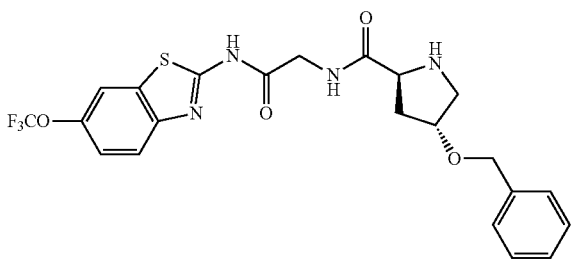 [SMILES: O=C(CNC(=O)[C@@H]1C[C@@H](OCc2ccccc2)CN1)Nc1nc2ccc(OC(F)(F)F)cc2s1]

(2S,4R)-4-(benzyloxy)-N-(2-oxo-2-((6-(trifluoromethoxy)benzo[d]thiazol-2-yl)amino) ethyl)pyrrolidine-2-carboxamide was prepared according to the procedure of example 18 from 2-amino-N-(6-(trifluoromethoxy)benzo[d] thiazol-2-yl)acetamide hydrochloride from example 1 above (20 mg, 61 µmol) and tert-butyl (2S,4R)-4-(benzyloxy)-2-carbamoylpyrrolidine-1-carboxylate (25 mg, 79 µmol). Yield=24 mg (74%). LC/MS method A: $R_t$=4.13 min., $(M+H)^+$=495.

Example 46: Synthesis of (S)—N-(2-oxo-2-((6-(trifluoromethoxy)benzo[d] thiazol-2-yl)amino) ethyl)piperazine-2-carboxamide

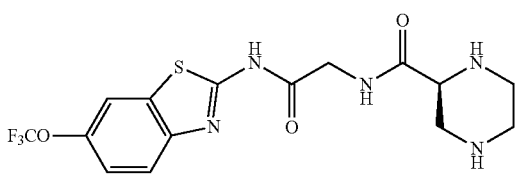 [SMILES: O=C(CNC(=O)[C@@H]1CNCCN1)Nc1nc2ccc(OC(F)(F)F)cc2s1]

(S)—N-(2-oxo-2-((6-(trifluoromethoxy)benzo[d] thiazol-2-yl)amino)ethyl)piperazine-2-carboxamide was prepared according to the procedure of example 18 from 2-amino-N-(6-(trifluoromethoxy)benzo[d] thiazol-2-yl)acetamide hydrochloride from example 1 above (20 mg, 61 µmol) and (S)—N,N'-di-(tert-butyloxycarbonyl) morpholine-2-carboxylic acid (26 mg, 79 µmol). Yield=23 mg (70%). LC/MS method A: $R_t$=3.23 min., $(M+H)^+$=404.

Example 47: Synthesis of (R)-2-amino-4-(benzyloxy)-N-(2-oxo-2-((6-(trifluoro methoxy)benzo[d] thiazol-2-yl)amino)ethyl)butanamide

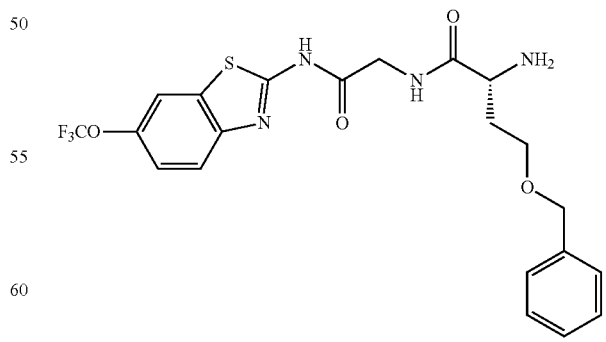

(R)-2-amino-4-(benzyloxy)-N-(2-oxo-2-((6-(trifluoromethoxy)benzo[d]thiazol-2-yl) amino)ethyl)butanamide was prepared according to the procedure of example 18 from 2-amino-N-(6-(trifluoromethoxy)benzo[d] thiazol-2-yl)acetamide hydrochloride from example 1 above (20 mg, 61 μmol) and N-t-butyloxycarbonyl-O-benzyl-D-homoserine (27 mg, 79 μmol). Yield=26 mg (77%). LC/MS method A: $R_t$=4.39 min $(M+H)^+$=482.

Example 48: Synthesis of (R)-1-(N,N-dimethyl-L-valyl)-N-(6-(trifluoromethoxy)benzo [d]thiazol-2-yl) pyrrolidine-2-carboxamide

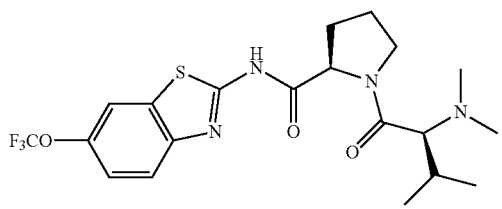 [SMILES: CC(C)[C@@H](C(=O)N1CCC[C@@H]1C(=O)Nc1nc2ccc(OC(F)(F)F)cc2s1)N(C)C]

A solution of (R)—N-(6-(trifluoromethoxy)benzo[d]thiazol-2-yl)pyrrolidine-2-carboxamide from example 6 above (0.11 g, 0.30 mmol), N,N-dimethyl-L-valine (52 mg, 0.36 mmol) and N,N-diisopropylethylamine (46 mg, 0.36 mmol, 65 μl) in N,N-dimethylformamide (2 ml) was treated with 1-[Bis(dimethylamino)methylene]-1H-1,2,3-triazolo[4,b]pyridinium 3-oxid hexafluorophosphate (137 mg, 0.36 mmol) and stirred 72 hours. The product was purified by reverse phase HPLC (method B, direct injection of the reaction mixture). The product fractions were combined and evaporated on a Genevac evaporator to leave the mono TFA salt product as a white powder (31 mg, 18%). LC/MS method A: $R_t$=4.06 min., $(M+H)^+$=459.

Example 49: Synthesis of (R)-1-(L-valyl)-N-(6-(trifluoromethoxy)benzo[d]thiazol-2-yl)pyrrolidine-2-carboxamide

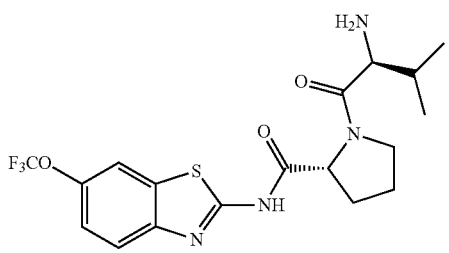 [SMILES: CC(C)[C@H](N)C(=O)N1CCC[C@@H]1C(=O)Nc1nc2ccc(OC(F)(F)F)cc2s1]

A solution of (R)—N-(6-(trifluoromethoxy)benzo[d]thiazol-2-yl)pyrrolidine-2-carboxamide from example 6 above (25 mg, 0.68 μmop, N-t-butyloxycarbonyl-L-valine (18 mg, 81 μmol) and N,N-diisopropylethylamine (10 μmol, 18 μl) in N,N-dimethylformamide (0.3 ml) was treated with 1-[Bis (dimethylamino)methylene]-1H-1,2,3-triazolo[4,5-b]pyridinium 3-oxid hexafluorophosphate (39 mg, 10 μmol) and stirred 72 hours. The product was purified by reverse phase HPLC (method B, direct injection of the reaction mixture). The product fractions were combined and evaporated on a Genevac evaporator to leave the product as a white powder which was stirred for 2 hours in 4N HCl/1,4-dioxane (2 ml). The solvents were evaporated to leave the product as a white solid (27 mg, 85% two steps). LC/MS method A: $R_t$=4.23 min., $(M+H)^+$=431.02.

Example 50: Synthesis of (R)-1-D-valyl-N-(6-(trifluoromethoxy)benzo[d]thiazol-2-yl) pyrrolidine-2-carboxamide

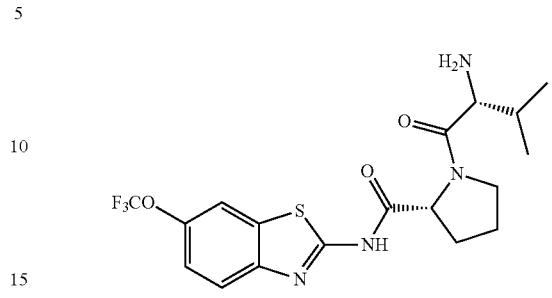

(R)-1-D-valyl-N-(6-(trifluoromethoxy)benzo[d]thiazol-2-yl) pyrrolidine-2-carboxamide was prepared according to the procedure of example 49 from (R)—N-(6-(trifluoromethoxy)benzo[d]thiazol-2-yl)pyrrolidine-2-carboxamide (37 mg, 0.1 mmol) and N-t-butyloxycarbonyl-D-valine (26 mg, 0.13 mmol). Yield=35 mg, 75% two steps. LC/MS method A: $R_t$=4.24 min., $(M+H)^+$=431.02.

Example 51: Synthesis of (R)-1-glycinyl-N-(6-(trifluoromethoxy)benzo[d]thiazol-2-yl) pyrrolidine-2-carboxamide

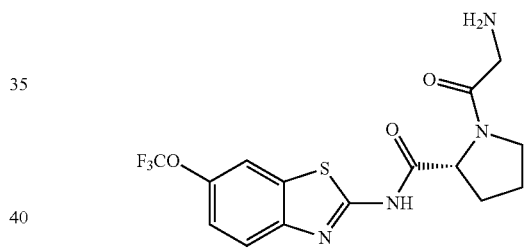

(R)-1-glycinyl-N-(6-(trifluoromethoxy)benzo[d]thiazol-2-yl) pyrrolidine-2-carboxamide was prepared according to the procedure of example 49 from (R)—N-(6-(trifluoromethoxy)benzo [d]thiazol-2-yl)pyrrolidine-2-carboxamide (37 mg, 0.1 mmol) and N-t-butyloxycarbonylglycine (25 mg, 0.13 mmol). Yield=42 mg, 100% two steps. LC/MS method A: $R_t$=3.78 min., $(M+H)^+$=388.94.

Example 52: (R)-1-N-ethylglycinyl-N-(6-(trifluoromethoxy)benzo [d]thiazol-2-yl) pyrrolidine-2-carboxamide

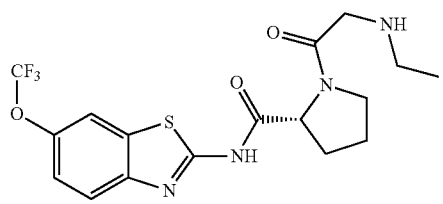 [SMILES: CCNCC(=O)N1CCC[C@@H]1C(=O)Nc1nc2ccc(OC(F)(F)F)cc2s1]

(R)-1-N-ethylglycinyl-N-(6-(trifluoromethoxy)benzo[d]thiazol-2-yl)pyrrolidine-2-carboxamide was prepared according to the procedure of example 49 from (R)—N-(6-(trifluoromethoxy)benzo[d]thiazol-2-yl) pyrrolidine-2-carboxamide (74 mg, 0.2 mmol) and N-Boc-N-ethyl glycine (61 mg, 0.30 mmol) Yield=88 mg, 97% two steps. LC/MS method A: $R_t$=3.94 min., $(M+H)^+$=417.02.

Example 53: Synthesis of (R)-1-N-isopropylglycinyl-N-(6-(trifluoromethoxy) benzo[d]thiazol-2-yl)pyrrolidine-2-carboxamide

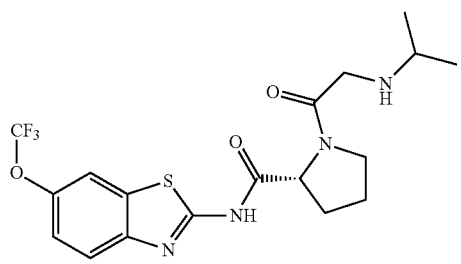 [SMILES: CC(C)NCC(=O)N1CCC[C@@H]1C(=O)Nc1nc2ccc(OC(F)(F)F)cc2s1]

(R)-1-N-isopropylglycinyl-N-(6-(trifluoromethoxy)benzo[d]thiazol-2-yl)pyrrolidine-2-carboxamide was prepared according to the procedure of example 49 from (R)—N-(6-(trifluoromethoxy)benzo[d]thiazol-2-yl) pyrrolidine-2-carboxamide (74 mg, 0.2 mmol) and N-t-butyloxycarbonyl-N-isopropyl glycine (65 mg, 0.30 mmol). Yield=98 mg, 100% two steps. LC/MS method A: $R_t$=4.03 min., $(M+H)^+$=431.09.

Example 54: Synthesis of (R)-1-N-t-butylglycinyl-N-(6-(trifluoromethoxy) benzo[d]thiazol-2-yl)pyrrolidine-2-carboxamide

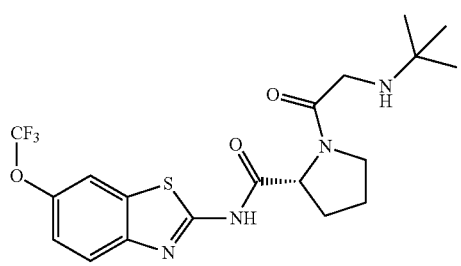 [SMILES: CC(C)(C)NCC(=O)N1CCC[C@@H]1C(=O)Nc1nc2ccc(OC(F)(F)F)cc2s1]

(R)-1-N-t-butylglycinyl-N-(6-(trifluoromethoxy) benzo[d]thiazol-2-yl)pyrrolidine-2-carboxamide was prepared according to the procedure of example 49 from (R)—N-(6-(trifluoromethoxy)benzo[d]thiazol-2-yl)pyrrolidine-2-carboxamide (74 mg, 0.2 mmol) and N-t-butyloxycarbonyl-N-tertbutyl glycine (69 mg, 0.30 mmol). Yield=86 mg, 89% two steps. LC/MS method A: $R_t$=4.13 min., $(M+H)^+$=445.10.

Example 55: Synthesis of (R)-1-(3-amino-2,2-dimethylpropanoyl)-N-(6-(trifluoromethoxy)benzo[d]thiazol-2-yl)pyrrolidine-2-carboxamide

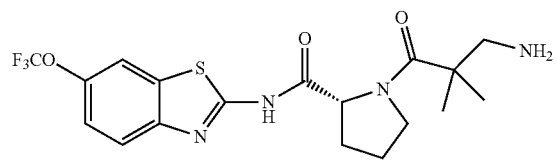 [SMILES: CC(C)(CN)C(=O)N1CCC[C@@H]1C(=O)Nc1nc2ccc(OC(F)(F)F)cc2s1]

(R)-1-(3-amino-2,2-dimethylpropanoyl)-N-(6-(trifluoromethoxy)benzo[d]thiazol-2-yl)pyrrolidine-2-carboxamide was prepared according to the procedure of example 49 from (R)—N-(6-(trifluoromethoxy)benzo[d] thiazol-2-yl) pyrrolidine-2-carboxamide (37 mg, 0.1 mmol) and N-t-butyloxycarbonyl-3-amino-2,2-dimethylpropanoic acid (29 mg, 0.13 mmol). Yield=53 mg, 100% two steps. LC/MS method A: $R_t$=4.01 min., $(M+H)^+$=431.02.

Example 56: Synthesis of (R)-1-(1-(aminomethyl)cyclopropane-1-carbonyl)-N-(6-(trifluoromethoxy)benzo[d]thiazol-2-yl)pyrrolidine-2-carboxamide

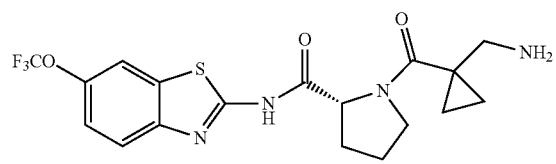 [SMILES: NCC1(C(=O)N2CCC[C@@H]2C(=O)Nc2nc3ccc(OC(F)(F)F)cc3s2)CC1]

(R)-1-(1-(aminomethyl)cyclopropane-1-carbonyl)-N-(6-(trifluoromethoxy)benzo[d] thiazol-2-yl)pyrrolidine-2-carboxamide was prepared according to the procedure of example 49 from (R)—N-(6-(trifluoromethoxy)benzo[d]thiazol-2-yl)pyrrolidine-2-carboxamide (74 mg, 0.2 mmol) and N-t-butyloxycarbonyl-1-(aminomethyl)cyclopropane carboxylic acid (56 mg, 0.26 mmol). Yield=93 mg, 100% two steps. LC/MS method A: 124=3.92 min., $(M+H)^+$=429.05.

Example 57: Synthesis of (R)-1-(1-(aminomethyl)cyclopentane-1-carbonyl)-N-(6-(trifluoromethoxy)benzo[d]thiazol-2-yl)pyrrolidine-2-carboxamide

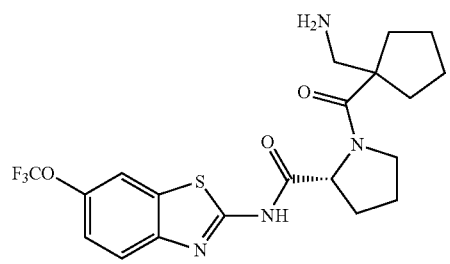 [SMILES: NCC1(C(=O)N2CCC[C@@H]2C(=O)Nc2nc3ccc(OC(F)(F)F)cc3s2)CCCC1]

(R)-1-(1-(aminomethyl)cyclopentane-1-carbonyl)-N-(6-(trifluoromethoxy)benzo [d]thiazol-2-yl)pyrrolidine-2-carboxamide was prepared according to the procedure of example 49 from (R)—N-(6-(trifluoromethoxy)benzo[d]thiazol-2-yl)pyrrolidine-2-carboxamide (74 mg, 0.2 mmol) and N-t-butyloxycarbonyl-1-(aminomethyl)cyclopentane carboxylic acid (63 mg, 0.26 mmol). Yield=91 mg, 92% two steps. LC/MS method A: $R_t$=4.21 min., $(M+H)^+$=457.13.

Example 58: Synthesis of (R)-1-(1-(aminomethyl) cyclohexane-1-carbonyl)-N-(6-(trifluoromethoxy) benzo[d]thiazol-2-yl)pyrrolidine-2-carboxamide

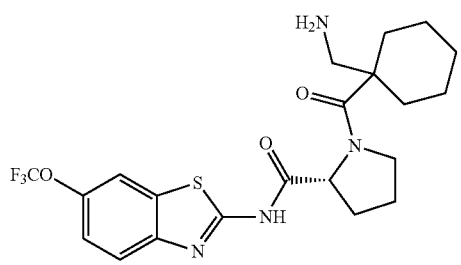 [SMILES: NCC1(C(=O)N2CCC[C@@H]2C(=O)Nc2nc3ccc(OC(F)(F)F)cc3s2)CCCCC1]

(R)-1-(1-(aminomethyl)cyclohexane-1-carbonyl)-N-(6-(trifluoromethoxy)benzo[d]thiazol-2-yl)pyrrolidine-2-carboxamide was prepared according to the procedure of example 49 from (R)—N-(6-(trifluoromethoxy)benzo[d]thiazol-2-yl)pyrrolidine-2-carboxamide (37 mg, 0.1 mmol) and N-t-butyloxycarbonyl-1-(aminomethyl)cyclohexane carboxylic acid (33 mg, 0.13 mmol). Yield=28 mg, 55% two steps. LC/MS method A: $R_t$=4.54 min., $(M+H)^+$=471.08.

Example 59: Synthesis of (S)-1-(3-amino-2,2-dimethylpropanoyl)-N-(6-(trifluoro methoxy)benzo[d]thiazol-2-yl)pyrrolidine-2-carboxamide

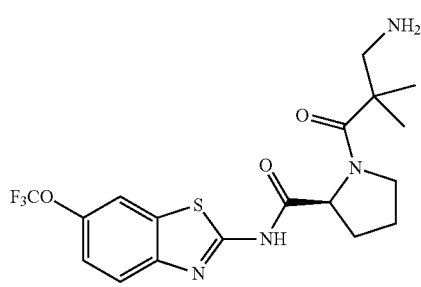 [SMILES: CC(C)(CN)C(=O)N1CCC[C@H]1C(=O)Nc1nc2ccc(OC(F)(F)F)cc2s1]

(S)-1-(3-amino-2,2-dimethylpropanoyl)-N-(6-(trifluoromethoxy)benzo[d]thiazol-2-yl) pyrrolidine-2-carboxamide was prepared according to the procedure of example 49 from (S)—N-(6-(trifluoromethoxy)benzo[d]thiazol-2-yl) pyrrolidine-2-carboxamide (37 mg, 0.1 mmol) and N-t-butyloxycarbonyl-2-amino-2,2-dimethylpropane carboxylic acid (29 mg, 0.13 mmol). Yield=45 mg, 96% two steps. LC/MS method A: $R_t$=4.03 min., $(M+H)^+$=431.02.

Example 60: Synthesis of (S)-1-(1-(aminomethyl) cyclopropane-1-carbonyl)-N-(6-(trifluoromethoxy) benzo[d]thiazol-2-yl)pyrrolidine-2-carboxamide

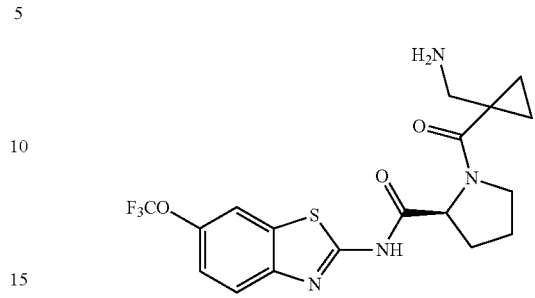

(S)-1-(1-(aminomethyl)cyclopropane-1-carbonyl)-N-(6-(trifluoromethoxy)benzo [d]thiazol-2-yl)pyrrolidine-2-carboxamide was prepared according to the procedure of example 49 from (S)—N-(6-(trifluoromethoxy)benzo[d]thiazol-2-yl)pyrrolidine-2-carboxamide (37 mg, 0.1 µmol) and N-t-butyloxycarbonyl-1-(aminomethyl)cyclopropane carboxylic acid (29 mg, 0.13 µmol). Yield=42 mg, 90% two steps. LC/MS method A: $R_t$=3.94 min., $(M+H)^+$=428.98.

Example 61: Synthesis of (S)-1-(1-(aminomethyl) cyclopentane-1-carbonyl)-N-(6-(trifluoromethoxy) benzo[d]thiazol-2-yl)pyrrolidine-2-carboxamide

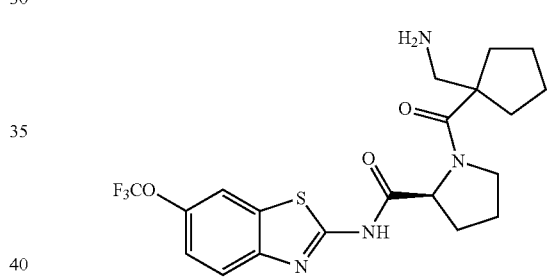

(S)-1-(1-(aminomethyl)cyclopentane-1-carbonyl)-N-(6-(trifluoromethoxy)benzo[d]thiazol-2-yl)pyrrolidine-2-carboxamide was prepared according to the procedure of example 49 from (S)—N-(6-(trifluoromethoxy)benzo[d]thiazol-2-yl)pyrrolidine-2-carboxamide (37 mg, 0.1 µmol) and N-t-butyloxycarbonyl-1-(aminomethyl)cyclopentane carboxylic acid (29 mg, 0.13 µmol). Yield=33 mg, 67% two steps. LC/MS method A: $R_t$=4.21 min., $(M+H)^+$=457.07.

Example 62: (S)-1-(D-valyl)-N-(6-(trifluoromethoxy)benzo[d]thiazol-2-yl)pyrrolidine-2-carboxamide

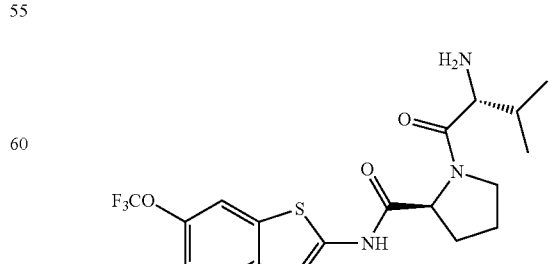

(S)-1-(D-valyl)-N-(6-(trifluoromethoxy)benzo[d]thiazol-2-yl)pyrrolidine-2-carboxamide was prepared according to the procedure of example 49 from (S)—N-(6-(trifluoromethoxy)benzo [d]thiazol-2-yl)pyrrolidine-2-carboxamide (25 mg, 68 μmol) and N-t-butyloxycarbonyl-D-valine (18 mg, 82 μmol). Yield=33 mg (48%, two steps). LC/MS method A: $R_t$=4.23 min., $(M+H)^+$=431.13.

Example 63: Synthesis of (S)-1-(L-valyl)-N-(6-(trifluoromethoxy)benzo[d]thiazol-2-yl)pyrrolidine-2-carboxamide

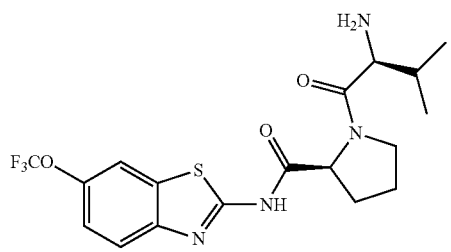 [SMILES: CC(C)[C@H](N)C(=O)N1CCC[C@H]1C(=O)Nc1nc2ccc(OC(F)(F)F)cc2s1]

(S)-1-(L-valyl)-N-(6-(trifluoromethoxy)benzo[d]thiazol-2-yl)pyrrolidine-2-carboxamide was prepared according to the procedure of example 49 from (S)—N-(6-(trifluoromethoxy)benzo [d]thiazol-2-yl)pyrrolidine-2-carboxamide (37 mg, 0.1 μmol) and N-(t-butyloxycarbonyl)valine (24 mg, 0.12 μmol). Yield=35 mg (75%, two steps). LC/MS method A: $R_t$=4.23 min., $(M+H)^+$=431.02.

Example 64: Synthesis of (S)-1-glycyl-N-(6-(trifluoromethoxy)benzo[d]thiazol-2-yl)pyrrolidine-2-carboxamide

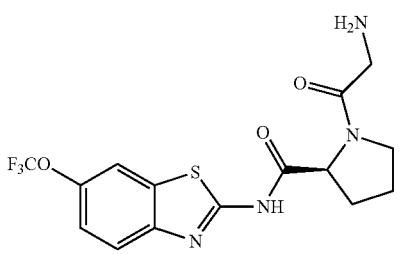 [SMILES: NCC(=O)N1CCC[C@H]1C(=O)Nc1nc2ccc(OC(F)(F)F)cc2s1]

(S)-1-glycyl-N-(6-(trifluoromethoxy)benzo[d]thiazol-2-yl)pyrrolidine-2-carboxamide was prepared according to the procedure of example 49 from (S)—N-(6-(trifluoromethoxy)benzo[d] thiazol-2-yl)pyrrolidine-2-carboxamide (37 mg, 0.1 μmol) and N-(t-butyloxycarbonyl)glycine (21 mg, 0.12 μmol). Yield=45 mg (100%, two steps). LC/MS method A: $R_t$=3.78 min., $(M+H)^+$=388.94.

Example 65: Synthesis of (S)-1-(D-alanyl)-N-(6-(trifluoromethoxy)benzo[d]thiazol-2-yl)pyrrolidine-2-carboxamide

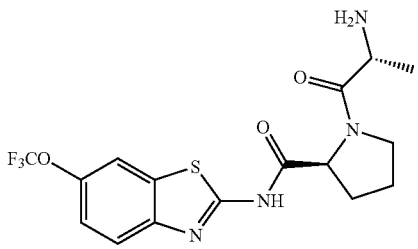 [SMILES: C[C@@H](N)C(=O)N1CCC[C@H]1C(=O)Nc1nc2ccc(OC(F)(F)F)cc2s1]

(S)-1-(D-alanyl)-N-(6-(trifluoromethoxy)benzo [d]thiazol-2-yl)pyrrolidine-2-carboxamide was prepared according to the procedure of example 49 from (S)—N-(6-(trifluoromethoxy)benzo [d]thiazol-2-yl)pyrrolidine-2-carboxamide (37 mg, 0.1 μmol) and N-(t-butyloxycarbonyl)-D-alanine (23 mg, 0.12 μmol). Yield=55 mg (100%, two steps). LC/MS method A: $R_t$=3.82 min., $(M+H)^+$=403.01.

Example 66: Synthesis of (S)-1-(methylglycyl)-N-(6-(trifluoromethoxy)benzo [d]thiazol-2-yl)pyrrolidine-2-carboxamide

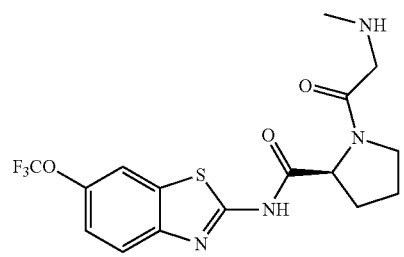 [SMILES: CNCC(=O)N1CCC[C@H]1C(=O)Nc1nc2ccc(OC(F)(F)F)cc2s1]

(S)-1-(methylglycyl)-N-(6-(trifluoromethoxy)benzo[d] thiazol-2-yl)pyrrolidine-2-carboxamide was prepared according to the procedure of example 49 from (S)—N-(6-(trifluoromethoxy)benzo[d]thiazol-2-yl)pyrrolidine-2-carboxamide (37 mg, 0.1 mmol) and N-(t-butyloxycarbonyl)sarcosine (23 mg, 0.12 mmol). Yield=31 mg (71%, two steps). LC/MS method A: $R_t$=3.85 min., $(M+H)^+$=403.01.

Example 67: Synthesis of (S)-1-(ethylglycyl)-N-(6-(trifluoromethoxy)benzo[d]thiazol-2-yl)pyrrolidine-2-carboxamide

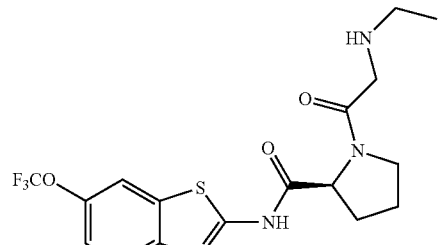

(S)-1-(ethylglycyl)-N-(6-(trifluoromethoxy)benzo[d]thiazol-2-yl)pyrrolidine-2-carboxamide was prepared according to the procedure of example 49 from (S)—N-(6-(trifluoromethoxy)benzo[d]thiazol-2-yl)pyrrolidine-2-carboxamide (37 mg, 0.1 mmol) and N-(t-butyloxycarbonyl)-N-ethylglycine (24 mg, 0.12 mmol). Yield=35 mg (65%, two steps). LC/MS method A: $R_f$=3.94 min., $(M+H)^+$=416.95.

Example 68: Synthesis of (S)-1-(isopropylglycyl)-N-(6-(trifluoromethoxy)benzo[d] thiazol-2-yl)pyrrolidine-2-carboxamide

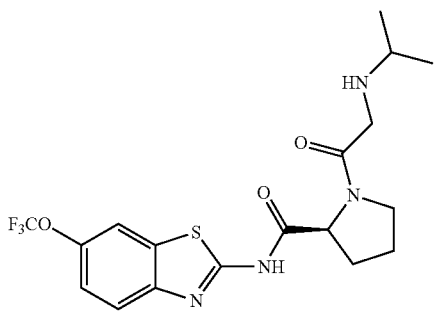 [SMILES: CC(C)NCC(=O)N1CCC[C@H]1C(=O)Nc1nc2ccc(OC(F)(F)F)cc2s1]

(S)-1-(isopropylglycyl)-N-(6-(trifluoromethoxy)benzo[d]thiazol-2-yl)pyrrolidine-2-carboxamide was prepared according to the procedure of example 49 from (S)—N-(6-(trifluoromethoxy)benzo[d]thiazol-2-yl)pyrrolidine-2-carboxamide (37 mg, 0.1 mmol) and N-(t-butyloxycarbonyl)-N-isopropylglycine (26 mg, 0.12 mmol). Yield=43 mg (79%, two steps). LC/MS method A: $R_f$=4.06 min., $(M+H)^+$=431.02.

Example 69: Synthesis of (S)-1-(tert-butylglycyl)-N-(6-(trifluoromethoxy)benzo[d] thiazol-2-yl)pyrrolidine-2-carboxamide

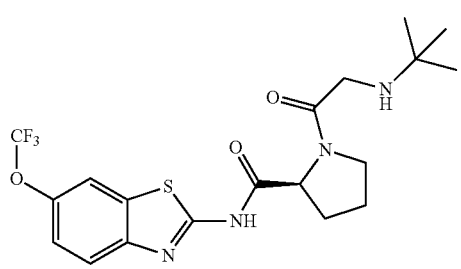 [SMILES: CC(C)(C)NCC(=O)N1CCC[C@H]1C(=O)Nc1nc2ccc(OC(F)(F)F)cc2s1]

(S)-1-(tert-butylglycyl)-N-(6-(trifluoromethoxy)benzo[d] thiazol-2-yl)pyrrolidine-2-carboxamide was prepared according to the procedure of example 49 from (S)—N-(6-(trifluoromethoxy)benzo[d]thiazol-2-yl)pyrrolidine-2-carboxamide (65 mg, 0.18 mmol) and N-(t-butyloxycarbonyl)-N-t-butylglycine (61 mg, 0.26 mmol). Yield=62 mg (73%, two steps). LC/MS method A: $R_f$=4.16 min., $(M+H)^+$=445.10.

Example 70: Synthesis of (S)-1-(D-leucyl)-N-(6-(trifluoromethoxy)benzo[d]thiazol-2-yl)pyrrolidine-2-carboxamide

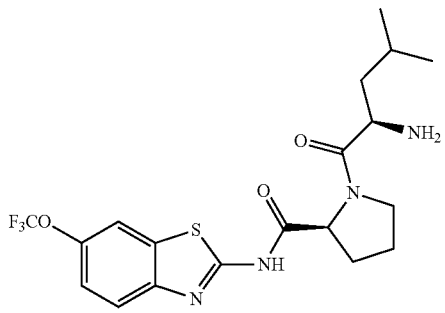 [SMILES: CC(C)C[C@@H](N)C(=O)N1CCC[C@H]1C(=O)Nc1nc2ccc(OC(F)(F)F)cc2s1]

(S)-1-(D-leucyl)-N-(6-(trifluoromethoxy)benzo[d]thiazol-2-yl)pyrrolidine-2-carboxamide: was prepared according to the procedure of example 49 from (S)—N-(6-(trifluoromethoxy)benzo [d]thiazol-2-yl)pyrrolidine-2-carboxamide (37 mg, 0.1 mmol) and N-(t-butyloxycarbonyl)-D-leucine (26 mg, 0.12 mmol). Yield=33 mg (69%, two steps). LC/MS method A: $R_f$=4.18 min., $(M+H)^+$=445.03.

Example 71: Synthesis of (S)-1-(3-aminopropanoyl)-N-(6-(trifluoromethoxy)benzo [d]thiazol-2-yl)pyrrolidine-2-carboxamide

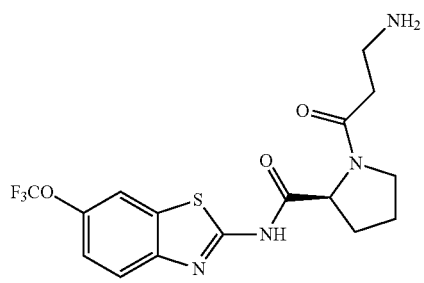 [SMILES: NCCC(=O)N1CCC[C@H]1C(=O)Nc1nc2ccc(OC(F)(F)F)cc2s1]

(S)-1-(3-aminopropanoyl)-N-(6-(trifluoromethoxy)benzo[d]thiazol-2-yl)pyrrolidine-2-carboxamide was prepared according to the procedure of example 49 from (S)—N-(6-(trifluoromethoxy)benzo[d] thiazol-2-yl) pyrrolidine-2-carboxamide (37 mg, 0.1 mmol) and N-t-butyloxycarbonyl-beta-alanine (23 mg, 0.12 mmol). Yield=46 mg (100%, two steps). LC/MS method A: $R_f$=3.64 min., $(M+H)^+$=403.01.

Example 72: Synthesis of (S)-1-glycyl-N-(6-(trifluoromethoxy)benzo[d]thiazol-2-yl)azetidine-2-carboxamide

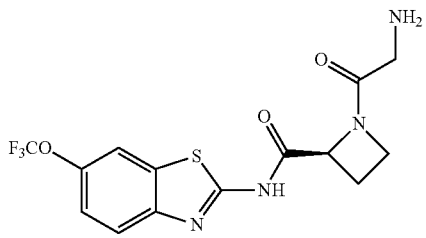 [SMILES: NCC(=O)N1CC[C@H]1C(=O)Nc1nc2ccc(OC(F)(F)F)cc2s1]

(S)-1-glycyl-N-(6-(trifluoromethoxy)benzo[d]thiazol-2-yl)azetidine-2-carboxamide was prepared according to the procedure of example 49 from (S)—N-(6-(trifluoromethoxy)benzo[d] thiazol-2-yl)azetidine-2-carboxamide (37 mg, 0.1 mmol) and N-t-butyloxycarbonylglycine (26 mg, 0.13 mmol). Yield=21 mg (43%, two steps). LC/MS method A: $R_t$=3.69 min., (M+H)$^+$=374.94.

Example 73: Synthesis of (S)-1-(3-aminopropanoyl)-N-(6-(trifluoromethoxy)benzo[d] thiazol-2-yl)azetidine-2-carboxamide

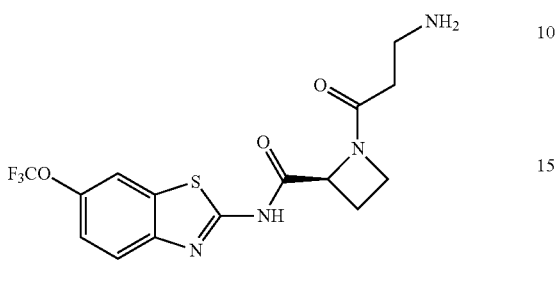

(S)-1-(3-aminopropanoyl)-N-(6-(trifluoromethoxy)benzo[d]thiazol-2-yl)azetidine-2-carboxamide was prepared according to the procedure of example 49 from (S)—N-(6-(trifluoromethoxy)benzo[d]thiazol-2-yl)azetidine-2-carboxamide (37 mg, 0.1 mmol) and N-t-butyloxycarbonyl-beta-alanine (29 mg, 0.13 mmol). Yield=18 mg (36%, two steps). LC/MS method A: $R_t$=3.76 min., (M+H)$^+$=388.94.

Example 74: Synthesis of (S)-1-(1-(aminomethyl)cyclopropane-1-carbonyl)-N-(6-(trifluoromethoxy)benzo[d]thiazol-2-yl)azetidine-2-carboxamide

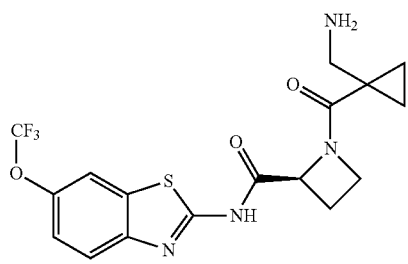 [SMILES: NCC1(C(=O)N2CC[C@H]2C(=O)Nc2nc3ccc(OC(F)(F)F)cc3s2)CC1]

(S)-1-(1-(aminomethyl)cyclopropane-1-carbonyl)-N-(6-(trifluoromethoxy)benzo [d] thiazol-2-yl)azetidine-2-carboxamide was prepared according to the procedure of example 49 from (S)—N-(6-(trifluoromethoxy)benzo[d]thiazol-2-yl)azetidine-2-carboxamide TFA salt (46 mg, 0.1 mmol) and N-t-butyloxycarbonyl-1-(aminomethyl)cyclopropane carboxylic acid (29 mg, 0.13 mmol). Yield=49 mg (93%, two steps). LC/MS method A: $R_t$=3.90 min., (M+H)$^+$=414.98.

Example 75: Synthesis of (S)-1-(1-(aminomethyl)cyclopentane-1-carbonyl)-N-(6-(trifluoromethoxy)benzo[d]thiazol-2-yl)azetidine-2-carboxamide

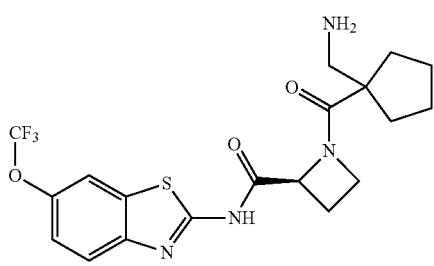 [SMILES: NCC1(C(=O)N2CC[C@H]2C(=O)Nc2nc3ccc(OC(F)(F)F)cc3s2)CCCC1]

(S)-1-(1-(aminomethyl)cyclopentane-1-carbonyl)-N-(6-(trifluoromethoxy)benzo [d]thiazol-2-yl)azetidine-2-carboxamide was prepared according to the procedure of example 49 from (S)—N-(6-(trifluoromethoxy)benzo[d]thiazol-2-yl)azetidine-2-carboxamide TFA salt (46 mg, 0.1 mmol) and N-t-butyloxycarbonyl-1-(aminomethyl)cyclopentane carboxylic acid (29 mg, 0.13 mmol). Yield=49 mg (88%, two steps). LC/MS method A: $R_t$=4.16 min., (M+H)$^+$=443.06.

Example 76: Synthesis of (S)-1-glycyl-N-(6-(trifluoromethoxy)benzo[d]thiazol-2-yl)piperidine-2-carboxamide

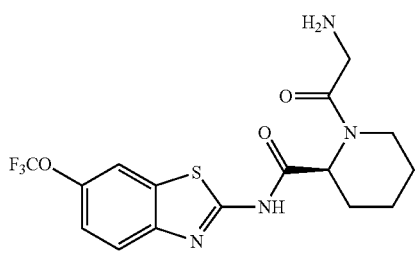 [SMILES: NCC(=O)N1CCCC[C@H]1C(=O)Nc1nc2ccc(OC(F)(F)F)cc2s1]

(S)-1-glycyl-N-(6-(trifluoromethoxy)benzo[d]thiazol-2-yl)piperidine-2-carboxamide was prepared according to the procedure of example 49 from (S)—N-(6-(trifluoromethoxy)benzo[d] thiazol-2-yl)cyclohexane-2-carboxamide hydrochloride (41 mg, 0.10 mmol) and N-t-butyloxycarbonylglycine (26 mg, 0.13 mmol). Yield=43 mg (98%, two steps). LC/MS method A: $R_t$=4.08 min., (M+H)$^+$=402.94.

Example 77: Synthesis of (S)-1-(3-aminopropanoyl)-N-(6-(trifluoromethoxy)benzo[d] thiazol-2-yl)piperidine-2-carboxamide

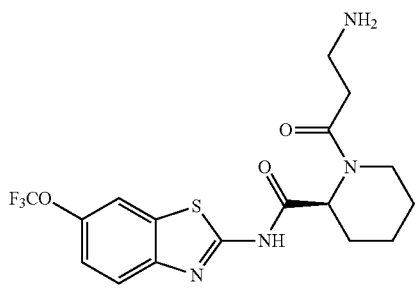 [SMILES: NCCC(=O)N1CCCC[C@H]1C(=O)Nc1nc2ccc(OC(F)(F)F)cc2s1]

(S)-1-(3-aminopropanoyl)-N-(6-(trifluoromethoxy)benzo[d]thiazol-2-yl)piperidine-2-carboxamide was prepared according to the procedure of example 49 from (S)—N-(6-(trifluoromethoxy)benzo[d]thiazol-2-yl)cyclohexane-2-carboxamide hydrochloride (41 mg, 0.10 mmol) and N-t-butyloxycarbonyl-beta-alanine (29 mg, 0.13 mmol). Yield=42 mg (98%, two steps). LC/MS method A: $R_t$=4.15 min., (M+H)$^+$=416.95.

Example 78: Synthesis of (S)-1-(3-aminopropanoyl)-N-(6-(trifluoromethoxy)benzo[d] thiazol-2-yl)piperidine-2-carboxamide

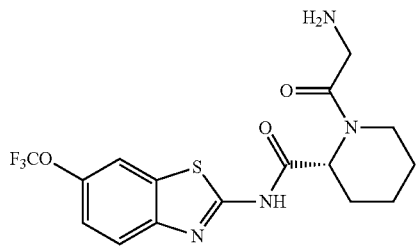 [SMILES: NCC(=O)N1CCCC[C@@H]1C(=O)Nc1nc2ccc(OC(F)(F)F)cc2s1]

(R)-1-glycyl-N-(6-(trifluoromethoxy)benzo[d]thiazol-2-yl)piperidine-2-carboxamide was prepared according to the procedure of example 49 from (R)—N-(6-(trifluoromethoxy)benzo[d] thiazol-2-yl)cyclohexane-2-carboxamide hydrochloride (30 mg, 0.073 mmol) and N-t-butyloxycarbonylglycine (17 mg, 0.098 mmol). Yield=18 mg (55%, two steps). LC/MS method A: $R_t$=4.17 min., $(M+H)^+$=402.94.

Example 79: Synthesis of (R)-1-(methylglycyl)-N-(6-(trifluoromethoxy)benzo[d] thiazol-2-yl)piperidine-2-carboxamide

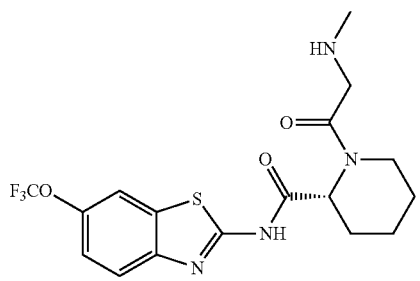 [SMILES: CNCC(=O)N1CCCC[C@@H]1C(=O)Nc1nc2ccc(OC(F)(F)F)cc2s1]

(R)-1-(methylglycyl)-N-(6-(trifluoromethoxy)benzo[d]thiazol-2-yl)piperidine-2-carboxamide was prepared according to the procedure of example 49 from (R)—N-(6-(trifluoromethoxy)benzo[d]thiazol-2-yl)cyclohexane-2-carboxamide hydrochloride (30 mg, 0.073 mmol) and N-t-butyloxycarbonylglycine (18 mg, 0.098 mmol). Yield=28 mg (82%, two steps). LC/MS method A: $R_t$=4.25 min., $(M+H)^+$=416.95.

Example 80: Synthesis of 1-(2-aminoacetamido)-N-(6-(trifluoromethoxy)benzo[d] thiazol-2-yl)cyclopropane-1-carboxamide

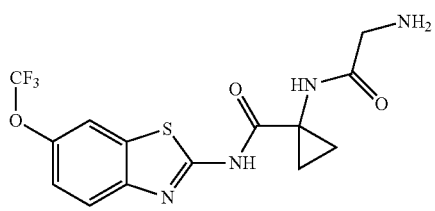 [SMILES: NCC(=O)NC1(C(=O)Nc2nc3ccc(OC(F)(F)F)cc3s2)CC1]

1-(2-aminoacetamido)-N-(6-(trifluoromethoxy)benzo[d]thiazol-2-yl)cyclopropane-1-carboxamide was prepared according to the procedure of example 49 from 1-amino-N-(6-(trifluoromethoxy)benzo[d] thiazol-2-yl)cyclopropanecarboxamide hydrochloride (36 mg, 0.10 mmol) and N-t-butyloxycarbonylglycine (23 mg, 0.13 mmol). Yield=35 mg (85%, two steps). LC/MS method A: $R_t$=3.90 min., $(M+H)^+$=375.01.

Example 81: Synthesis of 1-(2-(methylamino)acetamido)-N-(6-(trifluoromethoxy) benzo[d]thiazol-2-yl)cyclopropane-1-carboxamide

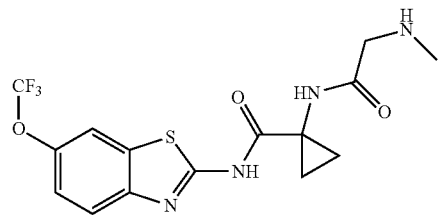 [SMILES: CNCC(=O)NC1(C(=O)Nc2nc3ccc(OC(F)(F)F)cc3s2)CC1]

1-(2-(methylamino)acetamido)-N-(6-(trifluoromethoxy) benzo [d]thiazol-2-yl)cyclopropane-1-carboxamide was prepared according to the procedure of example 49 from 1-amino-N-(6-(trifluoromethoxy)benzo[d]thiazol-2-yl)cyclopropanecarboxamide hydrochloride (36 mg, 0.10 mmol) and N-t-butyloxycarbonyl-N-methyl glycine (25 mg, 0.13 mmol). Yield=28 mg (66%, two steps). LC/MS method A: $R_t$=3.94 min., $(M+H)^+$=389.01.

Example 82: Synthesis of 1-(2-aminoacetamido)-N-(6-(trifluoromethoxy)benzo[d] thiazol-2-yl)cyclobutane-1-carboxamide

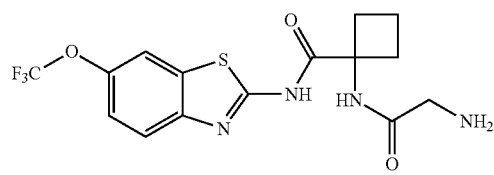 [SMILES: NCC(=O)NC1(C(=O)Nc2nc3ccc(OC(F)(F)F)cc3s2)CCC1]

1-(2-aminoacetamido)-N-(6-(trifluoromethoxy)benzo[d] thiazol-2-yl)cyclobutane-1-carboxamide was prepared according to the procedure of example 49 from 1-amino-N-(6-(trifluoromethoxy)benzo[d] thiazol-2-yl)cyclobutanecarboxamide hydrochloride (33 mg, 0.10 mmol) and N-t-butyloxycarbonylglycine (23 mg, 0.13 mmol). Yield=36 mg (85%, two steps). LC/MS method A: 1't, =4.06 min., $(M+H)^+$=388.94.

Example 83: Synthesis of 1-(2-(methylamino)acet-amido)-N-(6-(trifluoromethoxy) benzo[d]thiazol-2-yl)cyclobutane-1-carboxamide

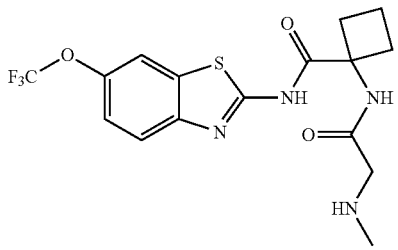 [SMILES: CNCC(=O)NC1(C(=O)Nc2nc3ccc(OC(F)(F)F)cc3s2)CCC1]

1-(2-(methylamino)acetamido)-N-(6-(trifluoromethoxy) benzo [d]thiazol-2-yl)cyclobutane-1-carboxamide was prepared according to the procedure of example 49 from 1-amino-N-(6-(trifluoromethoxy)benzo[d] thiazol-2-yl)cyclobutanecarboxamide hydrochloride (33 mg, 0.10 mmol) and N-t-butyloxycarbonyl-N-methylglycine (25 mg, 0.13 mmol). Yield=22 mg (50%, two steps). LC/MS method A: $R_t$=4.13 min., $(M+H)^+$=403.01.

Example 84: Synthesis of 1-(3-amino-2,2-dimethyl-propanamido)-N-(6-(trifluoro methoxy)benzo[d]thiazol-2-yl)cyclobutane-1-carboxamide

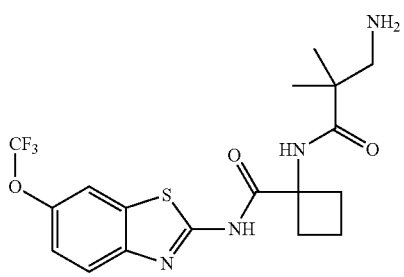 [SMILES: CC(C)(CN)C(=O)NC1(C(=O)Nc2nc3ccc(OC(F)(F)F)cc3s2)CCC1]

1-(3-amino-2,2-dimethylpropanamido)-N-(6-(trifluoromethoxy)benzo[d]thiazol-2-yl)cyclobutane-1-carboxamide was prepared according to the procedure of example 49 from 1-amino-N-(6-(trifluoromethoxy)benzo[d]thiazol-2-yl)cyclobutanecarboxamide hydrochloride (37 mg, 0.10 mmol) and N-t-butyloxycarbonyl-2,2-dimethyl-beta-alanine (30 mg, 0.15 mmol). Yield=30 mg (55%, two steps). LC/MS method A: $R_t$=4.20 min., $(M+H)^+$=431.16.

Example 85: Synthesis of 1-(aminomethyl)-N-(1-((6-(trifluoromethoxy)benzo[d]thiazol-2-yl)carbamoyl)cyclobutyl)cyclopentane-1-carboxamide

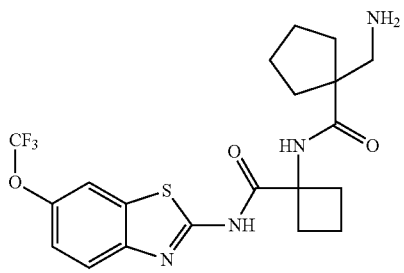 [SMILES: NCC1(C(=O)NC2(C(=O)Nc3nc4ccc(OC(F)(F)F)cc4s3)CCC2)CCCC1]

1-(aminomethyl)-N-(14(6-(trifluoromethoxy)benzo[d]thiazol-2-yl)carbamoyl)cyclobutyl) cyclopentane-1-carboxamide was prepared according to the procedure of example 49 from 1-amino-N-(6-(trifluoromethoxy)benzo[d] thiazol-2-yl)cyclobutanecarboxamide hydrochloride (37 mg, 0.10 mmol) and N-t-butyloxycarbonyl-1-(aminomethyl)cyclopentane carboxylic acid (33 mg, 0.15 mmol). Yield=23 mg (47%, two steps). LC/MS method A: $R_t$=4.40 min., $(M+H)^+$=457.13.

Example 86: Synthesis of 1-(2-(isopropylamino) acetamido)-N-(6-(trifluoromethoxy) benzo[d]thiazol-2-yl)cyclobutane-1-carboxamide

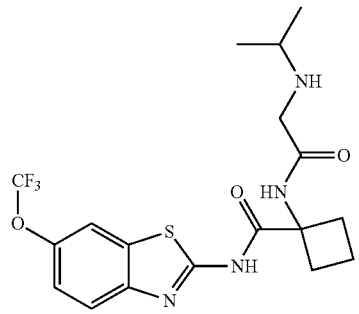 [SMILES: CC(C)NCC(=O)NC1(C(=O)Nc2nc3ccc(OC(F)(F)F)cc3s2)CCC1]

1-(2-(isopropylamino)acetamido)-N-(6-(trifluoromethoxy)benzo[d]thiazol-2-yl)cyclo butane-1-carboxamide was prepared according to the procedure of example 49 from 1-amino-N-(6-(trifluoromethoxy)benzo [d]thiazol-2-yl)cyclobutanecarboxamide hydrochloride (37 mg, 0.10 mmol) and N-t-butyloxycarbonyl-N-isopropylglycine (30 mg, 0.15 mmol). Yield=30 mg (64%, two steps). LC/MS method A: $R_t$=4.31 min., $(M+H)^+$=431.16.

Example 87: Synthesis of 1-(2-(isopropylamino) acetamido)-N-(6-(trifluoromethoxy) benzo[d]thiazol-2-yl)cyclobutane-1-carboxamide

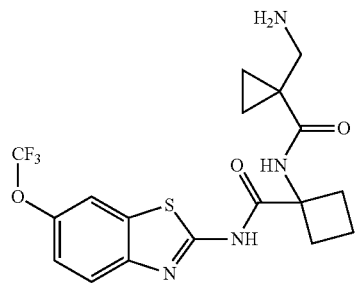 [SMILES: NCC1(C(=O)NC2(C(=O)Nc3nc4ccc(OC(F)(F)F)cc4s3)CCC2)CC1]

1-(1-(aminomethyl)cyclopropane-1-carboxamido)-N-(6-(trifluoromethoxy)benzo[d] thiazol-2-yl)cyclobutane-1-carboxamide was prepared according to the procedure of example 49 from 1-amino-N-(6-(trifluoromethoxy)benzo[d] thiazol-2-yl)cyclobutanecarboxamide hydrochloride (55 mg, 0.15 mmol) and N-t-butyloxycarbonyl-1-(aminomethyl)cyclopropane carboxylic acid (48 mg, 0.22 mmol). Yield=48 mg (69%, two steps). LC/MS method A: $R_t$=4.19 min., $(M+H)^+$=429.19.

Example 88: Synthesis of 1-(aminomethyl)-N-(1-((6-(trifluoromethoxy)benzo[d]thiazol-2-yl)carbamoyl)cyclobutyl)cyclohexane-1-carboxamide

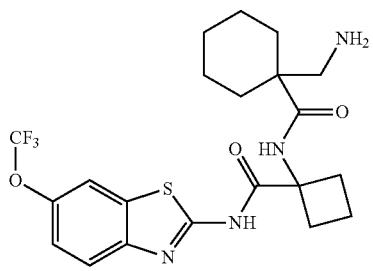 [SMILES: NCC1(C(=O)NC2(C(=O)Nc3nc4ccc(OC(F)(F)F)cc4s3)CCC2)CCCCC1]

1-(aminomethyl)-N-(1-((6-(trifluoromethoxy)benzo[d]thiazol-2-yl)carbamoyl)cyclobutyl) cyclohexane-1-carboxamide was prepared according to the procedure of example 49 from 1-amino-N-(6-(trifluoromethoxy)benzo[d]thiazol-2-yl)cyclobutanecarboxamide hydrochloride (55 mg, 0.15 mmol) and N-t-butyloxycarbonyl-1-(aminomethyl)cyclohexane carboxylic acid (58 mg, 0.22 mmol). Yield=43 mg (57%, two steps). LC/MS method A: $R_t$=4.50 min., $(M+H)^+$=471.21.

Example 89: Synthesis of (R)-1-(2-aminopropanamido)-N-(6-(trifluoromethoxy)benzo[d]thiazol-2-yl)cyclobutane-1-carboxamide

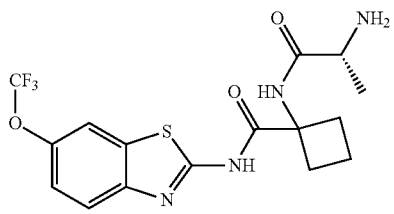 [SMILES: C[C@@H](N)C(=O)NC1(C(=O)Nc2nc3ccc(OC(F)(F)F)cc3s2)CCC1]

(R)-1-(2-aminopropanamido)-N-(6-(trifluoromethoxy)benzo[d]thiazol-2-yl)cyclobutane-1-carboxamide was prepared according to the procedure of example 49 from 1-amino-N-(6-(trifluoromethoxy)benzo[d]thiazol-2-yl)cyclobutanecarboxamide hydrochloride (55 mg, 0.15 mmol) and N-t-butyloxycarbonyl-D-alanine (42 mg, 0.22 mmol). Yield=27 mg (41%, two steps). LC/MS method A: $R_t$=4.10 min., $(M+H)^+$=403.15.

Example 90: Synthesis of (R)-1-(2-amino-3-methylbutanamido)-N-(6-(trifluoro methoxy)benzo[d]thiazol-2-yl)cyclobutane-1-carboxamide

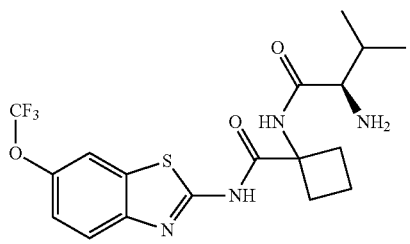 [SMILES: CC(C)[C@@H](N)C(=O)NC1(C(=O)Nc2nc3ccc(OC(F)(F)F)cc3s2)CCC1]

(R)-1-(2-amino-3-methylbutanamido)-N-(6-(trifluoromethoxy)benzo[d]thiazol-2-yl)cyclobutane-1-carboxamide was prepared according to the method of example 49 from 1-amino-N-(6-(trifluoromethoxy)benzo[d]thiazol-2-yl)cyclobutanecarboxamide hydrochloride (55 mg, 0.15 mmol) and N-t-butyloxycarbonyl-D-valine (49 mg, 0.22 mmol). Yield=57 mg (81%, two steps). LC/MS method A: $R_t$=4.32 min., $(M+H)^+$=431.16.

Example 91: Synthesis of (S)-2-(2-aminoacetamido)-3-phenyl-N-(6-(trifluoro methoxy)benzo[d]thiazol-2-yl)propanamide

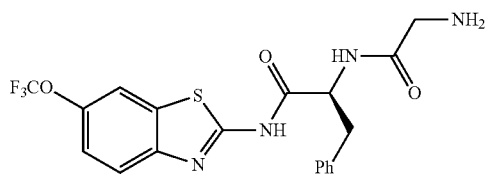 [SMILES: NCC(=O)N[C@@H](Cc1ccccc1)C(=O)Nc1nc2ccc(OC(F)(F)F)cc2s1]

(S)-2-(2-aminoacetamido)-3-phenyl-N-(6-(trifluoromethoxy)benzo[d]thiazol-2-yl)propanamide was prepared according to the procedure of example 49 from (S)-2-amino-3-phenyl-N-(6-(trifluoro methoxy)benzo[d]thiazol-2-yl)propanamide (19 mg, 0.05 mmol) and N-t-butyloxycarbonylglycine (13 mg, 0.065 mmol). Yield=20 mg (84%, two steps). LC/MS method A: $R_t$=4.36 min., $(M+H)^+$=438.98.

Example 92: Synthesis of (S)-2-(2-(methylamino)acetamido)-3-phenyl-N-(6-(trifluoromethoxy)benzo[d]thiazol-2-yl)propanamide

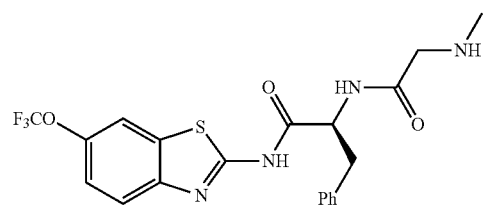 [SMILES: CNCC(=O)N[C@@H](Cc1ccccc1)C(=O)Nc1nc2ccc(OC(F)(F)F)cc2s1]

(S)-2-(2-(methylamino)acetamido)-3-phenyl-N-(6-(trifluoromethoxy)benzo[d]thiazol-2-yl)propanamide was prepared according to the procedure of example 49 from (S)-2-amino-3-phenyl-N-(6-(trifluoromethoxy)benzo[d]thiazol-2-yl)propanamide (19 mg, 0.05 mmol) and N-t-butyloxycarbonyl-N-methylglycine (14 mg, 0.065 mmol). Yield=13 mg (53%, two steps). LC/MS method A: $R_t$=4.41 min., $(M+H)^+$=453.05.

Example 92: Synthesis of (S)-2-((R)-2-aminopropanamido)-3-phenyl-N-(6-(trifluoromethoxy)benzo[d]thiazol-2-yl)propanamide

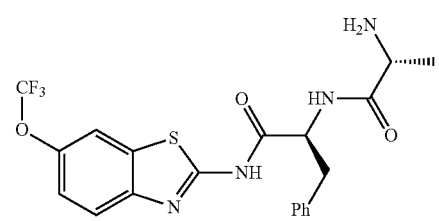 [SMILES: C[C@@H](N)C(=O)N[C@@H](Cc1ccccc1)C(=O)Nc1nc2ccc(OC(F)(F)F)cc2s1]

(S)-2-((R)-2-aminopropanamido)-3-phenyl-N-(6-(trifluoromethoxy)benzo[d]thiazol-2-yl)propanamide was prepared according to the procedure of example 49 from (S)-2-amino-3-phenyl-N-(6-(trifluoro methoxy)benzo[d]thiazol-2-yl)propanamide (42 mg, 0.10 mmol) and N-t-butyloxycarbonyl-D-alanine (28 mg, 0.15 mmol). Yield=43 mg (88%, two steps). LC/MS method A: $R_t$=4.32 min., (M−14+H)$^+$=438.98.

Example 93: Synthesis of (S)-2-((S)-2-aminopropanamido)-3-phenyl-N-(6-(trifluoro methoxy)benzo[d]thiazol-2-yl)propanamide

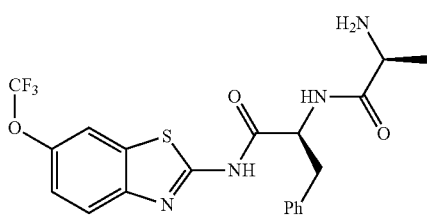 [SMILES: C[C@H](N)C(=O)N[C@@H](Cc1ccccc1)C(=O)Nc1nc2ccc(OC(F)(F)F)cc2s1]

(S)-2-((S)-2-aminopropanamido)-3-phenyl-N-(6-(trifluoromethoxy)benzo[d]thiazol-2-yl)propanamide was prepared according to the procedure of example 49 from (S)-2-amino-3-phenyl-N-(6-(trifluoro methoxy)benzo[d]thiazol-2-yl)propanamide (42 mg, 0.10 mmol) and N-t-butyloxycarbonyl-L-alanine (28 mg, 0.15 mmol). Yield=43 mg (88%, two steps). LC/MS method A: $R_t$=4.32 min., (M−14+H)$^+$=438.98.

Example 94: Synthesis of (R)-2-amino-3-methyl-N—((S)-1-oxo-3-phenyl-1-((6-(trifluoromethoxy)benzo[d]thiazol-2-yl)amino)propan-2-yl)butanamide

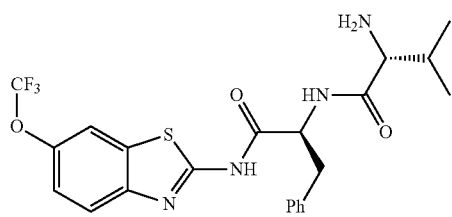 [SMILES: CC(C)[C@@H](N)C(=O)N[C@@H](Cc1ccccc1)C(=O)Nc1nc2ccc(OC(F)(F)F)cc2s1]

(R)-2-amino-3-methyl-N—((S)-1-oxo-3-phenyl-1-((6-(trifluoromethoxy)benzo[d]thiazol-2-yl)amino)propan-2-yl)butanamide was prepared according to the procedure of example 49 from (S)-2-amino-3-phenyl-N-(6-(trifluoromethoxy)benzo[d]thiazol-2-yl)propanamide (42 mg, 0.10 mmol) and N-t-butyloxycarbonyl-D-valine (33 mg, 0.15 mmol). Yield=46 mg (89%, two steps). LC/MS method A: $R_t$=3.62 min., (M−14+H)$^+$=467.06.

Example 95: Synthesis of (S)-2-amino-2-methyl-N-(1-oxo-3-phenyl-1-(((6-(trifluoromethoxy)benzo[d]thiazol-2-yl)amino)propan-2-yl)propanamide

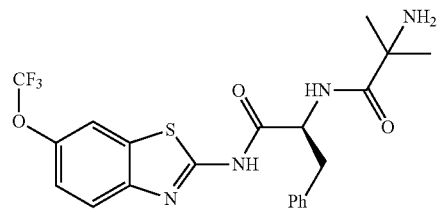 [SMILES: CC(C)(N)C(=O)N[C@@H](Cc1ccccc1)C(=O)Nc1nc2ccc(OC(F)(F)F)cc2s1]

(S)-2-amino-2-methyl-N-(1-oxo-3-phenyl-1-((6-(trifluoromethoxy)benzo[d]thiazol-2-yl)amino)propan-2-yl)propanamide was prepared according to the procedure of example 49 from (S)-2-amino-3-phenyl-N-(6-(trifluoromethoxy)benzo[d]thiazol-2-yl)propanamide (42 mg, 0.10 mmol) and N-t-butyloxycarbonylsarcosine (33 mg, 0.15 mmol). Yield=52 mg (100%, two steps). LC/MS method A: $R_t$=4.38 min., (M−14+H)$^+$=452.99.

Example 96: Synthesis of (S)-1-amino-N-(1-oxo-3-phenyl-1-((6-(trifluoromethoxy) benzo[d]thiazol-2-yl)amino)propan-2-yl)cyclopropane-1-carboxamide

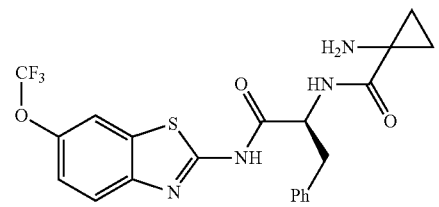 [SMILES: NC1(C(=O)N[C@@H](Cc2ccccc2)C(=O)Nc2nc3ccc(OC(F)(F)F)cc3s2)CC1]

(S)-1-amino-N-(1-oxo-3-phenyl-1-((6-(trifluoromethoxy) benzo [d]thiazol-2-yl)amino)propan-2-yl)cyclopropane-1-carboxamide was prepared according to the procedure of example 49 from (S)-2-amino-3-phenyl-N-(6-(trifluoromethoxy)benzo[d]thiazol-2-yl)propanamide (42 mg, 0.10 mmol) and 1-N-t-butyloxycarbonylaminocyclopropane carboxylic acid (30 mg, 0.15 mmol). Yield=41 mg (82%, two steps). LC/MS method A: $R_t$=4.33 min., (M−14+H)$^+$=451.01.

Example 97: Synthesis of (S)-1-amino-N-(1-oxo-3-phenyl-1-((6-(trifluoromethoxy) benzo[d]thiazol-2-yl)amino)propan-2-yl)cyclobutane-1-carboxamide

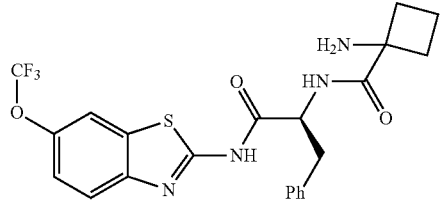 [SMILES: NC1(C(=O)N[C@@H](Cc2ccccc2)C(=O)Nc2nc3ccc(OC(F)(F)F)cc3s2)CCC1]

(S)-1-amino-N-(1-oxo-3-phenyl-1-((6-(trifluoromethoxy) benzo [d]thiazol-2-yl)amino) propan-2-yl)cyclobutane-1-carboxamide was prepared according to the procedure of example 49 from (S)-2-amino-3-phenyl-N-(6-(trifluoromethoxy)benzo[d]thiazol-2-yl)propanamide (42 mg, 0.10 mmol) and 1-(N-t-butyloxycarbonylamino)cyclobutanecarboxylic acid (32 mg, 0.15 mmol). Yield=41 mg (80%, two steps). LC/MS method A: $R_t$=4.43 min., (M−14+H)$^+$=465.16.

Example 98: Synthesis of 1-(3-amino-2,2-dimethylpropanamido)-N-(6-(trifluoro methoxy)benzo[d]thiazol-2-yl)cyclobutane-1-carboxamide

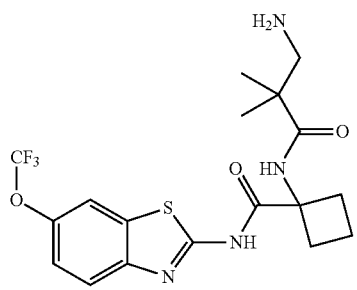

1-(3-amino-2,2-dimethylpropanamido)-N-(6-(trifluoromethoxy)benzo[d]thiazol-2-yl)cyclobutane-1-carboxamide was prepared according to the procedure of example 49 from 1-amino-N-(6-(trifluoromethoxy)benzo[d]thiazol-2-yl)cyclobutane-1-carboxamide (42 mg, 0.10 mmol) and 3-((N-t-butyloxycarbonyl)amino)-2,2-dimethylpropanoic acid (32 mg, 0.15 mmol). Yield=41 mg (80%, two steps). LC/MS method A: $R_t$=4.43 min., (M−14+H)$^+$=465.16.

Example 99: Synthesis of (R)-2-(2-aminopropanamido)-2-methyl-N-(6-(trifluoro methoxy)benzo[d]thiazol-2-yl)propanamide

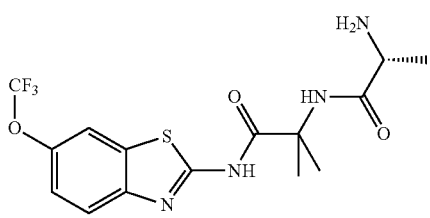 [SMILES: C[C@@H](N)C(=O)NC(C)(C)C(=O)Nc1nc2ccc(OC(F)(F)F)cc2s1]

(R)-2-(2-aminopropanamido)-2-methyl-N-(6-(trifluoromethoxy)benzo[d]thiazol-2-yl)propanamide was prepared according to the procedure of example 49 from 2-amino-2-methyl-N-(6-(trifluoromethoxy) benzo[d]thiazol-2-yl)propanamide (50 mg, 0.14 mmol) and N-t-butyloxycarbonyl-D-alanine (40 mg, 0.21 mmol). Yield=35 mg (59%, two steps). LC/MS method A: $R_t$=3.99 min., (M+H)$^+$=390.98.

Example 100: Synthesis of (S)-2-(2-aminopropanamido)-2-methyl-N-(6-(trifluoromethoxy)benzo[d]thiazol-2-yl)propanamide

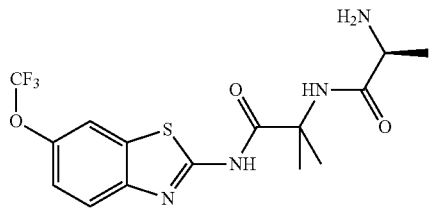 [SMILES: C[C@H](N)C(=O)NC(C)(C)C(=O)Nc1nc2ccc(OC(F)(F)F)cc2s1]

(S)-2-(2-aminopropanamido)-2-methyl-N-(6-(trifluoromethoxy)benzo[d]thiazol-2-yl)propanamide was prepared according to the procedure of example 49 from 2-amino-2-methyl-N-(6-(trifluoromethoxy)benzo[d]thiazol-2-yl)propanamide (50 mg, 0.14 mmol) and N-(t-butyloxycarbonyl)alanine (40 mg, 0.21 mmol). Yield=36 mg (60%, two steps). LC/MS method A: $R_t$=4.00 min., (M+H)$^+$=390.98.

Example 101: Synthesis of 2-(2-aminoacetamido)-2-methyl-N-(6-(trifluoro methoxy)benzo[d]thiazol-2-yl)propanamide

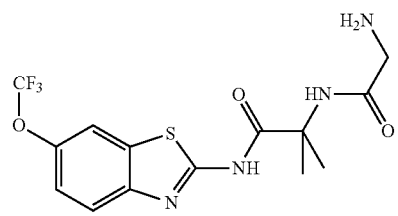 [SMILES: CC(C)(NC(=O)CN)C(=O)Nc1nc2ccc(OC(F)(F)F)cc2s1]

2-(2-aminoacetamido)-2-methyl-N-(6-(trifluoromethoxy)benzo[d]thiazol-2-yl)propanamide was prepared according to the procedure of example 49 from 2-amino-2-methyl-N-(6-(trifluoromethoxy) benzo[d]thiazol-2-yl)propanamide (50 mg, 0.14 mmol) and N-(t-butyloxycarbonyl)glycine (37 mg, 0.21 mmol). Yield=40 mg (69%, two steps). LC/MS method A: $R_t$=3.93 min., (M+H)$^+$=376.91.

Example 102: Synthesis of (R)-2-amino-N-(2-methyl-1-oxo-1-((6-(trifluoromethoxy) benzo[d]thiazol-2-yl)amino)propan-2-yl)-3-phenylpropanamide

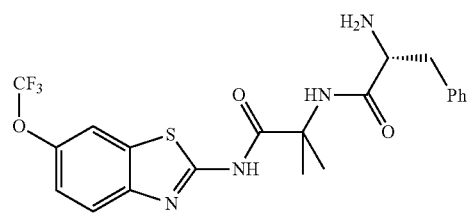 [SMILES: CC(C)(NC(=O)[C@H](N)Cc1ccccc1)C(=O)Nc1nc2ccc(OC(F)(F)F)cc2s1]

(R)-2-amino-N-(2-methyl-1-oxo-1-((6-(trifluoromethoxy)benzo [d]thiazol-2-yl)amino) propan-2-yl)-3-phenylpropanamide was prepared according to the procedure of example 49 from 2-amino-2-methyl-N-(6-(trifluoromethoxy)benzo[d]thiazol-2-yl)propanamide (36 mg, 0.10 mmol) and N-(t-butyloxycarbonyl)-D-phenylalanine (34 mg, 0.13 mmol). Yield=24 mg (49%, two steps). LC/MS method A: $R_t$=4.62 min., $(M+H)^+$=467.13.

Example 103: Synthesis of (S)-2-amino-3-(benzyloxy)-N-(2-methyl-1-oxo-1-((6-(trifluoromethoxy)benzo[d]thiazol-2-yl)amino)propan-2-yl)propanamide

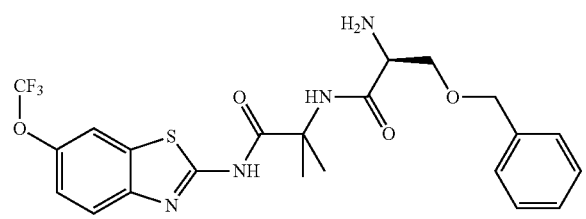 [SMILES: CC(C)(NC(=O)[C@@H](N)COCc1ccccc1)C(=O)Nc1nc2ccc(OC(F)(F)F)cc2s1]

(S)-2-amino-3-(benzyloxy)-N-(2-methyl-1-oxo-1-((6-(trifluoromethoxy)benzo[d]thiazol-2-yl)amino)propan-2-yl)propanamide was prepared according to the procedure of example 49 from 2-amino-2-methyl-N-(6-(trifluoromethoxy)benzo[d]thiazol-2-yl)propanamide (36 mg, 0.10 mmol) and (S)-2-(N-t-butyloxycarbonyl)amino-3-(benzyloxy)propanoic acid (38 mg, 0.13 mmol). Yield=51 mg (95%, two steps). LC/MS method A: $R_t$=4.76 min., $(M+H)^+$=497.13.

Example 104: Synthesis of 1-amino-N-(2-methyl-1-oxo-1-((6-(trifluoromethoxy) benzo[d]thiazol-2-yl) amino)propan-2-yl)cyclopropane-1-carboxamide

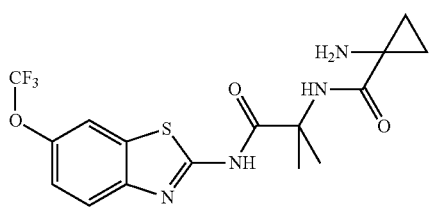 [SMILES: CC(C)(NC(=O)C1(N)CC1)C(=O)Nc1nc2ccc(OC(F)(F)F)cc2s1]

1-amino-N-(2-methyl-1-oxo-1-((6-(trifluoromethoxy) benzo [d]thiazol-2-yl)amino)propan-2-yl)cyclopropane-1-carboxamide was prepared according to the procedure of example 49 from 2-amino-2-methyl-N-(6-(trifluoro methoxy)benzo[d]thiazol-2-yl)propanamide (53 mg, 0.15 mmol) and 1-N-(t-butyloxycarbonyl)aminocyclopropanecarboxylic acid (40 mg, 0.19 mmol). Yield=41 mg (62%, two steps). LC/MS method A: $R_t$=4.03 min., $(M+H)^+$=403.01.

Example 105: Synthesis of 1-amino-N-(2-methyl-1-oxo-1-((6-(trifluoromethoxy) benzo[d]thiazol-2-yl) amino)propan-2-yl)cyclobutane-1-carboxamide

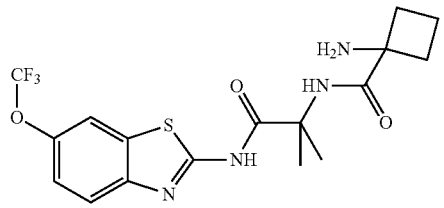 [SMILES: CC(C)(NC(=O)C1(N)CCC1)C(=O)Nc1nc2ccc(OC(F)(F)F)cc2s1]

1-amino-N-(2-methyl-1-oxo-1-((6-(trifluoromethoxy) benzo [d]thiazol-2-yl)amino)propan-2-yl)cyclobutane-1-carboxamide was prepared according to the procedure of example 49 from 2-amino-2-methyl-N-(6-(trifluoro methoxy)benzo[d]thiazol-2-yl)propanamide (53 mg, 0.15 mmol) and 1-N-(t-butyloxycarbonyl)aminocyclobutanecarboxylic acid (41 mg, 0.19 mmol). Yield=37 mg (54%, two steps). LC/MS method A: $R_t$=4.13 min., $(M+H)^+$=417.15.

Example 106: Synthesis of 2-amino-2-methyl-N-(2-methyl-1-oxo-1-((6-(trifluoro methoxy)benzo[d]thiazol-2-yl)amino)propan-2-yl)propanamide

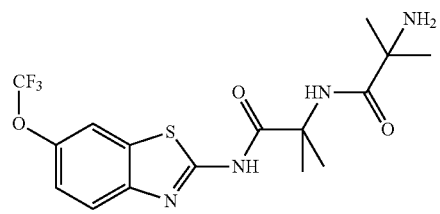 [SMILES: CC(C)(N)C(=O)NC(C)(C)C(=O)Nc1nc2ccc(OC(F)(F)F)cc2s1]

2-amino-2-methyl-N-(2-methyl-1-oxo-1-((6-(trifluoromethoxy)benzo[d]thiazol-2-yl)amino)propan-2-yl)propanamide was prepared according to the procedure of example 49 from 2-amino-2-methyl-N-(6-(trifluoromethoxy)benzo[d]thiazol-2-yl)propanamide (53 mg, 0.15 mmol) and 2-N-(t-butyloxycarbonyl)amino-2-methylpropanoic acid (40 mg, 0.19 mmol). Yield=10 mg (15%, two steps). LC/MS method A: $R_t$=4.02 min., $(M+H)^+$=405.05.

Example 107: Synthesis of 3-amino-2,2-dimethyl-N-(2-methyl-1-oxo-1-((6-(trifluoromethoxy)benzo [d]thiazol-2-yl)amino)propan-2-yl)propanamide

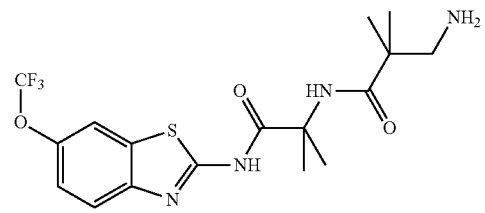 [SMILES: CC(C)(CN)C(=O)NC(C)(C)C(=O)Nc1nc2ccc(OC(F)(F)F)cc2s1]

3-amino-2,2-dimethyl-N-(2-methyl-1-oxo-1-((6-(trifluoromethoxy)benzo [d]thiazol-2-yl)amino)propan-2-yl)propanamide was prepared according to the procedure of example 49 from 2-amino-2-methyl-N-(6-(trifluoromethoxy)benzo[d]thiazol-2-yl)propanamide (53 mg, 0.15 mmol) and 3-N-(t-butyloxycarbonyl)amino-2,2-dimethylpropanoic acid (40 mg, 0.18 mmol). Yield=5.8 mg (8.5%, two steps). LC/MS method A: $R_t$=4.06 min., $(M+H)^+$=419.12.

Example 108: Synthesis of 1-(aminomethyl)-N-(2-methyl-1-oxo-1-((6-(trifluoro methoxy)benzo[d]thiazol-2-yl)amino)propan-2-yl)cyclopropane-1-carboxamide

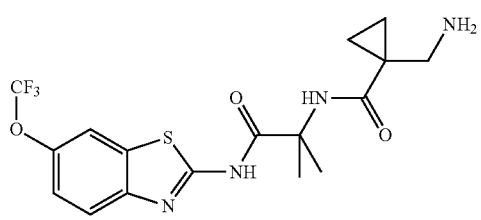 [SMILES: CC(C)(NC(=O)C1(CN)CC1)C(=O)Nc1nc2ccc(OC(F)(F)F)cc2s1]

1-(aminomethyl)-N-(2-methyl-1-oxo-1-((6-(trifluoromethoxy)benzo [d]thiazol-2-yl)amino)propan-2-yl)cyclopropane-1-carboxamide was prepared according to the procedure of example 49 from 2-amino-2-methyl-N-(6-(trifluoromethoxy)benzo[d]thiazol-2-yl)propanamide (53 mg, 0.15 mmol) and 1-((N-t-butyloxycarbonylamino)methyl)cyclopropanecarboxylic acid (39 mg, 0.18 mmol). Yield=20 mg (29%, two steps). LC/MS method A: $R_t$=4.05 min., $(M+H)^+$=417.09.

Example 109: Synthesis of 1-(aminomethyl)-N-(2-methyl-1-oxo-1-((6-(trifluoro methoxy)benzo[d]thiazol-2-yl)amino)propan-2-yl)cyclopentane-1-carboxamide

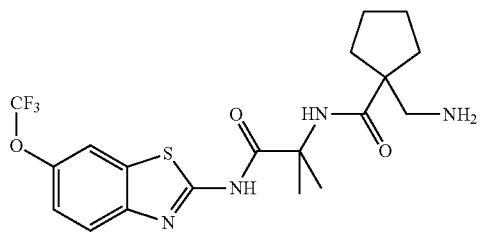 [SMILES: CC(C)(NC(=O)C1(CN)CCCC1)C(=O)Nc1nc2ccc(OC(F)(F)F)cc2s1]

1-(aminomethyl)-N-(2-methyl-1-oxo-1-((6-(trifluoromethoxy)benzo[d]thiazol-2-yl)amino) propan-2-yl)cyclopentane-1-carboxamide was prepared according to the procedure of example 49 from 2-amino-2-methyl-N-(6-(trifluoromethoxy)benzo[d]thiazol-2-yl)propanamide (53 mg, 0.15 mmol) and 1-((N-t-butyloxycarbonylamino)methyl)cyclopentanecarboxylic acid (44 mg, 0.18 mmol). Yield=8.0 mg (11%, two steps). LC/MS method A: $R_t$=4.24 min., $(M+H)^+$=445.17.

Example 110: Synthesis of 1-(aminomethyl)-N-(2-methyl-1-oxo-1-((6-(trifluoro methoxy)benzo[d]thiazol-2-371)amino)propan-2-yl)cyclohexane-1-carboxamide

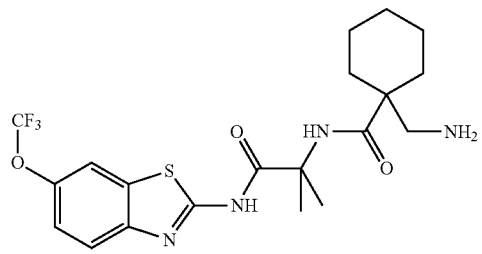 [SMILES: CC(C)(NC(=O)C1(CN)CCCCC1)C(=O)Nc1nc2ccc(OC(F)(F)F)cc2s1]

1-(aminomethyl)-N-(2-methyl-1-oxo-1-((6-(trifluoromethoxy)benzo[d]thiazol-2-yl)amino) propan-2-yl)cyclohexane-1-carboxamide was prepared according to the procedure of example 49 from 2-amino-2-methyl-N-(6-(trifluoromethoxy)benzo[d]thiazol-2-yl)propanamide (53 mg, 0.15 mmol) and 1-((N-t-butyloxycarbonyl)aminomethyl)cyclohexanecarboxylic acid (44 mg, 0.18 mmol). Yield=8.0 mg (11%, two steps). LC/MS method A: $R_t$=3.26 min., $(M+H)^+$=459.24.

Example 111: Synthesis of 2-methyl-2-(2-(methylamino)acetamido)-N-(6-(trifluoro methoxy)benzo[d]thiazol-2-yl)propanamide

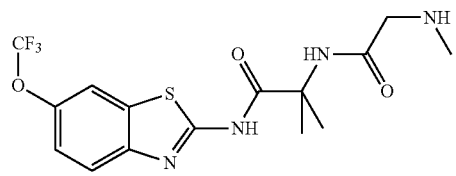 [SMILES: CNCC(=O)NC(C)(C)C(=O)Nc1nc2ccc(OC(F)(F)F)cc2s1]

2-methyl-2-(2-(methylamino)acetamido)-N-(6-(trifluoromethoxy)benzo[d]thiazol-2-yl)propanamide was prepared according to the procedure of example 49 from 2-amino-2-methyl-N-(6-(trifluoromethoxy)benzo[d]thiazol-2-yl)propanamide (53 mg, 0.15 mmol) and N-(t-butyloxycarbonyl)-N-methylglycine (34 mg, 0.18 mmol). Yield=25 mg (39%, two steps). LC/MS method A: $R_t$=3.99 min., $(M+H)^+$=391.05.

Example 112: Synthesis of 2-(2-(ethylamino)acetamido)-2-methyl-N-(6-(trifluoromethoxy)benzo[d]thiazol-2-yl)propanamide

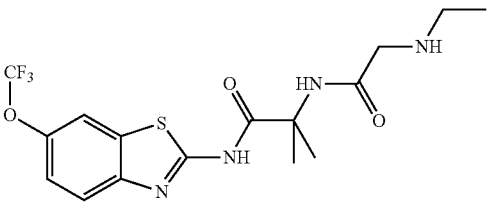 [SMILES: CCNCC(=O)NC(C)(C)C(=O)Nc1nc2ccc(OC(F)(F)F)cc2s1]

2-(2-(ethylamino)acetamido)-2-methyl-N-(6-(trifluoromethoxy)benzo[d]thiazol-2-yl) propanamide was prepared according to the procedure of example 49 from 2-amino-2-methyl-N-(6-(trifluoromethoxy)benzo[d]thiazol-2-yl)propanamide (53 mg, 0.15 mmol) and N-(t-butyloxycarbonyl)-N-ethylglycine (37 mg, 0.18 mmol). Yield=29 mg (44%, two steps). LC/MS method A: R$_f$=4.07 min., (M+H)$^+$=405.12.

Example 113: Synthesis of 2-(2-(isopropylamino)acetamido)-2-methyl-N-(6-(trifluoromethoxy)benzo[d]thiazol-2-yl)propanamide

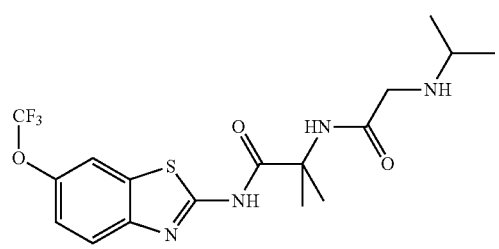 [SMILES: CC(C)NCC(=O)NC(C)(C)C(=O)Nc1nc2ccc(OC(F)(F)F)cc2s1]

2-(2-(isopropylamino)acetamido)-2-methyl-N-(6-(trifluoromethoxy)benzo[d]thiazol-2-yl)propanamide was prepared according to the procedure of example 49 from 2-amino-2-methyl-N-(6-(trifluoromethoxy)benzo[d]thiazol-2-yl)propanamide (53 mg, 0.15 mmol) and N-t-butyloxycarbonyl-N-isopropylglycine (39 mg, 0.18 mmol). Yield=29 mg (42%, two steps). LC/MS method A: R$_f$=4.17 min., (M+H)$^+$=419.12.

Example 114: Synthesis of 2-(2-(tert-butylamino)acetamido)-2-methyl-N-(6-(trifluoromethoxy)benzo[d]thiazol-2-yl)propanamide

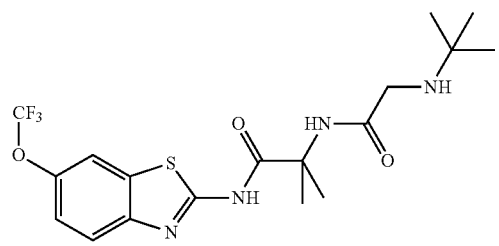 [SMILES: CC(C)(C)NCC(=O)NC(C)(C)C(=O)Nc1nc2ccc(OC(F)(F)F)cc2s1]

2-(2-(tert-butylamino)acetamido)-2-methyl-N-(6-(trifluoromethoxy)benzo[d]thiazol-2-yl)propanamide was prepared according to the procedure of example 49 from 2-amino-2-methyl-N-(6-(trifluoromethoxy)benzo[d]thiazol-2-yl)propanamide (53 mg, 0.15 mmol) and N-t-butyloxycarbonyl-N-t-butyl glycine (39 mg, 0.18 mmol). Yield=18 mg (22%, two steps). LC/MS method A: R$_f$=4.26 min., (M+H)$^+$=433.13

Example 115: Synthesis of (S)-2-(2-aminoacetamido)-N-(6-(trifluoromethoxy) benzo[d]thiazol-2-yl)propanamide

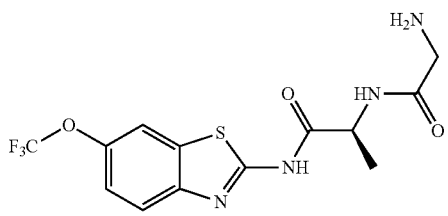 [SMILES: C[C@H](NC(=O)CN)C(=O)Nc1nc2ccc(OC(F)(F)F)cc2s1]

(S)-2-(2-aminoacetamido)-N-(6-(trifluoromethoxy)benzo[d]thiazol-2-yl)propanamide was prepared according to the procedure of example 49 from (S)-2-amino-N-(6-(trifluoromethoxy) benzo[d]thiazol-2-yl)propanamide (50 mg, 0.146 mmol) and N-t-butyloxycarbonylglycine (33 mg, 0.19 mmol). Yield=35 mg (50%, two steps). LC/MS method A: R$_f$=3.73 min., (M+H)$^+$=362.98.

Example 116: Synthesis of (S)-2-amino-N—((S)-1-oxo-1-((6-(trifluoromethoxy)benzo[d]thiazol-2-yl)amino)propan-2-yl)propanamide

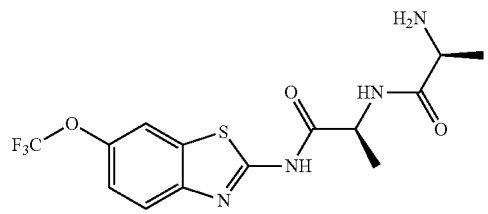 [SMILES: C[C@H](N)C(=O)N[C@@H](C)C(=O)Nc1nc2ccc(OC(F)(F)F)cc2s1]

(S)-2-amino-N—((S)-1-oxo-1-((6-(trifluoromethoxy)benzo[d]thiazol-2-yl)amino)propan-2-yl)propanamide was prepared according to the procedure of example 49 from (S)-2-amino-N-(6-(trifluoromethoxy) benzo[d]thiazol-2-yl)propanamide (50 mg, 0.146 mmol) and N-t-butyloxycarbonylalanine (41 mg, 0.22 mmol). Yield=38 mg (53%, two steps). LC/MS method A: R$_f$=3.76 min., (M+Na)$^+$=398.93.

Example 117: Synthesis of (R)-2-amino-N—((S)-1-oxo-1-((6-(trifluoromethoxy)benzo[d] thiazol-2-yl)amino)propan-2-yl)propanamide

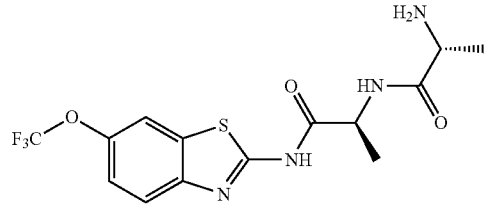 [SMILES: C[C@H](NC(=O)[C@@H](C)N)C(=O)Nc1nc2ccc(OC(F)(F)F)cc2s1]

(R)-2-amino-N—((S)-1-oxo-1-((6-(trifluoromethoxy)benzo[d]thiazol-2-yl)amino)propan-2-yl)propanamide was prepared according to the procedure of example 49 from (S)-2-amino-N-(6-(trifluoromethoxy) benzo[d]thiazol-2-yl)propanamide (50 mg, 0.146 mmol) and N-t-butyloxycarbonyl-D-alanine (41 mg, 0.22 mmol). Yield=23 mg (32%, two steps). LC/MS method A: $R_t$=3.76 min., (M+H)$^+$=376.98.

Example 118: Synthesis of 3-Amino-N,2,2-trimethyl-N-(2-oxo-2-((6-(trifluoromethoxy)benzo[d]thiazol-2-yl)amino)ethyl)propanamide

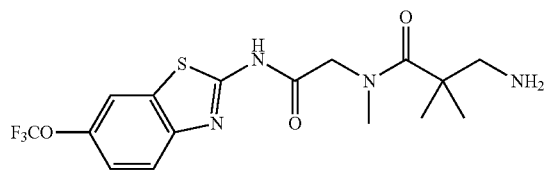 [SMILES: CN(CC(=O)Nc1nc2ccc(OC(F)(F)F)cc2s1)C(=O)C(C)(C)CN]

A solution of 2-(methylamino)-N-(6-(trifluoromethoxy) benzo[d]thiazol-2-yl)acetamide hydrochloride (25 mg, 73 µmol), 3-((tert-butoxycarbonyl)amino)-2,2-dimethylpropanoic acid (19 mg, 88 µmol) and N,N-diisopropylethylamine (24 mg, 180 µmol, 33 µl) in N,N-dimethylformamide (0.5 ml) was treated with 1-[Bis(dimethylamino)methylene]-1H-1,2,3-triazolo[4,5-b]pyridinium 3-oxid hexafluorophosphate (33 mg, 88 µmol) and stirred for 18 hours. The product was purified by reversed phase HPLC (method B, direct injection). The product was evaporated on a Genevac evaporator to leave 36 mg (81%). The purified product was dissolved in 4N HCl/1,4-dioxane (0.5 ml) and stirred for 2 hours. The HCl/1,4-dioxane was evaporated to leave the product as a white solid, mono HCl salt. Yield=33 mg (100%, 81% for two steps). LC/MS method A: $R_t$=3.88 min., (M+H)$^+$=405.

Examples 119-125 were prepared under identical scale and method as example 118 above:

Example 119: Synthesis of 1-(aminomethyl)-N-methyl-N-(2-oxo-2-((6-(trifluoromethoxy)benzo[d]thiazol-2-yl)amino)ethyl)cyclopropane-1-carboxamide

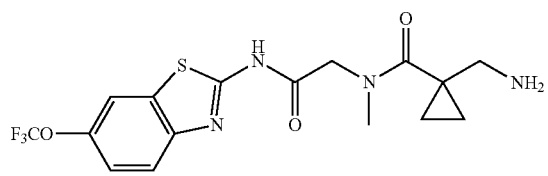 [SMILES: CN(CC(=O)Nc1nc2ccc(OC(F)(F)F)cc2s1)C(=O)C1(CN)CC1]

1-(aminomethyl)-N-methyl-N-(2-oxo-2-((6-(trifluoromethoxy)benzo[d]thiazol-2-yl) amino)ethyl)cyclopropane-1-carboxamide was prepared according to the procedure of example 118 from 1-(((tert-butoxycarbonyl)amino) methyl)cyclopropane-1-carboxylic acid (19 mg, 88 µmol). Yield=31 mg (98%, 80% for two steps). LC/MS method A: $R_t$=3.81 min., (M+H)$^+$=403.

Example 120: Synthesis of 1-(aminomethyl)-N-methyl-N-(2-oxo-2-((6-(trifluoro methoxy)benzo[d]thiazol-2-yl)amino)ethyl)cyclopentane-1-carboxamide

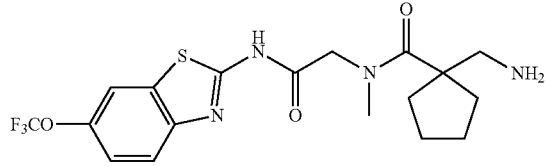 [SMILES: CN(CC(=O)Nc1nc2ccc(OC(F)(F)F)cc2s1)C(=O)C1(CN)CCCC1]

1-(aminomethyl)-N-methyl-N-(2-oxo-2-((6-(trifluoromethoxy)benzo [d]thiazol-2-yl) amino)ethyl)cyclopentane-1-carboxamide was prepared according to the procedure of example 118 from 1-(((tert-butoxycarbonyl)amino) methyl)cyclopentane-1-carboxylic acid (21 mg, 88 µmol). Yield=33 mg (100%, 77% for two steps). LC/MS method A: $R_t$=4.07 min., (M+H)$^+$=431.

Example 121: Synthesis of 1-(aminomethyl)-N-methyl-N-(2-oxo-2-((6-(trifluoro methoxy)benzo[d]thiazol-2-yl)amino)ethyl)cyclohexane-1-carboxamide

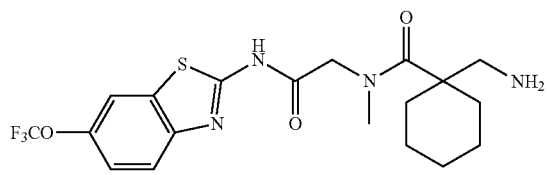 [SMILES: CN(CC(=O)Nc1nc2ccc(OC(F)(F)F)cc2s1)C(=O)C1(CN)CCCCC1]

1-(aminomethyl)-N-methyl-N-(2-oxo-2-((6-(trifluoromethoxy)benzo [d]thiazol-2-yl) amino)ethyl)cyclohexane-1-carboxamide was prepared according to the procedure of example 118 from 1-(((tert-butoxycarbonyl) amino)methyl)cyclohexane-1-carboxylic acid (23 mg, 88 µmol). Yield=23 mg (100%, 48% for two steps). LC/MS method A: $R_t$=4.21 min., (M+H)$^+$=445.

Example 122: Synthesis of N-methyl-2-(methylamino)-N-(2-oxo-2-((6-(trifluoro methoxy)benzo[d]thiazol-2-yl)amino)ethyl)acetamide

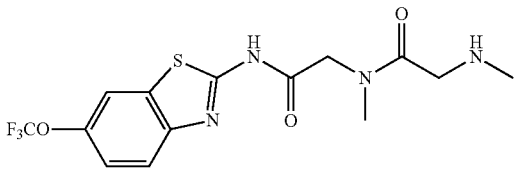 [SMILES: CNCC(=O)N(C)CC(=O)Nc1nc2ccc(OC(F)(F)F)cc2s1]

N-methyl-2-(methylamino)-N-(2-oxo-2-((6-(trifluoromethoxy)benzo[d]thiazol-2-yl) amino)acetamide was prepared according to the procedure of example 118 from N-(tert-butoxycarbonyl)-N-methylglycine (17 mg, 88 µmol). Yield=30 mg (100%, 86% for two steps). LC/MS method A: $R_t$=3.70 min., (M+H)$^+$=377.

Example 123: Synthesis of 2-(ethylamino)-N-methyl-N-(2-oxo-2-((6-(trifluoro methoxy)benzo[d]thiazol-2-yl)amino)ethyl)acetamide

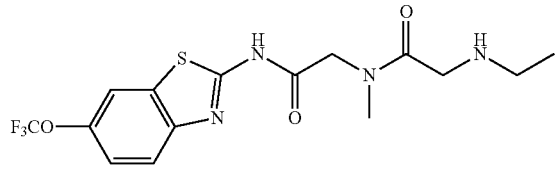 [SMILES: CCNCC(=O)N(C)CC(=O)Nc1nc2ccc(OC(F)(F)F)cc2s1]

2-(ethylamino)-N-methyl-N-(2-oxo-2-((6-(trifluoromethoxy)benzo [d]thiazol-2-yl)amino) ethyl)acetamide was prepared according to the procedure of example 118 from N-(tert-butoxycarbonyl)-N-ethylglycine (18 mg, 88 µmol). Yield=32 mg (100%, 86% for two steps). LC/MS method A: $R_f$=3.78 min., (M+H)$^+$=391.

Example 124: Synthesis of 2-(isopropylamino)-N-methyl-N-(2-oxo-2-((6-(trifluoro methoxy)benzo[d]thiazol-2-yl)amino)ethyl)acetamide

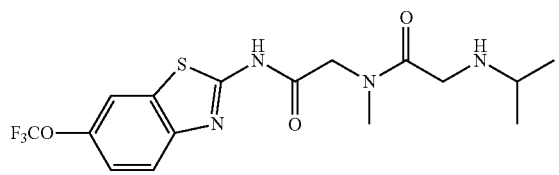 [SMILES: CC(C)NCC(=O)N(C)CC(=O)Nc1nc2ccc(OC(F)(F)F)cc2s1]

2-(isopropylamino)-N-methyl-N-(2-oxo-2-((6-(trifluoromethoxy)benzo [d]thiazol-2-yl)amino)ethyl)acetamide was prepared according to the procedure of example 118 from N-(tert-butoxycarbonyl)-N-isopropylglycine (19 mg, 88 µmol). Yield=34 mg (100%, 81% for two steps). LC/MS method A: $R_f$=3.88 min., (M+H)$^+$=405.

Example 125: Synthesis of 2-(tert-butylamino)-N-methyl-N-(2-oxo-2-((6-(trifluoromethoxy)benzo[d]thiazol-2-yl)amino)ethyl)acetamide

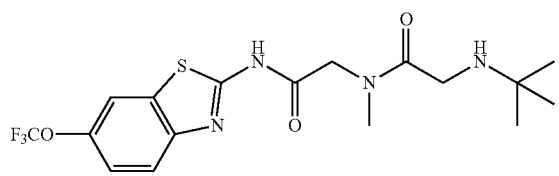 [SMILES: CN(CC(=O)Nc1nc2ccc(OC(F)(F)F)cc2s1)C(=O)CNC(C)(C)C]

2-(tert-butylamino)-N-methyl-N-(2-oxo-2-((6-(trifluoromethoxy)benzo[d]thiazol-2-yl)amino)ethyl)acetamide was prepared according to the procedure of example 118 from N-(tert-butoxycarbonyl)-N-tert-butylglycine (20 mg, 88 µmol). Yield=29 mg (100%, 68% for two steps). LC/MS method A: $R_f$=3.99 min., (M+H)$^+$=419.

Example 126: Synthesis of 2-(dimethylamino)-N-methyl-N-(2-oxo-2-((6-(trifluoro methoxy)benzo[d]thiazol-2-yl)amino)ethyl)acetamide

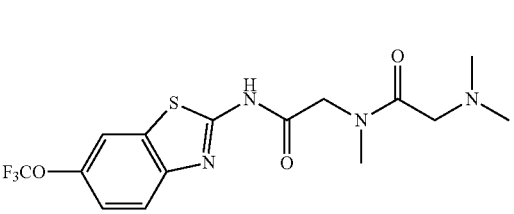 [SMILES: CN(C)CC(=O)N(C)CC(=O)Nc1nc2ccc(OC(F)(F)F)cc2s1]

2-(dimethyl amino)-N-methyl-N-(2-oxo-2-((6-(trifluoromethoxy)benzo [d]thiazol-2-yl) amino)ethyl)acetamide was prepared according to the procedure of example 49 from 2-(methylamino)-N-(6-(trifluoromethoxy)benzo[d]thiazol-2-yl)acetamide hydrochloride (50 mg, 0.16 mmol) and N,N-dimethylglycine hydrochloride (25 mg, 0.18 mmol). Purified by reverse phase HPLC to leave the product as a mono TFA salt. Yield=64 mg (79%). LC/MS method B: $R_f$=1.41 min., (M+H)$^+$=391.

Example 127: Synthesis of 2-amino-N-methyl-N-(2-oxo-2-((6-(trifluoromethoxy) benzo[d]thiazol-2-yl)amino)ethyl)acetamide

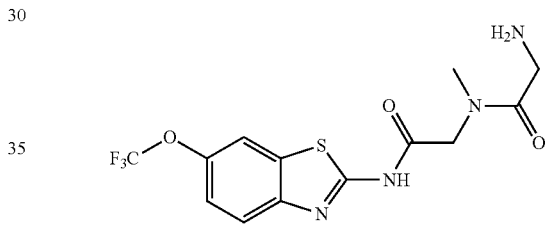

2-amino-N-methyl-N-(2-oxo-2-((6-(trifluoromethoxy) benzo [d]thiazol-2-yl)amino)ethyl) acetamide was prepared according to the procedure of example 49 from 2-(methylamino)-N-(6-(trifluoromethoxy)benzo[d]thiazol-2-yl)acetamide hydrochloride (50 mg, 0.16 mmol) and N-(tert-butoxycarbonyl)glycine (36 mg, 0.21 mmol). Yield=38 mg (65%, two steps). LC/MS method A: $R_f$=3.64 min., (M+H)$^+$=362.98.

Example 128: Synthesis of (S)-2-amino-N-methyl-N-(2-oxo-2-((6-(trifluoromethoxy) benzo[d]thiazol-2-yl)amino)ethyl)propanamide

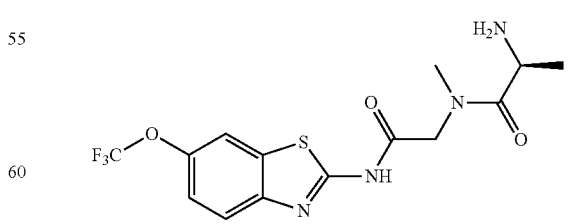

(S)-2-amino-N-methyl-N-(2-oxo-2-((6-(trifluoromethoxy)benzo [d]thiazol-2-yl)amino) ethyl)propanamide was prepared according to the procedure of example 49 from 2-(methylamino)-N-(6-(trifluoromethoxy)benzo [d]thiazol- 2-yl)acetamide hydrochloride (50 mg, 0.16 mmol) and N-(tert-butoxycarbonyl)alanine (41 mg, 0.22 mmol). Yield=45 mg (75%, two steps). LC/MS method A: $R_t$=3.76 min., $(M+Na)^+$=398.93.

Example 129: Synthesis of (R)-2-amino-N-methyl-N-(2-oxo-2-((6-(trifluoromethoxy)benzo[d]thiazol-2-yl)amino)ethyl)propanamide

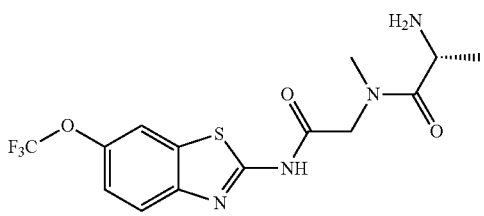 [SMILES: C[C@@H](N)C(=O)N(C)CC(=O)Nc1nc2ccc(OC(F)(F)F)cc2s1]

(R)-2-amino-N-methyl-N-(2-oxo-2-((6-(trifluoromethoxy)benzo[d]thiazol-2-yl)amino) ethyl)propanamide was prepared according to the procedure of example 49 from 2-(methylamino)-N-(6-(trifluoromethoxy)benzo[d]thiazol-2-yl)acetamide hydrochloride (50 mg, 0.16 mmol) and N-(tert-butoxycarbonyl)-D-alanine (41 mg, 0.22 mmol). Yield=45 mg (75%, two steps). LC/MS method A: $R_t$=3.76 min., $(M+Na)^+$=398.93.

Example 130: Synthesis of 3-amino-N-methyl-N-(2-oxo-2-((6-(trifluoromethoxy)benzo [d]thiazol-2-yl)amino)ethyl)propanamide

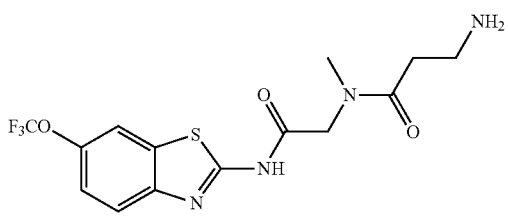 [SMILES: CN(CC(=O)Nc1nc2ccc(OC(F)(F)F)cc2s1)C(=O)CCN]

3-amino-N-methyl-N-(2-oxo-2-((6-(trifluoromethoxy)benzo[d]thiazol-2-yl)amino)ethyl) propanamide was prepared according to the procedure of example 49 from 2-(methylamino)-N-(6-(trifluoromethoxy)benzo[d]thiazol-2-yl)acetamide hydrochloride (34 mg, 0.10 mmol) and N-(tert-butoxycarbonyl)-beta-alanine (33 mg, 0.17 mmol). Yield=35 mg (58%, two steps). LC/MS method A: $R_t$=3.69 min., $(M+H)^+$=376.91.

Example 131: Synthesis of 2-amino-N-ethyl-N-(2-oxo-2-((6-(trifluoromethoxy)benzo [d]thiazol-2-yl)amino)ethyl)acetamide

2-amino-N-ethyl-N-(2-oxo-2-((6-(trifluoromethoxy)benzo [d]thiazol-2-yl)amino)ethyl) acetamide was prepared according to the procedure of example 49 from 2-(ethylamino)-N-(6-(trifluoromethoxy)benzo [d]thiazol-2-yl)acetamide hydrochloride (35 mg, 0.10 mmol) and N-(tert-butoxycarbonyl)glycine (23 mg, 0.13 mmol). Yield=32 mg (77%, two steps). LC/MS method A: $R_t$=3.76 min., $(M+H)^+$=376.98.

Example 132: Synthesis of 2-amino-N-isopropyl-N-(2-oxo-2-((6-(trifluoromethoxy) benzo[d]thiazol-2-yl)amino)ethyl)acetamide

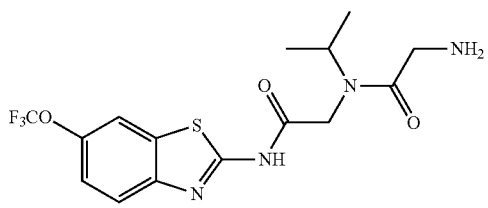 [SMILES: CC(C)N(CC(=O)Nc1nc2ccc(OC(F)(F)F)cc2s1)C(=O)CN]

2-amino-N-isopropyl-N-(2-oxo-2-((6-(trifluoromethoxy)benzo[d]thiazol-2-yl)amino) ethyl)acetamide was prepared according to the procedure of example 49 from 2-(isopropylamino)-N-(6-(trifluoromethoxy)benzo [d]thiazol-2-yl)acetamide hydrochloride (37 mg, 0.10 mmol) and N-(tert-butoxycarbonyl)glycine (23 mg, 0.13 mmol). Yield=32 mg (75%, two steps). LC/MS method A: $R_t$=3.88 min., $(M+H)^+$=390.91.

Example 133: Synthesis of 2-(aminomethyl)-N-(6-(trifluoromethoxy)benzo[d]thiazol-2-yl)benzamide

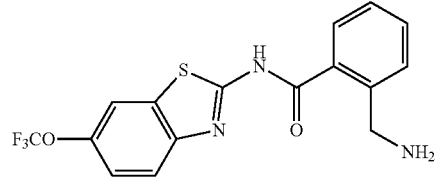 [SMILES: NCc1ccccc1C(=O)Nc1nc2ccc(OC(F)(F)F)cc2s1]

A solution of 2-amino-6-(trifluoromethoxy)benzo[d]thiazole (100 mg, 0.43 mmol), 2-N-((tert-butoxy carbonyl)aminomethyl)benzoic acid (161 mg, 0.64 mmol) and N,N-diisopropyl ethylamine (83 mg, 0.64 mmol, 115 µl) in N,N-dimethylformamide (2 ml) was treated with 1-[B is (dimethylamino) methylene]-1H-1,2,3-triazolo[4,5-b]pyridinium 3-oxid hexafluorophosphate (243 mg, 0.64 mmol) and stirred for 72 hours. The reaction mixture was diluted with ethyl acetate (50 ml), washed with water (2×25 ml) and 1N HCl (25 ml). The solvents were evaporated and the residue was chromatographed on silica gel eluted with a gradient of 10% ethyl acetate in hexanes to 50% ethyl acetate in hexanes. The product (87 mg, 43%) was dissolved in 4N HCl/1,4-dioxane, stirred for 2 hours then evaporated to dryness. The white powdery mono hydrochloride product weighed 77 mg (100%, 43% for two steps). LC/MS method A: $R_t$=3.97 min., $(M+H)^+$=368.

Example 134: Synthesis of tert-butyl (4-oxo-4-((6-(trifluoromethoxy)benzo[d]thiazol-2-yl)amino)butyl) carbamate

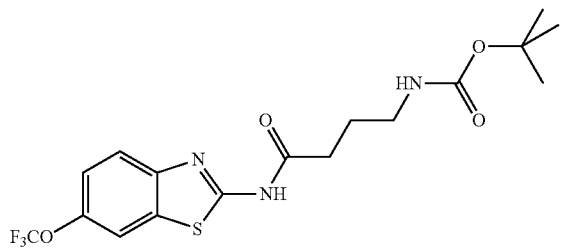 [SMILES: CC(C)(C)OC(=O)NCCCC(=O)Nc1nc2ccc(OC(F)(F)F)cc2s1]

A solution of 2-amino-6-(trifluoromethoxy)benzo[d]thiazole (2.0 g, 8.5 mmol), N-(tert-butyloxycarbonyl)-4-aminobutyric acid (2.6 g, 12.8 mmol) and N,N-diisopropylethylamine (1.7 g, 12.8 mmol, 2.3 ml) in N,N-dimethylformamide (40 ml) was treated with 1-[Bis(dimethylamino) methylene]-1H-1,2,3-triazolo[4,5-b]pyridinium 3-oxid hexafluorophosphate (4.9 g, 12.8 mmol) and stirred for 18 h. Ethyl acetate (200 ml) was added to the reaction mixture and it was washed with water (2×150 ml), 1N HCl (2×100 ml), saturated aqueous sodium bicarbonate (100 ml) and brine (100 ml). The organic layer was dried (Na$_2$SO$_4$) and evaporated to leave a light yellow crystalline solid (2.9 g, 81%). LC/MS method A: R$_t$=5.88 min., (M+H)$^+$=420.42.

Synthesis of 4-amino-N-(6-(trifluoromethoxy)benzo[d]thiazol-2-yl)butanamide

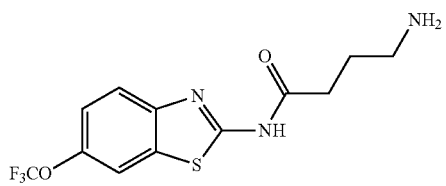 [SMILES: NCCCC(=O)Nc1nc2ccc(OC(F)(F)F)cc2s1]

A solution of tert-butyl (4-oxo-4-((6-(trifluoromethoxy)benzo[d]thiazol-2-yl)amino)butyl) carbamate (2.8 g, 6.7 mmol) in 1,4-dioxane (35 ml) and 4N HCl/1,4-dioxane (35 ml) was stirred for 18 h. The white precipitate was filtered on a medium glass frit and washed with 1,4-dioxane and ether. The solid was dried under vacuum to leave 2.55 g (97%). LC/MS method A: R$_t$=3.68 min., (M+H)$^+$=320.30.

Synthesis of (S)—N-(4-oxo-4-((6-(trifluoromethoxy)benzo[d]thiazol-2-yl)amino)butyl) pyrrolidine-2-carboxamide

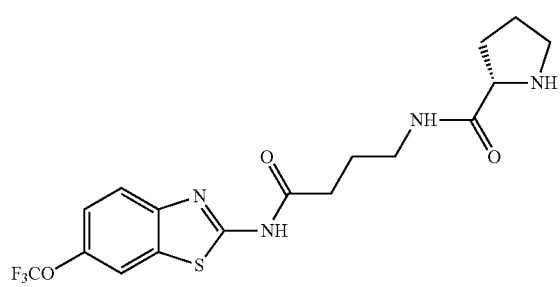 [SMILES: O=C(CCCNC(=O)[C@@H]1CCCN1)Nc1nc2ccc(OC(F)(F)F)cc2s1]

A solution of 4-amino-N-(6-(trifluoromethoxy)benzo[d]thiazol-2-yl)butanamide (25 mg, 65 μmop and N,N-diisopropylethylamine (17 mg, 0.13 mmol, 23 μl) in N,N-dimethylformamide (0.5 ml) was treated with 1-(tert-butyl) 2-(2,5-dioxopyrrolidin-1-yl) (S)-pyrrolidine-1,2-dicarboxylate (22 mg, 70 μmol) and stirred 18 h. The product was purified by direct injection reverse phase HPLC (method B) and the product fractions were evaporated on a Genevac evaporator to leave the product as a gum (29 mg) which was dissolved in 1,4-dioxane (1 ml) and 4N HCl/1,4-dioxane (1 ml). After stirring for 4 h the solvents were evaporated to leave the product as a white solid (26 mg, 83%). LC/MS method A: R$_t$=3.85 min., (M+H)$^+$=417.

Example 135: Synthesis of (S)-2-amino-4-methyl-N-(4-oxo-4-((6-(trifluoromethoxy) benzo[d]thiazol-2-yl)amino)butyl)pentanamide

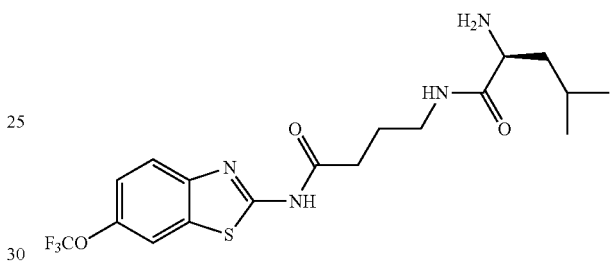

A solution of 4-amino-N-(6-(trifluoromethoxy)benzo[d]thiazol-2-yl)butanamide (25 mg, 65 μmol) and N,N-diisopropylethylamine (17 mg, 0.13 mmol, 23 μl) in N,N-dimethylformamide (0.5 ml) was treated with 2,5-dioxopyrrolidin-1-yl (tert-butoxycarbonyl)-L-leucinate (23 mg, 70 μmol) and stirred 18 h. The product was purified by direct injection reverse phase HPLC (method B) and the product fractions were evaporated on a Genevac evaporator to leave the product as a gum (29 mg) which was dissolved in 1,4-dioxane (1 ml) and 4N HCl/1,4-dioxane (1 ml). After stirring for 4 h the solvents were evaporated to leave the product as a white solid (28 mg, 87%). LC/MS method A: R$_t$=4.14 min., (M+H)$^+$=433.

Example 136: Synthesis of 4-(2-aminoacetamido)-N-(6-(trifluoromethoxy)benzo[d] thiazol-2-yl)butanamide

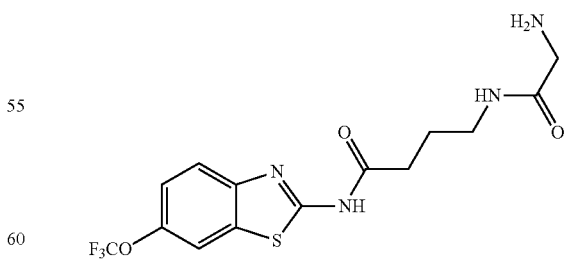

A solution of 4-amino-N-(6-(trifluoromethoxy)benzo[d]thiazol-2-yl)butanamide (25 mg, 65 μmop, N-(tert-butoxycarbonyl)-L-glycine (13 mg, 76 μmol) and N,N-diisopropylethylamine (18 mg, 0.14 mmol, 25 μl) in N,N-dimethylformamide (0.5 ml) was treated with 1-[Bis (dimethylamino)methylene]-1H-1,2,3-triazolo[4,5-b]pyridinium 3-oxid hexafluorophosphate (27 mg, 70 μmol) and stirred 18 hours. The product was purified by direct injection reverse phase HPLC (method B) and the product fractions were evaporated on a Genevac evaporator to leave the product as a gum (17 mg, 54%) which was dissolved in 1,4-dioxane (1 ml) and 4N HCl/1,4-dioxane (1 ml). After stirring for 4 hours the solvents were evaporated to leave the product as a white solid (12 mg, 46% for two steps). LC/MS method A: $R_t$=3.71 min., $(M+H)^+$=377. Examples 137-146 were prepared in identical scale and method to example 136 above.

Example 137: Synthesis of (S)-4-(2-aminopropanamido)-N-(6-(trifluoromethoxy)benzo [d]thiazol-2-yl)butanamide

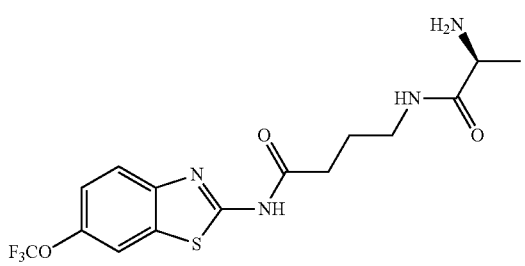 [SMILES: C[C@H](N)C(=O)NCCCC(=O)Nc1nc2ccc(OC(F)(F)F)cc2s1]

(S)-4-(2-aminopropanamido)-N-(6-(trifluoromethoxy)benzo[d]thiazol-2-yl)butanamide was prepared according to the procedure of example 136 from 4-amino-N-(6-(trifluoromethoxy) benzo[d]thiazol-2-yl)butanamide (25 mg, 65 μmol) and N-(tert-butoxycarbonyl)-L-alanine to leave 16 mg (59% for two steps). LC/MS method A: $R_t$=3.75 min., $(M+H)^+$=391.

Example 138: Synthesis of (S)-2-amino-3-methyl-N-(4-oxo-4-((6-(trifluoromethoxy) benzo[d]thiazol-2-yl)amino)butyl)butanamide

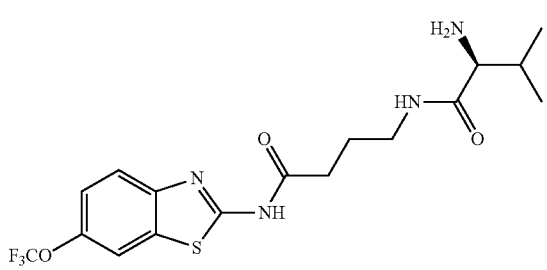 [SMILES: CC(C)[C@H](N)C(=O)NCCCC(=O)Nc1nc2ccc(OC(F)(F)F)cc2s1]

(S)-2-amino-3-methyl-N-(4-oxo-4-((6-(trifluoromethoxy)benzo[d]thiazol-2-yl)amino) butyl)butanamide was prepared according to the procedure of example 136 from 4-amino-N-(6-(trifluoromethoxy)benzo[d]thiazol-2-yl)butanamide (25 mg, 65 μmol) and N-(tert-butoxy carbonyl)-L-Valine to leave 16 mg (59% for two steps). LC/MS method A: $R_t$=3.95 min., $(M+H)^+$=419.

Example 139: Synthesis of (S)-5-oxo-N-(4-oxo-4-((6-(trifluoromethoxy)benzo[d]thiazol-2-yl)amino)butyl)pyrrolidine-2-carboxamide

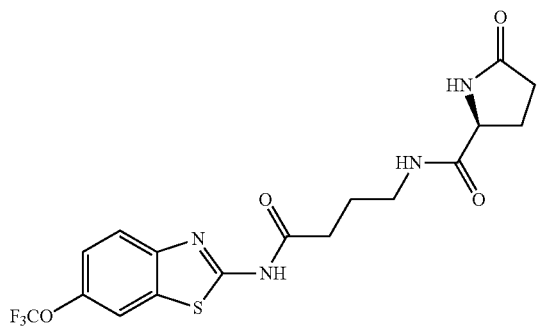 [SMILES: O=C(CCCNC(=O)[C@@H]1CCC(=O)N1)Nc1nc2ccc(OC(F)(F)F)cc2s1]

(S)-5-oxo-N-(4-oxo-4-((6-(trifluoromethoxy)benzo[d]thiazol-2-yl)amino)butyl)pyrrolidine-2-carboxamide was prepared according to the procedure of example 136 from 4-amino-N-(6-(trifluoromethoxy)benzo[d]thiazol-2-yl)butanamide (25 mg, 65 μmol) and L-pyroglutamate to leave 14 mg (47% for two steps). LC/MS method A: $R_t$=4.22 min., $(M+H)^+$=431.

Example 140: Synthesis of (2S,3S)-2-amino-3-methyl-N-(4-oxo-4-((6-(trifluoro methoxy)benzo[d]thiazol-2-yl)amino)butyl)pentanamide

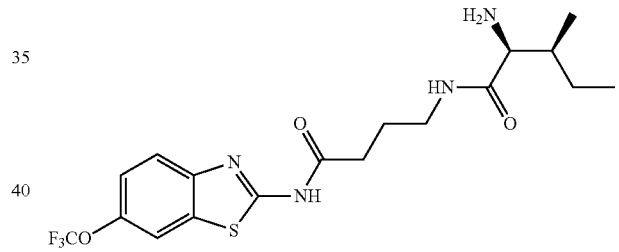

(2S,3S)-2-amino-3-methyl-N-(4-oxo-4-((6-(trifluoromethoxy)benzo [d]thiazol-2-yl)amino) butyl)pentanamide was prepared according to the procedure of example 136 from 4-amino-N-(6-(trifluoromethoxy)benzo[d]thiazol-2-yl)butanamide (25 mg, 65 μmol) and N-(tert-butoxy carbonyl)-L-isoleucine to leave 14 mg (47% for two steps). LC/MS method A: $R_t$=4.11 min., $(M+H)^+$=433.

Example 141: Synthesis of (S)-4-amino-5-oxo-5-((4-oxo-4-((6-(trifluoromethoxy)benzo [d]thiazol-2-yl)amino)butyl)amino)pentanoic Acid

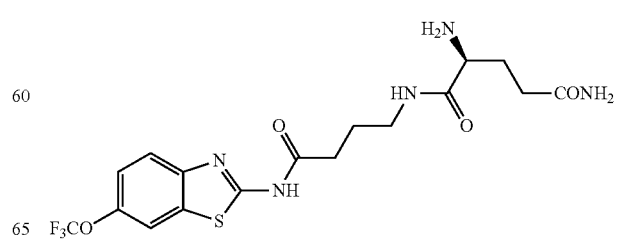

(S)-4-amino-5-oxo-5-((4-oxo-4-((6-(trifluoromethoxy) benzo[d]thiazol-2-yl)amino)butyl) amino)pentanoic acid was prepared according to the procedure of example 136 from 4-amino-N-(6-(trifluoromethoxy)benzo[d]thiazol-2-yl)butanamide (25 mg, 65 μmol) and N-(tert-butoxycarbonyl)-L-glutamine to leave 16 mg (52% for two steps). LC/MS method A: $R_t$=3.62 min. $(M+H)^+$=448.

Example 142: Synthesis of (S)-2-amino-4-(methyl-thio)-N-(4-oxo-4-((6-(trifluoro methoxy)benzo[d]thiazol-2-yl)amino)butyl)butanamide

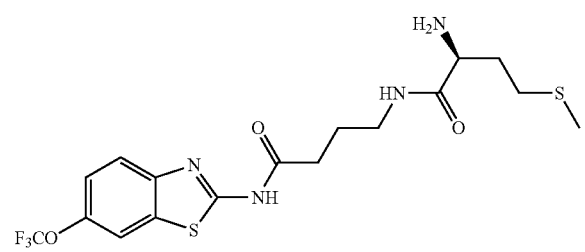 [SMILES: CSCC[C@H](N)C(=O)NCCCC(=O)Nc1nc2ccc(OC(F)(F)F)cc2s1]

(S)-2-amino-4-(methylthio)-N-(4-oxo-4-((6-(trifluoromethoxy)benzo[d]thiazol-2-yl) amino)butyl)butanamide was prepared according to the procedure of example 136 from 4-amino-N-(6-(trifluoromethoxy)benzo[d]thiazol-2-yl)butanamide (25 mg, 65 μmol) and N-(tert-butoxycarbonyl)-L-methionine to leave 16 mg (51% for two steps). LC/MS method A: $R_t$=4.02 min., $(M+H)^+$=451.

Example 143: (S)-4-(2-amino-3-phenylpropanamido)-N-(6-(trifluoromethoxy)benzo [d]thiazol-2-yl)butanamide

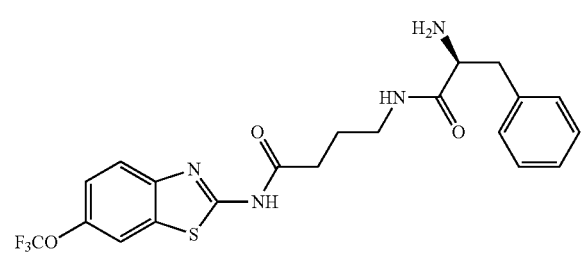 [SMILES: N[C@@H](Cc1ccccc1)C(=O)NCCCC(=O)Nc1nc2ccc(OC(F)(F)F)cc2s1]

(S)-4-(2-amino-3-phenylpropanamido)-N-(6-(trifluoromethoxy)benzo[d]thiazol-2-yl)butanamide was prepared according to the procedure of example 136 from 4-amino-N-(6-(trifluoromethoxy)benzo[d]thiazol-2-yl)butanamide (25 mg, 65 μmol) and N-(tert-butoxycarbonyl)-L-phenylalanine to leave 16 mg (50% for two steps). LC/MS method A: $R_t$=4.20 min., $(M+H)^+$=467.

Example 144: Synthesis of (S)-3-amino-4-oxo-4-((4-oxo-4-((6-(trifluoromethoxy)benzo [d]thiazol-2-yl)amino)butyl)amino)butanoic Acid

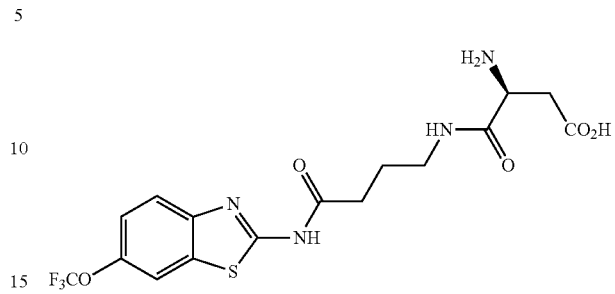

(S)-3-amino-4-oxo-4-((4-oxo-4-((6-(trifluoromethoxy) benzo[d]thiazol-2-yl)amino)butyl) amino)butanoic acid was prepared according to the procedure of example 136 from 4-amino-N-(6-(trifluoromethoxy)benzo[d]thiazol-2-yl)butanamide (25 mg, 65 μmol) and N-(tert-butoxycarbonyl)-aspartic acid beta tert-butyl ester to leave 18 mg (60% for two steps). LC/MS method A: $R_t$=3.72 min., $(M+H)^+$=435.

Example 145: Synthesis of (S)-4-amino-5-oxo-5-((4-oxo-4-((6-(trifluoromethoxy) benzo[d]thiazol-2-yl)amino)butyl)amino)pentanoic Acid

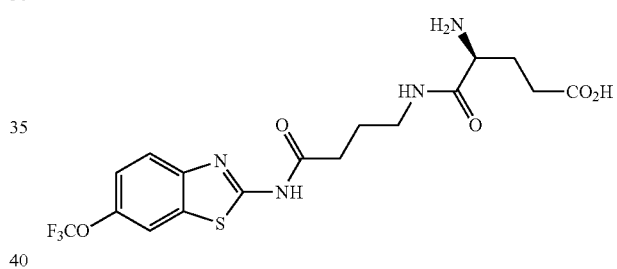

(S)-4-amino-5-oxo-5-((4-oxo-4-((6-(trifluoromethoxy) benzo[d]thiazol-2-yl)amino)butyl) amino)pentanoic acid was prepared according to the procedure of example 136 from 4-amino-N-(6-(trifluoromethoxy)benzo[d]thiazol-2-yl)butanamide (25 mg, 65 μmol) and N-(tert-butoxy carbonyl)-L-glutamine gamma tert butyl ester to leave 16 mg (52% for two steps). LC/MS method A: $R_t$=3.72 min., $(M+H)^+$=449.

Example 146: Synthesis of (S)-4-(2-amino-3-(1H-indol-3-yl)propanamido)-N-(6-(trifluoromethoxy) benzo[d]thiazol-2-yl)butanamide

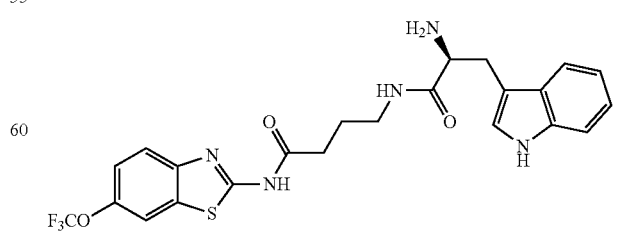

(S)-4-(2-amino-3-(1H-indol-3-yl)propanamido)-N-(6-(trifluoromethoxy)benzo [d] thiazol-2-yl)butanamide was prepared according to the procedure of example 136 from 4-amino-N-(6-(trifluoromethoxy)benzo[d]thiazol-2-yl)butanamide (25 mg, 65 µmol) and N-(tert-butoxy carbonyl)-L-tryptophan to leave 20 mg (71% for two steps). LC/MS method A: $R_t$=4.24 min., (M+H)$^+$=506.

Example 147: Synthesis of (S)—N-((1-(2-oxo-2-((6-(trifluoromethoxy)benzo[d]thiazol-2-yl)amino) ethyl)cyclohexyl)methyl)pyrrolidine-2-carboxamide Synthesis of tert-butyl ((1-(2-oxo-2-((6-(trifluoromethoxy)benzo[d] thiazol-2-yl)amino)ethyl)cyclohexyl)methyl)carbamate

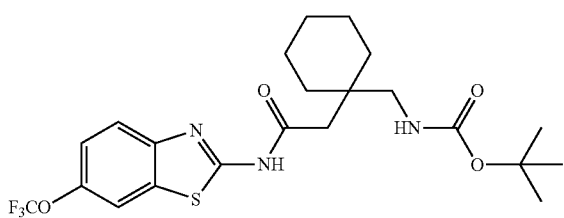 [SMILES: CC(C)(C)OC(=O)NCC1(CC(=O)Nc2nc3ccc(OC(F)(F)F)cc3s2)CCCCC1]

A solution of 2-amino-6-(trifluoromethoxy)benzo[d]thiazole (0.50 g, 2.1 mmol), 2-(1-(((tert-butoxycarbonyl)amino)methyl)cyclohexyl)acetic acid (0.74 g, 2.7 mmol) and N,N-diisopropylethylamine (0.35 g, 2.7 mmol, 2.30.48 ml) in N,N-dimethylformamide (10 ml) was treated with 1-[Bis(dimethylamino)methylene]-1H-1,2,3-triazolo[4,5-b] pyridinium 3-oxid hexafluorophosphate (1.0 g, 2.7 mmol) and stirred for 18 hours. Ethyl acetate (100 ml) was added to the reaction mixture and it was washed with water (2×50 ml), 1N HCl (100 ml), saturated aqueous sodium bicarbonate (100 ml) and brine (50 ml). The organic layer was dried (Na$_2$SO$_4$) and evaporated. The crude product was chromatographed on silica gel with a gradient of 20% to 25% ethyl acetate in hexanes to leave the product as a white crystalline solid (0.44 g, 43%). LC/MS method A: $R_t$=7.36 min., (M+H)$^+$=488.

Synthesis of 2-(1-(aminomethyl)cyclohexyl)-N-(6-(trifluoromethoxy)benzo[d]thiazol-2-yl)acetamide

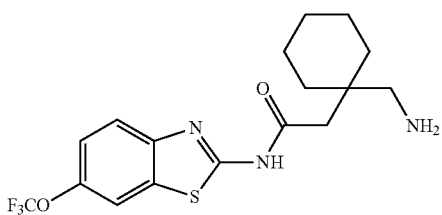 [SMILES: NCC1(CC(=O)Nc2nc3ccc(OC(F)(F)F)cc3s2)CCCCC1]

A solution of tert-butyl ((1-(2-oxo-2-((6-(trifluoromethoxy)benzo[d]thiazol-2-yl)amino) ethyl)cyclohexyl)methyl)carbamate (0.42 g, 0.86 mmol) in 1,4-dioxane (10 ml) and 4N HCl/1,4-dioxane (10 ml) was stirred for 18 hours. The solvents were evaporated to leave the product as a white solid (0.38 g, 100%). LC/MS method A: $R_t$=4.27 min., purity >95%, (M+H)$^+$=388.

Synthesis of (S)—N-((1-(2-oxo-2-((6-(trifluoromethoxy)benzo[d]thiazol-2-yl)amino) ethyl)cyclohexyl)methyl)pyrrolidine-2-carboxamide

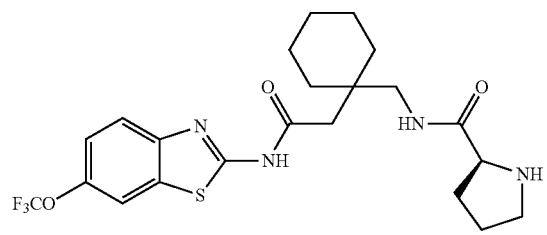 [SMILES: O=C(CC1(CNC(=O)[C@@H]2CCCN2)CCCCC1)Nc1nc2ccc(OC(F)(F)F)cc2s1]

A solution of 2-(1-(aminomethyl)cyclohexyl)-N-(6-(trifluoromethoxy)benzo [d]thiazol-2-yl)acetamide (20 mg, 47 µmol) and N,N-diisopropylethylamine (15 mg, 0.12 mmol, 21 µl) in N,N-dimethylformamide (0.5 ml) was treated with 1-(tert-butyl) 2-(2,5-dioxopyrrolidin-1-yl) (S)-pyrrolidine-1,2-dicarboxylate (18 mg, 56 µmol) and stirred 18 h. The product was purified by direct injection reverse phase HPLC (method B) and the product fractions were evaporated on a Genevac evaporator to leave the product which was dissolved in 1,4-dioxane (1 ml) and 4N HCl/1,4-dioxane (1 ml). After stirring for 4 h the solvents were evaporated to leave the product as a white solid (21 mg, 92%). LC/MS method A: $R_t$=4.75 min., (M+H)$^+$=485.

Examples 148-149 were prepared in identical scale and method to example 147 above.

Example 148: Synthesis of (S)-2-amino-4-methyl-N-((1-(2-oxo-2-((6-(trifluoromethoxy) benzo[d]thiazol-2-yl)amino)ethyl)cyclohexyl)methyl)pentanamide

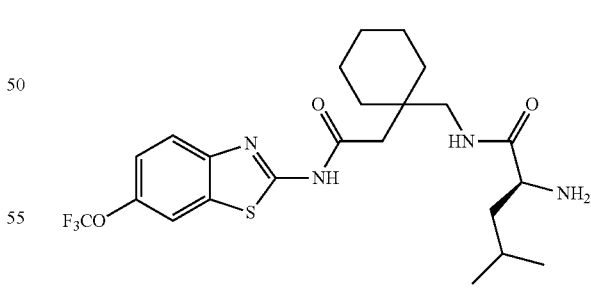

(S)-2-amino-4-methyl-N-((1-(2-oxo-2-((6-(trifluoromethoxy)benzo[d]thiazol-2-yl)amino)ethyl)cyclohexyl) methyl)pentanamide was prepared according to the procedure of example 147 from 2-(1-(aminomethyl)cyclohexyl)-N-(6-(trifluoromethoxy)benzo[d]thiazol-2-yl)acetamide (20 mg, 47 µmol) and 2,5-dioxopyrrolidin-1-yl L-leucinate to leave 23 mg (94% for two steps). LC/MS method A: $R_t$=5.04 min., (M+H)$^+$=501.

Example 149: Synthesis of (S)-2-amino-3-methyl-N-((1-(2-oxo-2-((6-(trifluoro methoxy)benzo[d]thiazol-2-yl)amino)ethyl)cyclohexyl)methyl)butanamide

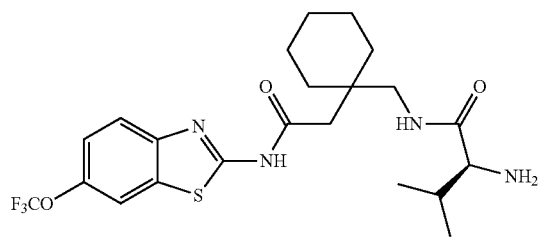 [SMILES: CC(C)[C@H](N)C(=O)NCC1(CC(=O)Nc2nc3ccc(OC(F)(F)F)cc3s2)CCCCC1]

(S)-2-amino-3-methyl-N-((1-(2-oxo-2-((6-(trifluoromethoxy)benzo[d]thiazol-2-yl)amino) ethyl)cyclohexyl)methyl)butanamide was prepared according to the procedure of example 147 from 2-(1-(aminomethyl)cyclohexyl)-N-(6-(trifluoromethoxy)benzo[d]thiazol-2-yl)acetamide (20 mg, 47 µmol) and 2,5-dioxopyrrolidin-1-yl L-valinate to leave 15 mg (66% for two steps). LC/MS method A: $R_t$=4.87 min., $(M+H)^+$=487.

Example 150: Synthesis of 2-amino-N-((1-(2-oxo-2-((6-(trifluoromethoxy)benzo[d] thiazol-2-yl)amino)ethyl)cyclohexyl)methyl)acetamide

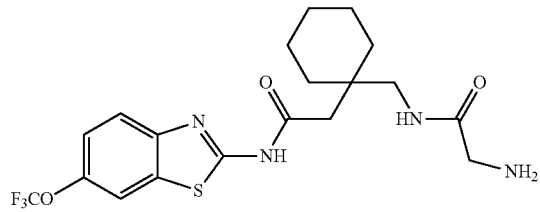 [SMILES: NCC(=O)NCC1(CC(=O)Nc2nc3ccc(OC(F)(F)F)cc3s2)CCCCC1]

A solution of 2-(1-(aminomethyl)cyclohexyl)-N-(6-(trifluoromethoxy)benzo[d]thiazol-2-yl)acetamide (20 mg, 47 µmol), N-(tert-butoxycarbonyl)-L-glycine (10 mg, 57 µmol) and N,N-diisopropylethylamine (15 mg, 0.12 mmol, 22 µl) in N,N-dimethylformamide (0.5 ml) was treated with 1-[Bis(dimethylamino)methylene]-1H-1,2,3-triazolo[4,5-b]pyridinium 3-oxid hexafluorophosphate (22 mg, 57 µmol) and stirred 18 hours. The product was purified by direct injection reverse phase HPLC (method B) and the product fractions were evaporated on a Genevac evaporator to leave the product as a gum (13 mg, 51%) which was dissolved in 1,4-dioxane (1 ml) and 4N HCl/1,4-dioxane (1 ml). After stirring for 4 hour the solvents were evaporated to leave the product as a white solid (10 mg, 47% for two steps). LC/MS method A: $R_t$=4.53 min., $(M+H)^+$=445.

Examples 151-160 were prepared in identical scale and method to example 150 above.

Example 151: Synthesis of (S)-2-amino-N-((1-(2-oxo-2-((6-(trifluoromethoxy)benzo[d] thiazol-2-yl)amino)ethyl)cyclohexyl)methyl)propanamide

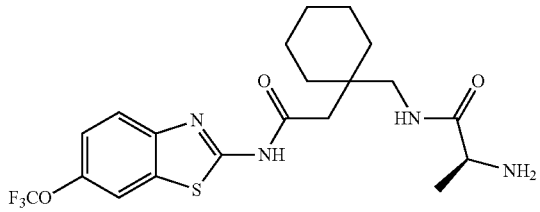 [SMILES: C[C@H](N)C(=O)NCC1(CC(=O)Nc2nc3ccc(OC(F)(F)F)cc3s2)CCCCC1]

(S)-2-amino-N-((1-(2-oxo-2-((6-(trifluoromethoxy)benzo [d]thiazol-2-yl)amino)ethyl) cyclohexyl)methyl)propanamide was prepared according to the procedure of example 150 from 2-(1-(aminomethyl)cyclohexyl)-N-(6-(trifluoromethoxy)benzo[d]thiazol-2-yl)acetamide (20 mg, 47 µmol) and (tert-butoxycarbonyl)-L-alanine to leave 9 mg (39% for two steps). LC/MS method A: $R_t$=4.61 min., $(M+H)^+$=459.

Example 152: Synthesis of 2-(methylamino)-N-((1-(2-oxo-2-((6-(trifluoromethoxy) benzo[d]thiazol-2-yl)amino)ethyl)cyclohexyl)methyl)acetamide

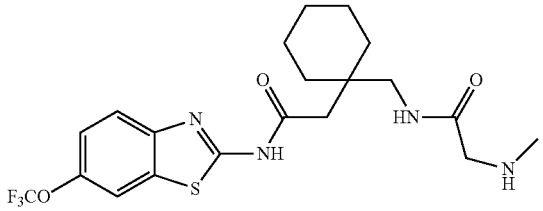 [SMILES: CNCC(=O)NCC1(CC(=O)Nc2nc3ccc(OC(F)(F)F)cc3s2)CCCCC1]

2-(methylamino)-N-((1-(2-oxo-2-((6-(trifluoromethoxy) benzo [d]thiazol-2-yl)amino)ethyl) cyclohexyl)methyl)acetamide was prepared according to the procedure of example 150 from 2-(1-(aminomethyl)cyclohexyl)-N-(6-(trifluoromethoxy)benzo[d]thiazol-2-yl)acetamide (20 mg, 47 µmol) and (tert-butoxycarbonyl)-sarcosine to leave 15 mg (65% for two steps). LC/MS method A: $R_t$=4.60 min., $(M+H)^+$=459.

Example 153: Synthesis of (R)-2-amino-3-methyl-N-((1-(2-oxo-2-((6-(trifluoro methoxy)benzo[d]thiazol-2-yl)amino)ethyl)cyclohexyl)methyl)butanamide

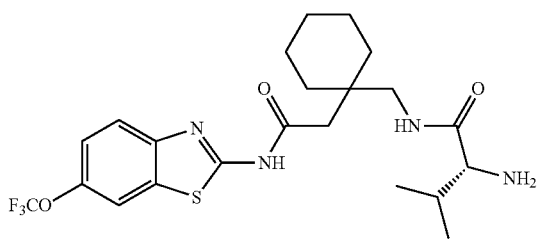 [SMILES: CC(C)[C@@H](N)C(=O)NCC1(CC(=O)Nc2nc3ccc(OC(F)(F)F)cc3s2)CCCCC1]

(R)-2-amino-3-methyl-N-((1-(2-oxo-2-((6-(trifluoromethoxy)benzo[d]thiazol-2-yl)amino)ethyl)cyclohexyl)methyl)butanamide was prepared according to the procedure of example 150 from 2-(1-(aminomethyl)cyclohexyl)-N-(6-(trifluoromethoxy)benzo[d]thiazol-2-yl)acetamide (20 mg, 47 μmol) and (tert-butoxycarbonyl)-D-valine to leave 11 mg (45% for two steps). LC/MS method A: $R_t$=4.86 min., $(M+H)^+$=487.

Example 154: Synthesis of (S)-5-oxo-N-((1-(2-oxo-2-((6-(trifluoromethoxy)benzo[d] thiazol-2-yl)amino)ethyl)cyclohexyl)methyl)pyrrolidine-2-carboxamide

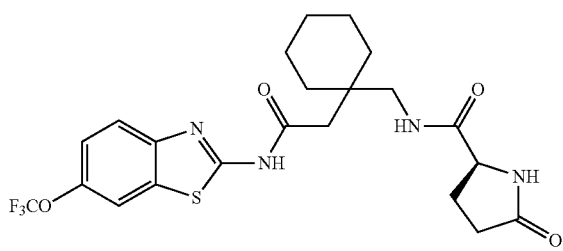 [SMILES: O=C(CC1(CNC(=O)[C@@H]2CCC(=O)N2)CCCCC1)Nc1nc2ccc(OC(F)(F)F)cc2s1]

(S)-5-oxo-N-((1-(2-oxo-2-((6-(trifluoromethoxy)benzo[d]thiazol-2-yl)amino)ethyl) cyclohexyl)methyl)pyrrolidine-2-carboxamide was prepared according to the procedure of example 150 from 2-(1-(aminomethyl)cyclohexyl)-N-(6-(trifluoromethoxy)benzo[d]thiazol-2-yl)acetamide (20 mg, 47 μmol) and L-pyroglutamate to leave 12 mg (45% for two steps). LC/MS method A: R, =4.41 min., $(M+H)^+$=499.

Example 155: Synthesis of (S)-2-amino-N1-(0-(2-oxo-2-((6-(trifluoromethoxy)benzo [d]thiazol-2-yl)amino)ethyl)cyclohexyl)methyl)pentanediamide

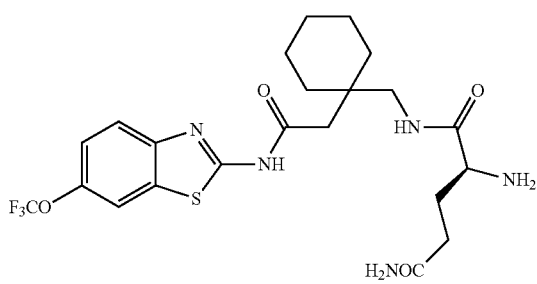 [SMILES: NC(=O)CC[C@H](N)C(=O)NCC1(CC(=O)Nc2nc3ccc(OC(F)(F)F)cc3s2)CCCCC1]

(S)-2-amino-N1-((1-(2-oxo-2-((6-(trifluoromethoxy)benzo [d]thiazol-2-yl)amino)ethyl) cyclohexyl)methyl)pentanediamide was prepared according to the procedure of example 150 from 2-(1-(aminomethyl)cyclohexyl)-N-(6-(trifluoromethoxy)benzo[d]thiazol-2-yl)acetamide (20 mg, 47 μmol) and (tert-butoxycarbonyl)-L-glutamine to leave 5 mg (19% for two steps). LC/MS method A: $R_t$=4.42 min., $(M+H)^+$=516.

Example 156: Synthesis of (S)-2-amino-4-(methylthio)-N-((1-(2-oxo-2-((6-(trifluoro methoxy)benzo[d]thiazol-2-yl)amino)ethyl)cyclohexyl)methyl)butanamide

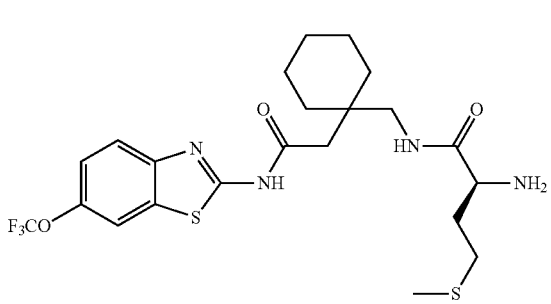 [SMILES: CSCC[C@H](N)C(=O)NCC1(CC(=O)Nc2nc3ccc(OC(F)(F)F)cc3s2)CCCCC1]

(S)-2-amino-4-(methylthio)-N-((1-(2-oxo-2-((6-(trifluoromethoxy)benzo[d]thiazol-2-yl)amino)ethyl)cyclohexyl)methyl)butanamide was prepared according to the procedure of example 150 from 2-(1-(aminomethyl)cyclohexyl)-N-(6-(trifluoromethoxy)benzo[d]thiazol-2-yl)acetamide (20 mg, 47 μmol) and (tert-butoxycarbonyl)-L-methionine to leave 12 mg (46% for two steps). LC/MS method A: $R_t$=4.90 min., $(M+H)^+$=519.

Example 157: Synthesis of (S)-2-amino-N-((1-(2-oxo-2-((6-(trifluoromethoxy)benzo[d] thiazol-2-yl)amino)ethyl)cyclohexyl)methyl)-3-phenylpropanamide

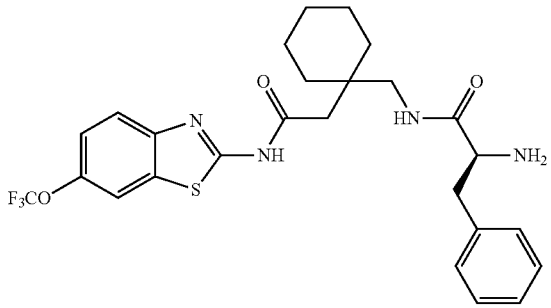 [SMILES: N[C@@H](Cc1ccccc1)C(=O)NCC1(CC(=O)Nc2nc3ccc(OC(F)(F)F)cc3s2)CCCCC1]

(S)-2-amino-N-((1-(2-oxo-2-((6-(trifluoromethoxy)benzo [d]thiazol-2-yl)amino)ethyl) cyclohexyl)methyl)-3-phenylpropanamide was prepared according to the procedure of example 150 from 2-(1-(aminomethyl)cyclohexyl)-N-(6-(trifluoromethoxy)benzo[d]thiazol-2-yl)acetamide (20 mg, 47 μmol) and (tert-butoxycarbonyl)-L-phenylalanine to leave 13 mg (49% for two steps). LC/MS method A: $R_t$=5.10 min., $(M+H)^+$=535.

Example 158: Synthesis of (S)-3-amino-4-oxo-4-(((1-(2-oxo-2-((6-(trifluoromethoxy) benzo[c]thiazol-2-yl)amino)ethyl)cyclohexyl)methyl)amino) butanoic Acid

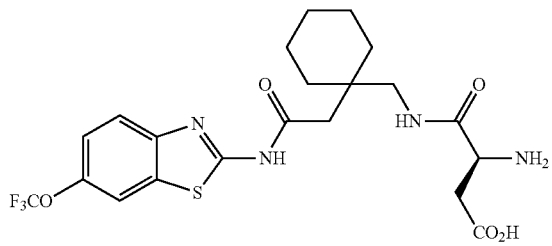 [SMILES: N[C@@H](CC(=O)O)C(=O)NCC1(CC(=O)Nc2nc3ccc(OC(F)(F)F)cc3s2)CCCCC1]

(S)-3-amino-4-oxo-4-(((1-(2-oxo-2-((6-(trifluoromethoxy)benzo[d]thiazol-2-yl)amino) ethyl)cyclohexyl)methyl)amino)butanoic acid was prepared according to the procedure of example 150 from 2-(1-(aminomethyl)cyclohexyl)-N-(6-(trifluoromethoxy)benzo[d]thiazol-2-yl)acetamide (20 mg, 47 µmol) and N-(tert-butoxycarbonyl)-L-aspartyl-beta-tert-butyl ester to leave 13 mg (51% for two steps). LC/MS method A: $R_t$=4.51 min., $(M+H)^+$=503.

Example 159: Synthesis of (S)-4-amino-5-oxo-5-(((1-(2-oxo-2-((6-(trifluoromethoxy) benzo[d]thiazol-2-yl)amino)ethyl)cyclohexyl)methyl)amino) pentanoic Acid

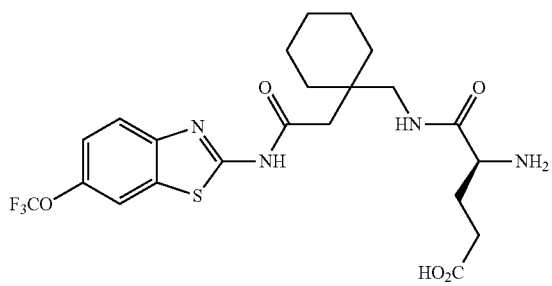 [SMILES: N[C@@H](CCC(=O)O)C(=O)NCC1(CC(=O)Nc2nc3ccc(OC(F)(F)F)cc3s2)CCCCC1]

(S)-4-amino-5-oxo-5-(((1-(2-oxo-2-((6-(trifluoromethoxy)benzo[d]thiazol-2-yl)amino) ethyl)cyclohexyl)methyl)amino)pentanoic acid was prepared according to the procedure of example 150 from 2-(1-(aminomethyl)cyclohexyl)-N-(6-(trifluoromethoxy)benzo[d]thiazol-2-yl)acetamide (20 mg, 47 µmol) and N-(tert-butoxycarbonyl)-L-glutamyl-gamma-tert-butyl ester to leave 14 mg (54% for two steps). LC/MS method A: $R_t$=4.52 min., $(M+H)^+$=517.

Example 160: Synthesis of (S)-2-amino-3-(1H-indol-3-yl)-N-((1-(2-oxo-2-((6-(trifluoro methoxy) benzo[d]thiazol-2-yl)amino)ethyl)cyclohexyl) methyl)propanamide

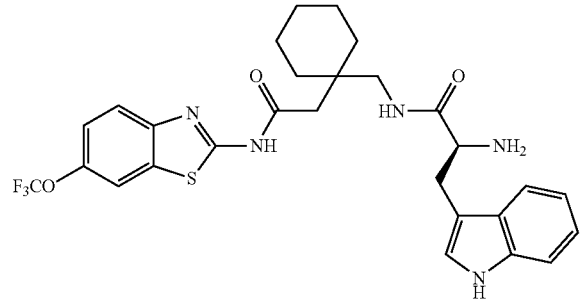 [SMILES: N[C@@H](Cc1c[nH]c2ccccc12)C(=O)NCC1(CC(=O)Nc2nc3ccc(OC(F)(F)F)cc3s2)CCCCC1]

(S)-2-amino-3-(1H-indol-3-yl)-N-((1-(2-oxo-2-((6-(trifluoromethoxy)benzo[d]thiazol-2-yl)amino)ethyl)cyclohexyl)methyl)propanamide was prepared according to the procedure of example 150 from 2-(1-(aminomethyl)cyclohexyl)-N-(6-(trifluoromethoxy)benzo[d]thiazol-2-yl)acetamide (20 mg, 47 µmol) and N-(tert-butoxycarbonyl)-L-tryptophan to leave 11 mg (38% for two steps). LC/MS method A: $R_t$=5.06 min., $(M+11)^+$=574.

Example 161: Synthesis of (R)-2-amino-3-methyl-N-(4-oxo-4-((6-(trifluoromethoxy)benzo[d]thiazol-2-yl)amino)butyl)butanamide

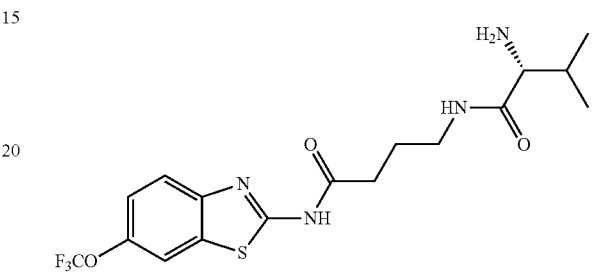

A solution of 4-amino-N-(6-(trifluoromethoxy)benzo[d]thiazol-2-yl)butanamide (20 mg, 56 µmol), N-(tert-butoxycarbonyl)-D-valine (16 mg, 73 µmol) and N,N-diisopropylethylamine (22 mg, 0.17 mmol, 30 µl) in N,N-dimethylformamide (0.5 ml) was treated with 1-[Bis(dimethylamino)methylene]-1H-1,2,3-triazolo[4,5-b]pyridinium 3-oxid hexafluorophosphate (28 mg, 73 µmol) and stirred 18 hours. The product was purified by direct injection reverse phase HPLC (method B) and the product fractions were evaporated on a Genevac evaporator to leave the product as a gum (21 mg, 72%) which was dissolved in 1,4-dioxane (1 ml) and 4N HCl/1,4-dioxane (1 ml). After stirring for 4 hours the solvents were evaporated to leave the product as a white solid (19 mg, 72% for two steps). LC/MS method A: $R_t$=4.01 min., $(M+H)^+$=419.

Examples 162-163 were prepared in identical scale and method to example 161 above.

Example 162: Synthesis of (R)—N-(4-oxo-4-((6-(trifluoromethoxy)benzo[d]thiazol-2-yl)amino)butyl) pyrrolidine-2-carboxamide

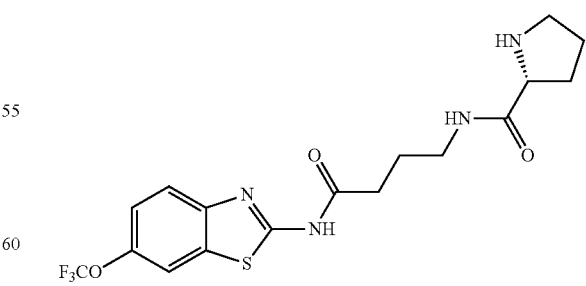

(R)—N-(4-oxo-4-((6-(trifluoromethoxy)benzo[d]thiazol-2-yl)amino)butyl)pyrrolidine-2-carboxamide was prepared according to the procedure of example 161 from 4-amino-N-(6-(trifluoromethoxy)benzo[d]thiazol-2-yl)butanamide (20 mg, 56 µmol) and N-(tert-butoxy carbonyl)-D-proline to leave 25 mg (76% for two steps). LC/MS method A: $R_t$=3.91 min., (M+H)$^+$=417.

Example 163: Synthesis of (R)-5-oxo-N-(4-oxo-4-((6-(trifluoromethoxy)benzo[d]thiazol-2-yl)amino)butyl)pyrrolidine-2-carboxamide

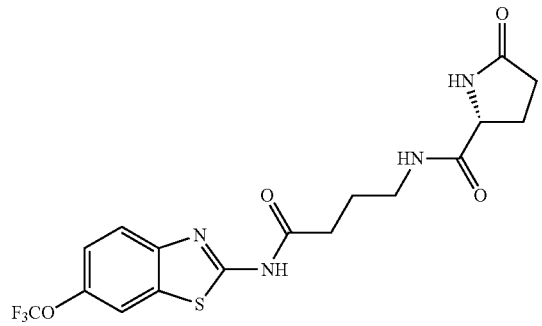 [SMILES: O=C(CCCNC(=O)[C@H]1CCC(=O)N1)Nc1nc2ccc(OC(F)(F)F)cc2s1]

(R)-5-oxo-N-(4-oxo-4-((6-(trifluoromethoxy)benzo[d]thiazol-2-yl)amino)butyl)pyrrolidine-2-carboxamide was prepared according to the procedure of example 161 from 4-amino-N-(6-(trifluoromethoxy)benzo[d]thiazol-2-yl)butanamide (20 mg, 56 µmol) and D-pyroglutamate to leave 9 mg (37% for two steps). LC/MS method A: $R_t$=4.28 min., (M+H)$^+$=431.

Example 164: Synthesis of (R)-2-amino-3-methyl-N-((1-(2-oxo-2-((6-(trifluoro methoxy)benzo[d]thiazol-2-yl)amino)ethyl)cyclohexyl)methyl)butanamide

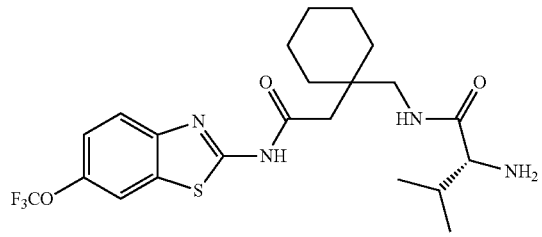 [SMILES: CC(C)[C@@H](N)C(=O)NCC1(CC(=O)Nc2nc3ccc(OC(F)(F)F)cc3s2)CCCCC1]

A solution of 2-(1-(aminomethyl)cyclohexyl)-N-(6-(trifluoromethoxy)benzo[d]thiazol-2-yl)acetamide (25 mg, 56 µmol), N-(tert-butoxycarbonyl)-D-valine (16 mg, 73 µmol) and N,N-diisopropylethylamine (22 mg, 0.17 mmol, 30 µl) in N,N-dimethylformamide (0.5 ml) was treated with 1-[Bis(dimethylamino)methylene]-1H-1,2,3-triazolo[4,5-b]pyridinium-3-oxid hexafluoro phosphate (28 mg, 73 µmol) and stirred 18 hours. The product was purified by direct injection reverse phase HPLC (method B) and the product fractions were evaporated on a Genevac evaporator to leave the product as a gum (10 mg, 30%) which was dissolved in 1,4-dioxane (1 ml) and 4N HCl/1,4-dioxane (1 ml). After stirring for 4 hours the solvents were evaporated to leave the product as a white solid (8 mg, 27% for two steps). LC/MS method A: $R_t$=4.86 min., (M+H)$^+$=487.

Examples 165-166 were prepared in identical scale and method to example 164 above.

Example 165: Synthesis of (S)—N-((1-(2-oxo-2-((6-(trifluoromethoxy)benzo[d]thiazol-2-yl)amino)ethyl)cyclohexyl)methyl)pyrrolidine-2-carboxamide

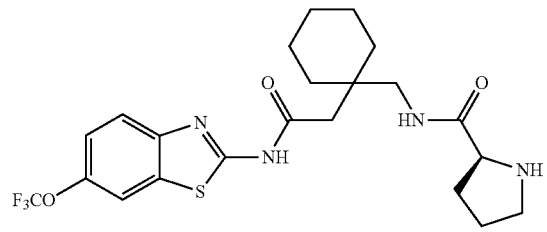 [SMILES: O=C(CC1(CNC(=O)[C@@H]2CCCN2)CCCCC1)Nc1nc2ccc(OC(F)(F)F)cc2s1]

(S)—N-((1-(2-oxo-2-((6-(trifluoromethoxy)benzo[d]thiazol-2-yl)amino)ethyl)cyclohexyl) methyl)pyrrolidine-2-carboxamide was prepared according to the procedure of example 164 from 2-(1-(aminomethyl)cyclohexyl)-N-(6-(trifluoromethoxy)benzo[d]thiazol-2-yl)acetamide (25 mg, 56 µmol) and (tert-butoxycarbonyl)-D-proline to leave 10 mg (34% for two steps). LC/MS method A: $R_t$=3.91 min., (M+H)$^+$=417.

Example 166: Synthesis of (R)-5-oxo-N-((1-(2-oxo-2-((6-(trifluoromethoxy)benzo[d] thiazol-2-yl)amino)ethyl)cyclohexyl)methyl)pyrrolidine-2-carboxamide

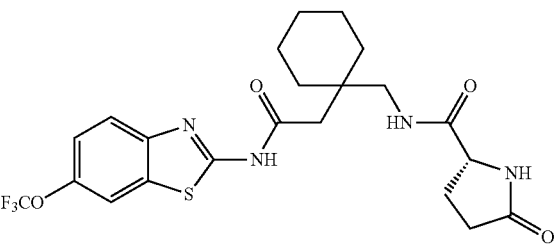 [SMILES: O=C(CC1(CNC(=O)[C@H]2CCC(=O)N2)CCCCC1)Nc1nc2ccc(OC(F)(F)F)cc2s1]

(R)-5-oxo-N-((1-(2-oxo-2-((6-(trifluoromethoxy)benzo[d]thiazol-2-yl)amino)ethyl) cyclohexyl)methyl)pyrrolidine-2-carboxamide: was prepared according to the procedure of example 164 from 2-(1-(aminomethyl)cyclohexyl)-N-(6-(trifluoromethoxy)benzo[d]thiazol-2-yl)acetamide (25 mg, 56 µmol) and D-pyroglutamate to leave 12 mg (43% for two steps). LC/MS method A: $R_t$=5.52 min., (M+H)$^+$=499.

Example 167: Synthesis of 4-amino-3,3-dimethyl-N-(6-(trifluoromethoxy)benzo[d] thiazol-2-yl)butanamide

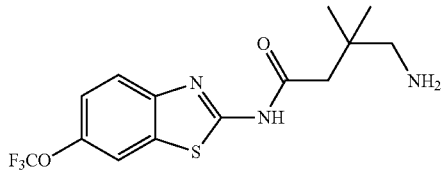 [SMILES: CC(C)(CN)CC(=O)Nc1nc2ccc(OC(F)(F)F)cc2s1]

A solution of 6-(trifluoromethoxy)benzo[d]thiazol-2-amine (37 mg, 0.16 mmol), 4-((tert-butoxycarbonyl)amino)-3,3-dimethylbutanoic acid (55 mg, 0.24 mmol), 1-hydroxy- 7-azabenzotriazole (33 mg, 0.24 mmol) and N,N-diisopropylethylamine (31 mg, 0.24 mmol, 43 µl) in N,N-dimethylformamide (0.5 ml) was treated with 1-methyl-2-chloropyridinium iodide (61 mg, 0.24 mmol) and stirred 4 days. The product was purified by direct injection reverse phase HPLC (method B) and the product fractions were evaporated on a Genevac evaporator to leave the product as a solid (38 mg, 53%) which was dissolved in 4N HCl/1,4-dioxane (1 ml). After stirring for 4 hours the solvents were evaporated to leave the product as a white solid (34 mg, 100%, 53% for two steps). LC/MS method A: $R_t$=3.95 min., $(M+H)^+$=348.

Example 168: Synthesis of (S)-3-(benzyloxy)-2-morpholino-N-(6-(trifluoromethoxy)benzo[d]thiazol-2-yl)propanamide Synthesis of (R)-3-(benzyloxy)-2-bromopropanoic Acid

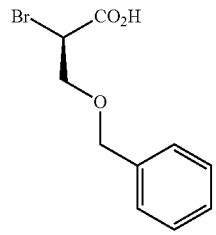

A solution of O-benzyl-D-serine (1.0 g, 5.1 mmol) and potassium bromide (3.6 g, 30.6 mmol) in 2.5 N sulfuric acid (35 ml) in an ice bath was stirred and treated with sodium nitrite (0.95 g, 14 mmol) in portions over 30 mins. The mixture stirred an additional 60 mins., then ether (50 ml) was added and the mixture stirred 30 mins. The organic layer was separated, washed with brine (25 ml), dried (Na$_2$SO$_4$) and evaporated to leave the product as a colorless oil (1.3 g, 98%).

Synthesis of Methyl (R)-3-(benzyloxy)-2-bromopropanoate

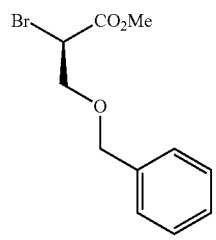 [SMILES: COC(=O)[C@H](Br)COCc1ccccc1]

A solution of (R)-3-(benzyloxy)-2-bromopropanoic acid (1.2 g, 4.6 mmol) in anhydrous tetrahydrofuran (30 ml) and methanol (5 ml) in an ice bath was treated with an ethereal solution of trimethylsilyldiazomethane (3.5 ml, 7.0 mmol) and stirred for 30 minutes. Acetic acid (1 ml) was added to the reaction mixture stirred an additional 30 mins. Approximately half of the solvent was evaporated in vacuo, ethyl acetate (50 ml) was added and the solution was washed with saturated sodium bicarbonate solution (25 ml) and brine (25 ml). The organic phase was dried (MgSO$_4$) and evaporated. The crude product was purified by silica gel chromatography eluted with 10% ethyl acetate in hexanes to leave a clear, colorless oil (0.90 g, 72%). LC/MS method A: $R_t$=5.57 min.

Synthesis of Methyl (R)-3-(benzyloxy)-2-morpholinopropanoate

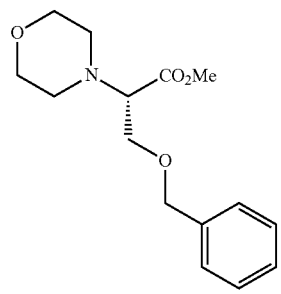 [SMILES: COC(=O)[C@H](COCc1ccccc1)N1CCOCC1]

A solution of Methyl (R)-3-(benzyloxy)-2-bromopropanoate (100 mg, 0.36 mmol) and morpholine (0.16 g, 1.8 mmol, 0.16 ml) in N,N-dimethylformamide (2 ml) was stirred for 5 days. The reaction mixture was diluted with ethyl acetate (25 ml) and washed with water (25 ml), saturated sodium bicarbonate solution (25 ml) and brine (25 ml). The organic phase was dried (MgSO$_4$) and evaporated to leave the product as an oil (0.10 g, 100%). LC/MS method A: $R_t$=2.95 min., $(M+H)^+$=280.

Synthesis of (S)-3-(benzyloxy)-2-morpholinepropanoic Acid

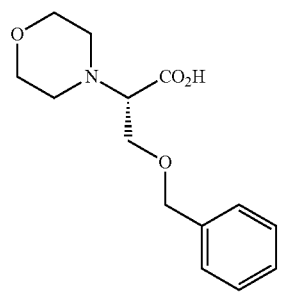 [SMILES: O=C(O)[C@H](COCc1ccccc1)N1CCOCC1]

A solution of Methyl (R)-3-(benzyloxy)-2-morpholinopropanoate (95 mg, 0.34 mmol) and lithium hydroxide monohydrate (57 mg, 1.4 mmol) in tetrahydrofuran (2 ml) and water (3 ml) was stirred for 1.5 hours. The reaction mixture was purified by reverse phase HPLC (method B) and the product fractions were evaporated on a Genevac evaporator to leave the pure product as a TFA salt (62 mg, 48%). LC/MS method A: $R_t$=2.5 min., $(M+H)^+$=266.

Synthesis of (S)-3-(benzyloxy)-2-morpholino-N-(6-(trifluoromethoxy)benzo[d]thiazol-2-yl)propanamide

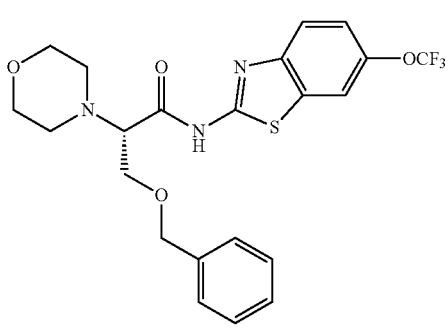 [SMILES: O=C(Nc1nc2ccc(OC(F)(F)F)cc2s1)[C@H](COCc1ccccc1)N1CCOCC1]

A solution of (S)-3-(benzyloxy)-2-morpholinepropanoic acid TFA salt (55 mg, 0.15 mmol), 6-(trifluoromethoxy)benzo[d]thiazol-2-amine (68 mg, 0.30 mmol), 1-hydroxy-7-azabenzotriazole (23 mg, 0.17 mmol) and N,N-diisopropylethylamine (58 mg, 0.45 mmol, 81 µl) in N,N-dimethylformamide (0.5 ml) was treated with 1-methyl-2-chloropyridinium iodide (43 mg, 0.17 mmol) and the mixture was stirred for 18 hours. The reaction mixture was purified by reverse phase HPLC. The acetonitrile was evaporated from the product fractions and the aqueous residue was diluted with saturated sodium bicarbonate solution (25 ml) and ethyl acetate (50 ml). The organic phase was separated, washed with brine (25 ml), dried (MgSO$_4$) and evaporated. The residue was dissolved in 1,4-dioxane (2 ml) and treated with 4N HCl in 1,4-dioxane (1 ml). The mixture was evaporated to leave the mono hydrochloride salt of the product (60 mg, 77%). LC/MS method A: R$_t$=4.82 min., (M+H)$^+$=482.

Example 169: Synthesis of (S)-3-(benzyloxy)-2-(dimethylamino)-N-(6-(trifluoro methoxy)benzo[d]thiazol-2-yl)propanamide Synthesis of Methyl O-Benzyl-N,N-Dimethyl-L-Serinate

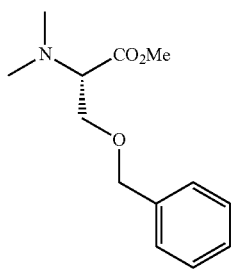 [SMILES: COC(=O)[C@H](COCc1ccccc1)N(C)C]

A solution of methyl (R)-3-(benzyloxy)-2-bromopropanoate (100 mg, 0.36 mmol) and dimethylamine (5.6 M in ethanol, 1.9 mmol, 0.34 ml) in N,N-dimethylformamide (2 ml) was stirred for 18 hours. The reaction mixture was diluted with ethyl acetate (25 ml) and washed with water (25 ml) and brine (25 ml). The organic phase was dried (MgSO$_4$) and evaporated to leave the product as an oil (83 mg, 95%). LC/MS method A: R$_t$=2.94 min., (M+H)$^+$=238.

Synthesis of O-Benzyl-N,N-Dimethyl-L-Serine

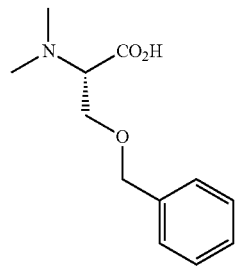 [SMILES: CN(C)[C@@H](COCc1ccccc1)C(=O)O]

A solution of methyl O-benzyl-N,N-dimethyl-L-serinate (75 mg, 0.32 mmol) and lithium hydroxide monohydrate (53 mg, 1.3 mmol) in tetrahydrofuran (2 ml) and water (3 ml) was stirred for 1 hour. The reaction mixture was purified by reverse phase HPLC (method B) and the product fractions were evaporated on a Genevac evaporator to leave the pure product as a TFA salt (110 mg, 100%). LC/MS method A: R$_t$=2.53 min.

Synthesis of (S)-3-(benzyloxy)-2-(dimethylamino)-N-(6-(trifluoromethoxy)benzo [d]thiazol-2-yl)propanamide

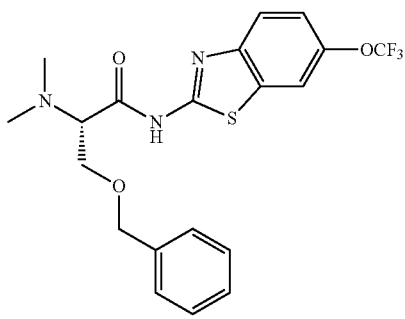 [SMILES: CN(C)[C@@H](COCc1ccccc1)C(=O)Nc1nc2ccc(OC(F)(F)F)cc2s1]

A solution of O-benzyl-N,N-dimethyl-L-serine TFA salt (52 mg, 0.22 mmol), 6-(trifluoromethoxy)benzo[d]thiazol-2-amine (50 mg, 0.15 mmol), 1-hydroxy-7-azabenzotriazole (29 mg, 0.22 mmol) and N,N-diisopropylethylamine (58 mg, 0.45 mmol, 81 µl) in N,N-dimethylformamide (0.5 ml) was treated with 1-methyl-2-chloropyridinium iodide (56 mg, 0.22 mmol) and the mixture was stirred for 18 hours. The reaction mixture was purified by reverse phase HPLC. The acetonitrile was evaporated from the product fractions and the aqueous residue was diluted with saturated sodium bicarbonate solution (25 ml) and ethyl acetate (50 ml). The organic phase was separated, washed with brine (25 ml), dried (MgSO$_4$) and evaporated. The residue was dissolved in 1,4-dioxane (2 ml) and treated with 4N HCl in 1,4-dioxane (1 ml). The mixture was evaporated to leave the mono hydrochloride salt of the product (21 mg, 29%). LC/MS method A: R$_t$=2.70 min., (M+H)$^+$=440.

Example 170: Synthesis of (S)-1-methyl-N-(6-(trifluoromethoxy)benzo[d]thiazol-2-yl)pyrrolidine-2-carboxamide

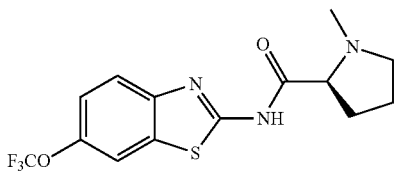 [SMILES: CN1CCC[C@H]1C(=O)Nc1nc2ccc(OC(F)(F)F)cc2s1]

A solution of N-methyl-L-proline (55 mg, 0.42 mmol), 6-(trifluoromethoxy)benzo[d] thiazol-2-amine (50 mg, 0.21 mmol), 1-hydroxy-7-azabenzotriazole (56 mg, 0.42 mmol) and N,N-diisopropylethylamine (54 mg, 0.42 mmol, 75 µl) in N,N-dimethylformamide (0.5 ml) was treated with 1-methyl-2-chloropyridinium iodide (107 mg, 0.42 mmol) and the mixture was stirred for 18 hours. The reaction mixture was purified by reverse phase HPLC. The product fractions were combined, treated with saturated sodium bicarbonate (25 ml) and extracted with ethyl acetate (2×25 ml). The combined extracts were washed with brine (25 ml), dried (MgSO$_4$) and evaporated. The residue was dissolved in 1,4-dioxane (2 ml) and treated with 4N HCl in 1,4-dioxane (1 ml). The mixture was evaporated to leave the mono hydrochloride salt of the product (67 mg, 84%). LC/MS method A: R$_t$=3.77 min., (M+H)$^+$=346.

Example 171: Synthesis of 2-(ethylamino)-N-methyl-N-(2-oxo-2-((6-(trifluoromethoxy) benzo[d]thiazol-2-yl)amino)ethyl)acetamide

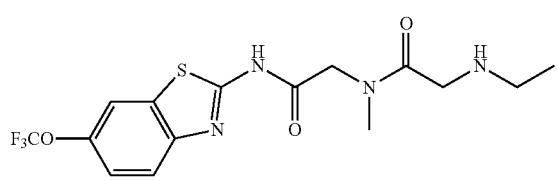 [SMILES: CCNCC(=O)N(C)CC(=O)Nc1nc2ccc(OC(F)(F)F)cc2s1]

A solution of 2-(methylamino)-N-(6-(trifluoromethoxy)benzo[d]thiazol-2-yl)acetamide (50 mg, 0.16 mmol), N-(tert-butoxycarbonyl)-N-ethylglycine (37 mg, 0.18 mmol) and N,N-diisopropylethylamine (46 mg, 0.36 mmol, 65 µl) in N,N-dimethylformamide (1 ml) was treated with 1-[Bis(dimethylamino)methylene]-1H-1,2,3-triazolo[4,5-b]pyridinium 3-oxid hexafluorophosphate (68 mg, 0.18 mmol) and stirred 18 hours. The product was purified by direct injection reverse phase HPLC (method B) and the product fractions were evaporated on a Genevac evaporator to leave the product as a gum (56 mg, 71%) which was dissolved in 4N HCl/1,4-dioxane (2 ml). After stirring for 2 hours the solvents were evaporated to leave the product as a white solid (43 mg, 63% for two steps). LC/MS method C: R$_t$=1.41 min., (M+H)$^+$=391. Example 172 was prepared under identical scale and conditions as example 171 above.

Example 172: Synthesis of 2-(isopropylamino)-N-methyl-N-(2-oxo-2-((6-(trifluoro methoxy)benzo[d]thiazol-2-yl)amino)ethyl)acetamide

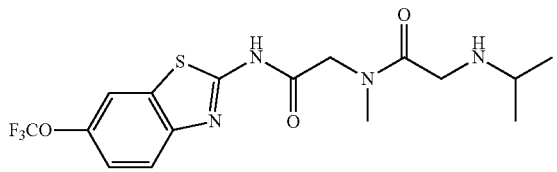 [SMILES: CC(C)NCC(=O)N(C)CC(=O)Nc1nc2ccc(OC(F)(F)F)cc2s1]

2-(isopropylamino)-N-methyl-N-(2-oxo-2-((6-(trifluoromethoxy)benzo[d]thiazol-2-yl)amino)ethyl)acetamide: was prepared according to the procedure of example 171 from 2-(methylamino)-N-(6-(trifluoromethoxy)benzo[d]thiazol-2-yl)acetamide (50 mg, 0.16 mmol) and N-(tert-butoxycarbonyl)-N-isopropylglycine to leave 43 mg (63% for two steps). LC/MS method C: R$_t$=1.44 min., (M+H)$^+$=405.

Example 173: Synthesis of (R)-1-(1-(aminomethyl)cyclohexane-1-carbonyl)-N-(6-(trifluoromethoxy)benzo[d]thiazol-2-yl)pyrrolidine-2-carboxamide

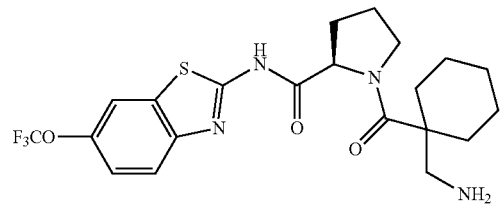 [SMILES: NCC1(C(=O)N2CCC[C@@H]2C(=O)Nc2nc3ccc(OC(F)(F)F)cc3s2)CCCCC1]

A solution of (R)—N-(6-(trifluoromethoxy)benzo[d]thiazol-2-yl)pyrrolidine-2-carboxamide (200 mg, 0.54 mmol), 1-(((tert-butoxycarbonyl)amino)methyl)cyclohexane-1-carboxylic acid (168 mg, 0.65 mmol) and N,N-diisopropylethylamine (168 mg, 1.3 mmol, 233 µl) in N,N-dimethylformamide (3 ml) was treated with 1-[Bis(dimethylamino)methylene]-1H-1,2,3-triazolo[4,5-b]pyridinium 3-oxid hexafluorophosphate (247 mg, 0.65 mmol) and stirred 18 hours. The reaction mixture was diluted with ethyl acetate (50 ml) and washed with water (50 ml), 1N HCl (50 ml), water (50 ml), saturated sodium bicarbonate solution (50 ml) and brine (25 ml). The organic layer was dried (MgSO$_4$) and evaporated. The product was purified by chromatography on silica gel eluted with a gradient of ethyl acetate in hexanes (10-40%) to leave the pure product as a foamy solid (220 mg, 71%). This product was dissolved in 4N HCl/1,4-dioxane (2 ml). After stirring for 2 hours the solvents were evaporated to leave the product as a white solid (188 mg, 69% for two steps). LC/MS method A: R$_t$=4.40 min., (M+H)$^+$=471.

Example 174: Synthesis of N-methyl-2-(methylsulfonamido)-N-(2-oxo-2-((6-(trifluoro methoxy)benzo[d]thiazol-2-yl)amino)ethyl)acetamide

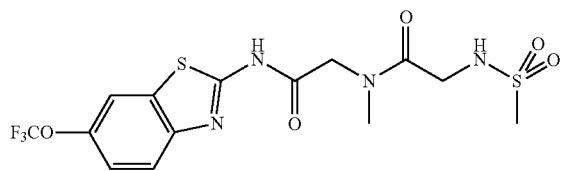 [SMILES: CN(CC(=O)Nc1nc2ccc(OC(F)(F)F)cc2s1)C(=O)CNS(C)(=O)=O]

A solution of 2-(methylamino)-N-(6-(trifluoromethoxy)benzo[d]thiazol-2-yl)acetamide (25 mg, 73 μmop, (methylsulfonyl)glycine (12 mg, 88 μmol) and N,N-diisopropylethylamine (24 mg, 183 lmo', 33 μl) in N,N-dimethylformamide (0.5 ml) was treated with 1-[Bis(dimethyl amino)methylene]-1H-1,2,3-triazolo[4,5-b]pyridinium 3-oxid hexafluorophosphate (33 mg, 88 μmop and stirred 18 hours. The reaction mixture was diluted with ethyl acetate (25 ml) and washed with water (25 ml), 1N HCl (25 ml) and brine (25 ml). The organic layer was dried (MgSO$_4$) and evaporated. The product was purified by reverse phase HPLC (method B) to leave the pure product as a crystalline solid (11 mg, 34%). LC/MS method C: $R_t$=2.06 min., $(M+H)^+$=441.

Example 175: Synthesis of 2-(tert-butoxy)-N-methyl-N-(2-oxo-2-((6-(trifluoromethoxy) benzo[d]thiazol-2-yl)amino)ethyl)acetamide

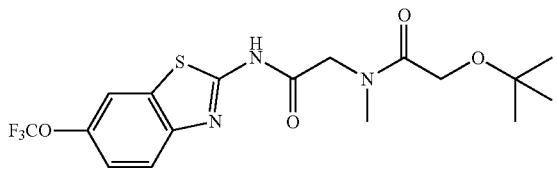 [SMILES: CN(CC(=O)Nc1nc2ccc(OC(F)(F)F)cc2s1)C(=O)COC(C)(C)C]

A solution of 2-(methylamino)-N-(6-(trifluoromethoxy)benzo[d]thiazol-2-yl)acetamide monohydrochloride (50 mg, 0.15 mmol), 2-(tert-butoxy)acetic acid (22 mg, 0.17 mmol) and N,N-diisopropylethylamine (45 mg, 0.35 mmol, 63 μl) in N,N-dimethylformamide (1 ml) was treated with 1-[Bis(dimethylamino)methylene]-1H-1,2,3-triazolo[4,5-b]pyridinium 3-oxid hexafluoro phosphate (57 mg, 0.15 mmol) and stirred 3 hours. The product was purified by reverse phase HPLC (method B) and the combined product fractions were evaporated to leave the pure product as a sticky solid (59 mg, 93%). LC/MS method C: $R_t$=2.26 min., $(M+H)^+$=420.

Example 176: Synthesis of N,4,4-trimethyl-N-(2-oxo-2-((6-(trifluoromethoxy)benzo[d] thiazol-2-yl)amino)ethyl)pentanamide

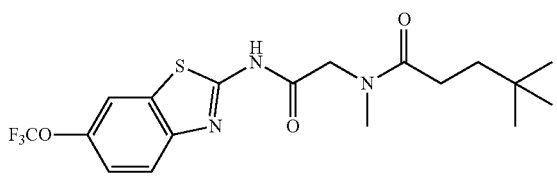 [SMILES: CN(CC(=O)Nc1nc2ccc(OC(F)(F)F)cc2s1)C(=O)CCC(C)(C)C]

N,4,4-trimethyl-N-(2-oxo-2-((6-(trifluoromethoxy)benzo[d]thiazol-2-yl)amino)ethyl) pentanamide was prepared according to the procedure of example 175 from 2-(methylamino)-N-(6-(trifluoromethoxy)benzo[d]thiazol-2-yl)acetamide monohydrochloride (50 mg, 0.15 mmol) and 4,4-dimethylpentanoic acid on the same scale as example 175 to leave 50 mg (80%) of product. LC/MS method C: $R_t$=2.50 min., $(M-f-H)^+$=418.

Example 177: Synthesis of tert-Butyl (2-(methyl(2-oxo-2-((6-(trifluoromethoxy)benzo [d]thiazol-2-yl)amino)ethyl)amino)-2-oxoethyl)(1-(trifluoromethyl)cyclopropyl)carbamate Synthesis of Benzyl (1-(trifluoromethyl)cyclopropyl)carbamate

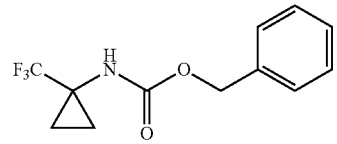 [SMILES: O=C(NC1(C(F)(F)F)CC1)OCc1ccccc1]

A solution of 1-(trifluoromethyl)cyclopropan-1-amine hydrochloride (0.15 g, 0.93 mmol) and N,N-diisopropylethylamine (0.28 g, 2.2 mmol, 0.39 ml) in dichloromethane (5 ml) was cooled in an ice bath and treated with benzyl chloroformate (0.17 g, 1.0 mmol, 0.143 ml). The mixture was allowed to warm to 20° C. over 2 hours and stirred an additional 72 hours. The mixture was diluted with ethyl acetate (50 ml), washed with 1N HCl (25 ml) and brine (25 ml). The organic phase was dried (MgSO$_4$) and evaporated to leave the product as a solid (135 mg, 56%).

Synthesis of tert-butyl N-((benzyloxy)carbonyl)-N-(1-(trifluoromethyl)cyclopropyl) glycinate

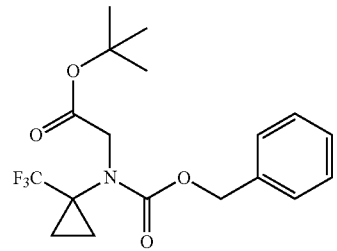 [SMILES: CC(C)(C)OC(=O)CN(C(=O)OCc1ccccc1)C1(C(F)(F)F)CC1]

A solution of benzyl (1-(trifluoromethyl)cyclopropyl)carbamate (130 mg, 0.50 mmol) in anhydrous tetrahydrofuran (4 ml) under nitrogen atmosphere in an ice bath was treated with a solution of lithium hexamethyldisilylamide (1.0 M in tetrahydrofuran, 0.60 ml, 0.60 mmol) dropwise over 5 minutes. The mixture stirred 30 minutes then 1-bromo tert-butylacetate was added and stirring continued for an additional 18 hours. The reaction mixture was treated with saturated aqueous ammonium chloride (1 ml) and stirred 30 minutes. Ethyl acetate (50 ml) was added and the mixture was washed with water (25 ml) and brine (25 ml). The organic phase was dried (MgSO$_4$) and evaporated. The crude product was purified by silica gel chromatography eluting with a gradient of ethyl acetate in hexanes (0-30%)

to leave the product as a colorless oil (143 mg, 77%). LC/MS method C: $R_t$=2.69 min.

Synthesis of N-((Benzyloxy)carbonyl)-N-(1-(trifluoromethyl)cyclopropyl)glycine

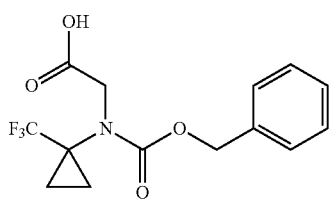 [SMILES: O=C(O)CN(C(=O)OCc1ccccc1)C1(C(F)(F)F)CC1]

A solution of tert-butyl N-((benzyloxy)carbonyl)-N-(1-(trifluoromethyl)cyclopropyl) glycinate (140 mg, 0.37 mmol) in TFA (1.5 ml) and dichloromethane (1.5 ml) was stirred 2 hours then evaporated. Left 117 mg (100%). LC/MS method C: $R_t$=2.13 min.

Synthesis of tert-Butyl (2-(methyl(2-oxo-2-((6-(trifluoromethoxy)benzo[d] thiazol-2-yl)amino)ethyl)amino)-2-oxoethyl)(1-(trifluoromethyl)cyclopropyl)carbamate

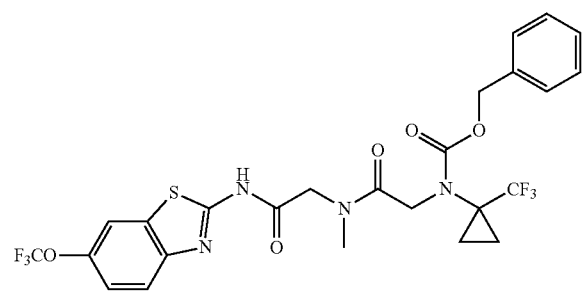 [SMILES: CN(CC(=O)Nc1nc2ccc(OC(F)(F)F)cc2s1)C(=O)CN(C(=O)OCc1ccccc1)C1(C(F)(F)F)CC1]

A solution of 2-(methylamino)-N-(6-(trifluoromethoxy)benzo[d]thiazol-2-yl)acetamide monohydrochloride (120 mg, 0.35 mmol), N-((benzyloxy)carbonyl)-N-(1-(trifluoromethyl) cyclopropyl)glycine (111 mg, 0.35 mmol) and N,N-diisopropylethylamine (181 mg, 1.4 mmol, 251 µl) in N,N-dimethylformamide (3 ml) was treated with 1-[Bis (dimethylamino)methylene]-1H-1,2,3-triazolo[4,5-b]pyridinium 3-oxid hexafluorophosphate (133 mg, 0.35 mmol) and stirred 4 hours. The mixture was diluted with ethyl acetate (50 ml), washed with water (25 ml), 1N HCl (25 ml) and brine (25 ml). The organic phase was dried (MgSO$_4$) and evaporated and the crude product was purified by chromatography on silica gel eluted with a gradient of ethyl acetate in hexanes (20%-100%) to leave the pure product as a gum (193 mg, 91%). LC/MS method C: $R_t$=2.60 min., $(M+H)^+$=605.

Synthesis of N-methyl-N-(2-oxo-2-((6-(trifluoromethoxy)benzo[d]thiazol-2-yl)amino)ethyl)-2-((1-(trifluoromethyl)cyclopropyl)amino)acetamide

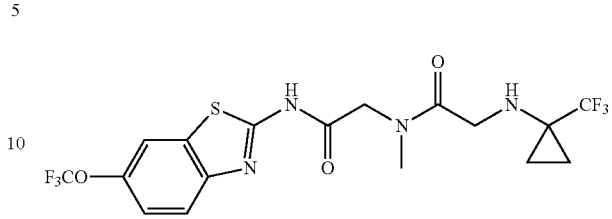

A solution of tert-Butyl (2-(methyl(2-oxo-2-((6-(trifluoromethoxy)benzo[d]thiazol-2-yl)amino)ethyl)amino)-2-oxoethyl)(1-(trifluoromethyl)cyclopropyl)carbamate (50 mg, 83 µmop in concentrated hydrobromic acid in acetic acid (2 ml) stirred for 18 hours and evaporated. The residue was dissolved in water (2 ml) and purified by reverse phase HPLC (method B). The product fractions were evaporated to leave the pure product as a TFA salt (25 mg, 52%). LC/MS method C: $R_t$=2.40 min., $(M+H)^+$=471.

Example 178: Synthesis of N-methyl-N-(2-oxo-2-((6-(trifluoromethoxy)benzo[d] thiazol-2-yl)amino) ethyl)-2-((2,2,2-trifluoroethyl)amino)acetamide hydrochloride Synthesis of tert-Butyl (2,2,2-trifluoroethyl)carbamate

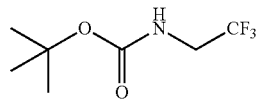

A solution of 2,2,2-trifluoroethylamine hydrochloride (1.0 g, 7.4 mmol) in 1,4-dioxane (15 ml) and water (15 ml) was treated with sodium carbonate (0.78 g, 7.4 mmol) and stirred 5 minutes. Di-tert-butyldicarbonate (1.4 g, 6.6 mmol) was added and the mixture stirred 20 hours. Dichloromethane (50 ml) was added to the reaction mixture and it was washed with saturated sodium bicarbonate solution (50 ml). The aqueous layer was back-extracted with dichloromethane (50 ml) and the combined dichloromethane layers were washed with brine, dried (MgSO$_4$) and evaporated to leave a white solid (964 mg, 65%).

Synthesis of Benzyl N-(tert-butoxycarbonyl)-N-(2,2,2-trifluoroethyl)glycinate

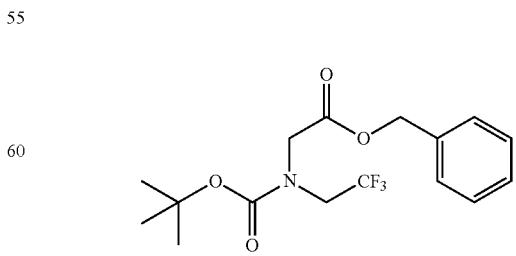

A solution of tert-Butyl (2,2,2-trifluoroethyl)carbamate (300 mg, 1.50 mmol) in anhydrous tetrahydrofuran (15 ml)

under nitrogen atmosphere in an ice bath was treated with a solution of lithium hexamethyldisilylamide (1.0 M in tetrahydrofuran, 1.8 ml, 1.8 mmol) dropwise over 5 minutes. The mixture stirred 30 minutes then 1-bromo benzylacetate (518 mg, 2.25 mmol, 0.357 ml) was added and stirring continued for an additional 18 hours. The reaction mixture was treated with saturated aqueous ammonium chloride (3 ml) and stirred 30 mins. Ethyl acetate (50 ml) was added and the mixture was washed with water (25 ml) and brine (25 ml). The organic phase was dried (MgSO$_4$) and evaporated. The crude product was purified by silica gel chromatography eluting with a gradient of ethyl acetate in hexanes (0-30%) to leave the product as a colorless oil (335 mg, 65%). LC/MS method C: R$_t$=2.62 min.

Synthesis of N-(tert-Butoxycarbonyl)-N-(2,2,2-trifluoroethyl)glycine

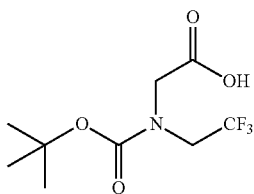 [SMILES: CC(C)(C)OC(=O)N(CC(=O)O)CC(F)(F)F]

Benzyl N-(tert-butoxycarbonyl)-N-(2,2,2-trifluoroethyl) glycinate (170 mg, 0.49 mmol) was hydrogenated (45 psi initial pressure) over 10% Pd/C (30 mg) in methanol (4 ml). After 18 hours the catalyst was filtered through celite (methanol wash) and the filtrate was evaporated to leave the product as a crystalline solid (126 mg, 100%).

Synthesis of N-methyl-N-(2-oxo-2-((6-(trifluoromethoxy)benzo[d]thiazol-2-yl)amino)ethyl)-2-((2,2,2-trifluoroethyl)amino)acetamide Hydrochloride

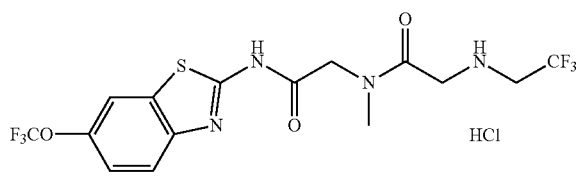 [SMILES: CN(CC(=O)Nc1nc2ccc(OC(F)(F)F)cc2s1)C(=O)CNCC(F)(F)F ; Cl]

A solution of 2-(methylamino)-N-(6-(trifluoromethoxy) benzo [d]thiazol-2-yl)acetamide monohydrochloride (160 mg, 0.47 mmol), N-(tert-butoxycarbonyl)-N-(2,2,2-trifluoroethyl) glycine (120 mg, 0.47 mmol) and N,N-diisopropylethylamine (152 mg, 1.2 mmol, 211 µl) in N,N-dimethylformamide (3 ml) was treated with 1-[Bis(dimethylamino) methylene]-1H-1,2,3-triazolo[4,5-b]pyridinium 3-oxid hexafluorophosphate (179 mg, 0.47 mmol) and stirred 18 hours.

The mixture was diluted with ethyl acetate (50 ml), washed with water (25 ml), 1N HCl (25 ml) and brine (25 ml). The organic phase was dried (MgSO$_4$) and evaporated and the crude product was purified by reverse phase HPLC. The product fractions were combined, treated with sodium bicarbonate solution and extracted with ethyl acetate (2×25 ml). The combined organic layers were washed with brine (25 ml), dried (MgSO$_4$) and evaporated. The product was dissolved in 4N HCl/1,4-dioxane and stirred 2 hours. The solid precipitate was filtered on a glass frit, washed with 1,4-dioxane and DCM, and dried under vacuum to leave 150 mg (66%). LC/MS method A: R$_t$=4.13 min., (M+H)$^+$=445.

Example 179: Synthesis of 2-acetamido-N-methyl-N-(2-oxo-2-((6-(trifluoromethoxy) benzo[d]thiazol-2-yl)amino)ethyl)acetamide

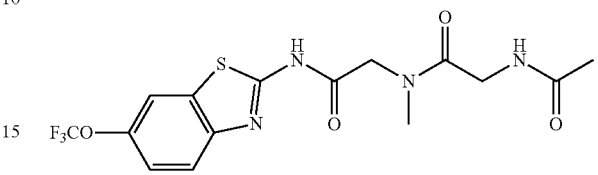

A solution of 2-amino-N-methyl-N-(2-oxo-2-((6-(trifluoromethoxy)benzo[d]thiazol-2-yl)amino)ethyl)acetamide hydrochloride (15 mg, 38 µmol) and N,N-diisopropylethylamine (17 mg, 132 µmol, 24 µl) in N,N-dimethylformamide (0.4 ml) was treated with acetic anhydride (8.0 mg, 76 µmol, 7.5 µl) and stirred 18 hours. Purified by reverse phase HPLC (direct injection of the reaction mixture) and the product fractions were evaporated to leave the pure product as a white solid (12 mg, 78%). LC/MS method B: R$_t$=1.82 min., (M+H)$^+$=405.

Examples 180-184 were prepared on an identical scale and with the same method as example 179 above.

Example 180: Synthesis of N-(2-(methyl(2-oxo-2-((6-(trifluoromethoxy)benzo[d] thiazol-2-yl)amino) ethyl)amino)-2-oxoethyl)propionamide

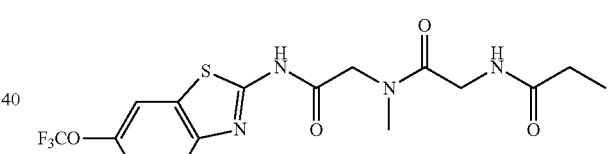

N-(2-(methyl(2-oxo-2-((6-(trifluoromethoxy)benzo[d] thiazol-2-yl)amino)ethyl)amino)-2-oxoethyl)propionamide was prepared according to the procedure of example 179 from 2-amino-N-methyl-N-(2-oxo-2-((6-(trifluoromethoxy) benzo [d]thiazol-2-yl)amino)ethyl)acetamide hydrochloride (15 mg, 38 µmol) and propionic anhydride to leave 12 mg (76%). LC/MS method B: R$_t$=1.90 min., (M+H)$^+$=419.

Example 181: Synthesis of N-(2-(methyl(2-oxo-2-((6-(trifluoromethoxy)benzo[d]thiazol-2-yl)amino) ethyl)amino)-2-oxoethyl)butyramide

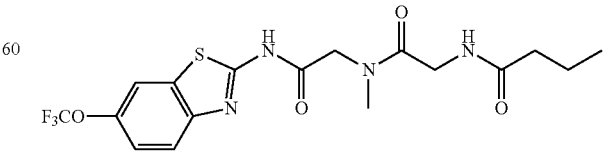

N-(2-(methyl(2-oxo-2-((6-(trifluoromethoxy)benzo [d]thiazol-2-yl)amino)ethyl)amino)-2-oxoethyl)butyramide was prepared according to the procedure of example 179 from 2-amino-N-methyl-N-(2-oxo-2-((6-(trifluoromethoxy)benzo [d]thiazol-2-yl)amino)ethyl)acetamide hydrochloride (15 mg, 38 µmol) and butyric anhydride to leave 12 mg (73%). LC/MS method B: $R_t$=1.99 min., (M+H)$^+$=433.

Example 182: Synthesis of N-(2-(methyl(2-oxo-2-((6-(trifluoromethoxy)benzo[d]thiazol-2-yl)amino)ethyl)amino)-2-oxoethyl)isobutyramide

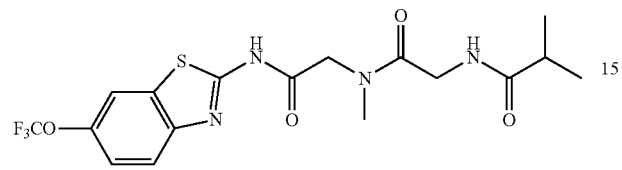

N-(2-(methyl(2-oxo-2-((6-(trifluoromethoxy)benzo [d]thiazol-2-yl)amino)ethyl)amino)-2-oxoethyl)isobutyramide was prepared according to the procedure of example 179 from 2-amino-N-methyl-N-(2-oxo-2-((6-(trifluoromethoxy)benzo [d]thiazol-2-yl)amino)ethyl)acetamide hydrochloride (15 mg, 38 µmol) and isobutyric anhydride to leave 12 mg (73%). LC/MS method B: $R_t$=1.98 min., purity >95%, (M+H)$^+$=433.

Example 183: Synthesis of N-(2-(methyl(2-oxo-2-((6-(trifluoromethoxy)benzo[d]thiazol-2-yl)amino)ethyl)amino)-2-oxoethyl)benzamide

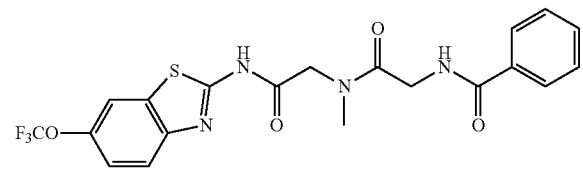 [SMILES: CN(CC(=O)Nc1nc2ccc(OC(F)(F)F)cc2s1)C(=O)CNC(=O)c1ccccc1]

N-(2-(methyl(2-oxo-2-((6-(trifluoromethoxy)benzo [d]thiazol-2-yl)amino)ethyl)amino)-2-oxoethyl)benzamide was prepared according to the procedure of example 179 from 2-amino-N-methy 1-N-(2-oxo-2-((6-(trifluoromethoxy)benzo[d]thiazol-2-yl)amino)ethyl)acetamide hydrochloride (15 mg, 38 µmol) and benzoic anhydride to leave 14 mg (79%). LC/MS method B: $R_t$=2.10 min., (M+H)$^+$=467.

Example 184: Synthesis of 2,2,2-trifluoro-N-(2-(methyl(2-oxo-2-((6-(trifluoromethoxy) benzo[d]thiazol-2-yl)amino)ethyl)amino)-2-oxoethyl)acetamide

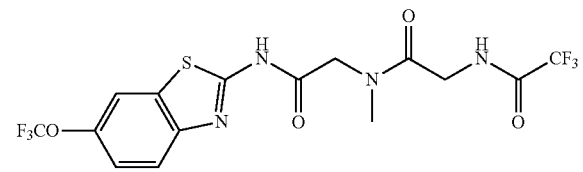 [SMILES: CN(CC(=O)Nc1nc2ccc(OC(F)(F)F)cc2s1)C(=O)CNC(=O)C(F)(F)F]

2,2,2-trifluoro-N-(2-(methyl(2-oxo-2-((6-(trifluoromethoxy)benzo[d]thiazol-2-yl)amino) ethyl)amino)-2-oxoethyl)acetamide was prepared according to the procedure of example 179 from 2-amino-N-methyl-N-(2-oxo-2-((6-(trifluoromethoxy)benzo[d]thiazol-2-yl)amino)ethyl)acetamide hydrochloride (15 mg, 38 µmol) and trifluoroacetic anhydride to leave 13 mg (75%). LC/MS method B: $R_t$=2.12 min., (M+H)$^+$=459.

Example 185: Synthesis of N-methyl-N-(2-oxo-2-((6-(trifluoromethoxy)benzo[d] thiazol-2-yl)amino) ethyl)-2-((1,1,1-trifluoro-2-methylpropan-2-yl)amino)acetamide Synthesis of Benzyl (1,1,1-trifluoro-2-methylpropan-2-yl)carbamate

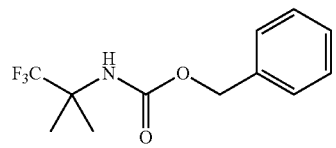 [SMILES: CC(C)(NC(=O)OCc1ccccc1)C(F)(F)F]

A solution of 1,1,1-trifluoro-2-methylpropan-2-amine (1.0 g, 7.9 mmol, 0.90 ml), N,N-diisopropylethylamine (1.5 g, 12 mmol, 1.7 ml) and 4-(dimethylamino)pyridine (50 mg) in dichloromethane (40 ml) was cooled in an ice bath and treated with a solution of benzyl chloroformate (2.0 g, 12 mmol, 1.7 ml) in dichloromethane (10 ml) dropwise over ten minutes. The mixture was allowed to warm to 20° C. over 2 hours and stirred an additional 24 hours. The mixture was washed with 1N HCl (25 ml) and brine (25 ml). The organic phase was dried (MgSO$_4$) and evaporated. The crude product was purified by chromatography on silica gel eluted with a gradient of ethyl acetate in hexanes (5-10-20%) to leave the product as a solid (1.12 g, 56%). LC/MS method C: $R_t$=2.32 min.

Synthesis of tert-butyl N-((benzyloxy)carbonyl)-N-(1,1,1-trifluoro-2-methylpropan-2-yl)glycinate

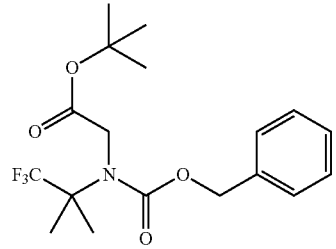 [SMILES: CC(C)(C)OC(=O)CN(C(=O)OCc1ccccc1)C(C)(C)C(F)(F)F]

A solution of benzyl (1,1,1-trifluoro-2-methylpropan-2-yl)carbamate (1.1 g, 4.2 mmol) in anhydrous tetrahydrofuran (40 ml) under nitrogen atmosphere in an ice bath was treated with a solution of lithium hexamethyldisilylamide (1.0 M in tetrahydrofuran, 5.0 ml, 5.0 mmol) dropwise over 15 minutes. The mixture stirred 30 minutes then 1-bromo tert-butylacetate (1.2 g, 6.3 mmol, 0.95 ml) was added and the mixture warmed to 20° C. over 2 hours. Stirring continued for an additional 72 hours. The reaction mixture was treated with saturated aqueous ammonium chloride (5 ml)

and stirred 30 mins. Approximately 75% of the solvents were evaporated and the remainder was treated with ethyl acetate (50 ml). The mixture was washed with water (25 ml) and brine (25 ml). The organic phase was dried (MgSO$_4$) and evaporated. The crude product was purified by silica gel chromatography eluting with a gradient of ethyl acetate in hexanes (0-30%) to leave the product as an impure mixture (600 mg) which was further purified by reverse phase HPLC to leave the product as an oil (165 mg, 10.5%). LC/MS method A: R$_t$=6.57 min.

Synthesis of N-((benzyloxy)carbonyl)-N-(1,1,1-trifluoro-2-methylpropan-2-yl)glycine

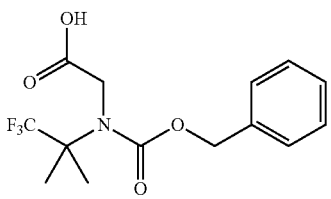 [SMILES: CC(C)(N(CC(=O)O)C(=O)OCc1ccccc1)C(F)(F)F]

A solution of tert-butyl N-((benzyloxy)carbonyl)-N-(1,1,1-trifluoro-2-methylpropan-2-yl)glycinate (160 mg, 0.43 mmol) in TFA (2 ml) and DCM (2 ml) was stirred 2 hours then evaporated. The residue was dissolved in toluene (5 ml) and evaporated (repeated 2×) to leave 132 mg (97%). LC/MS method A: R$_t$=4.87 min.

Synthesis of benzyl (2-(methyl(2-oxo-2-((6-(trifluoromethoxy)benzo[d]thiazol-2-yl)amino)ethyl)amino)-2-oxoethyl)(1,1,1-trifluoro-2-methylpropan-2-yl)carbamate

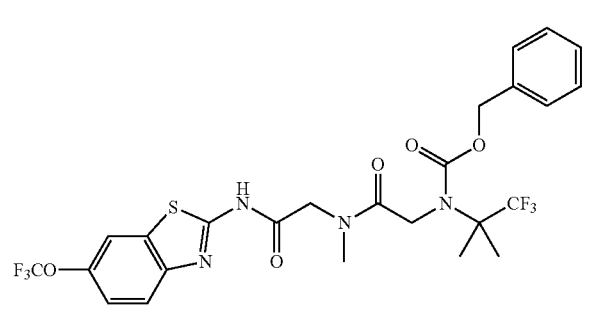 [SMILES: CN(CC(=O)Nc1nc2ccc(OC(F)(F)F)cc2s1)C(=O)CN(C(=O)OCc1ccccc1)C(C)(C)C(F)(F)F]

A solution of 2-(methylamino)-N-(6-(trifluoromethoxy)benzo[d]thiazol-2-yl)acetamide monohydrochloride (150 mg, 0.45 mmol), N-((benzyloxy)carbonyl)-N-(1,1,1-trifluoro-2-methylpropan-2-yl)glycine (130 mg, 0.41 mmol) and N,N-diisopropylethylamine (120 mg, 0.90 mmol, 160 µl) in N,N-dimethylformamide (2 ml) was treated with 1-[Bis(dimethylamino) methylene]-1H-1,2,3-triazolo[4,5-b]pyridinium 3-oxid hexafluorophosphate (170 mg, 0.45 mmol) and stirred 18 hours. The mixture was diluted with ethyl acetate (50 ml), washed with water (25 ml), 1N HCl (25 ml) and brine (25 ml). The organic phase was dried (MgSO$_4$) and evaporated and the crude product was purified by chromatography on silica gel eluted with a gradient of ethyl acetate in hexanes (20%-70%) to leave the pure product as a gum (188 mg, 76%). LC/MS method A: R$_t$=6.28 min., (M+H)$^+$=608.

Synthesis of N-methyl-N-(2-oxo-2-((6-(trifluoromethoxy)benzo[d]thiazol-2-yl)amino)ethyl)-2-((1,1,1-trifluoro-2-methylpropan-2-yl)amino)acetamide

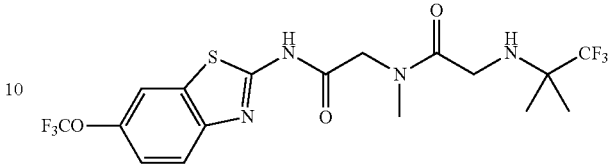

A solution of benzyl (2-(methyl(2-oxo-2-((6-(trifluoromethoxy)benzo[d]thiazol-2-yl)amino)ethyl)amino)-2-oxoethyl)(1,1,1-trifluoro-2-methylpropan-2-yl)carbamate (180 mg, 0.30 mmol) in concentrated hydrobromic acid in acetic acid (4 ml) stirred for 2 h and a precipitate has formed. The reaction mixture was diluted with ethyl acetate (50 ml) and washed with aqueous saturated sodium bicarbonate solution (200 ml). The organic phase was dried (MgSO$_4$) and evaporated to a solid. Dissolved in 1,4-dioxane (4 ml) and treated with 4N HCl/1,4-dioxane. The product hydrochloride salt precipitated and was collected on a medium glass frit, washed with dioxane and dichloromethane, and dried under vacuum to leave the product as a white powder (130 mg, 85%). LC/MS method A: R$_t$=4.45 min., (M+H)$^+$=473.

Example 186: Synthesis of 2-(2-oxopiperazin-1-yl)-N-(6-(trifluoromethoxy)benzo [d]thiazol-2-yl)

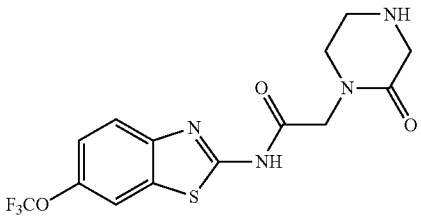 [SMILES: O=C(CN1CCNCC1=O)Nc1nc2ccc(OC(F)(F)F)cc2s1]

A solution of 6-(trifluoromethoxy)benzo[d]thiazol-2-amine (150 mg, 0.64 mmol), 2-(4-(tert-butoxycarbonyl)-2-oxopiperazin-1-yl)acetic acid (232 mg, 0.90 mmol) and N-hydroxybenzotriazole (122 mg, 0.90 mmol) in N,N-dimethylformamide (0.75 ml) was treated with 1-ethyl-3-(3-dimethylaminopropyl)carbodiimide (173 mg, 0.90 mmol) and stirred 18 hours. The mixture was diluted with ethyl acetate (25 ml) and washed with 0.5N HCl (25 ml) and saturated aqueous sodium bicarbonate solution (25 ml). The organic phase was dried (MgSO$_4$) and evaporated and the crude product was purified by silica gel chromatography eluted with a gradient of ethyl acetate in hexanes (0-100%) to leave the pure product which was dissolved in ethyl acetate (4 ml) and 4N HCl/1,4-dioxane (6 ml). The mixture stood for 3 hours and the precipitate was filtered, washed (ethyl acetate) and dries to leave the product as a white powder (98 mg, 37%). LC/MS method A: R$_t$=3.60 min., (M+H)$^+$=375.

Example 187: Synthesis of (S)—N-methyl-N-(2-oxo-2-((6-(trifluoromethoxy)benzo[d] thiazol-2-yl)amino)ethyl)piperazine-2-carboxamide

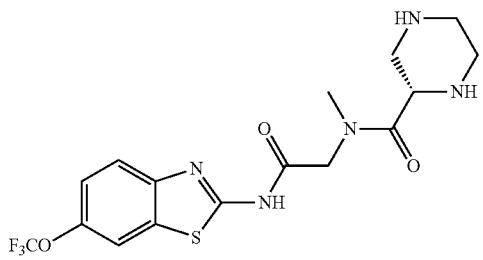 [SMILES: CN(CC(=O)Nc1nc2ccc(OC(F)(F)F)cc2s1)C(=O)[C@@H]1CNCCN1]

A solution of 2-(methylamino)-N-(6-(trifluoromethoxy)benzo[d]thiazol-2-yl)acetamide monohydrochloride (100 mg, 0.293 mmol), (S)-1,4-bis(tert-butoxycarbonyl)piperazine-2-carboxylic acid (135 mg, 0.41 mmol), N-hydroxybenzotriazole (55 mg, 0.41 mmol) and triethylamine (33 mg, 0.32 mmol) in N,N-dimethylformamide (0.50 ml) was treated with 1-ethyl-3-(3-dimethylaminopropyl)carbodiimide (79 mg, 0.41 mmol) and stirred 18 hours. The mixture was diluted with ethyl acetate (25 ml) and washed with 0.5N HCl (25 ml) and saturated aqueous sodium bicarbonate solution (25 ml). The organic phase was dried (MgSO$_4$) and evaporated and the crude product was purified by silica gel chromatography eluted with a gradient of ethyl acetate in hexanes (20-80%) to leave the pure product (120 mg) which was dissolved in ethyl acetate (3 ml) and 4N HCl/1,4-dioxane (4 ml). The mixture stood for 3 hours and the precipitate was filtered, washed (ethyl acetate) and dries to leave the product as a white powder (65 mg, 45%). LC/MS method A: R$_t$=3.39 min., (M+H)$^+$=418.

Example 188: Synthesis of (R)—N-methyl-N-(2-oxo-2-((6-(trifluoromethoxy)benzo[d]thiazol-2-yl)amino)ethyl)piperazine-2-carboxamide

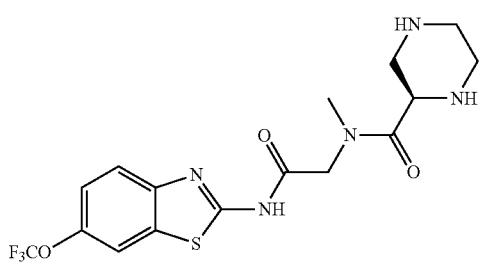 [SMILES: CN(CC(=O)Nc1nc2ccc(OC(F)(F)F)cc2s1)C(=O)[C@H]1CNCCN1]

(R)—N-methyl-N-(2-oxo-2-((6-(trifluoromethoxy)benzo[d]thiazol-2-yl)amino)ethyl) piperazine-2-carboxamide was prepared according to the procedure of example 187 from 2-(methylamino)-N-(6-(trifluoromethoxy)benzo[d]thiazol-2-yl)acetamide monohydrochloride (100 mg, 0.293 mmol) and (R)-1,4-bis(tert-butoxycarbonyl)piperazine-2-carboxylic acid on the same scale as example 187 to provide 60 mg (42%). LC/MS method A: R$_t$=3.39 min., (M+H)$^+$=418.

Example 189: Synthesis of Benzyl (2-(((6-(trifluoromethoxy)benzo[d]thiazol-2-yl)carbamoyl)oxy)ethyl)carbamate

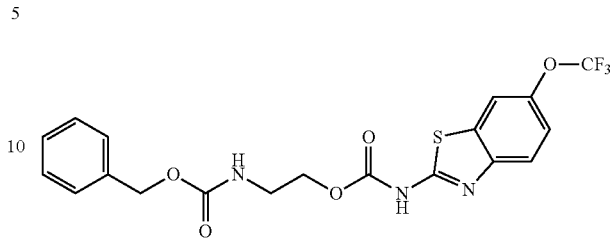

To a solution of benzyl 2-hydroxyethylcarbamate (98 mg, 0.5 mmol) in chloroform (1.0 mL) was added triphosgene (60 mg, 0.2 mmol). The mixture was stirred at 20° C. for 18 hours, then concentrated and dried under vacuum. The residue was dissolved in chloroform (1.0 mL) and was added to a mixture of 6-(trifluoromethoxy)benzo[d]thiazol-2-amine (117 mg, 0.5 mmol) and triethylamine (0.1 ml) in chloroform (2 mL). The resulting mixture was stirred at 20° C. for 18 hours. The mixture was concentrated and the residue was purified by reverse phase HPLC to give the desired product. Yield=54 mg (24%). LC/MS method A: R$_t$=5.87 min., (M+Na)$^+$=478.

Example 190: Synthesis of 2-aminoethyl (6-(trifluoromethoxy)benzo[d]thiazol-2-yl)carbamate

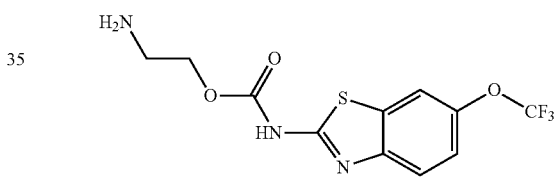

To a solution of benzyl (2-(((6-(trifluoromethoxy)benzo[d]thiazol-2-yl)carbamoyl)oxy) ethyl)carbamate (32.7 mg, 0.072 mmol) in isopropanol (3 mL) was added HBr in acetic acid (33%, 0.3 mL). The mixture was heated at 50° C. for overnight, and then concentrated. The residue was purified by reversed HPLC to give the desired product as TFA salt. Yield=28.8 mg (92%). LC/MS method A: R$_t$=3.74 min., (M+H)$^+$=322.

Example 191: Synthesis of Benzyl ethyl(2-(((6-(trifluoromethoxy)benzo[d]thiazol-2-yl)carbamoyl)oxy)ethyl)carbamate

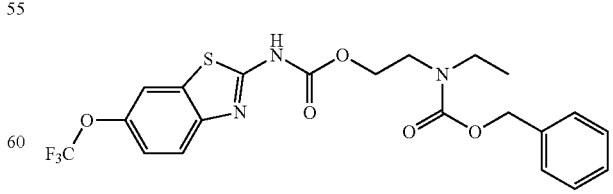

Benzyl ethyl(2-(((6-(trifluoromethoxy)benzo[d]thiazol-2-yl)carbamoyl)oxy)ethyl) carbamate was prepared according to the procedure of example 189 at the same scale from 6-(trifluoromethoxy)benzo[d]thiazol-2-amine and benzyl ethyl 2-hydroxyethylcarbamate. Yield=23 mg (9.5%). LC/MS method A: $R_t$=5.99 min., $(M+H)^+$=484.

Example 192: Synthesis of 2-(Ethylamino)ethyl (6-(trifluoromethoxy)benzo[d]thiazol-2-yl)carbamate

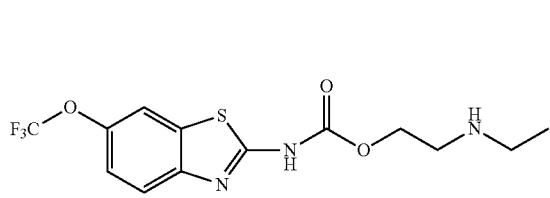 [SMILES: CCNCCOC(=O)Nc1nc2ccc(OC(F)(F)F)cc2s1]

2-(Ethylamino)ethyl (6-(trifluoromethoxy)benzo[d]thiazol-2-yl)carbamate. was prepared according to the procedure of example 190 at the same scale from benzyl ethyl (2-(((6-(trifluoromethoxy)benzo[d]thiazol-2-yl)carbamoyl)oxy)ethyl)carbamate (18 mg, 0.037 mmol). Yield=9.5 mg (58%). LC/MS method A: $R_t$=3.89 min., $(M+H)^+$=350.

Example 193: Synthesis of Benzyl methyl(2-(((6-(trifluoromethoxy)benzo[d]thiazol-2-yl)carbamoyl)oxy)ethyl)carbamate

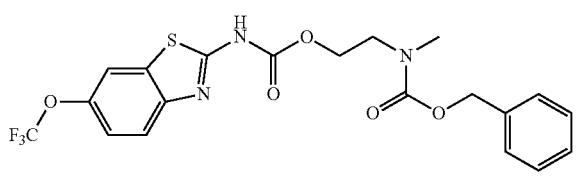 [SMILES: CN(CCOC(=O)Nc1nc2ccc(OC(F)(F)F)cc2s1)C(=O)OCc1ccccc1]

Benzyl methyl(2-(((6-(trifluoromethoxy)benzo[d]thiazol-2-yl)carbamoyl)oxy)ethyl) carbamate was prepared according to the procedure of example 189 at the same scale from 6-(trifluoromethoxy)benzo[d]thiazol-2-amine and benzyl methyl 2-hydroxyethylcarbamate. Yield=36 mg (15%). LC/MS method A: $R_t$=5.98 min., $(M+H)^+$=470.26.

Example 194: Synthesis of 2-(Methylamino)ethyl (6-(trifluoromethoxy)benzo[d]thiazol-2-yl)carbamate

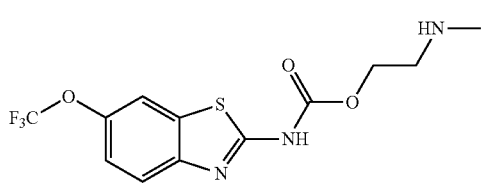 [SMILES: CNCCOC(=O)Nc1nc2ccc(OC(F)(F)F)cc2s1]

2-(Methylamino)ethyl (6-(trifluoromethoxy)benzo[d]thiazol-2-yl)carbamate was prepared according to the procedure of example 190 from benzyl methyl(2-(((6-(trifluoromethoxy)benzo[d]thiazol-2-yl)carbamoyl)oxy)ethyl) carbamate (18 mg, 0.037 mmol). Yield=19 mg (69%). LC/MS method A: $R_t$=3.80 min., $(M+H)^+$=336.06.

Example 195: Synthesis of Benzyl isopropyl(2-(((6-(trifluoromethoxy)benzo[d]thiazol-2-yl)carbamoyl)oxy)ethyl)carbamate

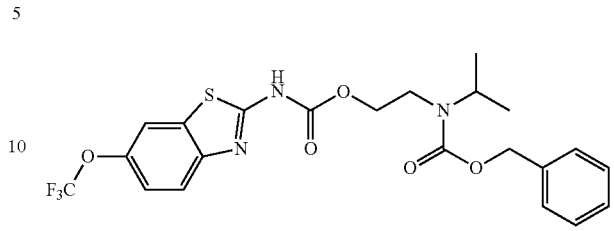

Benzyl isopropyl(2-(((6-(trifluoromethoxy)benzo[d]thiazol-2-yl)carbamoyl)oxy)ethyl) carbamate was prepared according to the procedure of example 189 at the same scale from 6-(trifluoromethoxy)benzo[d]thiazol-2-amine and benzyl isopropyl 2-hydroxyethylcarbamate. Yield=51 mg (21%). LC/MS method A: $R_t$=6.79 min., $(M+Na)^+$=520.12.

Example 196: Synthesis of 2-(Isopropylamino)ethyl (6-(trifluoromethoxy)benzo[d] thiazol-2-yl)carbamate

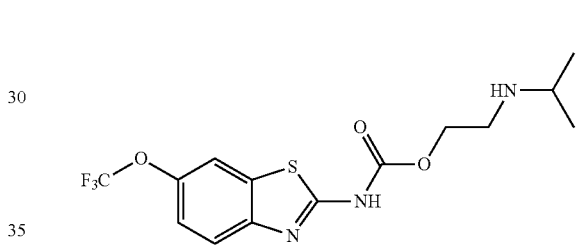

2-(Isopropylamino)ethyl (6-(trifluoromethoxy)benzo[d]thiazol-2-yl)carbamate was prepared according to the procedure and same scale as example 190 from benzyl isopropyl(2-(((6-(trifluoromethoxy)benzo[d]thiazol-2-yl)carbamoyl)oxy)ethyl) carbamate. Yield=26 mg (62%). LC/MS method A: $R_t$=3.96 min., $(M+H)^+$=364.

Example 197: Synthesis of (5-methyl-2-oxo-1,3-dioxol-4-yl)methyl (5-(trifluoro methoxy)benzo[d]thiazol-2-yl)carbamate

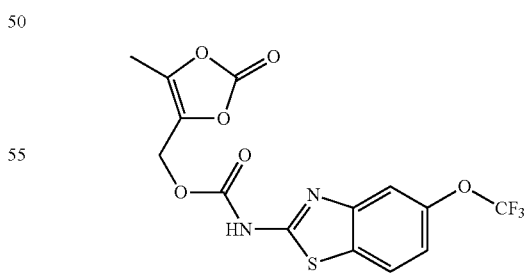

(5-methyl-2-oxo-1,3-dioxol-4-yl)methyl (5-(trifluoromethoxy)benzo[d]thiazol-2-yl)carbamate was prepared according to the procedure of example 189 at the same scale from 6-(trifluoromethoxy)benzo[d]thiazol-2-amine and 4-(hydroxymethyl)-5-methyl-1,3-dioxol-2-one. Yield=10 mg (5%). LC/MS method A: $R_t$=5.67 min.

Example 198: Synthesis of 4-amino-2,2-dimethyl-N-(6-(trifluoromethoxy)benzo[d] thiazol-2-yl)butanamide

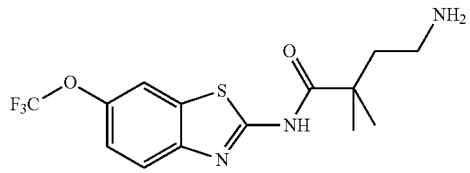 [SMILES: CC(C)(CCN)C(=O)Nc1nc2ccc(OC(F)(F)F)cc2s1]

4-Amino-2,2-dimethyl-N-(6-(trifluoromethoxy)benzo[d]thiazol-2-yl)butanamide was prepared according to the procedure of example 147 from 2-amino-6-(trifluoromethoxy) benzimidazole (0.10 g, 0.43 mmol) and N-Boc 4-amino-2,2-dimethylbutanoic acid (0.15 g, 0.64 mmol). Yield for Boc protected intermediate 138 mg (72%). LC/MS method A: $R_t$=6.43 min., purity >90%, $(M+H)^+$=448. Yield for final product (111 mg, 100%, 72% overall). LC/MS method A: $R_t$=4.03 min., $(M+H)^+$=348.

Example 199: Synthesis of (S)-2-amino-N1,N5-bis (6-(trifluoromethoxy)benzo[d] thiazol-2-yl)pentanediamide

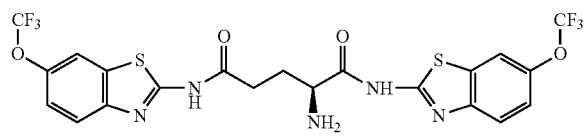 [SMILES: N[C@@H](CCC(=O)Nc1nc2ccc(OC(F)(F)F)cc2s1)C(=O)Nc1nc2ccc(OC(F)(F)F)cc2s1]

(S)-2-amino-N1,N5-bis(6-(trifluoromethoxy)benzo[d] thiazol-2-yl)pentanediamide was prepared according to the procedure of example 147 from 2-amino-6-(trifluoromethoxy) benzimidazole (117 mg, 0.5 mmol) and N-Boc (S)-2-aminopentanedioic acid (62 mg, 0.25 mmol). Yield for Boc protected intermediate 42 mg (25%). LC/MS method A: $R_t$=5.72 min., purity >90%, $(M+H)^+$=679. Yield for final product (17 mg, 40%, 10% overall). LC/MS method A: $R_t$=4.99 min., $(M+H)^+$=580.

Example 200: Synthesis of 2-(dimethylamino)-N-(6-(trifluoromethoxy)benzo[d]thiazol-2-yl)acetamide

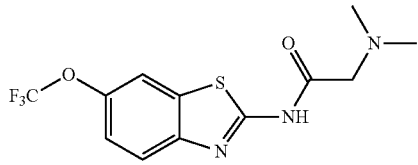 [SMILES: CN(C)CC(=O)Nc1nc2ccc(OC(F)(F)F)cc2s1]

2-(dimethylamino)-N-(6-(trifluoromethoxy)benzo[d]thiazol-2-yl) was prepared according to the procedure of example 147 from 2-amino-6-(trifluoromethoxy) benzimidazole (117 mg, 0.5 mmol) and 2-(dimethylamino)acetic acid (58 mg, 0.75 mmol). Yield=200 mg (93%). LC/MS method A: $R_t$=3.35 min., purity >90%, $(M+H)^+$=320.

Example 201: Synthesis of 1,3-bis(6-(trifluoromethoxy)benzo[d]thiazol-2-yl)urea

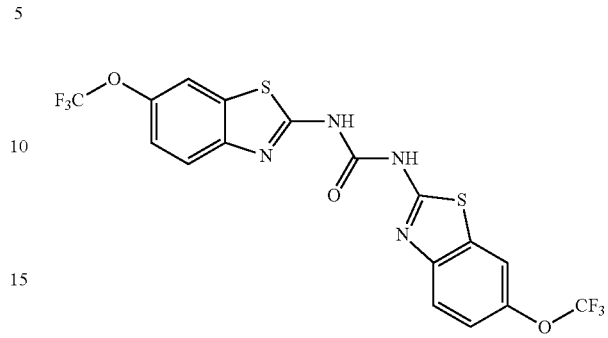

A mixture of 2-amino-6-(trifluoromethoxy) benzimidazole (936 mg, 4.0 mmol) and triphosgene (593 mg, 2.0 mmol) in chloroform (10 mL) was heated to 60° C. for 18 hours. The solid was filtered off (unreacted riluzole) and filtrate was diluted with ethyl acetate (50 ml), washed with 1N HCl (25 ml), saturated aqueous $NaHCO_3$ (25 ml) and brine (25 ml), dried over $MgSO_4$ and concentrated to give the isocyanide intermediate. Yield=375 mg (36%). LC/MS method A: $R_t$=6.41 min., purity >90%, $(M+H)^+$=261.19. A mixture of the isocyanide (26 mg, 0.1 mmol) and 2-amino-6-(trifluoromethoxy) benzimidazole (23 mg, 0.1 mmol) in 2-butanone (0.5 mL) was stirred at 60° C. for 72 hours. The mixture was concentrated and the residue was stirred in methylene chloride for 20 minutes, the solid was collected, washed with methylene chloride and dried under vacuum. Yield=23 mg (46%). LC/MS method A: $R_t$=6.90 min., $(M+H)^+$=496.

Example 202: Synthesis of Benzyl 2-(2-{[(tert-butoxy)carbonyl]amino}acetamido) acetate

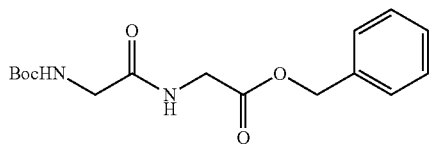 [SMILES: CC(C)(C)OC(=O)NCC(=O)NCC(=O)OCc1ccccc1]

A solution of (tert-butyloxycarbonyl)glycine (0.39 g, 2.3 mmol), glycine benzyl ester hydrochloride (0.50 g, 2.5 mmol) and triethylamine (0.51 g, 5.0 mmol, 0.70 ml) in N,N-dimethylformamide (10 ml) was treated with N-[(Dimethylamino)-1H-1,2,3-triazolo-[4,5-b]pyridin-1-ylmethylene]-N-methylmethanaminium hexafluorophosphate N-oxide (0.95 g, 2.5 mmol) and stirred 18 hours. The mixture was diluted with ethyl acetate (75 ml) and washed with 1N HCl (50 ml), water (50 ml), 1M sodium carbonate solution (50 ml), water (50 ml) and brine (25 ml). The organic phase was dried ($MgSO_4$) and evaporated to leave benzyl 2-(2-{[(tert-butoxy)carbonyl] amino}acetamido) acetate as a waxy solid (800 mg, 99%). LC/MS method A: $R_t$=4.30 min., $(M+H)^+$=323. $^1$H-NMR ($CDCl_3$): δ=7.36 (s, 5H), 6.55 (bs, 1H), 5.20 (s, 2H), 5.09 (bs, 1H), 4.11 (d, J=5.2 Hz, 2H), 3.86 (d, J=5.8 Hz, 2H), 1.46 (s, 9H).

Example 203: Synthesis of 2-(2-{[(tert-Butoxy)carbonyl]amino}acetamido)acetic Acid

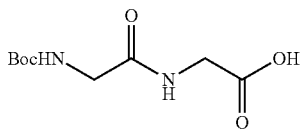 [SMILES: CC(C)(C)OC(=O)NCC(=O)NCC(=O)O]

Benzyl 2-(2-{[(tert-butoxy)carbonyl]amino}acetamido)acetate (790 mg, 2.4 mmol) was hydrogenated at one atmosphere hydrogen pressure over 10% Pd/C (100 mg) in methanol (25 ml) for 18 h. The catalyst was filtered over celite, washed with methanol (2×5 ml) and the filtrate evaporated under reduced pressure to leave 2-(2-{[(tert-butoxy)carbonyl]amino}acetamido)acetic acid as a solid (555 mg, 100%). $^1$H-NMR (CD$_3$OD): δ=3.92 (s, 2H), 3.75 (s, 2H), 1.45 (s, 9H).

Example 204: Synthesis of 2-Amino-N-{[methyl({[6-(trifluoromethoxy)-1,3-benzo thiazol-2-yl]carbamoyl}methyl)carbamoyl]methyl}acetamide

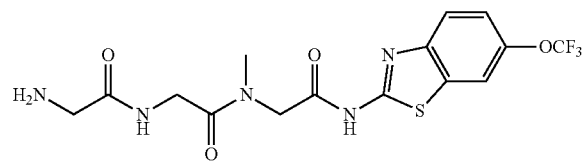 [SMILES: CN(CC(=O)Nc1nc2ccc(OC(F)(F)F)cc2s1)C(=O)CNC(=O)CN]

A solution of 2-(methylamino)-N-[6-(trifluoromethoxy)-1,3-benzothiazol-2-yl]acetamide dihydrochloride (40 mg, 0.11 mmol), (tert-butyloxycarbonyl)glycylglycine (28 mg, 0.12 mmol) and triethylamine (33 mg, 0.33 mmol, 46 µl) in N,N-dimethylformamide (1 ml) was treated with N-[(Dimethylamino)-1H-1,2,3-triazolo-[4,5-b]pyridin-1-ylmethylene]-N-methylmethanaminium hexafluorophosphate N-oxide (44 mg, 0.12 mmol) and the mixture was stirred for 18 hours. The mixture was then purified by RPHPLC without a workup procedure (method B) and the product fractions were combined, treated with saturated aqueous sodium bicarbonate solution (50 ml) and extracted with ethyl acetate (2×25 ml). The combined organic phases were washed with brine (2×25 ml), dried (MgSO$_4$) and evaporated under reduced pressure to leave a solid (34 mg, 60%). LC/MS method A: R$_t$=4.86 min., (M+H)$^+$=520.

The solid was dissolved in methylene chloride (1 ml) and trifluoroacetic acid (1 ml) and allowed to stand for 2 hours. The solvents were evaporated and the residue was dissolved in water (25 ml) and lyophilized to leave 2-amino-N-{[methyl({[6-(trifluoromethoxy)-1,3-benzothiazol-2-yl]carbamoyl}methyl) carbamoyl]methyl}acetamide as a light yellow powder trifluoroacetic acid salt (40 mg, 60% over two steps). LC/MS method A: R$_t$=3.69 min., (M+H)$^+$=420. $^1$H-NMR (CD$_3$OD): δ=7.84 (d, J=1.8 Hz, 1H), 3:1 conformers at 7.78 and 7.80 (d, J=8.8 Hz, 1H), 7.35 (dd, J=8.8 Hz, J=1.8 Hz, 11-1), 3:1 conformers at 4.45 and 4.38 (s, 2H), 3:1 conformers at 4.28 and 4.15 (s, 2H), 3.75 (s, 2H), 3:1 conformers at 3.20 and 3.02 (s, 3H).

Example 205: Synthesis of Benzyl 2-{[(tert-butoxy)carbonyl](oxan-4-yl)amino}acetate

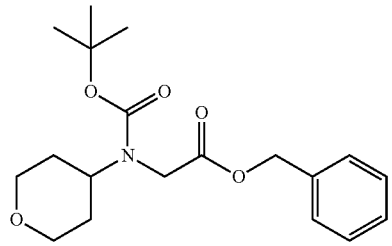 [SMILES: CC(C)(C)OC(=O)N(CC(=O)OCc1ccccc1)C1CCOCC1]

A solution of 4-aminotetrahydropyran (0.46 g, 4.6 mmol) in tetrahydrofuran (10 ml) was treated with triethylamine (0.59 g, 5.8 mmol, 0.80 ml) and bromobenzylacetate (1.3 g, 5.8 mmol, 0.91 ml) and stirred for 24 hours. tert-butyloxycarbonyl anhydride (1.0 g, 4.6 mmol) was added and the mixture stirred for 72 hours. The mixture was diluted with ethyl acetate (50 ml) and 1N HCl (50 ml) and separated. The organic layer was washed with water (30 ml), dried (MgSO$_4$) and evaporated to leave benzyl 2-{[(tert-butoxy)carbonyl](oxan-4-yl)amino}acetate as a solid (0.80 g, 50%). LC/MS method A: R$_t$=5.43 min., (M+H)$^+$=250 (M+H$^+$−100, (t-butyloxcarbonyl)). $^1$H-NMR (CDCl$_3$): δ=7.35 (s, 5H), 5.16 (s, 2H), 4.25-4.40 (m, 1H), 3.90-4.01 (m, 2H), 3.84 (s, 2H), 3.44 (t, 2H, J=11.7 Hz), 1.33-1.73 (m, 13H).

Example 206: Synthesis of 2-{[(tert-Butoxy)carbonyl](oxan-4-yl)amino}acetic Acid

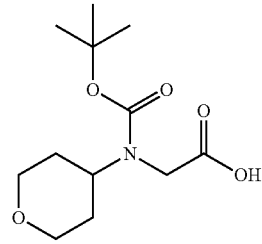 [SMILES: CC(C)(C)OC(=O)N(CC(=O)O)C1CCOCC1]

A solution of 2-{[(tert-butoxy)carbonyl](oxan-4-yl)amino}acetate (0.80 g, 2.3 mmol) was hydrogenated at 1 atmosphere hydrogen pressure over 5% Pd/C (100 mg) in methanol (25 ml) for 2 hours. The mixture was filtered over celite, washed with methanol (2×5 ml) and concentrated to yield 2-{[(tert-butoxy)carbonyl](oxan-4-yl)amino}acetic acid as a solid (0.61 g, 100%). $^1$H-NMR (CDCl$_3$): δ=conformers at 4.25-4.40 and 3.60-3.80 (m, 1H), 3.80-4.05 (m, 4H), 3.45 (t, J=14.3 Hz, 2H), 1.50-1.95 (m, 4H), 1.45 (s, 9H).

Example 207: Synthesis of tert-Butyl N-{[methyl({[6-(trifluoromethoxy)-1,3-benzothiazol-2-yl]carbamoyl}methyl)carbamoyl]methyl}-N-(oxan-4-yl)carbamate

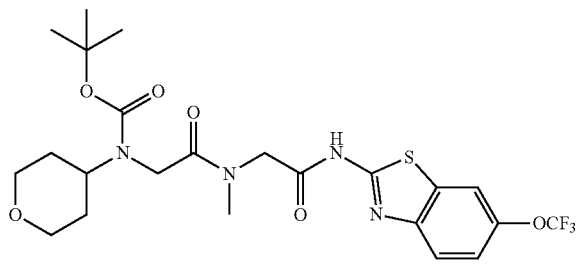 [SMILES: CN(CC(=O)Nc1nc2ccc(OC(F)(F)F)cc2s1)C(=O)CN(C(=O)OC(C)(C)C)C1CCOCC1]

A solution of 2-{[(tert-butoxy)carbonyl](oxan-4-yl)amino}acetic acid (52 mg, 0.15 mmol), 2-(methylamino)-N-[6-(trifluoromethoxy)-1,3-benzothiazol-2-yl]acetamide dihydrochloride (50 mg, 0.13 mmol) and N,N-diisopropylethylamine (50 mg, 0.39 mmol, 70 µl) in N,N-dimethylformamide (1 ml) was treated with N-[(Dimethylamino)-1H-1,2,3-triazolo-[4,5-b]pyridin-1-ylmethylene]-N-methylmethanaminium hexafluorophosphate N-oxide (57 mg, 0.15 mmol) and the mixture stirred for 18 hours. The product mixture was purified by reversed phase HPLC (RPHPLC, method B) without a workup to yield 66 mg (93%) of tert-butyl N-{[methyl({[6-(trifluoromethoxy)-1,3-benzothiazol-2-yl]carbamoyl}methyl)carbamoyl]methyl}-N-(oxan-4-yl)carbamate as a solid. LC/MS method A: $R_t$=5.46 min., (M+H)$^+$=547.

Example 208: Synthesis of N-Methyl-2-[(oxan-4-yl)amino]-N-({[6-(trifluoromethoxy)-1,3-benzothiazol-2-yl]carbamoyl}methyl)acetamide

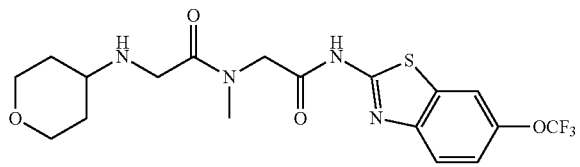 [SMILES: CN(CC(=O)Nc1nc2ccc(OC(F)(F)F)cc2s1)C(=O)CNC1CCOCC1]

A solution of tert-butyl N-{[methyl({[6-(trifluoromethoxy)-1,3-benzothiazol-2-yl]carbamoyl}methyl)carbamoyl]methyl}-N-(oxan-4-yl)carbamate (66 mg) in 1,4-dioxane (2 ml) was treated with 4N HCl in 1,4-dioxane (2 ml) and the mixture stirred for 2 hours. The product precipitated as a fine white powder which was collected by filtration, washed with dioxane and ether, and dried to yield 56 mg (83%) of N-methyl-2-[(oxan-4-yl)amino]-N-({[6-(trifluoromethoxy)-1,3-benzothiazol-2-yl]carbamoyl}methyl)acetamide dihydrochloride salt. LC/MS method A: $R_t$=3.89 min., (M+H)$^+$=447. $^1$H-NMR (CD$_3$OD): δ=7.85 (d, J=1.5 Hz, 1H), 3:1 conformers at 7.81 and 7.80 (d, J=9.1 Hz, 1H), 7.36 (dd, J=9.1 Hz and J=1.5 Hz, 1H), 4.44 (s, 2H), 3:1 conformers at 4.24 and 4.10 (s, 2H), 4.02 (dd, J=12.0 Hz, J=6.5 Hz, 2H), 3.35-3.50 (m, 3H), 3:1 conformers at 3.18 and 3.04 (s, 3H), 2.20-2.10 (m, 2H), 1.70 (ddd, J=17.0, J=12.4 Hz, J=5.0 Hz, 2H).

Example 209: Synthesis of tert-Butyl 3-{[2-(benzyloxy)-2-oxoethyl][(tert-butoxy) carbonyl]amino}azetidine-1-carboxylate

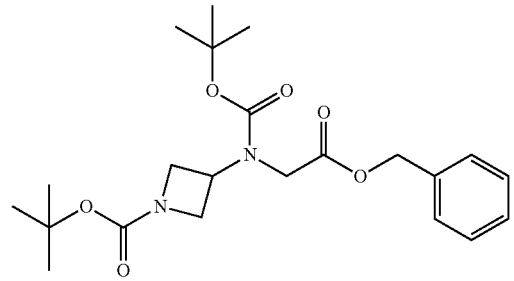 [SMILES: CC(C)(C)OC(=O)N1CC(N(CC(=O)OCc2ccccc2)C(=O)OC(C)(C)C)C1]

Tert-Butyl 3-{[2-(benzyloxy)-2-oxoethyl][(tert-butoxy)carbonyl]amino}azetidine-1-carboxylate was prepared according to the procedure for Example 205 from tert-butyl 3-aminoazetidine-1-carboxylate. (0.82 g, 42%). LC/MS method A: $R_t$=6.08 min., (M+Na)$^+$=423. $^1$H-NMR (CDCl$_3$): δ=7.36 (s, 5H), 5.17 (s, 2H), conformers at 4.90-4.50 and 4.35-4.50 (m, 1H), 3.80-4.20 (m, 6H), 3.84 (s, 2H), 1.33-1.53 (m, 18H).

Example 210: Synthesis of 2-{[(tert-Butoxy)carbonyl]({1-[(tert-butoxy)carbonyl]azetidin-3-yl})amino}acetic Acid

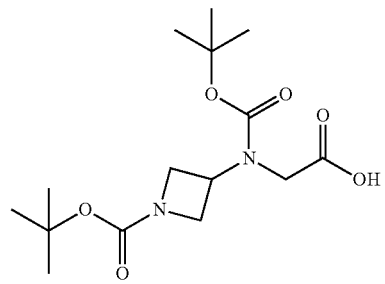 [SMILES: CC(C)(C)OC(=O)N1CC(N(CC(=O)O)C(=O)OC(C)(C)C)C1]

2-{[(tert-Butoxy)carbonyl]({1-[(tert-butoxy)carbonyl]azetidin-3-yl})amino}acetic acid was prepared according to the procedure for Example 206 from 0.82 g (2.0 mmol) of tert-butyl 3-{[2-(benzyloxy)-2-oxoethyl][(tert-butoxy)carbonyl]amino}azetidine-1-carboxy late (0.64 g, 97%). $^1$H-NMR (CDCl$_3$): δ=conformers at 4.93-5.02 and 4.45-4.53 (m, 1H), 3.83-4.22 (m, 6H), 1.44 (s, 18H).

Example 211: Synthesis of tert-Butyl 3-{[(tert-butoxy)carbonyl]({[methyl({[6-(trifluoromethoxy)-1,3-benzothiazol-2-yl]carbamoyl}methyl)carbamoyl]methyl})amino}azetidine-1-carboxylate

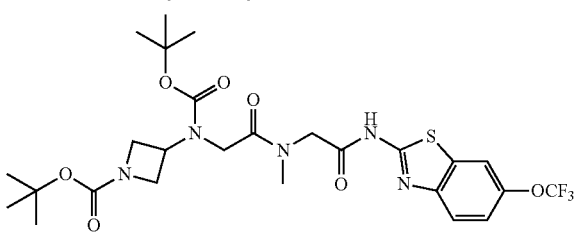 [SMILES: CN(CC(=O)Nc1nc2ccc(OC(F)(F)F)cc2s1)C(=O)CN(C(=O)OC(C)(C)C)C1CN(C(=O)OC(C)(C)C)C1]

Tert-Butyl 3-{[(tert-butoxy)carbonyl]({[methyl({[6-(trifluoromethoxy)-1,3-benzothiazol-2-yl]carbamoyl}methyl)carbamoyl]methyl})amino}azetidine-1-carboxylate was prepared according to the procedure for Example 207 from 2-{[(tert-butoxy)carbonyl]({1-[(tert-butoxy)carbonyl]azetidin-3-yl})amino}acetic acid and 2-(methylamino)-N-[6-(trifluoromethoxy)-1,3-benzothiazol-2-yl]acetamide dihydrochloride (75 mg 94%). LC/MS method A: R$_f$=6.01 min., (M+H)$^+$=618. NMR??

Example 212: Synthesis of 2-[(Azetidin-3-yl)amino]-N-methyl-N-({[6-(trifluoromethoxy)-1,3-benzothiazol-2-yl]carbamoyl}methyl)acetamid

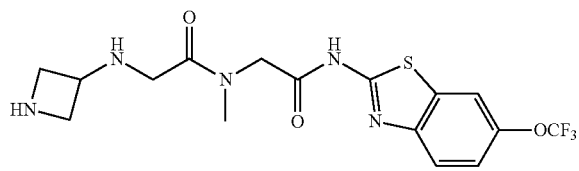 [SMILES: CN(CC(=O)Nc1nc2ccc(OC(F)(F)F)cc2s1)C(=O)CNC1CNC1]

2-[(Azetidin-3-yl)amino]-N-methyl-N-({[6-(trifluoromethoxy)-1,3-benzothiazol-2-yl]carbamoyl}methyl)acetamide was prepared according to the procedure for Example 208 from tert-butyl 3-{[(tert-butoxy)carbonyl]({[methyl({[6-(trifluoromethoxy)-1,3-benzothiazol-2-yl]carbamoyl}methyl) carbamoyl]methyl})amino}azetidine-1-carboxylate (75 mg) to yield 43 mg (63%) of 2-[(azetidin-3-yl)amino]-N-methyl-N-({[6-(trifluoromethoxy)-1,3-benzothiazol-2-yl]carbamoyl}methyl) acetamide as a white powder. LC/MS method A: $^1$H-NMR (CD$_3$OD): δ=7.85 (d, J=1.5 Hz, 1H), 3:1 conformers at 7.81 and 7.80 (d, J=8.8 Hz, 1H), 7.35 (dd, J=8.8 Hz and J=1.5 Hz, 1H), 4.20-4.60 (m, 9H), 3:1 conformers at 3.21 and 3.18 (s, 3H).

Example 213: Synthesis of tert-Butyl 4-{[2-(benzyloxy)-2-oxoethyl][(tert-butoxy)carbonyl]amino}piperidine-1-carboxylate

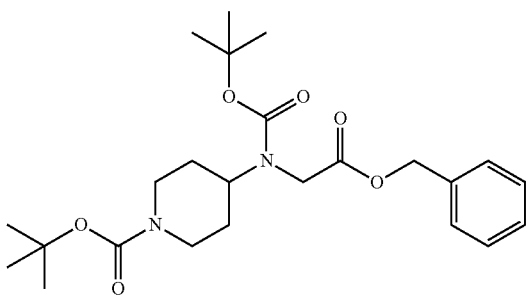 [SMILES: CC(C)(C)OC(=O)N1CCC(N(CC(=O)OCc2ccccc2)C(=O)OC(C)(C)C)CC1]

Tert-Butyl 4-{[2-(benzyloxy)-2-oxoethyl][(tert-butoxy)carbonyl]amino}piperidine-1-carboxylate was prepared according to the procedure for Example 205 from tert-butyl 4-aminopiperidine-1-carboxylate. Left tert-butyl 4-{[2-(benzyloxy)-2-oxoethyl][(tert-butoxy)carbonyl]amino}piperidine-1-carboxylate (1.3 g, 63%). LC/MS method A: R$_f$=5.43 min., (M+Na)$^+$=471. $^1$H-NMR (CDCl$_3$): δ=7.36 (s, 5H), 5.15 (s, 2H), 4.10-4.30 (m, 3H), conformers at 3.94 and 3.80 (s, 2H), 2.65-2.80 (m, 2H), 1.70-1.78 (m, 2H), conformers at 1.35-1.45 (s, 18H).

Example 214: Synthesis of 2-{[(tert-Butoxy)carbonyl]({1-[(tert-butoxy)carbonyl] piperidin-4-yl}) amino}acetic Acid

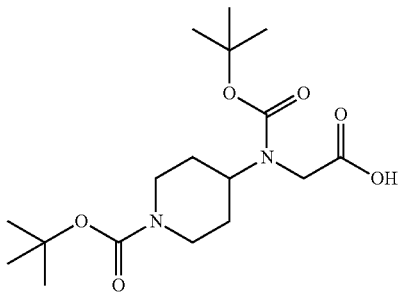 [SMILES: CC(C)(C)OC(=O)N1CCC(N(CC(=O)O)C(=O)OC(C)(C)C)CC1]

2-{[(tert-Butoxy)carbonyl]({1-[(tert-butoxy)carbonyl]piperidin-4-yl})amino}acetic acid was prepared according to the procedure for Example 206 from tert-butyl 4-{[2-(benzyloxy)-2-oxoethyl][(tert-butoxy)carbonyl]amino}piperidine-1-carboxylate (1.3 g, 2.9 mmol) to provide 2-[{(tert-butoxy)carbonyl}({1-[(tert-butoxy)carbonyl] piperidin-4-yl})amino}acetic acid (1.0 g, 96%) as a solid. $^1$H-NMR (CDCl$_3$): δ=4.10-4.32 (m, 3H), 3.78-3.95 (m, 2H), 2.65-2.81 (m, 2H), 1.75 (d, J=10.3 Hz, 2H), 1.52 (bs, 20H).

Example 215: Synthesis of tert-Butyl 4-{[(tert-butoxy)carbonyl]({[methyl({[6-(trifluoromethoxy)-1,3-benzothiazol-2-yl]carbamoyl}methyl)carbamoyl]methyl})amino}piperidine-1-carboxylate

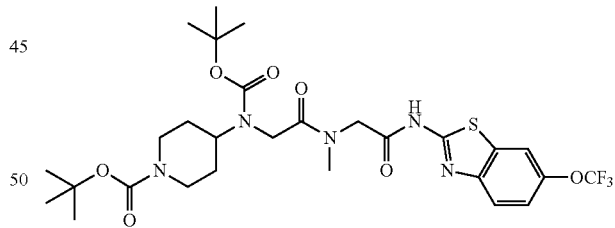

Tert-Butyl 4-{[(tert-butoxy)carbonyl]({[methyl({[6-(trifluoromethoxy)-1,3-benzothiazol-2-yl]carbamoyl}methyl)carbamoyl]methyl}) amino} piperidine-1-carboxylate was prepared according to the procedure for Example 207 from 2-{[(tert-butoxy)carbonyl]({1-[(tert-butoxy)carbonyl]piperidin-4-yl})amino}acetic acid and 2-(methylamino)-N-[6-(trifluoromethoxy)-1,3-benzothiazol-2-yl]acetamide dihydrochloride to yield 82 mg (98%) of tert-butyl 4-{[(tert-butoxy)carbonyl]({[methyl({[6-(trifluoromethoxy)-1,3-benzothiazol-2-yl]carbamoyl}methyl)carbamoyl]methyl}) amino}piperidine-1-carboxylate. LC/MS method A: R$_f$=6.20 min., (M+H)$^+$=646.

Example 216: Synthesis of N-Bethyl-2-[(piperidin-4-yl)amino]-N-({[6-(trifluoromethoxy)-1,3-benzothiazol-2-yl]carbamoyl}methyl)acetamide

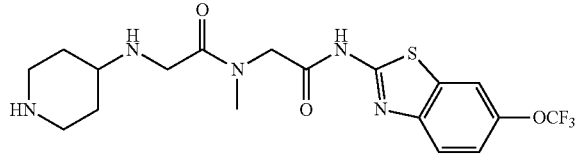 [SMILES: CN(CC(=O)Nc1nc2ccc(OC(F)(F)F)cc2s1)C(=O)CNC1CCNCC1]

N-Bethyl-2-[(piperidin-4-yl)amino]-N-({[6-(trifluoromethoxy)-1,3-benzothiazol-2-yl]carbamoyl}methyl)acetamide was prepared according to the procedure for Example 208 from tert-butyl 4-{[(tert-butoxy)carbonyl]({[methyl({[6-(trifluoromethoxy)-1,3-benzothiazol-2-yl]carbamoyl}methyl)carbamoyl]methyl})amino}piperidine-1-carboxylate (82 mg) to yield 57 mg (79%) of N-methyl-2-[(piperidin-4-yl)amino]-N-({[6-(trifluoromethoxy)-1,3-benzothiazol-2-yl]carbamoyl}methyl)acetamide as a white powder. LC/MS method A: $R_t$=3.47 min., (M+H)$^+$=447. $^1$H-NMR (CD$_3$OD): δ=7.85 (d, J=2.0 Hz, 1H), 3:1 conformers at 7.81 and 7.80 (d, J=8.8 Hz, 1H), 7.36 (dd, J=8.8 Hz and J=2.0 Hz, 1H), 3:1 conformers at 4.45 and 4.47 (s, 2H), 3:1 conformers at 4.32 and 4.18 (s, 2H), 3.50-3.61 (m, 3H), 3:1 conformers at 3.20 and 3.05 (s, 3H), 3.12 (ddd, J=13.2 Hz, J=13.2 Hz, J=3.0 Hz, 2H), 2.42 (d, J=13.2 Hz, 2H), 1.95 (ddd, J=20.1 Hz, J=13.2 Hz, J=4.1 Hz, 2H).

Example 217: Synthesis of 2-[N-Methyl-2-(morpholin-4-yl)acetamido]-N-[6-(trifluoromethoxy)-1,3-benzothiazol-2-yl]acetamide

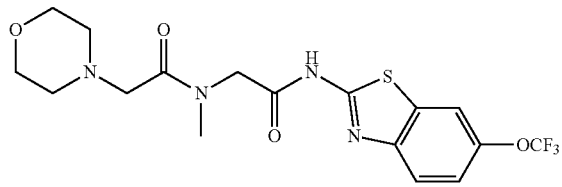 [SMILES: CN(CC(=O)Nc1nc2ccc(OC(F)(F)F)cc2s1)C(=O)CN1CCOCC1]

A solution of 2-(morpholin-4-yl)acetic acid (50 mg, 0.34 mmol), 2-(methylamino)-N-[6-(trifluoromethoxy)-1,3-benzothiazol-2-yl]acetamide dihydrochloride (106 mg, 0.31 mmol) and DIPEA (88 mg, 0.64 mmol, 122 µl) in N,N-dimethyl formamide (2 ml) was treated with N-[(Dimethylamino)-1H-1,2,3-triazolo-[4,5-b]pyridin-1-ylmethylene]-N-methylmethanaminium hexafluorophosphate N-oxide (129 mg, 0.34 mmol) and stirred for 72 hours. The mixture was purified by RPHPLC (method B) and the product fractions were combined and lyophilized to leave 2-[N-methyl-2-(morpholin-4-yl)acetamido]-N-[6-(trifluoromethoxy)-1,3-benzothiazol-2-yl]acetamide as a white powder (92 mg, 54%). LC/MS method A: $R_t$=3.87 min., (M+H)$^+$=433. $^1$H-NMR (CD$_3$OD): δ=7.85 (d, J=1.2 Hz, 1H), 3:1 conformers at 7.81 and 7.99 (d, J=9.0 Hz, 1H), 7.36 (dd, J=9.0 Hz, J=1.2 Hz, 1H), 3:1 conformers at 4.44 and 4.41 (s, 2H), 3:1 conformers at 4.43 and 4.25 (s, 2H), 3.80-4.10 (m, 4H), 3.20-3.60 (m, 4H), 3:1 conformers at 3.16 and 3.05 (s, 3H).

Example 218: Synthesis of 2-[N-Methyl-2-(piperazin-1-yl)acetamido]-N-[6-(trifluoromethoxy)-1,3-benzothiazol-2-yl]acetamide

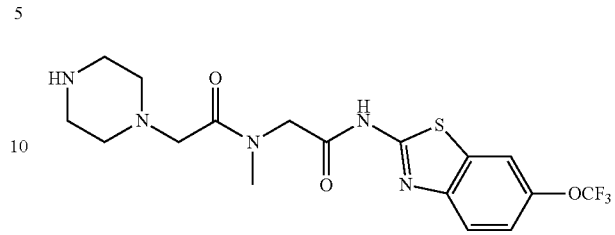

A solution of 2-{4-[(tert-butoxy)carbonyl]piperazin-1-yl}acetic acid (41 mg, 0.17 mmol), 2-(methylamino)-N-[6-(trifluoromethoxy)-1,3-benzothiazol-2-yl]acetamide dihydrochloride (50 mg, 0.15 mmol) and N,N-diisopropylethylamine (22 mg, 0.17 mmol, 30 µl) in N,N-dimethylformamide (1 ml) was treated with N-[(Dimethylamino)-1H-1,2,3-triazolo-[4,5-b]pyridin-1-ylmethylene]-N-methylmethanaminium hexafluorophosphate N-oxide (65 mg, 0.17 mmol) and stirred 3 hours. The mixture was diluted with ethyl acetate (25 ml) and washed with water (25 ml) and brine (25 ml). The organic phase was dried (MgSO$_4$) and evaporated. The crude product was purified by RPHPLC (method B) and the product fractions were combined, treated with saturated aqueous sodium bicarbonate solution and extracted with ethyl acetate (2×50 ml). The combined organic phases were washed with brine (25 ml) and dried (MgSO$_4$). The solvents were evaporated to leave a colorless glassy solid which was dissolved in dichloromethane and trifluoroacetic acid (1:1, 3 ml) and allowed to stand for 2 h. The solvents were evaporated and the residue was dissolved in water (10 ml) and lyophilized to leave 2-[N-methyl-2-(piperazin-1-yl)acetamido]-N-[6-(trifluoromethoxy)-1,3-benzothiazol-2-yl]acetamide as a white powder (74 mg, 75%). LC/MS method A: $R_t$=3.54 min., (M+H)$^+$=432. $^1$H-NMR (CD$_3$OD): δ=7.86 (d, J=10.3 Hz, 1H), 1:1 conformers at 7.81 and 7.99 (d, J=8.8 Hz, 1H), 7.36 (m, 1H), 1:1 conformers at 4.43 and 4.38 (s, 2H), 1:1 conformers at 3.71 and 3.40 (s, 2H), 3.35-3.39 (m, 2H), 1:1 conformers at 3.20 and 3.08 (s, 3H), 3.00-3.10 (m, 4H), 2.68-2.75 (m, 2H).

Example 219: Synthesis of Benzyl 2-[(2S)-2-{[(tert-butoxy)carbonyl]amino}propanamido]acetate

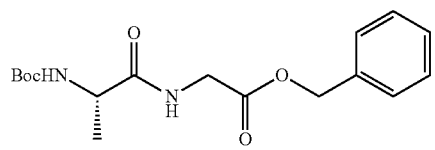 [SMILES: C[C@H](NC(=O)OC(C)(C)C)C(=O)NCC(=O)OCc1ccccc1]

Benzyl 2-[(2S)-2-{[(tert-butoxy)carbonyl]amino} propanamido]acetate was prepared according to the procedure for benzyl 2-(2-{[(tert-butoxy)carbonyl]amino}acetamido)acetate from (tert-butyloxycarbonyl)alanine to leave benzyl 2-[(2S)-2-{[(tert-butoxy)carbonyl]amino}propanamido]acetate as a solid. LC/MS method A: $R_t$=5.38 min., (M+H)$^+$=337. $^1$H-NMR (CDCl$_3$): δ=7.36 (s, 5H), 6.63 (bs, 1H), 5.20 (s, 2H), 4.94 (bs, 1H), 4.21 (q, J=7.0 Hz, 1H), 4.09 (ABq, J=5.3 Hz, 2H), 1.45 (s, 9H), 1.37 (d, J=7.0 Hz, 3H).

Example 220: Synthesis of 2-[(2S)-2-{[(tert-Butoxy)carbonyl]amino}propanamido]acetic Acid

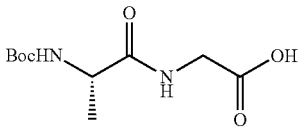 [SMILES: C[C@H](NC(=O)OC(C)(C)C)C(=O)NCC(=O)O]

Benzyl 2-[(2S)-2-{[(tert-butoxy)carbonyl]amino} propanamido]acetate was prepared according to the procedure for benzyl 2-(2-{[(tert-butoxy)carbonyl]amino}acetamido) acetate from Benzyl 2-[(2S)-2-{[(tert-butoxy)carbonyl]amino}propanamido]acetate to provide 2-[(2S)-2-{[(tert-butoxy)carbonyl]amino}propanamido] acetic acid as a solid. $^1$H-NMR (CDCl$_3$): δ=4.10 (q, J=7.3 Hz, 1H), 3.90 (ABq, J=17.9 Hz, 2H), 1.44 (s, 9H), 1.32 (d, J=7.0 Hz, 3H).

Example 221: Synthesis of (2S)-2-Amino-N-{[methyl({[6-(trifluoromethoxy)-1,3-benzothiazol-2-yl]carbamoyl}methyl)carbamoyl]methyl}propanamide

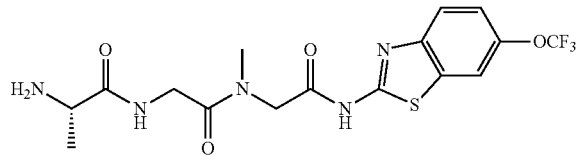 [SMILES: C[C@H](N)C(=O)NCC(=O)N(C)CC(=O)Nc1nc2ccc(OC(F)(F)F)cc2s1]

(2S)-2-Amino-N-{[methyl({[6-(trifluoromethoxy)-1,3-benzothiazol-2-yl]carbamoyl}methyl)carbamoyl]methyl}propanamide was prepared according to the procedure for 2-amino-N-{[methyl({[6-(trifluoromethoxy)-1,3-benzothiazol-2-yl]carbamoyl}methyl)carbamoyl]methyl}acetamide from (tert-butyloxycarbonyl)alanylglycine to provide (2 S)-2-amino-N-{[methyl({[6-(trifluoromethoxy)-1,3-benzothiazol-2-yl]carbamoyl}methyl)carbamoyl]methyl}propanamide. LC/MS method A: R$_t$=3.72 min., (M+H)$^+$=434. $^1$H-NMR (CD$_3$OD): δ=7.84 (d, J=1.8 Hz, 1H), 3:1 conformers at 7.78 and 7.80 (d, J=8.7 Hz, 1H), 7.35 (dd, J=8.7 Hz, J=1.8 Hz, 1H), 3:1 conformers at 4.46 and 4.38 (s, 2H), 4.26 (ABq, J=17.3 Hz, 2H), 4.00 (q, J=7.0 Hz, 1H), 3:1 conformers at 3.20 and 3.02 (s, 3H), 1.52 (d, J=7.0 Hz, 3H).

Example 222: Synthesis of Benzyl 2-[(2S)-2-{[(tert-butoxy)carbonyl]amino}-3-phenyl propanamido]acetate

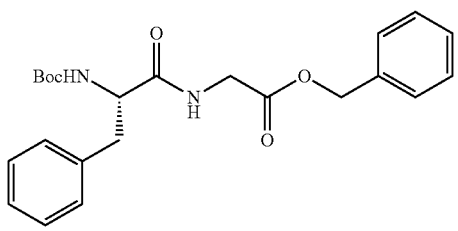 [SMILES: CC(C)(C)OC(=O)N[C@@H](Cc1ccccc1)C(=O)NCC(=O)OCc1ccccc1]

Benzyl 2-[(2S)-2-{[(tert-butoxy)carbonyl]amino}-3-phenyl propanamido]acetate was prepared according to the procedure for benzyl 2-(2-{[(tert-butoxy)carbonyl]amino}acetamido)acetate from (tert-butyloxycarbonyl)phenylalanine to provide benzyl 2-[(2S)-2-{[(tert-butoxy)carbonyl]amino}-3-phenylpropanamido]acetate. LC/MS method A: R$_t$=5.38 min., (M+Na)$^+$=435. $^1$H-NMR (CDCl$_3$): δ=7.18-7.40 (m, 10H), 6.37 (bs, 1H), 5.17 (s, 2H), 4.92 (bs, 1H), 4.03 (ABq, J=18.5 Hz, J=5.6 Hz, 1H), (ABq, J=18.4 Hz, J=5.0 Hz, 1H), 3.10 (doublet of ABq, J=14.0 Hz, J=6.7 Hz, J=4.7 Hz, 2H), 1.40 (s, 9H).

Example 223: Synthesis of 2-[(2S)-2-{[(tert-Butoxy)carbonyl]amino}-3-phenylpropanamido]acetic Acid

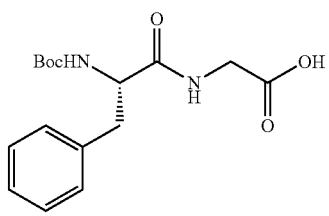 [SMILES: CC(C)(C)OC(=O)N[C@@H](Cc1ccccc1)C(=O)NCC(=O)O]

2-[(2S)-2-{[(tert-Butoxy)carbonyl]amino}-3-phenylpropanamido]acetic acid was prepared according to the procedure for 2-(2-{[(tert-butoxy)carbonyl]amino}acetamido)acetic acid from Benzyl 2-[(2S)-2-{[(tert-butoxy)carbonyl]amino}-3-phenylpropanamido]acetate to provide 2-[(2S)-2-{[(tert-butoxy)carbonyl]amino}-3-phenylpropanamido] acetic acid as a solid. $^1$H-NMR (CD$_3$OD): δ=7.18-7.30 (m, 5H), 4.34 (dd, J=9.7 Hz, J=5.3 Hz, 1H), 3.91 (s, 2H), 3.17 (dd, J=13.7 Hz, J=4.7 Hz, 1H), 2.80 (dd, J=13.7 Hz, J=9.7 Hz, 1H), 1.34 (s, 9H).

Example 224: Synthesis of (2S)-2-Amino-N-{[methyl({[6-(trifluoromethoxy)-1,3-benzothiazol-2-yl]carbamoyl}methyl)carbamoyl]methyl}-3-phenylpropanamide

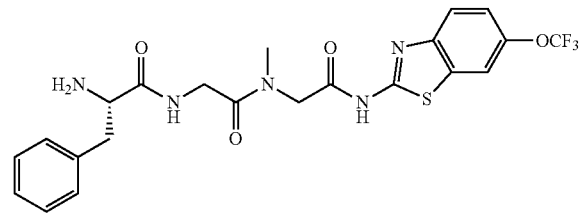 [SMILES: CN(CC(=O)Nc1nc2ccc(OC(F)(F)F)cc2s1)C(=O)CNC(=O)[C@@H](N)Cc1ccccc1]

(2S)-2-Amino-N-{[methyl({[6-(trifluoromethoxy)-1,3-benzothiazol-2-yl]carbamoyl}methyl)carbamoyl]methyl}-3-phenylpropanamide was prepared according to the procedure for 2-amino-N-{[methyl({[6-(trifluoromethoxy)-1,3-benzothiazol-2-yl]carbamoyl}methyl)carbamoyl]methyl}acetamide from (tert-butyloxycarbonyl)phenylalanylglycine. LC/MS method A: R$_t$=4.19 min., (M+H)$^+$=510. $^1$H-NMR (CD$_3$OD): δ=7.85 (bs, 1H), 3:1 conformers at 7.81 and 7.79 (d, J=7.4 Hz, J=8.8 Hz, 1H), 7.27-7.40 (m, 6H), 3:1 conformers at 4.45 and 4.38 (s, 2H), 3:1 conformers at 4.22 and 4.10 (ABq, J=17.3 Hz, J=15.0

Hz, 2H), 4.15 (obscured dd, 1H), 3.12 (obscured dd, 1H), 3:1 conformers at 3.20 and 3.02 (s, 3H), 3.04 (obscured dd, 1H).

Example 225: Synthesis of Benzyl 2-[(2S)-2-{[(tert-butoxy)carbonyl]amino}-3-methyl butanamido]acetate

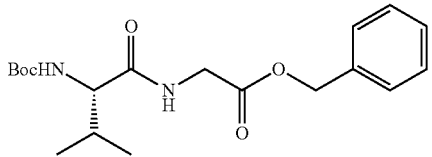 [SMILES: CC(C)[C@H](NC(=O)OC(C)(C)C)C(=O)NCC(=O)OCc1ccccc1]

A solution of (tert-butyloxycarbonyl)valine succinate ester (0.71 g, 2.3 mmol) and glycine benzyl ester hydrochloride (0.50 g, 2.5 mmol) in N,N-dimethylformamide (10 ml) was treated with triethylamine (0.51 g, 5.0 mmol, 0.70 ml) and stirred 18 hours. A white precipitate formed. The mixture was diluted with ethyl acetate (75 ml) and washed with 1N HCl (50 ml), water (50 ml) and brine (25 ml). The organic phase was dried (MgSO$_4$) and evaporated to leave benzyl 2-[(2S)-2-{[(tert-butoxy)carbonyl]amino}-3-methylbutanamido]acetate as a waxy solid (829 mg, 100%). LC/MS method A: R$_t$=5.03 min., (M+Na)$^+$=387. $^1$H-NMR (CDCl$_3$): δ=7.36 (s, 5H), 6.45 (bs, 1H), 5.19 (s, 2H), 5.00 (bs, 1H), 4.10 (dd, J=5.3 Hz, J=2.6 Hz, 2H), 3.00 (dd, J=7.2 Hz, J=5.6 Hz, 1H), 2.15-2.25 (m, 1H), 1.45 (s, 9H), 0.98 (d, J=6.8 Hz, 3H), 0.92 (d, J=7.1 Hz, 3H).

Example 226: Synthesis of 2-[(2S)-2-{[(tert-Butoxy)carbonyl]amino}-3-methyl butanamido]acetic Acid

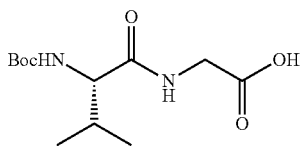 [SMILES: CC(C)[C@H](NC(=O)OC(C)(C)C)C(=O)NCC(=O)O]

2-[(2S)-2-{[(tert-butoxy)carbonyl]amino}-3-methylbutanamido]acetate (0.82 g, 2.2 mmol) was hydrogenolyzed (1 atmosphere hydrogen pressure) in methanol (25 ml) over 5% Pd/C (100 mg) for 18 hours. The catalyst was filtered through a bed of celite, washed with methanol (2×5 ml) and the filtrate was evaporated under reduced pressure to afford 2-[(2S)-2-{[(tert-butoxy)carbonyl]amino}-3-methylbutanamido]acetic acid as a solid (636 mg, 100%). $^1$H-NMR (CD$_3$OD): δ=8.20 (bs, 1H), 3.80-4.03 (m, 3H), 2.00-2.15 (m, 1H), 1.44 (s, 9H), 0.97 (d, J=6.8 Hz, 3H), 0.93 (d, J=6.8 Hz, 3H).

Example 227: Synthesis of (2S)-2-Amino-3-methyl-N-{[methyl({[6-(trifluoromethoxy)-1,3-benzothiazol-2-yl]carbamoyl}methyl)carbamoyl]methyl}butanamide

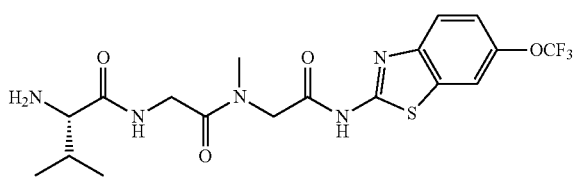 [SMILES: CC(C)[C@H](N)C(=O)NCC(=O)N(C)CC(=O)Nc1nc2ccc(OC(F)(F)F)cc2s1]

(2S)-2-Amino-3-methyl-N-{[methyl({[6-(trifluoromethoxy)-1,3-benzothiazol-2-yl]carbamoyl}methyl)carbamoyl]methyl}butanamide was prepared according to the procedure for 2-amino-N-{[methyl({[6-(trifluoromethoxy)-1,3-benzothiazol-2-yl]carbamoyl}methyl) carbamoyl] methyl} acetamide from (tert-butyloxycarbonyl)valylglycine. LC/MS method A: R$_t$=3.91 min., (M+H)$^+$=462. $^1$H-NMR (CD$_3$OD): δ=7.84 (d, J=1.2 Hz, 1H), 3:1 conformers at 7.79 and 7.80 (d, J=8.8 Hz, 1H), 7.35 (dd, J=8.8 Hz, J=1.2 Hz, 1H), 3:1 conformers at 4.46 and 4.39 (s, 2H), 3:1 conformers at 4.28 and 4.15 (ABq, J=10.0 Hz, J=4.7 Hz, 2H), 3:1 conformers at 4.15 and 3.71 (d, J=5.9 Hz, 1H), 3:1 conformers at 3.20 and 3.02 (s, 3H), 2.15-2.25 (m, 1H), 1.07 (d, J=6.8 Hz, 3H), 1.06 (d, J=7.0 Hz, 3H).

Example 228: Synthesis of Benzyl 2-[(2S)-2-{[(tert-butoxy)carbonyl]amino}-4-methylpentanamido]acetate

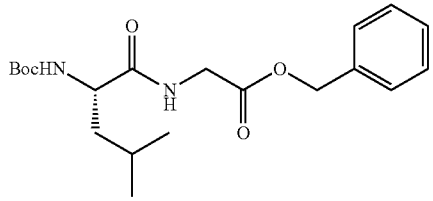 [SMILES: CC(C)C[C@H](NC(=O)OC(C)(C)C)C(=O)NCC(=O)OCc1ccccc1]

Benzyl 2-[(2S)-2-{[(tert-butoxy)carbonyl]amino}-4-methylpentanamido]acetate was prepared according to the procedure for benzyl 2-[(2S)-2-{[(tert-butoxy)carbonyl]amino}-3-methylbutanamido]acetate from (tert-butyloxycarbonyl)leucine succinate ester to provide benzyl 2-[(2S)-2-{[(tert-butoxy)carbonyl]amino}-4-methylpentanamido]acetate as an oil. LC/MS method A: R$_t$=5.32 min., (M+Na)$^+$=401. $^1$H-NMR (CDCl$_3$): δ=7.36 (s, 5H), 6.61 (bs, 1H), 5.18 (s, 2H), 4.84 (bd, J=8.5 Hz, 1H), 4.15 (bs, 1H), 4.08 (d, J=5.2 Hz, 2H), 1.65-1.75 (m, 3H), 1.44 (s, 9H), 0.95 (d, J=6.1 Hz, 3H), 0.92 (d, J=6.1 Hz, 3H).

Example 229: Synthesis of 2-[(2S)-2-{[(tert-Butoxy)carbonyl]amino}-4-methyl pentanamido]acetic Acid

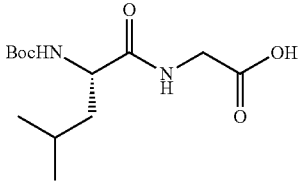 [SMILES: CC(C)C[C@H](NC(=O)OC(C)(C)C)C(=O)NCC(=O)O]

2-[(2S)-2-{[(tert-Butoxy)carbonyl]amino}-4-methyl pentanamido]acetic acid was prepared according to the procedure for 2-[(2S)-2-{[(tert-butoxy)carbonyl]amino}-3-methylbutanamido]acetic acid from Benzyl 2-[(2 S)-2-{[(tert-butoxy)carbonyl]amino}-4-methylpentanamido]acetate to provide 2-[(2S)-2-{[(tert-butoxy)carbonyl]amino}-4-methylpentanamido]acetic acid as a solid. $^1$H-NMR (CD$_3$OD): δ=4.11 (dd, J=10.4 Hz, J=5.0 Hz, 1H), 3.90 (ABq, J=17.9 Hz, 2H), 1.50-1.80 (m, 3H), 1.44 (s, 9H), 0.95 (d, J=6.4 Hz, 3H), 0.93 (d, J=6.2 Hz, 3H).

Example 230: Synthesis of (2S)-2-Amino-4-methyl-N-{[methyl({[6-(trifluoromethoxy)-1,3-benzothiazol-2-yl]carbamoyl}methyl)carbamoyl]methyl}pentanamide

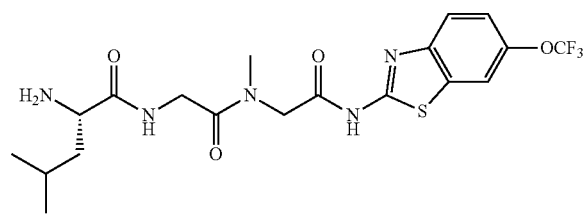 [SMILES: CC(C)C[C@H](N)C(=O)NCC(=O)N(C)CC(=O)Nc1nc2ccc(OC(F)(F)F)cc2s1]

(2S)-2-Amino-4-methyl-N-{[methyl({[6-(trifluoromethoxy)-1,3-benzothiazol-2-yl]carbamoyl}methyl)carbamoyl]methyl}pentanamide was prepared according to the procedure for 2-amino-N-{[methyl({[6-(trifluoromethoxy)-1,3-benzothiazol-2-yl]carbamoyl}methyl)carbamoyl]methyl}acetamide from (tert-butyloxycarbonyl)leucylglycine. LC/MS method A: R$_t$=4.09 min., (M+H)$^+$=476. $^1$H-NMR (CD$_3$OD): δ=7.84 (d, J=2.1 Hz, 1H), 3:1 conformers at 7.79 and 7.77 (d, J=8.8 Hz, J=7.2 Hz, 1H), 7.35 (dm, J=7.8 Hz, 1H), 3:1 conformers at 4.46 and 4.38 (s, 2H), 3:1 conformers at 4.26 and 4.13 (ABq, J=15.2 Hz, J=9.1 Hz, 2H), 3.93 (dd, J=7.6 Hz, J=6.2 Hz, 1H), 3:1 conformers at 3.20 and 3.02 (s, 3H), 1.65-1.80 (m, 3H), 1.01 (d, J=5.6 Hz, 3H), 0.99 (d, J=5.0 Hz, 3H).

Example 231: Synthesis of Benzyl 2-[(oxetan-3-yl)amino]acetate

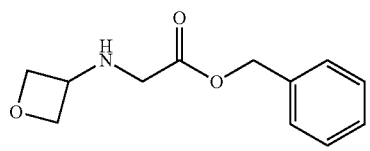 [SMILES: O=C(CNC1COC1)OCc1ccccc1]

A solution of 4-aminooxetane (300 mg, 4.1 mmol) and benzyl 2-bromoacetate (1.3 g, 5.8 mmol, 0.91 ml) in acetonitrile (10 ml) was stirred 72 hours. The mixture was diluted with 1N HCl (50 ml) and extracted with ethyl acetate (50 ml). The aqueous layer was neutralized (pH=9) with solid sodium carbonate and extracted with ethyl acetate (2×50 ml). The combined organic layers were washed with brine, dried (MgSO$_4$) and evaporated under reduced pressure to leave benzyl 2-[(oxetan-3-yl)amino]acetate as an oil (160 mg, 17%). $^1$H-NMR (CDCl$_3$): δ=7.36 (m, 5H), 5.16 (s, 2H), 4.76 (t, J=7.0 Hz, 2H), 4.48 (t, J=6.4 Hz, 2H), 3.92-4.01 (m, 1H), 3.45 (s, 2H).

Example 232: Synthesis of Benzyl 2-{[(tert-butoxy)carbonyl](oxetan-3-yl)amino}acetate

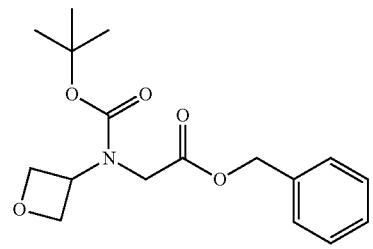 [SMILES: CC(C)(C)OC(=O)N(CC(=O)OCc1ccccc1)C1COC1]

A solution of 2-[(oxetan-3-yl)amino]acetate (155 mg, 0.66 mmol) in methylene chloride (5 ml) was treated with tert-butyloxycarbonyl anhydride (168 mg, 0.79 mmol) and stirred 18 hours. The solvents were evaporated and the residue was purified by chromatography on silica gel eluted with a gradient of ethyl acetate in hexanes (10% to 20% to 40%) to leave benzyl 2-{[(tert-butoxy)carbonyl](oxetan-3-yl)amino}acetate as a colorless oil (200 mg, 90%). LC/MS method A: R$_t$=5.13 min. $^1$H-NMR (CDCl$_3$): δ=7.36 (bs, 5H), 1:1 conformers at 5.22-5.35 and 4.90-5.00 (m, 1H), 5.18 (s, 2H), 4.58-4.85 (m, 4H), 4.12 (s, 2H), 1:1 conformers at 1.45 and 1.37 (s, 9H).

Example 233: Synthesis of 2-{[(tert-Butoxy)carbonyl](oxetan-3-yl)amino}acetic Acid

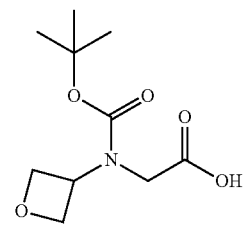 [SMILES: CC(C)(C)OC(=O)N(CC(=O)O)C1COC1]

2-{[(tert-butoxy)carbonyl](oxetan-3-yl)amino}acetate (195 mg, 0.58 mmol) was hydrogenated (1 atmosphere hydrogen pressure) over 10% Pd/C (30 mg) in methanol (5 ml) for 18 hours. The catalyst was filtered and washed with methanol (2×5 ml) and the filtrate was evaporated to leave 2-{[(tert-butoxy)carbonyl](oxetan-3-yl)amino}acetic acid as a white solid (135 mg, 100%). $^1$H-NMR (CDCl$_3$): δ=1:1 conformers at 5.22-5.35 and 4.90-5.05 (m, 1H), 4.60-4.90 (m, 4H), 4.12 (s, 2H), 1.45 (s, 9H).

Example 234: Synthesis of N-Methyl-2-[(oxetan-3-yl)amino]-N-({[6-(trifluoromethoxy)-1,3-benzothiazol-2-yl]carbamoyl}methyl)acetamide

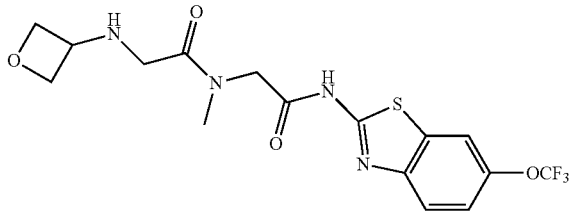 [SMILES: CN(CC(=O)Nc1nc2ccc(OC(F)(F)F)cc2s1)C(=O)CNC1COC1]

A solution of 2-{[(tert-butoxy)carbonyl](oxetan-3-yl)amino}acetic acid (30 mg, 0.13 mmol), 2-(methylamino)-N-[6-(trifluoromethoxy)-1,3-benzothiazol-2-yl]acetamide dihydrochloride (40 mg, 0.12 mmol) and triethylamine (26 mg, 0.26 mmol, 36 µl) in N,N-dimethylformamide (1 ml) was treated with N-[(Dimethylamino)-1H-1,2,3-triazolo-[4,5-b]pyridin-1-ylmethylene]-N-methylmethanaminium hexafluorophosphate N-oxide (49 mg, 0.13 mmol) and stirred 18 hours. The product was purified by reversed phase HPLC (method B) and the product fractions were combined, treated with saturated sodium bicarbonate solution (50 ml) and extracted with ethyl acetate (2×50 ml). The combined organic phases were washed with brine (25 ml), dried (MgSO$_4$) and evaporated to a thick gum (47 mg, 76%). This was dissolved in 4N HCl in 1,4-dioxane (3 ml) and stirred for 2 hours. The solvents were evaporated and the residue was dissolved in water (8 ml) and acetonitrile (2 ml) and lyophilized to leave a white powder (36 mg, 56% over two steps). LC/MS method A: R$_t$=4.23 min., (M+H)$^+$=419. $^1$H-NMR (CD$_3$OD): δ=7.85 (bs, 1H), 3:1 conformers at 7.81 and 7.79 (d, J=7.9 Hz, J=8.8 Hz, 1H), 7.35 (dm, J=7.9 Hz, 1H), 4.00-4.50 (m, 7H), 3:1 conformers at 3.20 and 3.02 (s, 3H).

Example 235: Synthesis of (2,2,2-Trifluoro-ethylamino)-acetic Acid Ethyl Ester

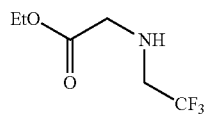

A flask was charged with 2,2,2-Trifluoroethylamine hydrochloride (2.81 g, 20.7 mmol) and potassium iodide (340 mg, 2.07 mmol). DIEA (14.5 mL) was added to the flask and the mixture was stirred for 5 minutes before adding ethyl bromoacetate (3.46 g, 20.7 mmol, 2.3 mL). The slurry was stirred overnight at room temperature. The slurry was diluted with diethyl ether (75 mL) and stirred for 1 hour. The reaction mixture was filtered and the filtrate was concentrated in vacuo. The crude residue was dissolved in methylene chloride (30 mL) and extracted into 1N HCl (2×30 mL). The aqueous layer was neutralized with sat. aqueous NaHCO$_3$ and the product was extracted with methylene chloride (3×30 mL). The combined organic extracts were dried over Na$_2$SO$_4$, filtered, and concentrated in vacuo to provide (2,2,2-Trifluoro-ethylamino)-acetic acid ethyl ester as a brown oil. $^1$H NMR (300 MHz, CDCl$_3$) δ=4.27-4.14 (m, 2H), 3.56-3.48 (m, 2H), 3.31-3.17 (m, 2H), 1.29 (t, J=7.0 Hz, 3H)

Example 236: Synthesis of [(2-Chloro-acetyl)-(2,2,2-trifluoro-ethyl)-amino]acetic Acid Ethyl Ester

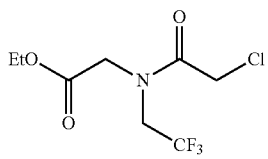 [SMILES: CCOC(=O)CN(CC(F)(F)F)C(=O)CCl]

Chloroacetyl chloride (358 mg, 3.17 mmol, 252 µL) was added dropwise to a solution of (2,2,2-trifluoro-ethylamino)-acetic acid ethyl ester (489 mg, 2.64 mmol) and diisopropylethylamine (751 mg, 5.81 mmol, 1.01 mL) in dichloromethane (13 mL) at 0° C., keeping the temperature <5° C. during the addition. The mixture was stirred for 30 minutes then quenched with 1N HCl (13 mL). The layers were separated and the aqueous layer was extracted with methylene chloride (2×13 mL). The combined organic extracts were dried over Na$_2$SO$_4$, filtered, and concentrated in vacuo to give 672 mg (97%) of ethyl [(2-Chloro-acetyl)-(2,2,2-trifluoro-ethyl)-amino]-acetate as a brown oil. $^1$H NMR (300 MHz, CDCl$_3$) δ=4.45-3.99 (m, 8H), 1.37-1.24 (m, 3H)

Example 237: Synthesis of [(2-tert-Butylamino-acetyl)-(2,2,2-trifluoro-ethyl)-amino]-acetic Acid Ethyl Ester

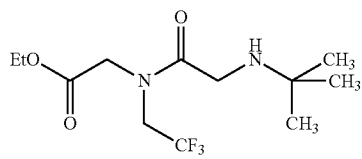

tert-Butylamine (296 mg, 4.05 mmol, 426 µL) was added to a solution of [(2-chloro-acetyl)-(2,2,2-trifluoro-ethyl)-amino]-acetic acid ethyl ester (265 mg, 1.01 mmol,) and diisopropylethylamine (131 mg, 1.01 mmol, 176 lit) in dichloromethane (5 mL) and the reaction was stirred overnight. The product was extracted into 1N HCl (2×10 mL). The aqueous layer was neutralized with sat. aqueous NaHCO$_3$ and the product was extracted with methylene chloride (3×10 mL). The combined organic extracts were dried over Na$_2$SO$_4$, filtered, and concentrated in vacuo to 130 mg (43%) of [(2-tert-butylamino-acetyl)-(2,2,2-trifluoro-ethyl)-amino]-acetic acid ethyl ester as a brown oil. $^1$H NMR (300 MHz, CDCl$_3$) δ=4.22 (d, J=17.6 Hz, 4H), 4.17-4.02 (m, 2H), 3.56-3.35 (m, 2H), 1.36-1.24 (m, 3H), 1.10 (d, J=5.0 Hz, 9H)

Example 238: Synthesis of 2-tert-Butylamino-N-(2,2,2-trifluoro-ethyl)-N-[(6-trifluoromethoxy-benzothiazol-2-ylcarbamoyl)-methyl]-acetamide

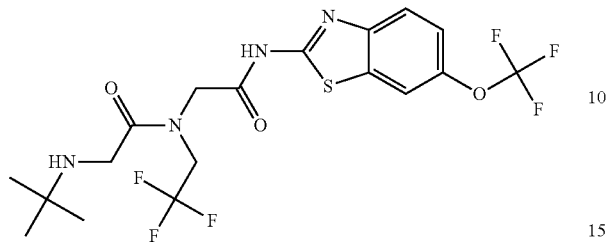

Sodium ethoxide (45 mg, 0.65 mmol) was added to a stirred solution of 2-amino-6-(trifluoromethoxy)benzothiazole (102 mg, 0.44 mmol) in ethanol (2.5 mL) at room temperature. After stirring for 10 minutes, a solution of [(2-tert-butylamino-acetyl)-(2,2,2-trifluoro-ethyl)-amino]-acetic acid ethyl ester (130 mg, 0.44 mmol,) in ethanol (1 mL) was added. The mixture was stirred overnight. The reaction was quenched with water (500 µL) then concentrated to dryness in vacuo. The residue was diluted with N,N-dimethylformamide and purified by prep HPLC (method B). The purified product was freeze dried from dioxane to obtain 97 mg (37%) of the trifluoroacetic acid salt of 2-tert-butylamino-N-(2,2,2-trifluoro-ethyl)-N-[(6-trifluoromethoxy-benzothiazol-2-ylcarbamoyl)-methyl]-acetamide as a white powder. LC/MS method A: $R_f$=4.42 min., $(M+H)^+$=487. 1H NMR (300 MHz, DMSO-d6) δ=12.91-12.56 (m, 1H), 9.08-8.63 (m, 2H), 8.32-7.97 (m, 1H), 7.93-7.75 (m, 1H), 7.54-7.25 (m, 1H), 4.69-4.52 (m, 2H), 4.49-4.32 (m, 2H), 4.13-3.95 (m, 2H), 1.38-1.19 (m, 9H).

Example 239: Synthesis of Benzyl 2-{[(tert-butoxy)carbonyl](cyclohexyl)amino}acetate

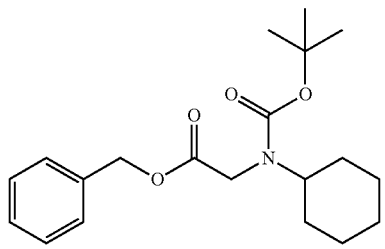 [SMILES: CC(C)(C)OC(=O)N(CC(=O)OCc1ccccc1)C1CCCCC1]

A solution of benzyl 2-bromoacetate (1.3 g, 5.8 mmol), cyclohexylamine (456.5 mg, 4.6 mmol) and triethylamine (0.59 g, 5.8 mmol) in tetrahydrofuran (10 mL) was stirred 18 h. Di-tert-butyl dicarbonate (1 g, 4.6 mmol) was added and the reaction stirred for 24 hours. Ethyl acetate (100 ml) was added and the mixture was washed with water (2×50 ml), 1N HCl (50 ml), and brine (25 ml). The organic solution was dried over sodium sulfate and evaporated to give a crude product. Purification by silica gel chromatography afforded benzyl 2-{[(tert-butoxy)carbonyl](cyclohexyl)amino}acetate as a colorless oil (1.03 g, 65%). LC/MS method A: $R_f$=6.44 min., $(M+H)^+$−100 (t-butoxycarbonyl)=248. $^1$H NMR (300 MHz, CDCl$_3$): δ 7.40-7.24 (m, 5H), 5.15 (s, 2H), 4.03-3.95 (m, 1H), 3.82 (s, 2H), 1.77-1.74 (m, 4H), 1.47-1.44 (m, 2H), 1.34 (s, 9H), 1.31-1.17 (m, 4H).

Example 240: Synthesis of 2-{[(tert-Butoxy)carbonyl](cyclohexyl)amino}acetic Acid

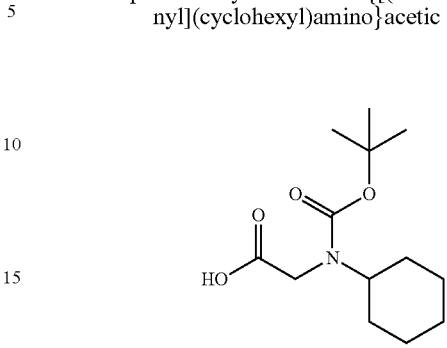

Benzyl 2-{[(tert-butoxy)carbonyl](cyclohexyl)amino}acetate (1.035 g, 2.98 mmol) in methanol (20 mL) was hydrogenated (1 atmosphere H$_2$ pressure) over Pd/C (100 mg) for 18 hours. The mixture was filtered through celite and the filtrate was evaporated to give 2-{[(tert-butoxy)carbonyl](cyclohexyl)amino}acetic acid as a white solid (0.75 g, 98%). LC/MS method A: $R_f$=5.20 min., $(M+Na)^+$=280. $^1$H NMR (300 MHz, CDCl$_3$): δ 4.03-3.84 (m, 3H), 1.81-1.61 (m, 4H), 1.44 (s, 9H), 1.43-1.07 (m, 6H).

Example 241: Synthesis of 2-(Cyclohexylamino)-N-(2-oxo-2-((6-(trifluoromethoxy)benzo[d]thiazol-2-yl)amino)ethyl)acetamide

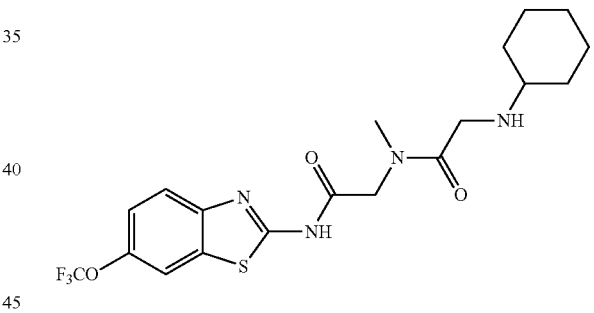

To a solution of 2-(methylamino)-N-(6-(trifluoromethoxy)benzo[d]thiazol-2-yl)acetamide dihydrochloride (50 mg, 0.13 mmol), 2-{[(tert-butoxy)carbonyl](cyclohexyl)amino}acetic acid (38.6 mg, 0.15 mmol) and N,N-diisopropylethylamine (50 mg, 0.39 mmol, 70 ul) in N,N-dimethylformamide (I ml) was added 1-[Bis(dimethylamino)methylene]-1H-1,2,3-triazolo[4,5-b]pyridinium 3-oxid hexafluorophosphate (HATU, 57 mg, 0.15 mmol) and the reaction mixture stirred for 18 hours. The crude material was purified via RPHPLC (method B) to give a light yellow foamy solid (LC/MS method A; $R_f$=6.07 min., $(M+Na)^+$=566.6). The solid was dissolved in 4N HCl in 1,4-dioxane. The mixture stirred 18 h and the white precipitate was filtered on a glass frit (medium), washed with 1,4-dioxane and ether and dried under vacuum to leave 2-(cyclohexylamino)-N-(2-oxo-2-((6-(trifluoromethoxy)benzo[d]thiazol-2-yl)amino)ethyl)acetamide as a white crystalline solid (49.1 mg, 70%). LC/MS method A: $R_f$=4.00 min., $(M+H)^+$=445. $^1$H NMR (300 MHz, CD$_3$OD): δ 7.96-7.73 (m, 2H), 7.36 (d, J=8.80 Hz, 1H), 4.43 (s, 2H), 4.20 (s, 2H), 3.17 (s, 3H), 3.04 (m, 1H), 2.13 (m, 2H), 1.89 (m, 2H), 1.72 (d, J=11.73 Hz, 1H), 1.49-1.20 (m, 5H).

Example 242: Synthesis of Benzyl 2-{[(tert-butoxy)carbonyl](1-methanesulfonylpiperidin-4-yl)amino}acetate

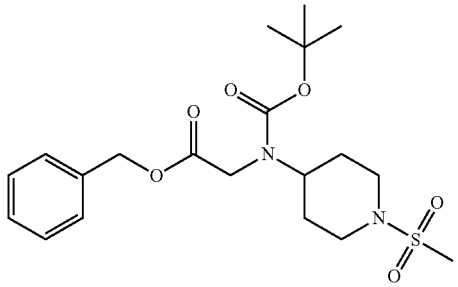 [SMILES: CC(C)(C)OC(=O)N(CC(=O)OCc1ccccc1)C1CCN(S(C)(=O)=O)CC1]

A mixture of benzyl 2-bromoacetate (1.3 g, 5.8 mmol), 4-Amino-1-methanesulfonylpiperidine (820 mg, 4.6 mmol) and triethylamine (0.59 g, 5.8 mmol) in tetrahydrofuran (10 mL) was stirred for 18 hours. Di-tert-butyl dicarbonate (1 g, 4.6 mmol) was added and the mixture stirred for another 20 hours. Ethyl acetate (100 ml) was added and the mixture was washed with water (2×50 ml), 1N HCl (50 ml), and brine (25 ml). The organic solution was dried over sodium sulfate and evaporated to give a crude product which was purified by chromatography on silica gel to give benzyl 2-{[(tert-butoxy)carbonyl](1-methanesulfonyl piperidin-4-yl)amino}acetate as a colorless oil (1.56 g, 79.5%). LC/MS method A: $R_f$=5.24 min., (M+H)$^+$-100 (t-butyloxycarbonyl)=327. $^1$H NMR (300 MHz, CDCl$_3$): δ 7.36 (s, 5H), 5.16 (s, 2H), 3.97-3.87 (m, 1H), 3.82 (s, 2H), 2.78 (s, 3H), 2.77-2.68 (m, 2H), 1.89-1.85 (m, 2H), 1.71-1.61 (m, 2H), 1.48-1.45 (m, 2H), 1.35 (s, 9H).

Example 243: Synthesis of 2-{[(tert-Butoxy)carbonyl](1-methanesulfonylpiperidin-4-yl)amino}acetic Acid

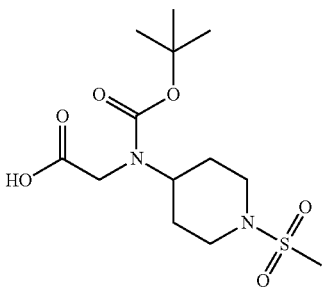 [SMILES: CC(C)(C)OC(=O)N(CC(=O)O)C1CCN(S(C)(=O)=O)CC1]

Benzyl 2-{[(tert-butoxy)carbonyl](1-methanesulfonylpiperidin-4-yl)amino}acetate (1.56 g, 3.66 mmol) was hydrogenated (1 atmosphere hydrogen pressure) in methanol (20 mL) over Pd/C (100 mg) for 20 hours. The mixture was filtered through celite and evaporated to give 2-{[(tert-butoxy)carbonyl](1-methanesulfonylpiperidin-4-yl)amino}acetic acid as a white solid (0.97 g, 79%). LC/MS method A: $R_f$=3.37 min., (M+Na)$^+$=359. $^1$H NMR (300 MHz, CDCl$_3$): δ 3.88-3.84 (m, 1H), 3.81 (s, 2H), 2.80 (s, 3H), 2.76-2.71 (m, 2H), 1.90-1.87 (m, 2H), 1.64-1.60 (m, 2H), 1.59-1.45 (m, 2H), 1.43 (s, 9H).

Example 244: Synthesis of 2-[(1-Methanesulfonylpiperidin-4-yl)amino]-N-methyl-N-({[6-(trifluoromethoxy)-1,3-benzothiazol-2-yl]carbamoyl}methyl)acetamide

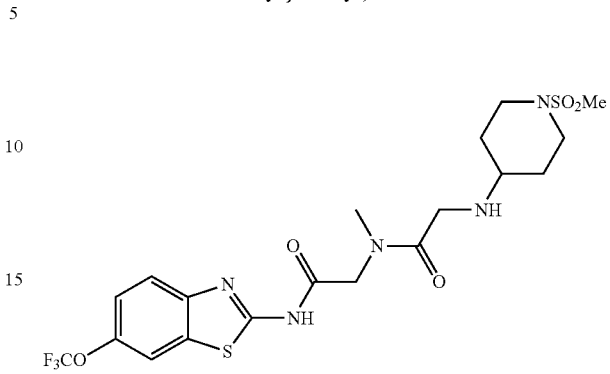

To a solution of 2-(methylamino)-N-(6-(trifluoromethoxy)benzo[d]thiazol-2-yl)acetamide dihydrochloride (50 mg, 0.13 mmol), 2-{[(tert-butoxy)carbonyl](1-methanesulfonylpiperidin-4-yl)amino}acetic acid (50.46 mg, 0.15 mmol) and N,N-diisopropylethylamine (50 mg, 0.39 mmol, 70 ul) in N,N-dimethylformamide (1 ml) was added 1-[Bis(dimethylamino)methylene]-1H-1,2,3-triazolo[4,5-b]pyridinium 3-oxid hexafluorophosphate (HATU, 57 mg, 0.15 mmol) and the reaction mixture stirred for 18 hours. The crude mixture was purified by RPHPLC (method B) and the product fractions were evaporated to give a light yellow foamy solid (LC/MS, method A; $R_f$=5.12 min., (M+Na)$^+$=646). The solid was dissolved in 4N HCl in 1,4-dioxane. The mixture stirred overnight and the white precipitate was filtered on a glass frit (medium), washed with 1,4-dioxane and ether and dried under vacuum to leave 61.1 mg (59%) of 2-[(1-methanesulfonylpiperidin-4-yl)amino]-N-methyl-N-({[6-(trifluoromethoxy)-1,3-benzothiazol-2-yl]carbamoyl}methyl)acetamide as a white crystalline solid. LC/MS method A: $R_f$=3.72 min., (M+H)$^+$=524. $^1$H NMR (300 MHz, CD$_3$OD): δ 7.95-7.70 (m, 2H), 7.36 (d, J=8.21 Hz, 1H), 4.44 (s, 2H), 4.34-4.06 (m, 2H), 3.87 (d, J=12.31 Hz, 2H), 3.36 (m, 1H), 3.18 (s, 3H), 2.87 (s, 3H), 2.81 (m, 2H), 2.25 (d, J=9.97 Hz, 2H), 1.88-1.55 (m, 2H)

Example 245: Synthesis of tert-Butyl N-(2-amino-2-methylpropyl)carbamate

A mixture of 2-methylpropane-1,2-diamine (1.1 g, 12.5 mmol) in dichloromethane (10 mL) was cooled to 0° C., Di-tert-butyl dicarbonate (2.7 g, 12.5 mmol) was added and the mixture was stirred 20 hours. The solvent was evaporated to give tert-butyl N-(2-amino-2-methylpropyl)carbamate as a white solid (2.4 g, 100%) which was used directly for the next step without characterization. LC/MS method A: $R_f$=3.70 min., (M+H)$^+$=327. $^1$H NMR (300 MHz, CDCl$_3$): δ 7.38-7.27 (m, 5H), 5.17 (s, 2H), 3.41 (s, 2H), 3.01-2.99 (d, J=5.8 Hz, 2H), 1.44 (s, 9H), 1.24 (s, 6H).

Example 246: Synthesis of Benzyl 2-{[(tert-butoxy)carbonyl](1-{[(tert-butoxy)carbonyl]amino}-2-methylpropan-2-yl)amino}acetate

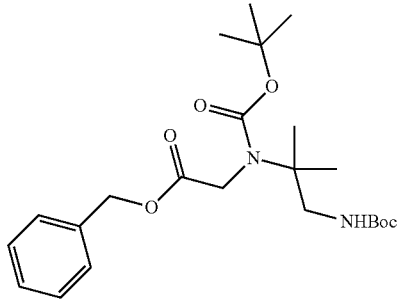 [SMILES: CC(C)(C)OC(=O)NCC(C)(C)N(CC(=O)OCc1ccccc1)C(=O)OC(C)(C)C]

A mixture of benzyl 2-bromoacetate (3.04 g, 13 mmol), tert-butyl N-(2-amino-2-methylpropyl)carbamate (2.5 g, 13 mmol), triethylamine (1.7 g, 16 mmol) in tetrahydrofuran (15 mL) was stirred 18 h. Di-tert-butyldicarbonate (2.8 g, 13 mmol) was added and the mixture stirred for another 24 hours. Ethyl acetate (100 ml) was added and the mixture was washed with water (2×50 ml), 1N HCl (50 ml), and brine (25 ml). The organic solution was dried over sodium sulfate and evaporated to give a crude product which was purified by silica gel chromatography elute with a hexanes/ethyl acetate gradient to give benzyl 2-1[(tert-butoxy)carbonyl](1-{[(tert-butoxy)carbonyl]aminol-2-methylpropan-2-yl) amino}acetate as a colorless oil (1.27 g, 23%) along with amine starting material (0.74 g, 17%). LC/MS method A: $R_t$=6.26 min., (M+Na)$^+$=459. $^1$H NMR (300 MHz, CD$_3$OD): δ 7.40-7.31 (m, 5H), 5.19 (s, 2H), 4.07 (s, 2H), 3.46 (s, 2H), 1.42 (s, 9H), 1.35 (s, 6H), 1.32 (s, 9H).

Example 247: Synthesis of 2-{[(tert-Butoxy)carbonyl](1-{[(tert-butoxy)carbonyl]amino}-2-methylpropan-2-yl)amino}acetic Acid

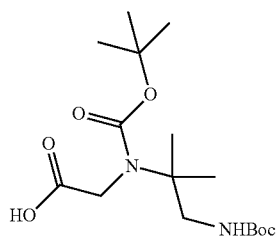

Benzyl 2-{[(tert-butoxy)carbonyl](1-1[(tert-butoxy)carbonyl]amino}-2-methylpropan-2-yl)amino}acetate (178 mg, 0.41 mmol) in methanol (20 mL) was hydrogenated (1 atmosphere hydrogen pressure) over Pd/C (50 mg) for 20 hours. The mixture was filtered through celite and evaporated to give 2-{[(tert-butoxy)carbonyl](1-{[(tert-butoxy)carbonyl]amino}-2-methylpropan-2-yl)amino}acetic acid as a colorless oil (161 mg, 100%). LC/MS method A: $R_t$=4.7 min., (M+Na)$^+$=369.

Example 248: Synthesis of 2-[(1-Amino-2-methylpropan-2-yl)amino]-N-methyl-N-({[6-(trifluoromethoxy)-1,3-benzothiazol-2-yl]carbamoyl}methyl)acetamide

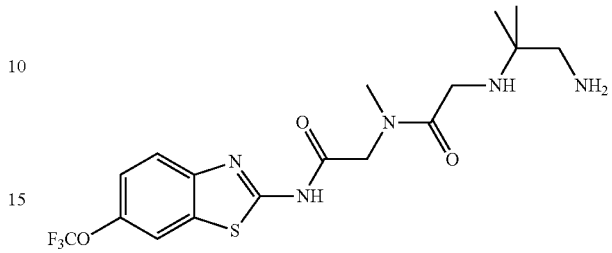

To a solution of 2-(methylamino)-N-(6-(trifluoromethoxy)benzo[d]thiazol-2-yl)acetamide dihydrochloride (51.68 mg, 0.14 mmol), 2-{[(tert-butoxy)carbonyl](1-{[(tert-butoxy)carbonyl]amino}-2-methylpropan-2-yl) amino}acetic acid (52 mg, 0.15 mmol) and N,N-diisopropylethylamine (53 mg, 0.41 mmol, 70 ul) in N,N-dimethylformamide (1 ml) was added 1-[Bis(dimethylamino)methylene]-1H-1,2,3-triazolo[4,5-b]pyridinium 3-oxid hexafluorophosphate (HATU, 57 mg, 0.15 mmol) and the reaction mixture stirred for 18 hours. The crude product was purified by RPHPLC (method B) to give a light yellow foamy solid (LC/MS method A, $R_t$=6.0 min., (M+H)$^+$ =634.33). This was dissolved in 4N HCl in 1,4-dioxane. The mixture was stirred 20 hours and the white precipitate was filtered on a glass frit (medium), washed with 1,4-dioxane and ether and dried under vacuum to leave 49 mg (72%) of 2-[(1-amino-2-methylpropan-2-yl)amino]-N-methyl-N-({[6-(trifluoromethoxy)-1,3-benzothiazol-2-yl]carbamoyl}methyl)acetamide as a white crystalline solid. LC/MS method A: $R_t$=3.27 min., (M+H)$^+$=434. $^1$H NMR (300 MHz, CD$_3$OD): δ 7.93-7.73 (m, 2H), 7.36 (d, J=8.21 Hz, 1H), 4.55-4.42 (m, 2H), 4.36-4.16 (m, 2H), 3.37 (m, 2H), 3.22 (s, 3H), 1.60-1.49 (in, 6H).

Example 249: Synthesis of tert-Butyl 4-{[2-(benzyloxy)-2-oxoethyl](methyl)amino}piperidine-1-carboxylate

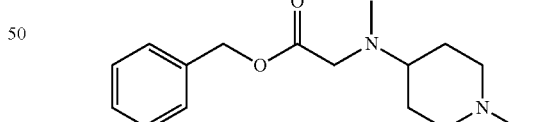

A mixture of benzyl 2-bromoacetate (1.3 g, 5.8 mmol), 1-(tert-butyloxcarbonyl)-4-(methylamino)piperidine (1.24 g, 5.8 mmol) and triethylamine (0.59 g, 5.8 mmol) in tetrahydrofuran (10 mL) was stirred overnight. Water (50 ml) was added followed by ethyl acetate extraction 2×100 ml). The organic solution was dried over sodium sulfate and evaporated to give a crude product which was purified by chromatography on silica gel using a gradient of ethyl acetate in hexanes to give tert-butyl 4-{[2-(benzyloxy)-2-oxoethyl](methyl)amino}piperidine-1-carboxylate as a colorless oil (1.87 g, 84%). LC/MS method A: $R_t$=3.76 min., (M+Na)$^+$=385. $^1$H NMR (300 MHz, CDCl$_3$): δ 7.34 (m, 5H), 5.14 (s, 2H), 4.11-4.09 (m, 2H), 3.37 (s, 2H), 2.68-2.60 (m, 3H), 2.40 (s, 3H), 1.79-1.74 (m, 2H), 1.43 (s, 9H), 1.36-1.31 (m, 2H).

Example 250: Synthesis of 2-({1-[(tert-Butoxy) carbonyl]piperidin-4-yl}(methyl)amino) acetic Acid

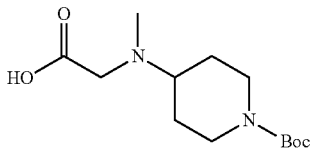 [SMILES: CN(CC(=O)O)C1CCN(C(=O)OC(C)(C)C)CC1]

tert-Butyl 4-{[2-(benzyloxy)-2-oxoethyl](methyl) amino}piperidine-1-carboxylate (1.87 g, 5.17 mmol) in methanol (20 mL) was hydrogenated (one atmosphere hydrogen pressure) over Pd/C (150 mg) for 18 hours. The mixture was filtered through celite and the filtrate was evaporated to give 2-({1-[(tert-butoxy)carbonyl]piperidin-4-yl}(methyl)amino)acetic acid as a colorless oil (1.365 g, 97%). LC/MS method A: $R_t$=2.62 min., (M+H)$^+$=273. $^1$H NMR (300 MHz, CDCl$_3$): δ 4.25 (m, 2H), 3.45 (s, 2H), 3.38-3.30 (m, 1H), 2.74 (m, 5H), 2.04-2.00 (m, 2H), 1.57-1.52 (m, 2H), 1.48 (s, 9H).

Example 251: Synthesis of 2-{N-Methyl-2-[methyl (piperidin-4-yl)amino]acetamido}-N-[6-(trifluoromethoxy)-1,3-benzothiazol-2-yl]acetamide

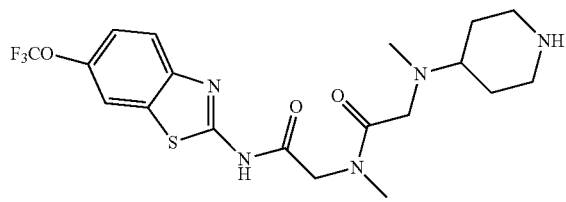 [SMILES: CN(CC(=O)Nc1nc2ccc(OC(F)(F)F)cc2s1)C(=O)CN(C)C1CCNCC1]

To a solution of 2-(methylamino)-N-(6-(trifluoromethoxy)benzo[d]thiazol-2-yl)acetamide dihydrochloride (55.5 mg, 0.15 mmol), 2-({1-[(tert-butoxy)carbonyl]piperidin-4-yl}(methyl)amino)acetic acid (44 mg, 0.16 mmol) and N,N-diisopropylethylamine (57 mg, 0.44 mmol, 73 ul) in N,N-dimethylformamide (1 ml) was added 1-[Bis(dimethylamino)methylene]-1H-1,2,3-triazolo[4,5-b]pyridinium 3-oxid hexafluorophosphate (HATU, 61.6 mg, 0.15 mmol) and the reaction mixture stirred for 18 hours. The crude material was purified by RPHPLC (method B) to give tert-butyl 4-[methyl({[methyl({[6-(trifluoromethoxy)-1,3-benzothiazol-2-yl]carbamoyl}methyl)carbamoyl]methyl}) amino] piperidine-1-carboxylate as a white foamy solid. $R_t$=4.19 min, (M+H)$^+$=560.20).

tert-Butyl 4-[methyl({[methyl({[6-(trifluoromethoxy)-1,3-benzothiazol-2-yl]carbamoyl}methyl) carbamoyl] methyl})amino]piperidine-1-carboxylate was dissolved in 4N HCl in 1,4-dioxane. The mixture stirred overnight and the white precipitate was filtered on a glass frit (medium), washed with 1,4-dioxane and ether and dried under vacuum to leave 2-{N-methyl-2-[methyl(piperidin-4-yl)amino]acetamido}-N-[6-(trifluoromethoxy)-1,3-benzothiazol-2-yl]acetamide as a white solid (61 mg, 73%). LC/MS method A: $R_t$=3.45 min., (M+H)$^+$=460. $^1$H NMR (300 MHz, CD$_3$OD): δ 7.93-7.71 (m, 2H), 7.37 (d, J=8.80 Hz, 1H), 4.47 (m, 2H), 4.09 (m, 2H), 3.19 (s, 3H), 3.06 (m, 1H), 2.37 (m, 1H), 2.02 (m, 6H), 1.33-1.16 (m, 4H).

Example 252: Synthesis of Benzyl 2-{[(tert-butoxy) carbonyl](1-methylpiperidin-4-yl) amino}acetate

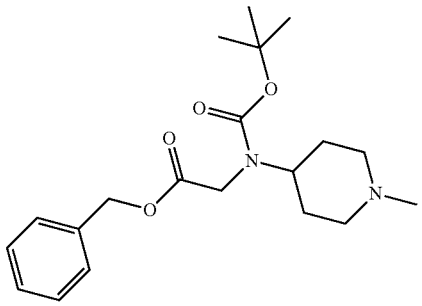 [SMILES: CN1CCC(N(CC(=O)OCc2ccccc2)C(=O)OC(C)(C)C)CC1]

A mixture of benzyl 2-bromoacetate (1.3 g, 5.8 mmol), 4-amino-1-methylpiperidine (2.5 g, 13 mmol) and triethylamine (0.59 g, 5.8 mmol) in tetrahydrofuran (10 mL) was stirred 20 hours. Di-tert-butyl dicarbonate (1 g, 4.6 mmol) was added and stirring continued for 20 hours. Ethyl acetate (100 ml) was added and the mixture was washed with water (2×50 ml), 1N HCl (50 ml), and brine (25 ml). The organic solution was dried over sodium sulfate and evaporated to give a crude product which was purified by chromatography on silica gel using a gradient of ethyl acetate in hexanes to give benzyl 2-{[(tert-butoxy)carbonyl](1-methylpiperidin-4-yl)amino}acetate as a colorless oil (0.116 g, 7%). LC/MS method A: $R_t$=3.74 min., (M+H)$^+$=363. $^1$H NMR (300 MHz, CDCl$_3$): δ 7.34 (m, 5H), 5.14 (s, 2H), 4.10-3.96 (m, 1H), 3.83 (s, 1H), 2.88-2.84 (m, 2H), 2.25 (s, 3H), 2.06-1.99 (m, 2H), 1.74-1.71 (m, 2H), 1.59-1.55 (m, 1H), 1.47 (s, 3H), 1.36 (s, 6H).

Example 253: Synthesis of 2-{[(tert-Butoxy)carbonyl](1-methylpiperidin-4-yl)amino} acetic Acid

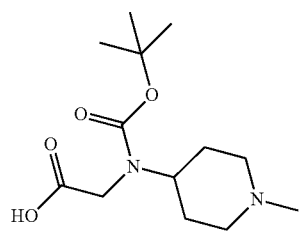 [SMILES: CN1CCC(N(CC(=O)O)C(=O)OC(C)(C)C)CC1]

A solution of benzyl 2-{[(tert-butoxy)carbonyl](1-methylpiperidin-4-yl)amino}acetate (116.2 mg, 0.32 mmol) in methanol (20 mL) was hydrogenated (1 atmosphere hydrogen pressure) over 10% Pd/C (100 mg) for 20 hours. The mixture was filtered through celite and the filtrate was evaporated to give 2-{[(tert-butoxy)carbonyl](1-methylpiperidin-4-yl)amino}acetic acid as a colorless oil (89 mg, 100%). LC/MS method A: $R_t$=2.36 min., (M+H)$^+$=273.

Example 254: Synthesis of N-Methyl-2-[(1-methyl-piperidin-4-yl)amino]-N-({[6-(trifluoro methoxy)-1,3-benzothiazol-2-yl]carbamoyl}methyl)acetamide

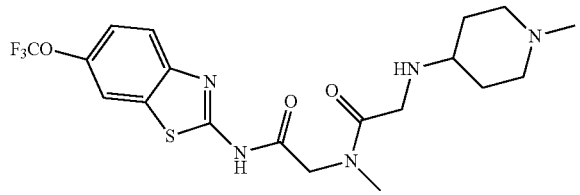 [SMILES: CN1CCC(NCC(=O)N(C)CC(=O)Nc2nc3ccc(OC(F)(F)F)cc3s2)CC1]

To a solution of 2-(methylamino)-N-(6-(trifluoromethoxy)benzo[d]thiazol-2-yl)acetamide dihydrochloride (71.8 mg, 0.19 mmol), 2-{[(tert-butoxy)carbonyl](1-methylpiperidin-4-yl)amino}acetic acid (56.9 mg, 0.21 mmol) and N,N-diisopropylethylamine (73.6 mg, 0.57 mmol, 94 ul) in N,N-dimethylformamide (1 ml) was added 1-[Bis(dimethylamino)methylene]-1H-1,2,3-triazolo[4,5-b]pyridinium 3-oxid hexafluorophosphate (HATU, 79.5 mg, 0.21 mmol) and the reaction mixture stirred for 18 hours. The crude material was purified by RPHPLC (method B) to give tert-butyl N-[methyl({[6-(trifluoromethoxy)-1,3-benzothiazol-2-yl]carbamoyl methyl)carbamoyl]methyl}-N-(1-methylpiperidin-4-yl)carbamate a light yellow foamy solid (138 mg). LC/MS (method A); $R_t$=4.02 min., $(M+H)^+$=560. tert-Butyl N-{[methyl({[6-(trifluoromethoxy)-1,3-benzothiazol-2-yl]carbamoyl}methyl) carbamoyl]methyl}-N-(1-methylpiperidin-4-yl)carbamate was dissolved in 4N HCl in 1,4-dioxane. The mixture stirred 18 hours and the white precipitate was filtered on a glass frit (medium), washed with 1,4-dioxane and ether and dried under vacuum to leave N-methyl-2-[(1-methylpiperidin-4-yl)amino]-N-({[6-(trifluoromethoxy)-1,3-benzothiazol-2-yl]carbamoyl}methyl) acetamide as a white powder (55 mg, 51%). LC/MS method A: $R_t$=3.26 min., $(M+H)^+$=460. $^1$H NMR (300 MHz, CD$_3$OD): δ 7.72-7.94 (m, 2H), 7.36 (d, J=8.80 Hz, 1H), 4.47 (m, 2H), 4.31-4.16 (m, 2H), 3.49-3.44 (m, 1H), 3.19 (s, 3H), 2.89 (s, 3H), 2.46-2.41 (m, 2H), 2.06-2.02 (m, 2H), 1.30-1.44 (m, 4H).

Example 255: Synthesis of tert-Butyl N-(1-acetylpiperidin-4-yl)carbamate

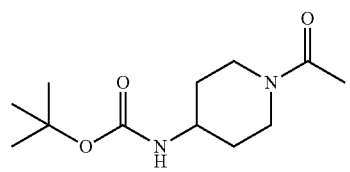 [SMILES: CC(=O)N1CCC(NC(=O)OC(C)(C)C)CC1]

A mixture of tert-butyl piperidin-4-ylcarbamate (3.69 g, 18.4 mmol) and triethylamine (5.57 g, 55 mmol) in tetrahydrofuran (10 mL) was cooled to 0° C. Acetic anhydride (2.25 g, 22 mmol) was added and stirred for 18 hours. Ethyl acetate (100 ml) was added and the mixture was washed with water (2×50 ml), 1N HCl (50 ml), and brine (25 ml). The organic solution was dried over sodium sulfate and evaporated to give tert-butyl N-(1-acetylpiperidin-4-yl)carbamate as a beige solid (4.7 g, 100%). LC/MS method A: $R_t$=3.39 min., $(M+H)^+$=243. $^1$H NMR (300 MHz, CDCl$_3$): δ 4.47 (d, J=11.4 Hz, 2H), 3.77-3.75 (m, 2H), 3.15-3.06 (m, 1H), 2.80-2.66 (m, 2H), 2.07 (s, 3H), 1.99-1.89 (m, 2H), 1.42 (s, 9H).

Example 256: Synthesis of N-(1-Acetylpiperidin-4-yl)amine

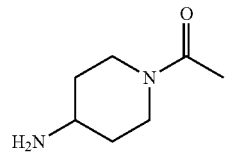

A solution of tert-butyl N-(1-acetylpiperidin-4-yl)carbamate (4.0 g, 17 mmol) stood in 1:1 trifluoroacetic acid-methylene chloride (50 ml) for 2 hours and was then evaporated to dryness to leave N-(1-acetylpiperidin-4-yl) amine as a solid (4.4 g, 100%) which was used without characterization for the next step.

Example 257: Synthesis of Benzyl 2-[(1-acetylpiperidin-4-yl)amino]acetate

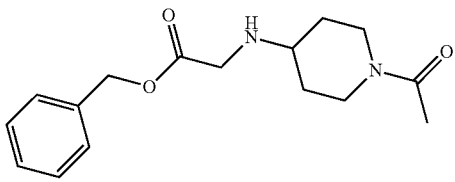 [SMILES: CC(=O)N1CCC(NCC(=O)OCc2ccccc2)CC1]

A mixture of benzyl 2-bromoacetate (1.3 g, 5.8 mmol), 1-(4-aminopiperidin-1-yl)ethan-1-one (1.8 g, 10 mmol), and triethylamine (3 g, 30 mmol) in tetrahydrofuran (10 mL) was stirred 18 hours. Saturated sodium bicarbonate solution (50 ml) was added followed by addition of ethyl acetate (50 ml). The organic layer was washed with water (2×50 ml) and brine (25 ml). The organic solution was dried over sodium sulfate and evaporated to give benzyl 2-[(1-acetylpiperidin-4-yl)amino]acetate as a colorless oil (1.56 g, 54%). LC/MS method A: $R_t$=2.76 min., $(M+H)^+$=291.

Example 258: Synthesis of Benzyl 2-[(1-acetylpiperidin-4-yl)[(tert-butoxy)carbonyl]amino]acetate

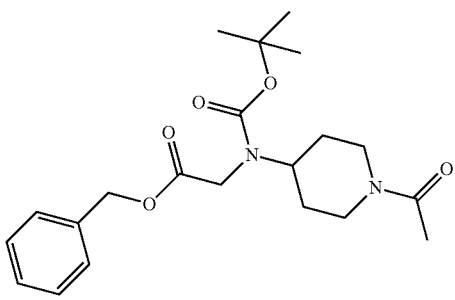 [SMILES: CC(=O)N1CCC(N(CC(=O)OCc2ccccc2)C(=O)OC(C)(C)C)CC1]

A mixture of benzyl 2-[(1-acetylpiperidin-4-yl)amino]acetate (1.56 g, 5.4 mmol) and triethylamine (1.09 g, 10.8 mmol) in tetrahydrofuran (10 mL) was cooled to 0° C. Di-tert-butyl dicarbonate (1.17 g, 5.4 mmol) was added and stirred for 20 hours. Ethyl acetate (100 ml) was added and the mixture was washed with water (2×50 ml), 1N HCl (50 ml), and brine (25 ml). The organic solution was dried over sodium sulfate and evaporated to give a crude product which was purified by silica gel chromatography eluted with a gradient of ethyl acetate in hexanes to leave benzyl 2-[(1-acetylpiperidin-4-yl)[(tert-butoxy)carbonyl]amino]acetate as a colorless oil (0.8 g, 38%). LC/MS method A: $R_t$=4.73 min., $(M+H)^+$=391.

Example 259: Synthesis of 2-[(1-Acetylpiperidin-4-yl)[(tert-butoxy)carbonyl]amino]acetic Acid

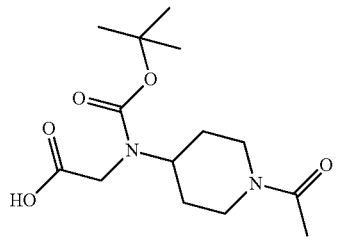 [SMILES: CC(=O)N1CCC(N(CC(=O)O)C(=O)OC(C)(C)C)CC1]

A solution of benzyl 2-[(1-acetylpiperidin-4-yl)[(tert-butoxy)carbonyl]amino]acetate (0.8 g, 2 mmol) in methanol (50 mL) was hydrogenated (1 atmosphere hydrogen pressure) over 10% Pd/C (100 mg) for 20 hours. The mixture was filtered through celite and the filtrate was evaporated to give 2-[(1-acetylpiperidin-4-yl)[(tert-butoxy)carbonyl]amino]acetic acid as an oil (550 mg, 92%). LC/MS method A: $R_t$=3.15 min., $(M+H)^+$=301.

Example 260: Synthesis of 21(1-Acetylpiperidin-4-yl)aminol-N-methyl-N-({[6-(trifluoromethoxy)-1,3-benzothiazol-2-yl]carbamoyl}methyl)acetamide

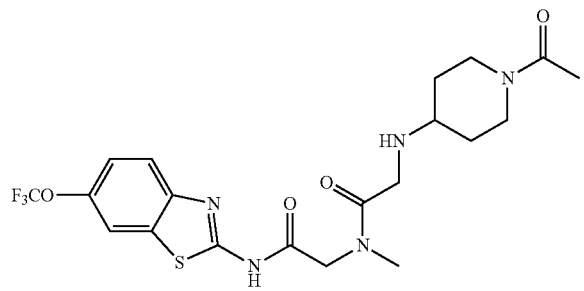 [SMILES: CC(=O)N1CCC(NCC(=O)N(C)CC(=O)Nc2nc3ccc(OC(F)(F)F)cc3s2)CC1]

To a solution of 2-(methylamino)-N-(6-(trifluoromethoxy)benzo[d]thiazol-2-yl)acetamide dihydrochloride (66.8 mg, 0.18 mmol), 2-[(1-acetylpiperidin-4-yl)[(tert-butoxy)carbonyl]amino]acetic acid (58.4 mg, 0.19 mmol) and N,N-diisopropylethylamine (69 mg, 0.53 mmol, 88 ul) in N,N-dimethylformamide (1 ml) was added 1-[Bis(dimethylamino)methylene]-1H-1,2,3-triazolo[4,5-b]pyridinium 3-oxid hexafluorophosphate (HATU, 73.8 mg, 0.19 mmol) and the reaction mixture stirred for 18 hours. The crude material was purified by RPHPLC (method B) to give tert-butyl N-(1-acetylpiperidin-4-yl)-N-{[methyl({[6-(trifluoromethoxy)-1,3-benzothiazol-2-yl]carbamoyl}methyl) carbamoyl]methyl}carbamate as a light yellow foamy solid (LC/MS method A: $R_t$=4.74 min., $(M+H)^+$=588). tert-Butyl N-(1-acetylpiperidin-4-yl)-N-{[methyl({[6-(trifluoromethoxy)-1,3-benzothiazol-2-yl]carbamoyl}methyl)carbamoyl]methyl}carbamate was dissolved in 4N HCl in 1,4-dioxane. The mixture stirred overnight and the white precipitate was filtered on a glass frit (medium), washed with 1,4-dioxane and ether and dried under vacuum to leave 2-[(1-acetylpiperidin-4-yl)amino]-N-methyl-N-({[6-(trifluoromethoxy)-1,3-benzothiazol-2-yl]carbamoyl}methyl) acetamide (68 mg, 68.5%) as a white solid. LC/MS method A: $R_t$=3.52 min., $(M+H)^+$=488. $^1$H NMR (300 MHz, CD$_3$OD): δ 7.88-7.78 (m, 2H), 7.38-7.35 (m, 1H), 4.68-4.65 (m, 1H), 4.44 (s, 2H), 4.27-4.12 (m, 2H), 3.19 (s, 3H), 2.71-2.63 (m, 1H), 2.23-2.20 (m, 1H), 2.11 (s, 3H), 1.65-1.51 (m, 2H), 1.39-1.34 (m, 4H).

Example 261: Synthesis of tert-Butyl 4-{[2-(benzyloxy)-2-oxoethyl]amino}-4-methyl piperidine-1-carboxylate

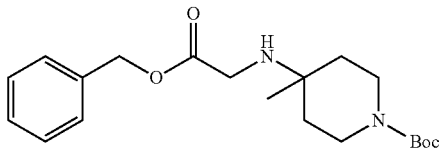 [SMILES: CC1(NCC(=O)OCc2ccccc2)CCN(C(=O)OC(C)(C)C)CC1]

A mixture of 4-methylpiperidin-4-amine (1 g, 8.76 mmol) in dichloromethane (20 mL) was cooled to 0° C., Di-tert-butyl dicarbonate (1.9 g, 8.76 mmol) was added and the mixture was stirred 20 h. The solvent was evaporated to give a crude product to which was added tetrahydrofuran (20 mL), followed by addition of triethylamine (3 mL, 22 mmol) and benzyl 2-bromoacetate (2 g, 8.76 mmol). The mixture was stirred 20 h. Ethyl acetate (100 ml) was added and the mixture was washed with saturated sodium bicarbonate solution (50 ml), and brine (25 ml). The organic solution was dried over sodium sulfate and evaporated to give a crude product which was purified by RPHPLC (method B) to give tert-butyl 4-{[2-(benzyloxy)-2-oxoethyl]amino}-4-methylpiperidine-1-carboxylate as a light yellowish oil (0.55 g, 17.3%). LC/MS method A: $R_t$=3.71 min., $(M+H)^+$=363.

Example 262: Synthesis of tert-Butyl 4-{[2-(benzyloxy)-2-oxoethyl][(benzyloxy) carbonyl]amino}-4-methylpiperidine-1-carboxylate

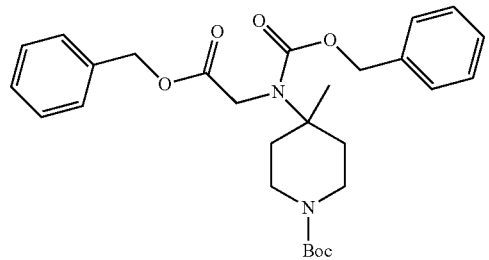 [SMILES: CC(C)(C)OC(=O)N1CCC(C)(N(CC(=O)OCc2ccccc2)C(=O)OCc2ccccc2)CC1]

To a solution of tert-butyl 4-{[2-(benzyloxy)-2-oxoethyl]amino}-4-methylpiperidine-1-carboxylate (0.51 g, 1.4 mmol) in dichloromethane (5 mL) at 0° C. was added N,N-diisopropylethylamine (0.7 mL, 4.2 mmol), followed by Benzyl chloroformate (0.29 g, 1.69 mmol). The reaction mixture was stirred at 0° C. and naturally warmed to room temperature overnight. More N, N-diisopropylethylamine (0.7 mL, 4.2 mmol) and benzyl chloroformate (0.29 g, 1.69 mmol) was added and the reaction was stirred for 24 hours. The reaction mixture was diluted with dichloromethane (50 ml) and washed with saturated sodium bicarbonate (50 ml) solution and brine (50 ml). The organic solution was dried over sodium sulfate and evaporated to give a crude product which was purified by RPHPLC (method B) to give tert-butyl 4-{[2-(benzyloxy)-2-oxoethyl][(benzyloxy)carbonyl]amino}-4-methyl piperidine-1-carboxylate (256 mg, 37%). LC/MS method A: $R_t$=6.34 min., (M+Na)$^+$=519.

Example 263: Synthesis of 2-{[(Benzyloxy)carbonyl]({1-[(tert-butoxy)carbonyl]-4-methyl piperidin-4-yl})amino}acetic Acid

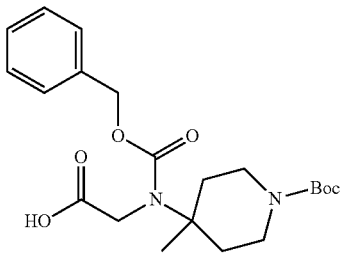 [SMILES: CC(C)(C)OC(=O)N1CCC(C)(N(CC(=O)O)C(=O)OCc2ccccc2)CC1]

To a solution of tert-butyl 4-{[2-(benzyloxy)-2-oxoethyl][(benzyloxy)carbonyl]amino}-4-methylpiperidine-1-carboxylate (256 mg, 0.50 mmol) in dioxane (5 mL) was added 2N LiOH (1 mL). The mixture was stirred for 20 h. 1N HCl was added slowly till the pH was 7. Extracted with ethyl acetate (100 ml) and the organic solution was dried over sodium sulfate and evaporated to give 2-{[(benzyloxy)carbonyl]({1-[(tert-butoxy)carbonyl]-4-methylpiperidin-4-yl})amino}acetic acid as a colorless oil (226 mg, 100%). Used for the next step without further purification. LC/MS method A: $R_t$=5.02 min., (M+Na)$^+$=429.

Example 264: Synthesis of tert-Butyl 4-{[(benzyloxy)carbonyl]({[(2-ethoxy-2-oxoethyl)(methyl) carbamoyl]methyl})amino}-4-methylpiperidine-1-carboxylate

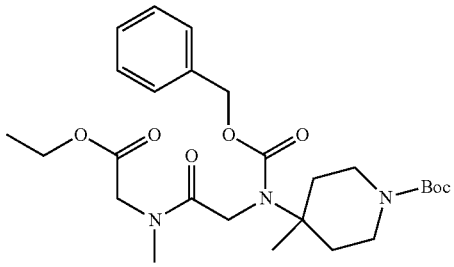 [SMILES: CCOC(=O)CN(C)C(=O)CN(C(=O)OCc1ccccc1)C1(C)CCN(C(=O)OC(C)(C)C)CC1]

To a solution of Sarcosine ethyl ester hydrochloride (94 mg, 0.61 mmol), 2-{[(benzyloxy)carbonyl]({1-[(tert-butoxy)carbonyl]-4-methylpiperidin-4-yl})amino}acetic acid (226 mg, 0.56 mmol) and N,N-diisopropylethylamine (217 mg, 1.68 mmol, 300 ul) in N,N-dimethylformamide (4 ml) was added 1-[Bis(dimethylamino)methylene]-1H-1,2,3-triazolo[4,5-b]pyridinium 3-oxid hexafluorophosphate (HATU, 233 mg, 0.61 mmol) and the reaction mixture stirred for 18 hours. The crude material was purified by RPHPLC (method B) to give tert-butyl 4-{[(benzyloxy)carbonyl]({[(2-ethoxy-2-oxoethyl)(methyl)carbamoyl]methyl})amino}-4-methyl piperidine-1-carboxylate as a colorless oil (218 mg, 77%). LC/MS method A: $R_t$=5.5 min., (M+H)$^+$=506.

Example 265: Synthesis of 2-(2-{[(Benzyloxy)carbonyl]({1-[(tert-butoxy)carbonyl]-4-methylpiperidin-4-yl})amino}-N-methylacetamido)acetic Acid

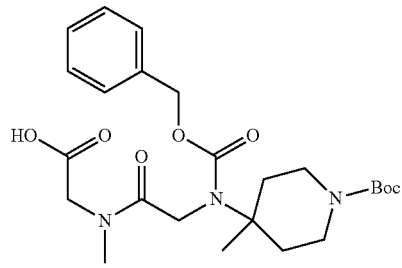 [SMILES: CN(CC(=O)O)C(=O)CN(C(=O)OCc1ccccc1)C1(C)CCN(C(=O)OC(C)(C)C)CC1]

To a solution of tert-butyl 4-{[(benzyloxy)carbonyl]({[(2-ethoxy-2-oxoethyl)(methyl) carbamoyl]methyl})amino}-4-methylpiperidine-1-carboxylate (142 mg, 0.28 mmol) in dioxane (1 mL) was added 2N NaOH. The mixture was stirred 20 h. 1N HCl was added slowly until the pH reached 7. The product was extracted with ethyl acetate (100 ml) and the organic solution was dried over sodium sulfate and evaporated to give a crude product which was purified by silica gel chromatography to give 2-(2-{[(benzyloxy)carbonyl]({1-[(tert-butoxy)carbonyl]-4-methyl piperidin-4-yl})amino}-N-methylacetamido)acetic acid as a colorless oil (100 mg, 75%). LC/MS method A: $R_t$=4.72 min., (M+Na)$^+$=500.

Example 266: Synthesis of tert-Butyl 4-{[(benzyloxy)carbonyl]({[methyl({[6-(trifluoro methoxy)-1,3-benzothiazol-2-yl]carbamoyl}methyl)carbamoyl]methyl}amino}-4-methyl piperidine-1-carboxylate

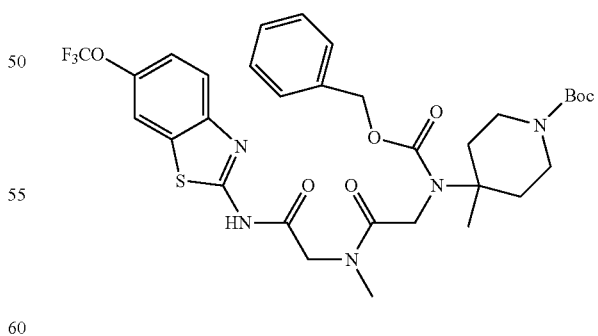

To a solution of 2-(methylamino)-N-(6-(trifluoromethoxy)benzo[d]thiazol-2-yl)acetamide dihydrochloride (59 mg, 0.252 mmol), 2-(2-{[(benzyloxy)carbonyl]({1-[(tert-butoxy)carbonyl]-4-methylpiperidin-4-yl})amino}-N-methylacetamido)acetic acid (100 mg, 0.21 mmol) and N,N-diisopropylethylamine (81.4 mg, 0.63 mmol, 104 ul) in N,N-dimethylformamide (2 ml) was added 1-[Bis(dimethylamino)methylene]-1H-1,2,3-triazolo[4,5-b]pyridinium 3-oxid hexafluoro phosphate (HATU, 95.8 mg, 0.252 mmol) and the reaction mixture stirred for 18 hours. The crude material was purified by RPHPLC (method B) to give tert-butyl 4-{[(benzyloxy)carbonyl]({[methyl({[6-(trifluoromethoxy)-1,3-benzothiazol-2-yl]carbamoyl} methyl)carbamoyl]methyl}) amino}-4-methylpiperidine-1-carboxylate as a white solid (114 mg, 78%). LC/MS method A: $R_t$=6.13 min., (M+H)$^+$=694. $^1$H NMR (300 MHz, CD$_3$OD): δ 7.84-7.77 (m, 2H), 7.35-7.27 (m, 6H), 5.06 (s, 2H), 4.39 (s, 2H), 4.32-4.28 (m, 2H), 3.71-3.65 (m, 2H), 3.24-3.18 (m, 2H), 3.13 (s, 3H), 2.15-2.12 (m, 2H), 1.93-1.89 (m, 2H), 1.48 (s, 3H), 1.41 (s, 9H).

Example 267: Synthesis of tert-Butyl 4-methyl-4-({[methyl({[6-(trifluoromethoxy)-1,3-benzothiazol-2-yl]carbamoyl}methyl)carbamoyl]methyl}amino)piperidine-1-carboxylate

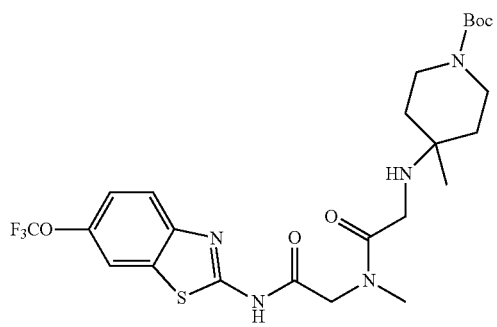 [SMILES: CN(CC(=O)Nc1nc2ccc(OC(F)(F)F)cc2s1)C(=O)CNC1(C)CCN(C(=O)OC(C)(C)C)CC1]

A solution of tert-butyl 4-{[(benzyloxy)carbonyl]({[methyl({[6-(trifluoromethoxy)-1,3-benzothiazol-2-yl]carbamoyl}methyl)carbamoyl]methyl})amino}-4-methylpiperidine-1-carboxylate (114 mg, 2 mmol) in methanol (20 mL) was hydrogenated (1 atmosphere hydrogen pressure) over 10% Pd/C (100 mg) for 20 hours. The mixture was filtered through celite and the filtrate was evaporated to give tert-butyl 4-methyl-4-({[methyl({[6-(trifluoromethoxy)-1,3-benzothiazol-2-yl]carbamoyl}methyl)carbamoyl]methyl}amino)piperidine-1-carboxylate as a colorless oil (100 mg, 100%). LC/MS method A: $R_t$=4.22 min., (M+H)$^+$=560.

Example 268: Synthesis of N-Methyl-2-[(4-methylpiperidin-4-yl)amino]-N-(([6-(trifluoromethoxy)-1,3-benzothiazol-2-yl]carbamoyl}methyl)acetamide

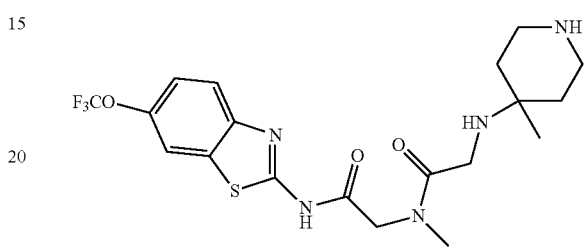

To a solution of tert-butyl 4-methyl-4-({[methyl({[6-(trifluoromethoxy)-1,3-benzothiazol-2-yl]carbamoyl}methyl)carbamoyl]methyl}amino)piperidine-1-carboxylate (100 mg, 0.179 mmol) in dioxane (1 mL) was added 4N HCl in 1,4-dioxane (2 mL). The mixture stirred overnight and the white precipitate was filtered, washed with 1,4-dioxane and ether and dried under vacuum to leave 22 mg (22%) of N-methyl-2-[(4-methylpiperidin-4-yl)amino]-N-({[6-(trifluoromethoxy)-1,3-benzothiazol-2-yl]carbamoyl} methyl)acetamide as a white powder. LC/MS method A: $R_t$=3.28 min., (M+H)$^+$=460. $^1$H NMR (300 MHz, CD$_3$OD): δ 7.73-7.91 (m, 2H), 7.36 (d, J=8.50 Hz, 1H), 4.45-4.51 (m, 2H), 3.48-3.52 (m, 2H), 3.23 (s, 3H), 2.07-2.38 (m, 6H), 1.45-1.64 (m, 5H).

TABLE 1

| | Non-limiting exemplary compounds of the disclosure. |
|---|---|
| Entry | Structure |
| 1 | ![structure] |
| 2 | ![structure] |
| 3 | ![structure] |

TABLE 1-continued

Non-limiting exemplary compounds of the disclosure.

| Entry | Structure |
|---|---|
| 4 | (6-trifluoromethoxy-benzothiazol-2-yl)-NH-C(O)-CH$_2$-N(CH$_3$)-S(O)$_2$-CH$_2$-NH-Pr |
| 5 | (6-trifluoromethoxy-benzothiazol-2-yl)-NH-C(O)-CH$_2$-N(CH$_3$)-S(O)$_2$-CH$_2$-NH-i-Pr |
| 6 | (6-trifluoromethoxy-benzothiazol-2-yl)-NH-C(O)-CH$_2$-N(CH$_3$)-S(O)$_2$-CH$_2$-NH-t-Bu |
| 7 | (6-trifluoromethoxy-benzothiazol-2-yl)-NH-C(O)-CH$_2$-N(CH$_3$)-C(=NH)-NH$_2$ |
| 8 | (6-trifluoromethoxy-benzothiazol-2-yl)-NH-C(O)-CH$_2$-N(CH$_3$)-(4,5-dihydro-1H-imidazol-2-yl) |
| 9 | (6-trifluoromethoxy-benzothiazol-2-yl)-NH-C(O)-CH$_2$-N(CH$_3$)-C(O)-CH$_2$-NH-(3-methylazetidin-3-yl) |
| 10 | (6-trifluoromethoxy-benzothiazol-2-yl)-NH-C(O)-CH$_2$-N(CH$_3$)-C(O)-CH$_2$-NH-(oxetan-3-yl) |
| 11 | (6-trifluoromethoxy-benzothiazol-2-yl)-NH-C(O)-CH$_2$-N(CH$_3$)-C(O)-CH$_2$-NH-(1-acetyl-3-methylazetidin-3-yl) |

TABLE 1-continued

Non-limiting exemplary compounds of the disclosure.

| Entry | Structure |
|---|---|
| 12 | 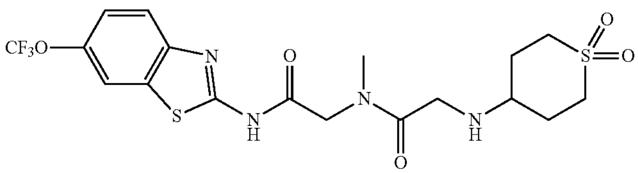 |
| 13 | 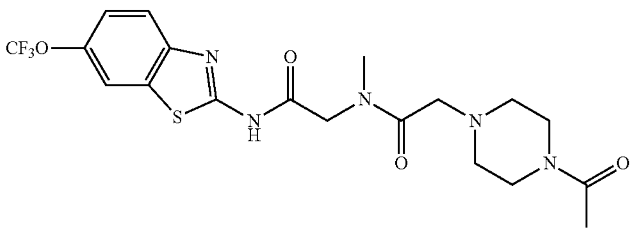 |
| 14 | 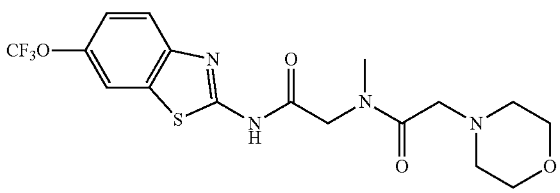 |
| 15 | 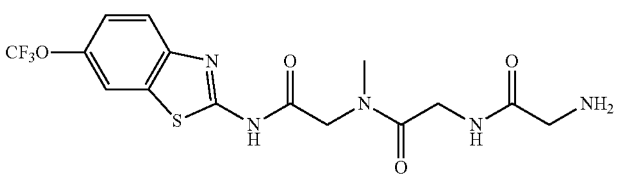 |
| 16 | 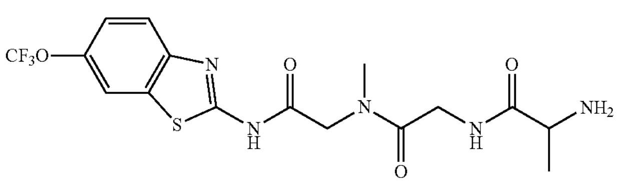 |
| 17 | 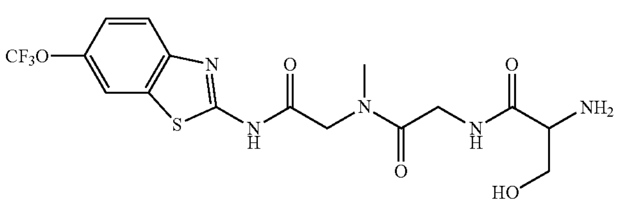 |
| 18 | 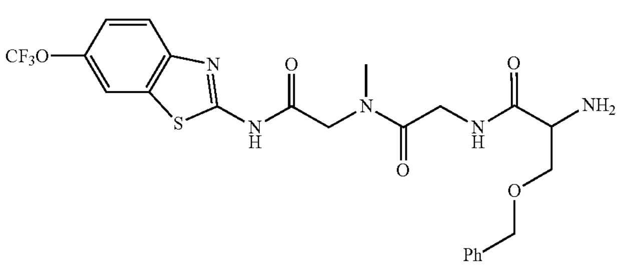 |

TABLE 1-continued
Non-limiting exemplary compounds of the disclosure.
| Entry | Structure |
|---|---|
| 19 | 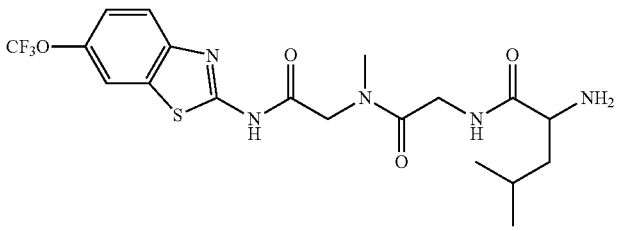 |
| 20 | 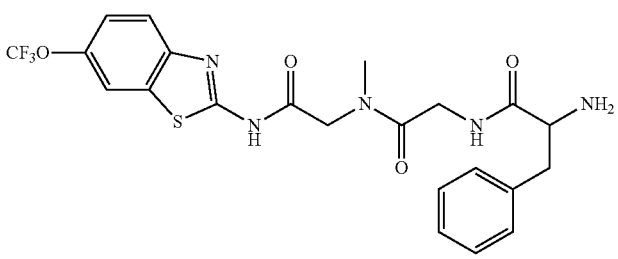 |
| 21 | 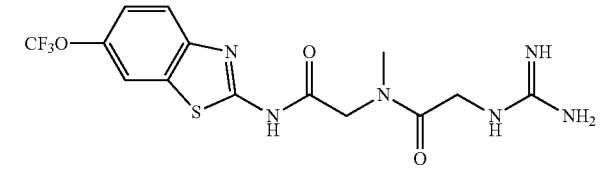 |
| 22 | 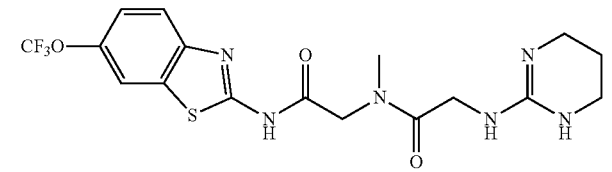 |
| 23 | 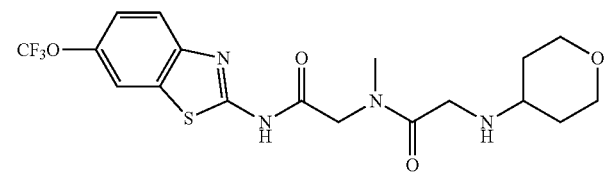 |
| 24 | 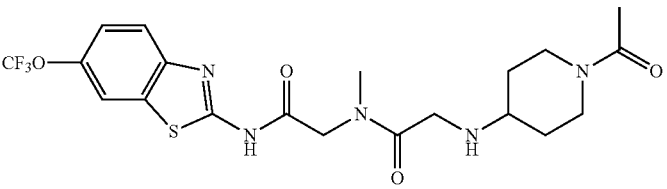 |
| 25 | 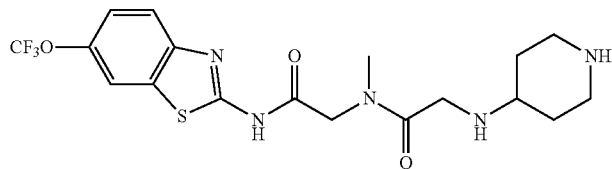 |

TABLE 1-continued

Non-limiting exemplary compounds of the disclosure.

| Entry | Structure |
|---|---|
| 26 | 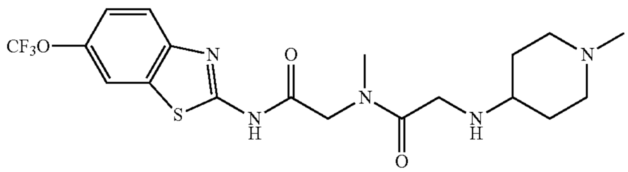 |
| 27 | 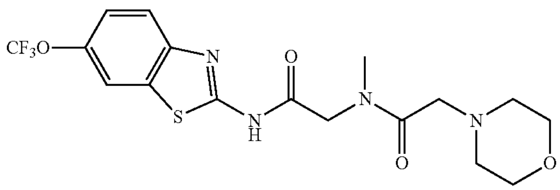 |
| 28 | 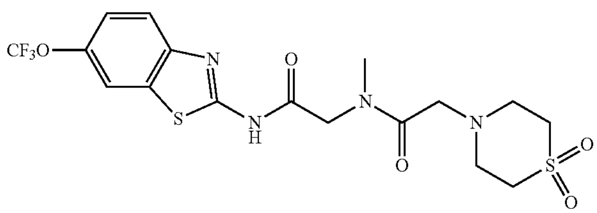 |

TABLE 2

Further non-limiting exemplary compounds of the disclosure.

| Entry | Structure |
|---|---|
| 1 | 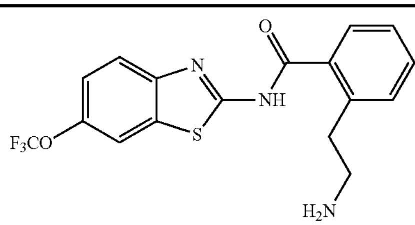 |
| 2 | 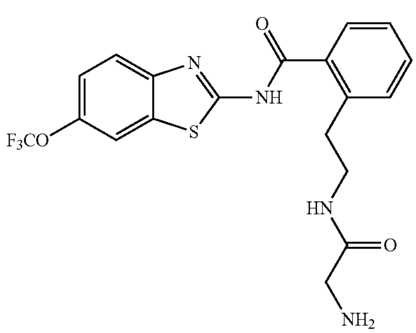 [SMILES: NCC(=O)NCCc1ccccc1C(=O)Nc1nc2ccc(OC(F)(F)F)cc2s1] |
| 3 | 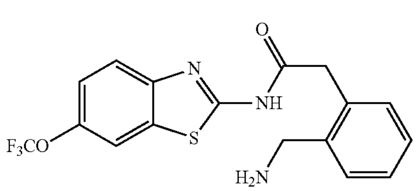 |

TABLE 2-continued

Further non-limiting exemplary compounds of the disclosure.

| Entry | Structure |
|---|---|
| 4 | 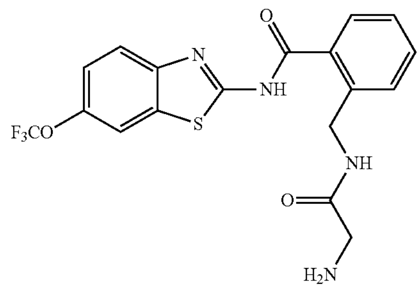 [SMILES: NCC(=O)NCc1ccccc1C(=O)Nc1nc2ccc(OC(F)(F)F)cc2s1] |
| 5 | 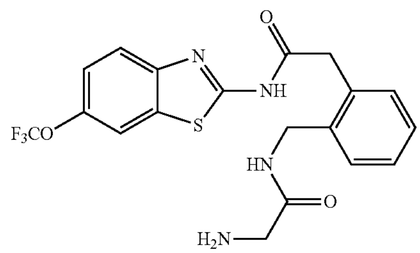 [SMILES: NCC(=O)NCc1ccccc1CC(=O)Nc1nc2ccc(OC(F)(F)F)cc2s1] |
| 6 | 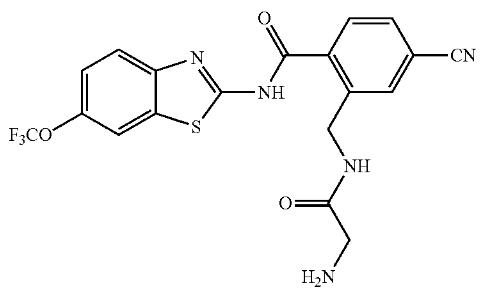 [SMILES: N#Cc1ccc(C(=O)Nc2nc3ccc(OC(F)(F)F)cc3s2)c(CNC(=O)CN)c1] |
| 7 | 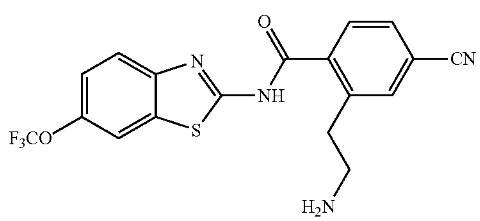 [SMILES: N#Cc1ccc(C(=O)Nc2nc3ccc(OC(F)(F)F)cc3s2)c(CCN)c1] |
| 8 | 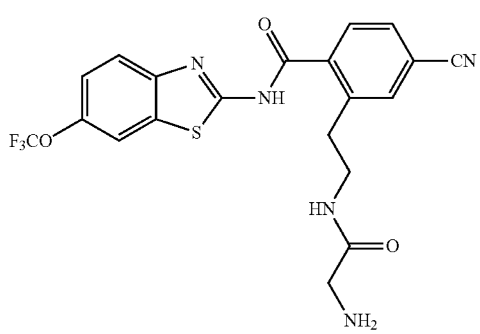 [SMILES: N#Cc1ccc(C(=O)Nc2nc3ccc(OC(F)(F)F)cc3s2)c(CCNC(=O)CN)c1] |
| 9 | 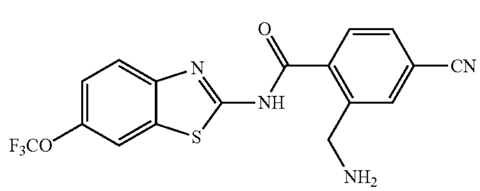 [SMILES: N#Cc1ccc(C(=O)Nc2nc3ccc(OC(F)(F)F)cc3s2)c(CN)c1] |

TABLE 2-continued

Further non-limiting exemplary compounds of the disclosure.

| Entry | Structure |
|---|---|
| 10 | 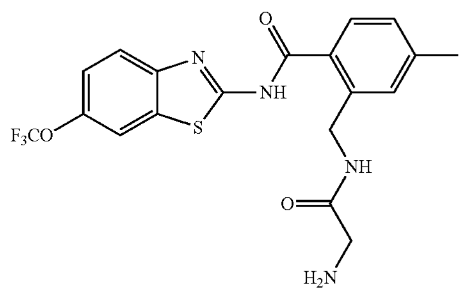 [SMILES: Cc1ccc(C(=O)Nc2nc3ccc(OC(F)(F)F)cc3s2)c(CNC(=O)CN)c1] |
| 11 | 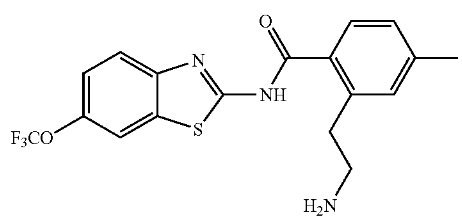 [SMILES: Cc1ccc(C(=O)Nc2nc3ccc(OC(F)(F)F)cc3s2)c(CCN)c1] |
| 12 | 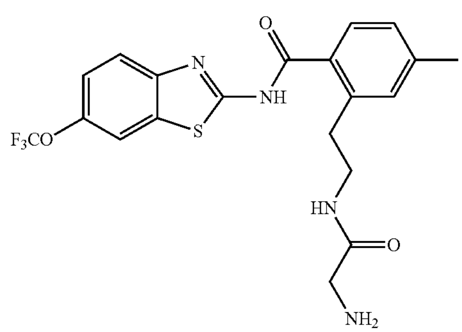 [SMILES: Cc1ccc(C(=O)Nc2nc3ccc(OC(F)(F)F)cc3s2)c(CCNC(=O)CN)c1] |
| 13 | 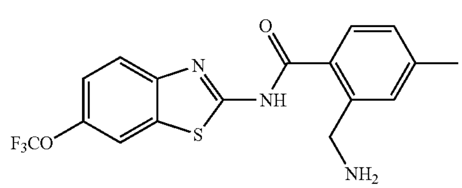 [SMILES: Cc1ccc(C(=O)Nc2nc3ccc(OC(F)(F)F)cc3s2)c(CN)c1] |
| 14 | 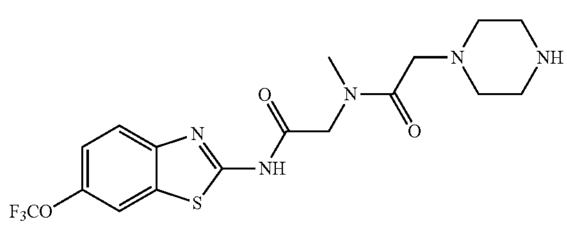 [SMILES: CN(CC(=O)Nc1nc2ccc(OC(F)(F)F)cc2s1)C(=O)CN1CCNCC1] |
| 15 | 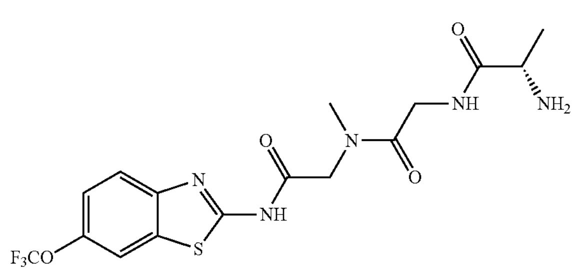 [SMILES: C[C@H](N)C(=O)NCC(=O)N(C)CC(=O)Nc1nc2ccc(OC(F)(F)F)cc2s1] |

TABLE 2-continued

Further non-limiting exemplary compounds of the disclosure.

| Entry | Structure |
|---|---|
| 16 | 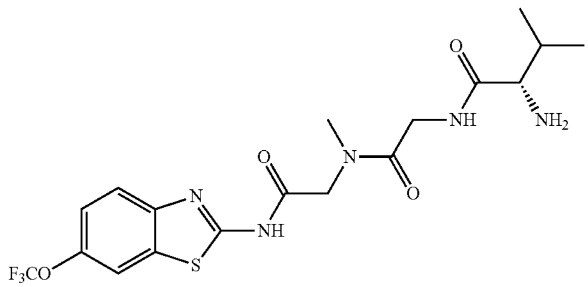 [SMILES: CC(C)[C@H](N)C(=O)NCC(=O)N(C)CC(=O)Nc1nc2ccc(OC(F)(F)F)cc2s1] |
| 17 | 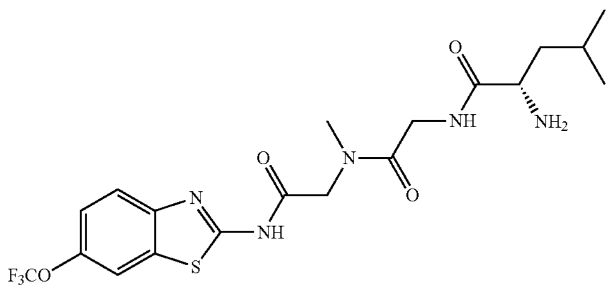 [SMILES: CC(C)C[C@H](N)C(=O)NCC(=O)N(C)CC(=O)Nc1nc2ccc(OC(F)(F)F)cc2s1] |
| 18 | 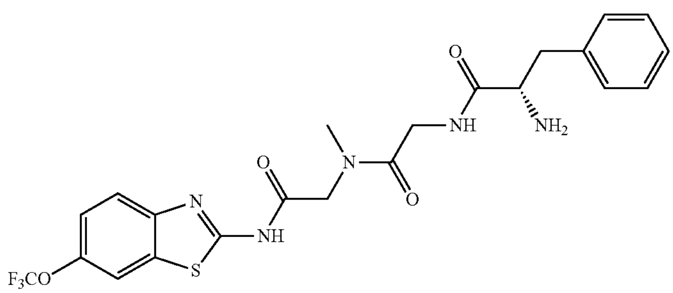 [SMILES: CN(CC(=O)Nc1nc2ccc(OC(F)(F)F)cc2s1)C(=O)CNC(=O)[C@@H](N)Cc1ccccc1] |
| 19 | 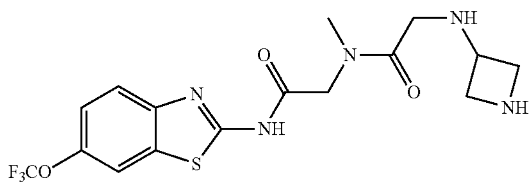 [SMILES: CN(CC(=O)Nc1nc2ccc(OC(F)(F)F)cc2s1)C(=O)CNC1CNC1] |
| 20 | 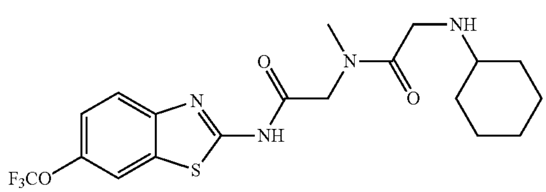 [SMILES: CN(CC(=O)Nc1nc2ccc(OC(F)(F)F)cc2s1)C(=O)CNC1CCCCC1] |
| 21 | 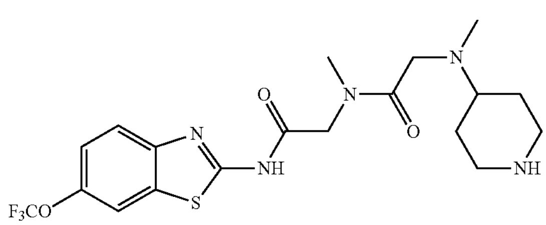 [SMILES: CN(CC(=O)Nc1nc2ccc(OC(F)(F)F)cc2s1)C(=O)CN(C)C1CCNCC1] |

TABLE 2-continued

Further non-limiting exemplary compounds of the disclosure.

| Entry | Structure |
|---|---|
| 22 | [structure] |
| 23 | [structure] |
| 24 | [structure] |
| 25 | [structure] |
| 26 | [structure] |

FORMULATIONS

The present invention also relates to compositions or formulations which comprise the riluzole prodrug agents according to the present invention. In general, the compositions of the present invention comprise an effective amount of one or more riluzole prodrug agents and salts thereof according to the present invention which are effective and one or more excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability. The formulation can be used for once-a-day or multiple time per day dosage.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington's Pharmaceutical Sciences,* 17th edition, ed. Alfonoso R. Gennaro, Mack Publishing Company, Easton, Pa. (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions. Compounds of the present teachings can be administered orally, parenterally or as orally dissolvable tablets ("ODT's") or sublingual preparations neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known prodrug agents. Oral formulations containing a compound disclosed herein can comprise any conventionally used oral form, including tablets, capsules, buccal forms, ODTs or other sublingual formulations, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound(s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intra-bronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.

Compounds described herein can be administered parenterally or intraperitoneally. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils. Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature. Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound with other agents effective in the treatment of the target disease. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of compositions according to the present invention include from about 0.001 mg to about 1000 mg of one or more riluzole prodrug according to the present invention and one or more excipients; from about 0.01 mg to about 100 mg of one or more riluzole prodrug according to the present invention and one or more excipients; and from about 0.1 mg to about 10 mg of one or more riluzole prodrug according to the present invention; and one or more excipients.

PROCEDURES

The following procedures can be utilized in evaluating and selecting compounds as riluzole prodrugs.
Stability in Simulated Gastric Fluid (SGF) and Simulated Intestinal Fluid (SIF).

Procedure from Baudy et. al. (J. Med. Chem. 2009, 52, 771-778) used. The physiological stability of prodrugs was determined by examining the stability of the compound in SGF, and SIF at 37° C. The compounds were prepared in a 9:1 mixture of the appropriate test component (SGF, SIF) and acetonitrile to a final concentration of 0.01 mg/mL. The samples were thoroughly mixed and maintained at 37° C. Each sample was injected consecutively onto an Agilent 1100 system (Luna C18, 3 µm, 50 mm×3 mm; 1 mL/min; mobile phase of 0.1% trifluoroacetic acid in water/0.1% trifluoroacetic acid in acetonitrile) after a 3 h period. The percent remaining of prodrug was calculated by comparing the area of prodrug compound versus riluzole generated. The identities of the parent compounds and conversion products were confirmed by LC/MS.
Plasma Stability:

Assessment of plasma stability was carried out by individual incubations of drug candidates in fresh mouse or human control plasma at a concentration of 1 uM for 1 hour at 37° C. After which, the samples were de-proteinized by addition of 2 volumes of acetonitrile containing 0.1% formic acid and internal standard, vortex mixed for 2 minutes and centrifuged at 4000 rpm for 10 minutes to pellet precipitated protein. The resulting supernatant containing the drug candidates was diluted 5-fold with water containing 0.1% formic acid and submitted to LC-MS/MS analysis. All determinations were done in triplicate. Plasma stability was expressed as percent of control remaining.

Metabolic Stability:

In vitro metabolic stability was determined in pooled mouse or human liver microsomes (BD Gentest) at a protein concentration of 0.5 mg/mL in reaction buffer (100 mM $KH_2PO_4$, pH 7.4 and 12 mM $MgCl_2$). Each drug candidate was added to a final concentration of 1 uM. This mixture was pre-warmed to 37° C. for 10 minutes prior to starting the reaction with the addition of (3-Nicotinamide adenine dinucleotide 2'-phosphate reduced (NADPH) to a final concentration of 1 mM. A parallel incubation lacking NADPH served as the control. After incubation for 30 min at 37° C., the reactions were quenched by the addition of acetonitrile containing 0.1% formic acid and internal standard, vortex mixed for 2 minutes and centrifuged at 4000 rpm for 10 minutes to pellet the precipitated protein. The resulting supernatant containing the drug candidate and its potential metabolites was diluted 5-fold with water containing 0.1% formic acid and submitted to LC-MS/MS analysis. Metabolic stability was expressed as percent of control remaining.

LC-MS/MS Analysis:

An aliquot from each incubation was analyzed by LC-MS/MS with SRM detection in the positive ionization mode using an ABSciex API 5500 QTrap Mass Spectrometer interfaced via the ABSciex Turbo V IonSpray source (ESI) to an Eksigent ExpressHT LC system. Best peak shape and separation from interfering matrix species was afforded by an Eksigent 3C18-CL-300, 3μ, 50×1 mm column. A fast gradient, from 15 to 85% organic in 2.5 minutes, with run time of 5.0 minutes, and flow rate of 50 uL/min was utilized. Peak areas were integrated using MultiQuant v2.0 software from ABSciex.

Rat Pharmacokinetic Studies of the Compounds of the Disclosure:

The pharmacokinetics of the compounds of the disclosure and released riluzole were evaluated following either a single intravenous or oral administration of the prodrug to fasted male Sprague-Dawley rats at suggested dose levels (mg/Kg body weight). Blood samples were collected at pre-determined time points including a 0 h time point and usually between 7 and 8 additional time points not exceeding a 24 h period. Plasma concentrations of the prodrug and riluzole were determined by LC-MS/MS and pharmacokinetic parameters were determined using WinNonlin (v6.3).

Plasma samples were extracted and analyzed using the methods described in Plasma Sample Extraction and Analysis. Average plasma concentrations for selected examples and plasma pharmacokinetic parameters are shown in Tables 2. All data are expressed as ng/mL of the free base. Samples that were below the limit of quantification (0.5 ng/mL) were not used in the calculation of averages.

Pharmacokinetic parameters were calculated from the time course of the plasmaconcentrations. Pharmacokinetic parameters were determined with Phoenix Winnonlin (v6.3) software using a non-compartmental model. The maximum plasma concentration (Cmax) and time to the maximum plasma concentration (Tmax) of the compound of the disclosure were observed from the data. The area under the concentration-time curve (AUC) of the compound of the disclosure was calculated using the trapezoidal formula with calculation to the last quantifiable data point, and to infinity if applicable. Plasma half-life (t½) was calculated from 0.693/slope of the terminal elimination phase. Mean residence time, MRT, was calculated by dividing the area under the moment curve (AUMC) by the AUC. Any samples below the limit of quantitation (0.5 ng/mL) were treated as zero for pharmacokinetic data analysis.

Plasma Sample Extraction and Analysis:

Analytical stock solutions (1.00 mg/mL of the free compound of the disclosure) were prepared in DMSO. Standards were prepared in diluted matrix containing 1 part 10% formic acid and 9 parts Sprague-Dawley rat plasma containing sodium heparin as the anticoagulant (pre-diluted with 1 part of 0.5M citric acid and 9 parts whole blood). Working solutions were prepared in 50:50 acetonitrile:water. Working solutions were then added to plasma to make calibration standards to final concentrations of 1000, 500, 100, 50, 10, 5, 1, and 0.5 ng/mL. Standards contained both the test article and riluzole. Standards were treated identically to the study samples.

Sample Extraction:

Plasma samples were extracted via acetonitrile precipitation on a Tomtec Quadra 96-Model 320 liquid handling system in a 96-well plate format.

Step 1
1) Standards: Add 10 μL of appropriate working solution to 50 μL of blank matrix in a 96-well plate.
2) Blanks: Add 10 μL 50:50 acetonitrile:water to 50 μL of blank matrix in a 96-well plate.
3) Samples: Add 10 μL 50:50 acetonitrile:water to 50 μL of study sample in a 96-well plate.
4) Cap and mix.

Step 2: Using the Tomtec, add 50 μL of sample to 150 μL of acetonitrile (containing 100 ng/mL propranolol as an internal standard) that has been pre-loaded onto a Sirocco Protein Precipitation plate (Waters Corp.)

Step 3: Using the Tomtec, mix the samples via air aspiration

Step 4: Apply vacuum and collect filtrates into clean polypropylene 96-well plate. Cap for analysis.

HPLC Conditions:
Instrument: Waters Acquity UPLC
Column: Waters Acquity BEH C18, 100×2.1 mm id, 1.7 μm
Mobile Phase Buffer: 40 mM ammonium formate, pH 3.5
Aqueous Reservoir (A): 10% buffer, 90% water
Organic Reservoir (B): 10% buffer, 90% acetonitrile
Gradient Program:

| Time (min) | Grad. Curve | % A | % B |
|---|---|---|---|
| 0.00 | 6 | 90 | 10 |
| 3.75 | 6 | 0 | 100 |
| 4.00 | 6 | 90 | 10 |
| 5.00 | 6 | 90 | 10 |

Flow Rate: 400 μL/min
Injection Volume: 5 μL
Run Time: 5.0 min
Column Temperature: 40° C.
Sample Temperature: 8° C.
Strong Autosampler Wash: 1:1:1 (v:v:v) water:methanol:isopropanol with 0.2% formic acid
Weak Autosampler Wash: 4 mM ammonium formate
Mass Spectrometer Conditions
Instrument: PE Sciex API4000
Interface: Electrospray ("Turbo Ion Spray")
Mode: Multiple Reaction Monitoring (MRM)
Gases: CUR 30, CAD 10, GS1 50, GS2 50
Source Temperature: 550° C.

Polarity: positive

Pharmacokinetic data for various examples via intravenous administration is shown in Table 3. Table 4 shows pharmacokinetic data for Example 125 via oral administration. FIG. 1 shows the time-concentration curves for Example 125 and released riluzole via both intravenous and oral administration. These data demonstrate that the compounds of the disclosure in Table 3 are converted to riluzole when given intravenously. These data further demonstrate that the prodrug Example 125 is converted to Riluzole with moderate to long half life during intravenous administration and the prodrug Example 125 is converted to Riluzole with long half life, high oral bioavailability during oral administration. Table 5 shows pharmacokinetic data for Example 204 via oral administration. FIG. 3 shows the time-concentration curves for Example 204 and released riluzole via both intravenous and oral administration. Table 6 shows pharmacokinetic data for Example 216 via oral administration. Tables 7, 8, and 9 and FIGS. 5 and 6 show PK data for example 204 in mice and cynomolgus monkey

TABLE 3

PK in fasted male Sprague Dawley Rats, IV administration. Monitor disappearance of Prodrug and appearance of riluzole.[a]

| | Compound of the disclosure values | | | | released riluzole values | | | |
|---|---|---|---|---|---|---|---|---|
| Example | Cl (L/h/Kg) | $t_{1/2}$ (h) | $AUC_{last}$ (hr · ng/mL) | $V_{ss}$ (L/Kg) | $t_{1/2}$ (h) | $T_{max}$ (h) | $C_{max}$ (ng/mL) | $AUC_{last}$ (hr · ng/mL) |
| 52 | 0.54 | 4.75 | 3623 | 3.55 | ND | 6.67 | 42.4 | 280 |
| 59 | 0.64 | 6.2 | 2766 | 5.11 | ND | 8 | 39.9 | 222 |
| 82 | 4.28 | 1.03 | 663 | 4.14 | 3.07 | 2 | 198 | 1121 |
| 83 | 0.68 | 5.56 | 1725 | 5.06 | ND | 5.33 | 24.8 | 171 |
| 111 | 0.345 | 6.51 | 4647 | 3.19 | ND | 5.33 | 24.6 | 153 |
| 113 | 0.69 | 5.45 | 2758 | 4.88 | ND | 6.67 | 92 | 530 |
| 118 | 1.13 | 10.4 | 2484 | 3.35 | 16.8 | 0.083 | 49.5 | 165 |
| 119 | 1.63 | 9.3 | 1721 | 4.7 | ND | 2.92 | 16.9 | 118 |
| 120 | 1.14 | 8.66 | 2465 | 3.63 | 76.7 | 0.083 | 30.7 | 132 |
| 121 | 2.18 | 4.83 | 1294 | 6.15 | ND | 1.39 | 49.6 | 286 |
| 122 | 3.98 | 0.28 | 219 | 0.861 | 4.01 | 0.08 | 560 | 2017 |
| 123 | 3.54 | 0.68 | 787 | 2.04 | 4.13 | 0.14 | 375 | 1655 |
| 124 | 4.87 | 0.63 | 580 | 2.67 | 2.99 | 1.33 | 324 | 1577 |
| 125 | 1.78 | 1.93 | 1526 | 3.57 | 7.83 | 0.78 | 187 | 1137 |
| 125 | 1.67 | 1.92 | 1602 | 3.51 | 4.71 | 0.19 | 324 | 1452 |
| 173 | 1.34 | 6.7 | 1444 | 9.66 | ND | 8 | 26 | 159 |
| 204 | 13.2 | 0.237 | 232 | 2.47 | 3.77 | 0.53 | 392 | 1300 |
| 212 | 6.26 | 2.43 | 218 | 6.21 | 4.64 | .083 | 315 | 208 |
| 216 | 1.38 | 3.98 | 1907 | 2.53 | 9.05 | .42 | 156 | 830 |
| 234 | 0.853 | 1.5 | 3245 | 1.10 | 5.39 | 0.78 | 18.3 | 73.3 |

IV administration of prodrug at dose of 2.8 mg/Kg except example 83 which was 1.8 mg/Kg and Example 212 which was dosed at 1.4 mg/Kg
ND = not determined
CL = Clearance
$t_{1/2}$ = Terminal Half Life
$V_{SS}$ = Volume of distribution
Tmax = Time at maximum concentration
Cmax = Maximum concentration

TABLE 4

PK in fasted male Sprague Dawley Rats for Example 125, PO administration at 14.6 mg/kg. Monitor disappearance of Prodrug and appearance of riluzole.

| | Example 125 | | Released Riluzole | |
|---|---|---|---|---|
| | Mean | SD | Mean | SD |
| $C_{max}$ (ng/mL) | 213 | 39.0 | $C_{max}$ (ng/mL) | 1587 | 150 |
| $t_{max}$ (hr) | 1.80 | 2.00 | $t_{max}$ (hr) | 8.00 | 0 |
| $t_{1/2}$ (hr) | 3.8 | 0.40 | $t_{1/2}$ (hr) | ND | ND |
| $AUC_{last}$ | 2259 | 305 | $AUC_{last}$ | 20518 | 1437 |

TABLE 4-continued

PK in fasted male Sprague Dawley Rats for Example 125, PO administration at 14.6 mg/kg. Monitor disappearance of Prodrug and appearance of riluzole.

| | Example 125 | | Released Riluzole | |
|---|---|---|---|---|
| | Mean | SD | Mean | SD |
| (hr · ng/mL) | | | (hr · ng/mL) | | |
| $AUC_{inf}$ (hr · ng/mL) | 2289 | 32 | $AUC_{inf}$ (hr · ng/mL) | ND | ND |
| % F | 26 | | % F | >100 | |

% F = bioavailability

TABLE 5

PK in fasted male Sprague Dawley Rats for Example 204, PO administration 5 mg/kg. Monitor disappearance of Prodrug and appearance of riluzole.

| | Example 204 | | Riluzole | |
|---|---|---|---|---|
| | Mean | SD | Mean | SD |
| $C_{max}$ (ng/mL) | 1.84 | 0.27 | $C_{max}$ (ng/mL) | 442 | 104.0 |
| $t_{max}$ (hr) | 0.28 | 0.21 | $t_{max}$ (hr) | 5.33 | 2.31 |
| $t_{1/2}$ (hr) | ND | ND | $t_{1/2}$ (hr) | ND | ND |

TABLE 5-continued

PK in fasted male Sprague Dawley Rats for Example 204, PO administration 5 mg/kg. Monitor disappearance of Prodrug and appearance of riluzole.

| | Example 204 | | Riluzole | | |
|---|---|---|---|---|---|
| | Mean | SD | | Mean | SD |
| $AUC_{last}$ (hr · ng/mL) | 0.90 | ND | $AUC_{last}$ (hr · ng/mL) | 2332 | 791 |

TABLE 6

PK in fasted male Sprague Dawley Rats for Example 216, PO administration 5 mg/kg. Monitor disappearance of Prodrug and appearance of riluzole.

| | Example 216 | | Riluzole | | |
|---|---|---|---|---|---|
| | Mean | SD | | Mean | SD |
| $C_{max}$ (ng/mL) | 2.96 | 0.56 | $C_{max}$ (ng/mL) | 81.8 | 43 |
| $t_{max}$ (hr) | 2.17 | 1.76 | $t_{max}$ (hr) | 5.33 | 2.31 |
| $t_{1/2}$ (hr) | ND | ND | $t_{1/2}$ (hr) | ND | ND |
| $AUC_{last}$ (hr · ng/mL) | 16.6 | 1.77 | $AUC_{last}$ (hr · ng/mL) | 426 | 226 |

TABLE 7

PK in fasted male mice for Example 204, IV administration, 1 mg/kg. Monitor disappearance of Prodrug and appearance of riluzole.

| | Example 204 | | | Riluzole | |
|---|---|---|---|---|---|
| | Mean | SD | | Mean | SD |
| $T_{1/2}$ (hr) | 0.29 | 0.06 | $C_{max}$(ng/mL) | 45 | 13 |
| CL (L/hr/kg) | 1.94 | 0.44 | Tmax(hr) | 083 | 0 |
| Vss (L/kg) | 0.46 | 0.14 | $T_{1/2}$ (hr) | 2.3 | 0.20 |
| $AUC_{last}$ (hr · ng/mL) | 532.0 | 109.0 | $AUC_{last}$ (hr · ng/mL) | 118 | 6 |
| $AUC_{inf}$ (hr · ng/mL) | 533 | 109.0 | $AUC_{inf}$ (hr · ng/mL) | 130 | 5 |

TABLE 8

PK in fasted male mice for Example 204, PO administration, 5 mg/kg. Monitor disappearance of Prodrug and appearance of riluzole.

| | Example 204 | | | Riluzole | |
|---|---|---|---|---|---|
| | Mean | SD | | Mean | SD |
| $C_{max}$(ng/mL) | 4.71 | 1.52 | $C_{max}$(ng/mL) | 79 | 26.1 |
| Tmax(hr) | 0.33 | 0.14 | Tmax(hr) | 2.0 | 0.0 |
| $T_{1/2}$ (hr) | ND | ND | $T_{1/2}$ (hr) | ND | ND |
| $AUC_{last}$ (hr · ng/mL) | 3.85 | 2.36 | $AUC_{last}$ (hr · ng/mL) | 332 | 52 |
| $AUC_{inf}$ (hr · ng/mL) | ND | ND | $AUC_{inf}$ (hr · ng/mL) | ND | ND |

TABLE 9

PK in Cynomolgus Monkey for Example 204, IV administration 1 mg/kg and PO administration, 3 mg/kg. Monitor the appearance of riluzole.

| | Riluzole from example 204 (IV, 1 mg/kg) | | Riluzole from example 204 (PO, 3 mg/kg) | | |
|---|---|---|---|---|---|
| | Mean | SD | | Mean | SD |
| $C_{max}$ (ng/mL) | 60 | 5.7 | $C_{max}$ (ng/mL) | 200 | 89.2 |
| $t_{max}$ (hr) | 0.75 | 0.3 | $t_{max}$ (hr) | 2.33 | 0.82 |
| $t_{1/2}$ (hr) | 6.2 | 1.3 | $t_{1/2}$ (hr) | 5.9 | 2.11 |
| $AUC_{last}$ (hr · ng/mL) | 293 | 97.9 | $AUC_{last}$ (hr · ng/mL) | 2110 | 920 |

Inhibition of Human Melanoma Cell Xenograft Growth by Riluzole:

Melanoma C8161 cells were inoculated s.c. into nude mice at 10 per site. The mice were treated with 7.5 mg/kg riluzole (control), an equimolar amount of prodrug (Example 125, 14.6 mg/kg), and a dose of prodrug Example 125 threefold lower in molar terms (4.9 mg/kg) than the dose of riluzole, by p.o. gavage when tumor volume had reached 6 mm³. Mice were treated every day for 21 days, and tumor sizes were measured twice weekly with a Vernier caliper. The results are shown in FIG. 2. These data demonstrate a significant reduction in tumor volume in mictreated with riluzole and both doses of prodrug Example 125 compared with untreated or vehicle-treated controls. Bars represent SD; *, P<0.01, compared with untreated and DMSO treated (t test). An additional study was conducted using the composition of example 204 with doses of 5.0 mg/kg, 1.7 mg/kg, and 0.56 mg/kg. The results of these studies are shown in FIG. 4.

What is claimed is:

1. A compound having formula (I):

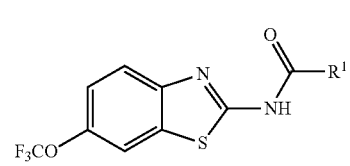

I including enantiomers, diastereomers, hydrates, solvates, pharmaceutically acceptable salts, and complexes thereof, wherein:
  $R^1$ is $CR^{10a}R^{10b}NR^{11}R^{12}$,
  $R^{10a}$ and $R^{10b}$ are hydrogen,
  $R^{11}$ is hydrogen,
  $R^{12}$ is $COCR^{13a}R^{13b}NR^{15a}R^{15b}$,
  $R^{13a}$ and $R^{13b}$ are hydrogen,
  $R^{15a}$ is hydrogen, and
  $R^{15b}$ is $C_1$-$C_6$ alkyl.

2. A compound according to claim 1 selected from the group consisting of:
  N-methyl-2-(methylamino)-N-(2-oxo-2-((6-(trifluoromethoxy)benzo[d]thiazol-2-yl)amino) ethyl)acetamide;
  2-(ethylamino)-N-methyl-N-(2-oxo-2-((6-(trifluoromethoxy)benzo[d]thiazol-2-yl)amino) ethyl)acetamide;
  2-(isopropylamino)-N-methyl-N-(2-oxo-2-((6-(trifluoromethoxy)benzo[d]thiazol-2-yl)amino) ethyl)acetamide;

2-(tert-butylamino)-N-methyl-N-(2-oxo-2-((6-(trifluoromethoxy)benzo[d]thiazol-2-yl)amino) ethyl)acetamide;

or a pharmaceutically acceptable form thereof.

3. A composition comprising an effective amount of at least one compound according to claim 1 and at least one excipient.

4. A method for treating or preventing a non-cancerous disease in which riluzole is clinically relevant said method comprising administering to a subject an effective amount of at least one compound according to claim 1.

5. The method of claim 4, wherein the at least one compound is administered in a composition further comprising at least one excipient.

6. The method of claim 4 wherein the disease in which riluzole is clinically relevant is selected from the group consisting of amyotrophic lateral sclerosis, bipolar disorder, treatment resistant and major depression, general anxiety disorder, panic disorder, social anxiety, mood disorders, cognitive disorders, dementia, agitation, apathy, psychoses, post-traumatic stress disorders, irritability, disinhibition, learning disorders, memory loss, personality disorders, bipolar disorders, Rett syndrome, eating disorders, conduct disorder, neurodegenerative disorders, pain disorders, supranuclear palsy, frontotemporal dementia, frontotemporal lobar degeneration, delirium, Alzheimer's disease, mild cognitive impairment, mild cognitive impairment due to Alzheimer's disease, drug addiction, tinnitus, mental retardation, obsessive-compulsive disorder, spinal muscular atrophy, radiation therapy, multiple sclerosis, chronic cerebellar ataxia, hereditary spinocerebellar ataxia, spinocerebellar ataxia, sporadic ataxia, episodic ataxia, Friedreich Ataxia, Multisystem Atrophy, ataxia associated with Anti-GAD antibodies target and oncoveural antigen, essential tremor, cervical spondylotic myelopathy, spinal cord injury, hereditary cerebellar ataxia, Tourette syndrome, autism spectrum disorder, schizophrenia, fragile X syndrome, Parkinson's Disease, Progressive Supranuclear Palsy, Dementia with Lewy Bodies, and Huntington's disease.

7. A method of attenuating presynaptic glutamate release said method comprising administering to a subject an effective amount of at least one compound according to claim 1.

8. A method of normalizing, enhancing, or potentiating the uptake of glutamate by glia, said method comprising administering to a subject an effective amount of at least one compound according to claim 1.

9. A method for treating or preventing disease in which riluzole is clinically relevant, said method comprising administering to a subject an effective amount of at least one compound according to claim 1 and a serotonin reuptake inhibitor.

10. The method of claim 9 wherein the disease in which riluzole is clinically relevant, is selected from the group consisting of amyotrophic lateral sclerosis, bipolar disorder, treatment resistant and major depression, general anxiety disorder, panic disorder, social anxiety, mood disorders, cognitive disorders, dementia, agitation, apathy, psychoses, post-traumatic stress disorders, irritability, disinhibition, learning disorders, memory loss, personality disorders, bipolar disorders, Rett syndrome, eating disorders, conduct disorder, neurodegenerative disorders, pain disorders, supranuclear palsy, frontotemporal dementia, frontotemporal lobar degeneration, delirium, Alzheimer's disease, mild cognitive impairment, mild cognitive impairment due to Alzheimer's disease, drug addiction, tinnitus, mental retardation, obsessive-compulsive disorder, spinal muscular atrophy, radiation therapy, multiple sclerosis, chronic cerebellar ataxia, hereditary spinocerebellar ataxia, spinocerebellar ataxia, sporadic ataxia, episodic ataxia, Friedreich Ataxia, Multisystem Atrophy, ataxia associated with Anti-GAD antibodies target and onconeural antigen, essential tremor, cervical spondylotic myelopathy, spinal cord injury, hereditary cerebellar ataxia, Tourette syndrome, autism spectrum disorder, schizophrenia, fragile X syndrome, Parkinson's Disease, Progressive Supranuclear Palsy, Dementia with Lewy Bodies, and Huntington's disease.

\* \* \* \* \*